(12) United States Patent
Damiano et al.

(10) Patent No.: US 12,201,803 B2
(45) Date of Patent: *Jan. 21, 2025

(54) INFUSION SYSTEM AND COMPONENTS THEREOF

(71) Applicant: Trustees of Boston University, Boston, MA (US)

(72) Inventors: Edward R. Damiano, Acton, MA (US); Firas H. El-Khatib, Allston, MA (US); Rajendranath Selagamsetty, Allston, MA (US); Kirk D. Ramey, Tallahassee, FL (US)

(73) Assignee: Trustees of Boston University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/215,438

(22) Filed: Jun. 28, 2023

(65) Prior Publication Data
US 2024/0165388 A1    May 23, 2024

Related U.S. Application Data

(63) Continuation of application No. 17/988,449, filed on Nov. 16, 2022, now abandoned, which is a
(Continued)

(51) Int. Cl.
*A61M 39/10* (2006.01)
*A61M 5/14* (2006.01)
(Continued)

(52) U.S. Cl.
CPC ........ *A61M 39/105* (2013.01); *A61M 5/1407* (2013.01); *A61M 5/1408* (2013.01);
(Continued)

(58) Field of Classification Search
CPC .............. A61M 39/105; A61M 5/1407; A61M 5/1408; A61M 5/142; A61M 5/14248;
(Continued)

(56) References Cited

U.S. PATENT DOCUMENTS 1,930,929 A    10/1933  Eisenberg
3,807,467 A    4/1974   Tascher et al.
(Continued)

FOREIGN PATENT DOCUMENTS

CN    106061528    10/2016
EP    2678056      1/2014
(Continued)

OTHER PUBLICATIONS

Kolind et al., "Preservation-free drug for insulin pumps", Novo Nordisk Pharmaceutical Company, Pump Partner Meeting ATTD 2020, WOP Technology Presentation, 26 pages.
(Continued)

*Primary Examiner* — Theodore J Stigell
(74) *Attorney, Agent, or Firm* — BainwoodHuang

(57) ABSTRACT

Certain embodiments provide multi-medicament infusion systems for preventing the cross-channeling of medicaments. The system may include one or more of an infusion pump, medicament reservoirs, collars, a multi-channel fluid conduit, and an infusion set. The medicament reservoirs and/or collars may be sized and shaped differently such that the medicament reservoirs can only be inserted into the system selected configurations.

15 Claims, 61 Drawing Sheets

Related U.S. Application Data continuation of application No. 17/723,769, filed on Apr. 19, 2022, now abandoned, which is a continuation of application No. 15/848,933, filed on Dec. 20, 2017, now Pat. No. 11,331,463, which is a continuation of application No. PCT/US2016/041395, filed on Jul. 7, 2016.

(60) Provisional application No. 62/353,210, filed on Jun. 22, 2016, provisional application No. 62/254,950, filed on Nov. 13, 2015, provisional application No. 62/190,212, filed on Jul. 8, 2015.

(51) Int. Cl.
- A61M 5/142 (2006.01)
- A61M 5/158 (2006.01)
- A61M 5/162 (2006.01)
- A61M 39/02 (2006.01)

(52) U.S. Cl.
CPC ........ *A61M 5/142* (2013.01); *A61M 5/14248* (2013.01); *A61M 5/158* (2013.01); *A61M 5/162* (2013.01); *A61M 39/02* (2013.01); *A61M 39/10* (2013.01); *A61M 2005/1586* (2013.01); *A61M 2039/1044* (2013.01); *A61M 2039/1072* (2013.01); *A61M 2039/1094* (2013.01); *A61M 2205/43* (2013.01); *A61M 2205/583* (2013.01); *A61M 2205/584* (2013.01); *A61M 2205/6018* (2013.01)

(58) Field of Classification Search
CPC ...... A61M 5/158; A61M 5/162; A61M 39/02; A61M 39/10; A61M 2005/1586; A61M 2039/1044; A61M 2039/1072; A61M 2039/1094; A61M 2205/43; A61M 2205/583; A61M 2205/584; A61M 2205/6018

See application file for complete search history.

(56) References Cited

U.S. PATENT DOCUMENTS

| | | |
|---|---|---|
| 4,150,673 A | 4/1979 | Watt |
| 4,253,501 A | 3/1981 | Ogle |
| 4,515,584 A | 5/1985 | Abe et al. |
| 4,585,439 A | 4/1986 | Michel |
| 4,608,042 A | 8/1986 | Vanderveen et al. |
| 4,675,006 A | 6/1987 | Hrushesky |
| 5,085,643 A | 2/1992 | Larkin et al. |
| 5,243,982 A | 9/1993 | Moestl et al. |
| 5,298,023 A | 3/1994 | Haber et al. |
| 5,356,380 A | 10/1994 | Hoekwater et al. |
| 5,411,480 A | 5/1995 | Kriesel |
| 5,472,403 A | 12/1995 | Cornacchia et al. |
| 5,505,704 A | 4/1996 | Pawelka et al. |
| 5,522,803 A | 6/1996 | Teissen-Simony |
| 5,545,152 A | 8/1996 | Funderburk et al. |
| 5,616,124 A | 4/1997 | Hague et al. |
| 5,916,494 A | 6/1999 | Widman et al. |
| 5,954,697 A | 9/1999 | Srisathapat et al. |
| 5,961,494 A | 10/1999 | Hogan |
| 5,971,972 A | 10/1999 | Rosenbaum |
| 6,106,498 A | 8/2000 | Friedli et al. |
| 6,132,416 A | 10/2000 | Broselow |
| 6,248,067 B1 | 6/2001 | Causey, III et al. |
| 6,259,587 B1 | 7/2001 | Sheldon et al. |
| 6,360,784 B1 | 3/2002 | Philippens et al. |
| 6,362,591 B1 | 3/2002 | Moberg |
| 6,368,314 B1 | 4/2002 | Kipfer et al. |
| 6,390,130 B1 | 5/2002 | Guala |
| 6,485,465 B2 | 11/2002 | Moberg et al. |
| 6,551,276 B1 | 4/2003 | Mann et al. |
| 6,551,298 B1 | 4/2003 | Zhang et al. |
| 6,554,798 B1 | 4/2003 | Mann et al. |
| 6,555,986 B2 | 4/2003 | Moberg |
| 6,558,320 B1 | 5/2003 | Causey, III et al. |
| 6,572,545 B2 | 6/2003 | Knobbe et al. |
| 6,585,695 B1 | 7/2003 | Adair et al. |
| 6,620,138 B1 | 9/2003 | Marrgi et al. |
| 6,641,533 B2 | 11/2003 | Causey, III et al. |
| 6,652,483 B2 | 11/2003 | Slate et al. |
| 6,656,148 B2 | 12/2003 | Das et al. |
| 6,659,980 B2 | 12/2003 | Moberg et al. |
| 6,719,728 B2 | 4/2004 | Mason et al. |
| 6,736,797 B1 | 5/2004 | Larsen et al. |
| 6,752,787 B1 | 6/2004 | Causey, III et al. |
| 6,801,420 B2 | 10/2004 | Talbot et al. |
| 6,809,653 B1 | 10/2004 | Mann et al. |
| 6,811,534 B2 | 11/2004 | Bowman, IV et al. |
| 6,821,421 B2 | 11/2004 | Murakami |
| 6,854,620 B2 | 2/2005 | Ramey |
| 6,872,200 B2 | 3/2005 | Mann et al. |
| 6,878,132 B2 | 4/2005 | Kipfer |
| 6,936,029 B2 | 8/2005 | Mann et al. |
| 6,939,329 B1 | 9/2005 | Verkaart |
| 6,958,705 B2 | 10/2005 | Lebel et al. |
| 6,960,198 B2 | 11/2005 | Sarmiento |
| 6,979,326 B2 | 12/2005 | Mann et al. |
| 6,997,920 B2 | 2/2006 | Mann et al. |
| 7,025,226 B2 | 4/2006 | Ramey |
| 7,025,743 B2 | 4/2006 | Mann et al. |
| 7,098,803 B2 | 8/2006 | Mann et al. |
| 7,109,878 B2 | 9/2006 | Mann et al. |
| 7,187,528 B2 | 3/2007 | Talbot et al. |
| 7,193,521 B2 | 3/2007 | Moberg et al. |
| 7,281,314 B2 | 10/2007 | Hess et al. |
| 7,285,105 B2 | 10/2007 | Kim et al. |
| 7,291,133 B1 | 11/2007 | Kindler et al. |
| 7,324,012 B2 | 1/2008 | Mann et al. |
| 7,342,508 B2 | 3/2008 | Morgan et al. |
| 7,460,350 B2 | 12/2008 | Talbot et al. |
| 7,534,226 B2 | 5/2009 | Mernoe et al. |
| 7,602,310 B2 | 10/2009 | Mann et al. |
| 7,621,893 B2 | 11/2009 | Moberg et al. |
| 7,625,354 B2 | 12/2009 | Hochman |
| 7,628,772 B2 | 12/2009 | McConnell et al. |
| 7,628,782 B2 | 12/2009 | Adair et al. |
| 7,648,494 B2 | 1/2010 | Kornerup et al. |
| 7,654,127 B2 | 2/2010 | Krulevitch et al. |
| 7,655,618 B2 | 2/2010 | Green et al. |
| 7,658,734 B2 | 2/2010 | Adair et al. |
| 7,678,762 B2 | 3/2010 | Green et al. |
| 7,678,763 B2 | 3/2010 | Green et al. |
| 7,683,027 B2 | 3/2010 | Green et al. |
| 7,708,717 B2 | 5/2010 | Estes et al. |
| 7,749,185 B2 | 7/2010 | Wilson et al. |
| 7,760,481 B2 | 7/2010 | Talbot et al. |
| 7,766,873 B2 | 8/2010 | Moberg et al. |
| 7,776,030 B2 | 8/2010 | Estes et al. |
| 7,789,859 B2 | 9/2010 | Estes et al. |
| 7,794,427 B2 | 9/2010 | Estes et al. |
| 7,794,428 B2 | 9/2010 | Estes et al. |
| 7,815,602 B2 | 10/2010 | Mann et al. |
| 7,819,843 B2 | 10/2010 | Mann et al. |
| 7,831,310 B2 | 11/2010 | Lebel et al. |
| 7,833,196 B2 | 11/2010 | Estes et al. |
| 7,879,010 B2 | 2/2011 | Hunn et al. |
| 7,879,026 B2 | 2/2011 | Estes et al. |
| 7,887,512 B2 | 2/2011 | Estes et al. |
| 7,892,206 B2 | 2/2011 | Moberg et al. |
| 7,914,449 B2 | 3/2011 | Kouchi et al. |
| 7,922,708 B2 | 4/2011 | Estes et al. |
| 7,938,803 B2 | 5/2011 | Mernoe et al. |
| 7,951,112 B2 | 5/2011 | Patzer |
| 7,967,785 B2 | 6/2011 | Morgan et al. |
| 7,981,084 B2 | 7/2011 | Estes et al. |
| 7,981,105 B2 | 7/2011 | Adair et al. |
| 7,988,683 B2 | 8/2011 | Adair et al. |
| 7,998,111 B2 | 8/2011 | Moberg et al. |
| 7,998,131 B2 | 8/2011 | Adair et al. |
| 8,004,422 B2 | 8/2011 | Morgan et al. |

(56) References Cited

U.S. PATENT DOCUMENTS

| | | |
|---|---|---|
| 8,034,026 B2 | 10/2011 | Grant et al. |
| 8,057,436 B2 | 11/2011 | Causey et al. |
| 8,062,257 B2 | 11/2011 | Moberg et al. |
| 8,065,096 B2 | 11/2011 | Moberg et al. |
| 8,088,096 B2 | 1/2012 | Lauchard et al. |
| 8,105,279 B2 | 1/2012 | Mernoe et al. |
| 8,106,534 B2 | 1/2012 | Spurlin et al. |
| 8,142,397 B2 | 3/2012 | Patzer |
| 8,167,846 B2 | 5/2012 | Chong et al. |
| 8,177,767 B2 | 5/2012 | Kristensen et al. |
| 8,182,447 B2 | 5/2012 | Moberg et al. |
| 8,192,394 B2 | 6/2012 | Estes et al. |
| 8,197,444 B1 | 6/2012 | Bazargan et al. |
| 8,206,350 B2 | 6/2012 | Mann et al. |
| 8,206,353 B2 | 6/2012 | Chong et al. |
| 8,211,059 B2 | 7/2012 | Kriesel et al. |
| 8,211,062 B2 | 7/2012 | Estes et al. |
| 8,251,959 B2 | 8/2012 | Johner et al. |
| 8,257,345 B2 | 9/2012 | Adair et al. |
| 8,267,893 B2 | 9/2012 | Moberg et al. |
| 8,273,061 B2 | 9/2012 | McConnell et al. |
| 8,282,601 B2 | 10/2012 | Mernoe et al. |
| 8,287,495 B2 | 10/2012 | Michaud et al. |
| 8,287,516 B2 | 10/2012 | Kornerup et al. |
| 8,298,184 B2 | 10/2012 | Diperna et al. |
| 8,303,572 B2 | 11/2012 | Adair et al. |
| 8,372,039 B2 | 2/2013 | Mernoe et al. |
| 8,409,142 B2 | 4/2013 | Causey et al. |
| 8,430,847 B2 | 4/2013 | Mernoe et al. |
| 8,430,849 B2 | 4/2013 | Smith et al. |
| 8,454,575 B2 | 6/2013 | Estes et al. |
| 8,469,942 B2 | 6/2013 | Kow et al. |
| 8,475,408 B2 | 7/2013 | Mernoe et al. |
| 8,480,623 B2 | 7/2013 | Mernoe et al. |
| 8,483,980 B2 | 7/2013 | Moberg et al. |
| 8,500,716 B2 | 8/2013 | Adair et al. |
| 8,512,276 B2 | 8/2013 | Talbot et al. |
| 8,512,289 B2 | 8/2013 | Chong et al. |
| 8,523,803 B1 | 9/2013 | Favreau |
| 8,551,045 B2 | 10/2013 | Sie et al. |
| 8,556,856 B2 | 10/2013 | Bazargan et al. |
| 8,556,866 B2 | 10/2013 | Krulevitch et al. |
| 8,562,565 B2 | 10/2013 | Fonacier et al. |
| 8,562,587 B2 | 10/2013 | Kovatchev et al. |
| 8,568,349 B2 | 10/2013 | Shergold |
| 8,573,027 B2 | 11/2013 | Rosinko et al. |
| 8,579,813 B2 | 11/2013 | Causey, III et al. |
| 8,597,269 B2 | 12/2013 | Chong et al. |
| 8,603,026 B2 | 12/2013 | Favreau |
| 8,603,027 B2 | 12/2013 | Favreau |
| 8,603,033 B2 | 12/2013 | Bazargan et al. |
| 8,613,726 B2 | 12/2013 | Causey, III et al. |
| 8,613,731 B2 | 12/2013 | Hansen et al. |
| 8,617,110 B2 | 12/2013 | Moberg et al. |
| 8,622,966 B2 | 1/2014 | Causey et al. |
| 8,628,510 B2 | 1/2014 | Bazargan et al. |
| 8,641,671 B2 | 2/2014 | Michaud et al. |
| 8,647,074 B2 | 2/2014 | Moberg et al. |
| 8,647,296 B2 | 2/2014 | Moberg et al. |
| 8,663,103 B2 | 3/2014 | Causey, III et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| 8,696,633 B2 | 4/2014 | Estes et al. |
| 8,747,368 B2 | 6/2014 | Mernoe et al. |
| 8,747,369 B2 | 6/2014 | Mernoe et al. |
| 8,758,323 B2 | 6/2014 | Michaud et al. |
| 8,771,229 B2 | 7/2014 | Amirouche et al. |
| 8,777,901 B2 | 7/2014 | Smith et al. |
| 8,790,307 B2 | 7/2014 | Amirouche et al. |
| 8,821,442 B2 | 9/2014 | Haar |
| 8,823,528 B2 | 9/2014 | Blomquist |
| 8,834,420 B2 | 9/2014 | Estes et al. |
| 8,841,012 B2 | 9/2014 | Fonacier et al. |
| 8,864,726 B2 | 10/2014 | Halili et al. |
| 8,864,737 B2 | 10/2014 | Hasegawa et al. |
| 8,864,739 B2 | 10/2014 | Moberg et al. |
| 8,870,829 B2 | 10/2014 | Halili et al. |
| 8,876,770 B2 | 11/2014 | Kraft et al. |
| 8,900,206 B2 | 12/2014 | Halili et al. |
| 8,905,972 B2 | 12/2014 | Smith et al. |
| 8,915,879 B2 | 12/2014 | Smith et al. |
| 8,936,573 B2 | 1/2015 | Blomquist |
| 8,945,068 B2 | 2/2015 | Halili et al. |
| 8,974,435 B2 | 3/2015 | Friedli |
| 8,992,475 B2 | 3/2015 | Mann et al. |
| 8,992,507 B2 | 3/2015 | Aeschlimann et al. |
| 8,998,840 B2 | 4/2015 | Hanson et al. |
| 8,998,842 B2 | 4/2015 | Lauchard et al. |
| 8,998,858 B2 | 4/2015 | Chong et al. |
| 9,011,371 B2 | 4/2015 | Moberg et al. |
| 9,033,925 B2 | 5/2015 | Moberg et al. |
| 9,033,951 B2 | 5/2015 | Kow et al. |
| 9,050,406 B2 | 6/2015 | Kow et al. |
| 9,101,710 B2 | 8/2015 | Yavorsky et al. |
| 9,101,715 B2 | 8/2015 | Causey, III et al. |
| 9,107,999 B2 | 8/2015 | Moberg et al. |
| 9,114,209 B2 | 8/2015 | Estes et al. |
| 9,114,213 B2 | 8/2015 | Murakami et al. |
| 9,119,917 B2 | 9/2015 | Blomquist |
| 9,132,228 B2 | 9/2015 | Yan |
| 9,173,998 B2 | 11/2015 | Rosinko et al. |
| 9,180,242 B2 | 11/2015 | Metzmaker et al. |
| 9,180,243 B2 | 11/2015 | Michaud |
| 9,180,254 B2 | 11/2015 | Avery et al. |
| 9,184,490 B2 | 11/2015 | Crouther et al. |
| 9,194,388 B2 | 11/2015 | Laermer et al. |
| 9,205,192 B2 | 12/2015 | Estes et al. |
| 9,211,376 B2 | 12/2015 | Kouyoumjian et al. |
| 9,211,377 B2 | 12/2015 | Diperna et al. |
| 9,216,249 B2 | 12/2015 | Smith et al. |
| 9,220,835 B2 | 12/2015 | Cane' |
| 9,250,106 B2 | 2/2016 | Rosinko et al. |
| 9,272,009 B2 | 3/2016 | Spencer |
| 9,283,318 B2 | 3/2016 | Yavorsky et al. |
| 9,295,826 B2 | 3/2016 | Bertrand et al. |
| 9,308,320 B2 | 4/2016 | Smith et al. |
| 9,308,321 B2 | 4/2016 | Alderete, Jr. et al. |
| 9,314,569 B2 | 4/2016 | Causey et al. |
| 9,320,849 B2 | 4/2016 | Smith et al. |
| 9,327,073 B2 | 5/2016 | Moberg et al. |
| 9,335,910 B2 | 5/2016 | Farnan et al. |
| 9,339,639 B2 | 5/2016 | Halili et al. |
| 9,344,024 B2 | 5/2016 | Favreau |
| 9,345,643 B2 | 5/2016 | Okiyama |
| 9,364,608 B2 | 6/2016 | Moberg et al. |
| 9,379,652 B2 | 6/2016 | Favreau |
| 9,379,653 B2 | 6/2016 | Favreau |
| 9,381,297 B2 | 7/2016 | Brown et al. |
| 9,381,300 B2 | 7/2016 | Smith et al. |
| 9,393,399 B2 | 7/2016 | Yavorsky et al. |
| 9,415,157 B2 | 8/2016 | Mann et al. |
| 9,427,519 B2 | 8/2016 | Kraft et al. |
| 9,433,731 B2 | 9/2016 | Trock et al. |
| 9,433,732 B2 | 9/2016 | Moberg et al. |
| 9,433,733 B2 | 9/2016 | Moberg et al. |
| 9,452,255 B2 | 9/2016 | Tieck et al. |
| 9,452,256 B2 | 9/2016 | Tieck et al. |
| 9,463,309 B2 | 10/2016 | Yavorsky et al. |
| 9,494,147 B2 | 11/2016 | Chong et al. |
| 9,498,573 B2 | 11/2016 | Smith et al. |
| 9,514,518 B2 | 12/2016 | Gillespie et al. |
| 9,517,299 B2 | 12/2016 | Tieck et al. |
| 9,517,301 B2 | 12/2016 | Estes et al. |
| 9,533,132 B2 | 1/2017 | Halili et al. |
| 9,539,385 B2 | 1/2017 | Mathys |
| 9,539,388 B2 | 1/2017 | Causey et al. |
| 9,554,967 B2 | 1/2017 | Moia et al. |
| 9,579,452 B2 | 2/2017 | Adair et al. |
| 9,592,339 B2 | 3/2017 | Zhou |
| 9,597,462 B2 | 3/2017 | Moore |
| 9,610,431 B2 | 4/2017 | Halili et al. |
| 9,629,992 B2 | 4/2017 | Halili et al. |
| 9,636,453 B2 | 5/2017 | Monirabbasi et al. |

(56) References Cited

U.S. PATENT DOCUMENTS

| | | |
|---|---|---|
| 9,682,189 B2 | 6/2017 | Good et al. |
| 9,687,612 B2 | 6/2017 | Avery et al. |
| 9,707,339 B2 | 7/2017 | Chartrand et al. |
| 9,715,327 B2 | 7/2017 | Rosinko et al. |
| 9,717,845 B2 | 8/2017 | Istoc |
| 9,717,848 B2 | 8/2017 | Geismar et al. |
| 9,731,067 B2 | 8/2017 | Pananen |
| 9,744,290 B2 | 8/2017 | Tieck et al. |
| 9,744,291 B2 | 8/2017 | Tieck et al. |
| 9,744,301 B2 | 8/2017 | Mann et al. |
| 9,750,871 B2 | 9/2017 | Metzmaker et al. |
| 9,750,873 B2 | 9/2017 | Brown et al. |
| 9,750,875 B2 | 9/2017 | Smith et al. |
| 9,770,553 B2 | 9/2017 | Bazargan et al. |
| 9,782,543 B2 | 10/2017 | Groeschke et al. |
| 9,789,245 B2 | 10/2017 | Tieck et al. |
| 9,795,732 B2 | 10/2017 | Trock et al. |
| 9,801,787 B2 | 10/2017 | Py |
| 9,814,830 B2 | 11/2017 | Mernoe et al. |
| 9,814,872 B2 | 11/2017 | Eggert et al. |
| 9,839,741 B2 | 12/2017 | Yavorsky et al. |
| 9,841,014 B2 | 12/2017 | Yap et al. |
| 9,863,837 B2 | 1/2018 | Rule et al. |
| 9,872,957 B2 | 1/2018 | Causey et al. |
| 9,883,834 B2 | 2/2018 | Amirouche et al. |
| 9,889,256 B2 | 2/2018 | Cabiri et al. |
| 9,895,490 B2 | 2/2018 | Kow et al. |
| 9,925,330 B2 | 3/2018 | Tieck et al. |
| 9,931,459 B2 | 4/2018 | Tieck et al. |
| 9,931,460 B2 | 4/2018 | Tieck et al. |
| 9,943,645 B2 | 4/2018 | Monirabbasi et al. |
| 9,950,113 B2 | 4/2018 | Franke et al. |
| 9,987,420 B2 | 6/2018 | Pananen |
| 9,993,592 B2 | 6/2018 | Amirouche et al. |
| 9,993,594 B2 | 6/2018 | Bazargan et al. |
| 10,010,674 B2 | 7/2018 | Rosinko et al. |
| 10,010,678 B2 | 7/2018 | Schildt et al. |
| 10,016,564 B2 | 7/2018 | Piehl et al. |
| 10,029,045 B2 | 7/2018 | Smith et al. |
| 10,064,933 B2 | 9/2018 | Bird et al. |
| 10,071,200 B2 | 9/2018 | Alderete, Jr. et al. |
| 10,080,839 B2 | 9/2018 | Cole et al. |
| 10,086,133 B2 | 10/2018 | Pananen et al. |
| 10,086,134 B2 | 10/2018 | Pananen et al. |
| 10,092,701 B2 | 10/2018 | Johansen et al. |
| 10,105,483 B2 | 10/2018 | Mernoe |
| 10,105,497 B2 | 10/2018 | Dreier et al. |
| 10,130,759 B2 | 11/2018 | Amirouche et al. |
| 10,130,763 B2 | 11/2018 | Lauchard et al. |
| 10,137,243 B2 | 11/2018 | Wang et al. |
| 10,141,882 B2 | 11/2018 | Favreau |
| 10,146,911 B2 | 12/2018 | Trock |
| 10,166,327 B2 | 1/2019 | Tieck et al. |
| 10,172,998 B2 | 1/2019 | Tieck et al. |
| 10,172,999 B2 | 1/2019 | Tieck et al. |
| 10,207,047 B2 | 2/2019 | Estes |
| 10,213,549 B2 | 2/2019 | Amirouche et al. |
| 10,220,143 B2 | 3/2019 | Moberg et al. |
| 10,228,663 B2 | 3/2019 | Favreau |
| 10,232,109 B2 | 3/2019 | Deak et al. |
| 10,238,030 B2 | 3/2019 | Urbani |
| 10,238,793 B2 | 3/2019 | Deak et al. |
| 10,252,001 B2 | 4/2019 | Geismar et al. |
| 10,258,736 B2 | 4/2019 | Metzmaker et al. |
| 10,272,196 B2 | 4/2019 | Smith et al. |
| 10,279,110 B2 | 5/2019 | Mann et al. |
| 10,300,264 B2 | 5/2019 | Halili et al. |
| 10,307,536 B2 | 6/2019 | Causey et al. |
| 10,322,227 B2 | 6/2019 | Piehl et al. |
| 10,363,365 B2 | 7/2019 | Bazargan |
| 10,376,631 B2 | 8/2019 | Tieck et al. |
| 10,376,632 B2 | 8/2019 | Tieck et al. |
| 10,384,013 B2 | 8/2019 | Krusell et al. |
| 10,391,257 B2 | 8/2019 | Piehl et al. |
| 10,478,554 B2 | 11/2019 | Bazargan et al. |
| 10,517,892 B2 | 12/2019 | Chattaraj et al. |
| 10,532,156 B2 | 1/2020 | Istoc |
| 10,552,580 B2 | 2/2020 | Bazargan |
| 10,603,431 B2 | 3/2020 | Mernoe et al. |
| 10,772,796 B2 | 9/2020 | Kavazov |
| 10,850,032 B2 | 12/2020 | Steck et al. |
| 10,857,287 B2 | 12/2020 | Damiano et al. |
| 10,861,591 B2 | 12/2020 | Grosman et al. |
| 10,960,136 B2 | 3/2021 | Palerm et al. |
| 11,331,463 B2 * | 5/2022 | Damiano .............. A61M 5/162 |
| 2002/0019608 A1 | 2/2002 | Mason et al. |
| 2002/0038392 A1 | 3/2002 | De La Huerga |
| 2002/0055711 A1 | 5/2002 | Lavi et al. |
| 2002/0065484 A1 | 5/2002 | Douglas et al. |
| 2002/0161332 A1 * | 10/2002 | Ramey .................. A61M 5/158 |
| | | 604/180 |
| 2003/0009133 A1 | 1/2003 | Ramey |
| 2005/0015056 A1 | 1/2005 | Duchon et al. |
| 2005/0020980 A1 | 1/2005 | Inoue et al. |
| 2005/0038387 A1 | 2/2005 | Kriesel et al. |
| 2005/0051580 A1 | 3/2005 | Ramey |
| 2005/0154434 A1 | 7/2005 | Simon et al. |
| 2005/0215979 A1 | 9/2005 | Kornerup et al. |
| 2005/0256461 A1 | 11/2005 | Difiore et al. |
| 2006/0102174 A1 | 5/2006 | Hochman |
| 2006/0264908 A1 | 11/2006 | Ishii et al. |
| 2007/0088271 A1 | 4/2007 | Richards |
| 2007/0142786 A1 | 6/2007 | Lampropoulos et al. |
| 2007/0161955 A1 | 7/2007 | Bynum et al. |
| 2007/0273671 A1 | 11/2007 | Zadesky et al. |
| 2007/0282294 A1 | 12/2007 | Sidler |
| 2008/0051710 A1 * | 2/2008 | Moberg .............. A61M 5/1456 |
| | | 604/131 |
| 2008/0119792 A1 | 5/2008 | Kornerup et al. |
| 2008/0188813 A1 | 8/2008 | Miller et al. |
| 2008/0243085 A1 | 10/2008 | Destefano |
| 2008/0262425 A1 | 10/2008 | Mogensen |
| 2008/0319383 A1 | 12/2008 | Byland et al. |
| 2009/0099523 A1 | 4/2009 | Grant et al. |
| 2009/0281505 A1 | 11/2009 | Hansen et al. |
| 2009/0326506 A1 | 12/2009 | Hasegawa et al. |
| 2010/0004603 A1 | 1/2010 | Kristensen et al. |
| 2010/0049144 A1 | 2/2010 | McConnell et al. |
| 2010/0191165 A1 | 7/2010 | Appling et al. |
| 2010/0217241 A1 | 8/2010 | Mann et al. |
| 2011/0021905 A1 | 1/2011 | Patrick et al. |
| 2011/0118659 A1 | 5/2011 | Maaskamp et al. |
| 2011/0230838 A1 | 9/2011 | Adams et al. |
| 2011/0288494 A1 | 11/2011 | Mendels |
| 2012/0078170 A1 | 3/2012 | Smith et al. |
| 2012/0078185 A1 | 3/2012 | Smith et al. |
| 2012/0078197 A1 | 3/2012 | O'Connor et al. |
| 2012/0211946 A1 | 8/2012 | Halili et al. |
| 2012/0211947 A1 | 8/2012 | Halili et al. |
| 2012/0215177 A1 | 8/2012 | Halili et al. |
| 2012/0215178 A1 | 8/2012 | Halili et al. |
| 2012/0215179 A1 | 8/2012 | Halili et al. |
| 2012/0215180 A1 | 8/2012 | Halili et al. |
| 2012/0215183 A1 | 8/2012 | Halili et al. |
| 2012/0226234 A1 | 9/2012 | Bazargan et al. |
| 2012/0323188 A1 | 12/2012 | Yavorsky et al. |
| 2013/0046252 A1 | 2/2013 | Yavorsky et al. |
| 2013/0046253 A1 | 2/2013 | Yavorsky et al. |
| 2013/0066281 A1 | 3/2013 | Yavorsky et al. |
| 2013/0085470 A1 | 4/2013 | O'Connor et al. |
| 2013/0090602 A1 | 4/2013 | Avery et al. |
| 2013/0116632 A1 | 5/2013 | Yavorsky et al. |
| 2013/0183170 A1 | 7/2013 | Laermer et al. |
| 2013/0237947 A1 | 9/2013 | Amirouche et al. |
| 2013/0245604 A1 | 9/2013 | Kouyoumjian et al. |
| 2013/0274576 A1 | 10/2013 | Amirouche et al. |
| 2013/0345641 A1 | 12/2013 | Cerman et al. |
| 2014/0052079 A1 | 2/2014 | Eggert et al. |
| 2014/0194815 A1 | 7/2014 | Kouyoumjian et al. |
| 2014/0276563 A1 | 9/2014 | Cole et al. |
| 2014/0378912 A1 | 12/2014 | Halili et al. |
| 2014/0378913 A1 | 12/2014 | Halili et al. |
| 2015/0045735 A1 | 2/2015 | Halili et al. |
| 2015/0057615 A1 | 2/2015 | Mernoe, V et al. |

(56) References Cited

U.S. PATENT DOCUMENTS

| | | |
|---|---|---|
| 2015/0073384 A1 | 3/2015 | Limaye |
| 2015/0202375 A1 | 7/2015 | Schabbach et al. |
| 2015/0265826 A1 | 9/2015 | Dudley |
| 2015/0314063 A1 | 11/2015 | Nagar et al. |
| 2015/0357683 A1 | 12/2015 | Lohr et al. |
| 2016/0015885 A1 | 1/2016 | Pananen et al. |
| 2016/0015886 A1 | 1/2016 | Pananen et al. |
| 2016/0015887 A1 | 1/2016 | Pananen et al. |
| 2016/0015911 A1 | 1/2016 | Bazargan et al. |
| 2016/0051760 A1 | 2/2016 | Krusell et al. |
| 2016/0058668 A1 | 3/2016 | Metzmaker et al. |
| 2016/0074587 A1 | 3/2016 | Searle et al. |
| 2016/0082182 A1 | 3/2016 | Gregory et al. |
| 2016/0089493 A1 | 3/2016 | Crouther et al. |
| 2016/0106919 A1 | 4/2016 | Hayter et al. |
| 2016/0151563 A1 | 6/2016 | Yavorsky et al. |
| 2016/0184519 A1 | 6/2016 | Blundred et al. |
| 2016/0220754 A1 | 8/2016 | Shaanan et al. |
| 2016/0235910 A1 | 8/2016 | Damiano et al. |
| 2016/0263324 A1 | 9/2016 | Shaanan et al. |
| 2016/0271322 A1 | 9/2016 | Ramey et al. |
| 2016/0361494 A1 | 12/2016 | Jürg et al. |
| 2017/0056590 A1 | 3/2017 | Diperna et al. |
| 2017/0065768 A1 | 3/2017 | Moore |
| 2017/0182307 A1 | 6/2017 | Halili et al. |
| 2017/0189666 A1 | 7/2017 | Sealfon et al. |
| 2017/0192506 A1 | 7/2017 | Andersen et al. |
| 2017/0216523 A1 | 8/2017 | Neftel et al. |
| 2017/0232203 A1 | 8/2017 | Krusell et al. |
| 2017/0235920 A1 | 8/2017 | Bauss et al. |
| 2017/0239422 A1 | 8/2017 | Kodgule et al. |
| 2017/0286638 A1 | 10/2017 | Searle et al. |
| 2017/0312454 A1 | 11/2017 | Chattaraj et al. |
| 2018/0036475 A1 | 2/2018 | Lin |
| 2018/0043104 A1 | 2/2018 | Mueller-Pathle |
| 2018/0043105 A1 | 2/2018 | Nazzaro et al. |
| 2018/0103897 A1 | 4/2018 | Amirouche |
| 2018/0104417 A1 | 4/2018 | Nessel et al. |
| 2018/0117248 A1 | 5/2018 | Cabiri et al. |
| 2018/0207366 A1 | 7/2018 | Marcoz et al. |
| 2018/0228979 A1 | 8/2018 | Schildt et al. |
| 2018/0280624 A1 | 10/2018 | Bitton et al. |
| 2018/0311435 A1 | 11/2018 | Galasso |
| 2018/0318498 A1 | 11/2018 | Grant et al. |
| 2018/0318506 A1 | 11/2018 | Oakes et al. |
| 2018/0326164 A1 | 11/2018 | Bauss et al. |
| 2018/0353699 A1 | 12/2018 | Helmer et al. |
| 2019/0001060 A1 | 1/2019 | Gylleby et al. |
| 2019/0009032 A1 | 1/2019 | Hautaviita et al. |
| 2019/0015582 A1 | 1/2019 | Naftalovitz et al. |
| 2019/0030247 A1 | 1/2019 | Edwards et al. |
| 2019/0054251 A1 | 2/2019 | Pieronek et al. |
| 2019/0091460 A1 | 3/2019 | Yavorsky et al. |
| 2019/0134305 A1 | 5/2019 | Srinivasan et al. |
| 2019/0151559 A1 | 5/2019 | Byerly et al. |
| 2019/0167900 A1 | 6/2019 | Friedli et al. |
| 2019/0192762 A1 | 6/2019 | Metzmaker et al. |
| 2019/0209775 A1 | 7/2019 | Merchant |
| 2019/0217007 A1 | 7/2019 | Sasaki |
| 2019/0344009 A1 | 11/2019 | Damiano et al. |
| 2020/0330719 A1 | 10/2020 | Segal et al. |
| 2021/0030949 A1 | 2/2021 | Damiano et al. |
| 2021/0030957 A1 | 2/2021 | Beckstein et al. |
| 2021/0093777 A1 | 4/2021 | Damiano et al. |
| 2021/0106750 A1 | 4/2021 | Damiano et al. |
| 2021/0283328 A1 | 9/2021 | Damiano et al. |

FOREIGN PATENT DOCUMENTS

| | | |
|---|---|---|
| EP | 3060276 | 8/2016 |
| EP | 3060277 | 8/2016 |
| EP | 3062841 | 9/2016 |
| EP | 3150241 | 6/2018 |
| EP | 3378516 | 9/2018 |
| EP | 3319662 | 3/2019 |
| HK | 1230529 | 12/2017 |
| HK | 1254602 | 7/2019 |
| JP | 57124151 | 8/1982 |
| JP | S5930241 | 2/1984 |
| JP | 2004538118 | 12/2004 |
| JP | 2007511252 | 5/2007 |
| JP | 2013524905 | 6/2013 |
| JP | 2014515673 | 7/2014 |
| JP | 2016538098 | 8/2016 |
| JP | 2018525060 | 9/2018 |
| RU | 2549310 | 4/2015 |
| WO | 9964103 | 12/1999 |
| WO | 03017915 | 3/2003 |
| WO | 2004045704 | 6/2004 |
| WO | 2005000378 | 1/2005 |
| WO | 2005004973 | 1/2005 |
| WO | 2006054367 | 5/2006 |
| WO | 2009029511 | 4/2009 |
| WO | 2007086186 | 5/2009 |
| WO | 2009060741 | 5/2009 |
| WO | 2011131778 | 10/2011 |
| WO | 2012008285 | 1/2012 |
| WO | 2012072555 | 6/2012 |
| WO | 2012110474 | 8/2012 |
| WO | 20120115911 | 8/2012 |
| WO | 2012146670 | 11/2012 |
| WO | 2012160104 | 11/2012 |
| WO | 2013161979 | 10/2013 |
| WO | 2014104027 | 3/2014 |
| WO | 2015061690 | 4/2015 |
| WO | 2015061691 | 4/2015 |
| WO | 2015061693 | 4/2015 |
| WO | WO-2015/06190 | * 4/2015 |
| WO | 2015166993 | 5/2015 |
| WO | 2015155229 | 10/2015 |
| WO | 2017007968 | 1/2017 |
| WO | 2017199012 | 11/2017 |
| WO | 2017217105 | 12/2017 |
| WO | 2018129354 | 7/2018 |
| WO | 2019021985 | 1/2019 |
| WO | 2019046593 | 3/2019 |

OTHER PUBLICATIONS

Ping One Touch Owner's Booklet, Dated Oct. 2014, (360 pages).
Renesas Synergy™ Platform, "Capacitive Touch Hardware Design and Layout Guidelines for Synergy, RX200, and RX100". R01AN3825EU0101 Rev.1.01, Jun. 14, 2017, pp. 1-18.
International Search Report and Written Opinion in PCT/US2016/041395 dated Nov. 4, 2016 in 23 pages.
Boston University, Jan. 2014, Bionic Pancreas: Introducing the iLet 1294 1000, http://sites.bu.edu/bionicpacreas/introducing-the-ilet-1294-1000/, 3 pp.
Brown et al, Apr. 2016, Introducing Beta Bionics: bringing the iLet bionic pancreas to market, https://diatribe.org/introducing-beta-bionics-bringing-ilet-bionic-pancreas-market, 3 pp.
Hoskins, Oct. 2, 2018, iLet "Bionic Pancreas" making progress with gen 4 device, Healthline, https://www.healthline.com/diabetesmine/beta-bionics-ilet-update#1, 15 pp.
Idlebrook, Jul. 30, 2019, Beta Bionics secures funding for pivotal iLet bionic pancreas trials, https://t1dexchange.org/welcome-glu-users/articles/beta-bionics-secures-funding-for-pivotal-ilet-bionic-pancreas-trials, 4 pp.
Krugman, Aug. 25, 2018, iLet Bionic Pancreas Interface, sarakrugman.com/ilet-interface, 3 pp.
Sifferlin, Apr. 1, 2016, The bionic pancreas is getting closer to reality, time.com, https://time.com/4278068/bionic-pancreas-company, 5 pp.

* cited by examiner

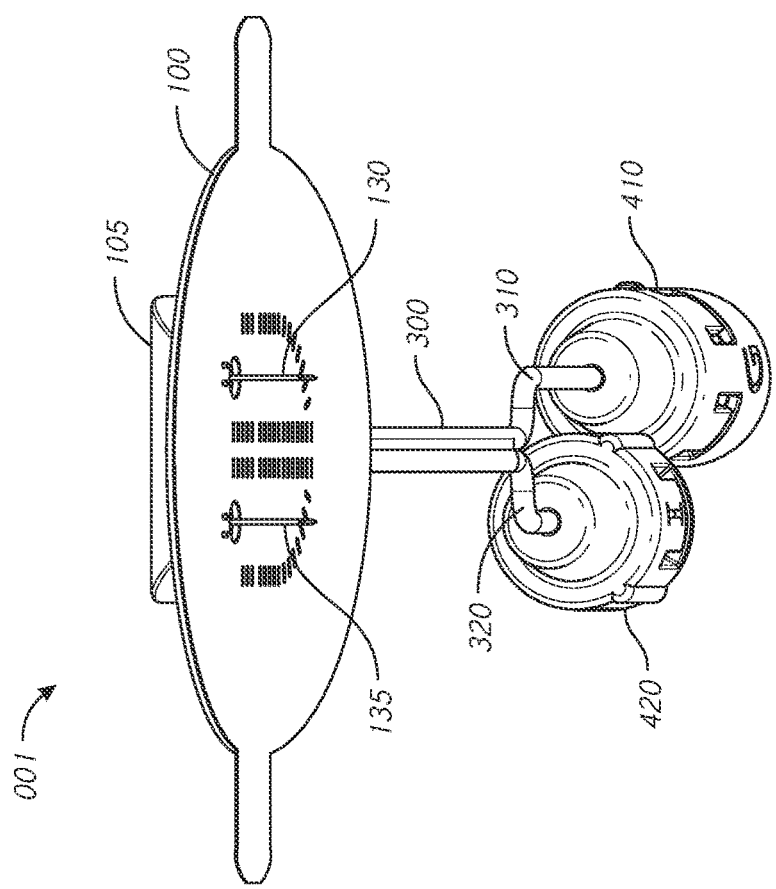
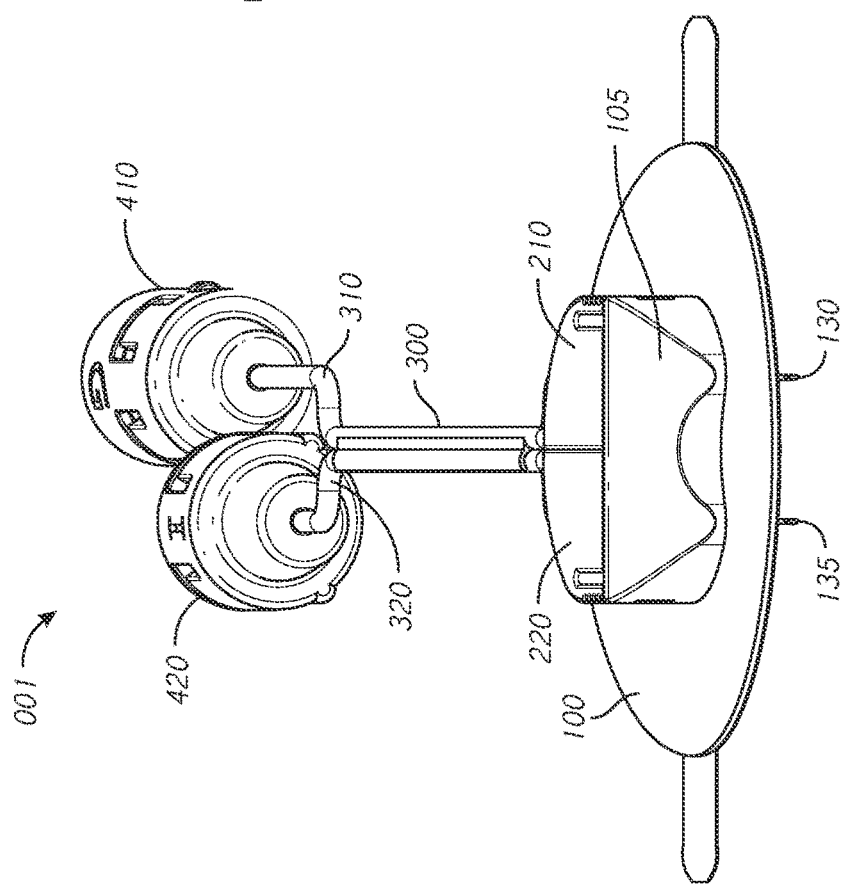
FIG. 3B
FIG. 3A

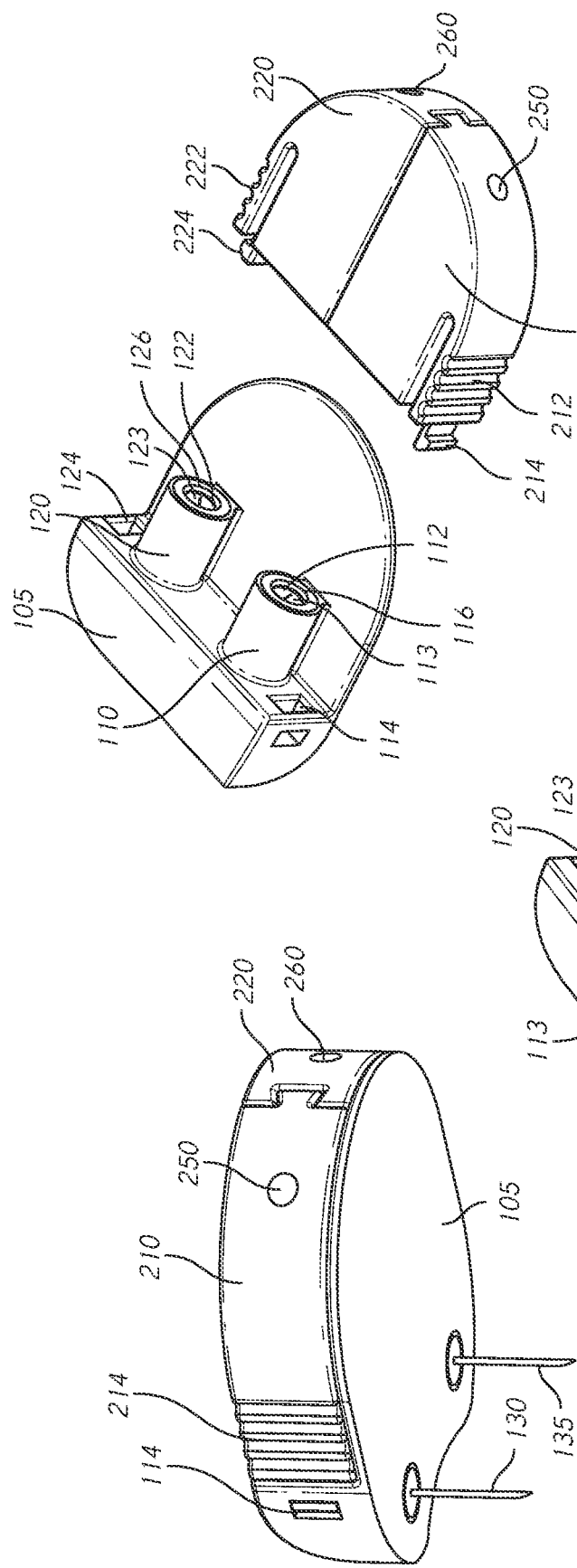

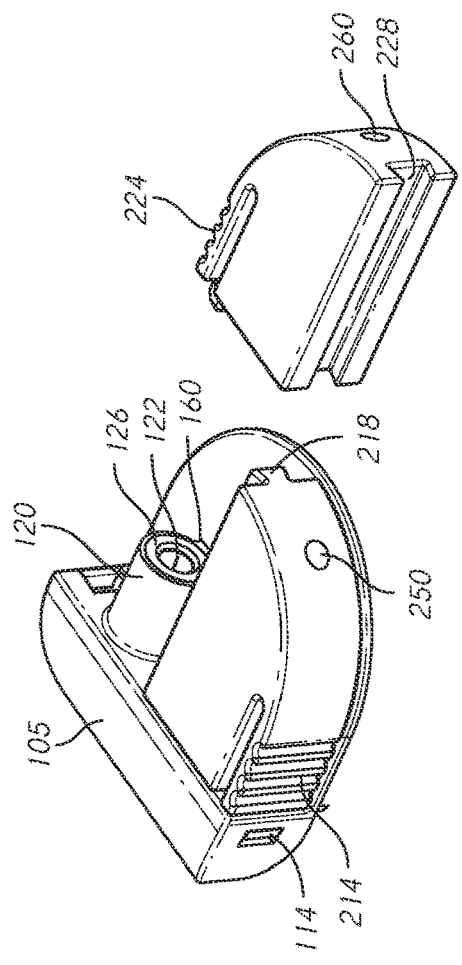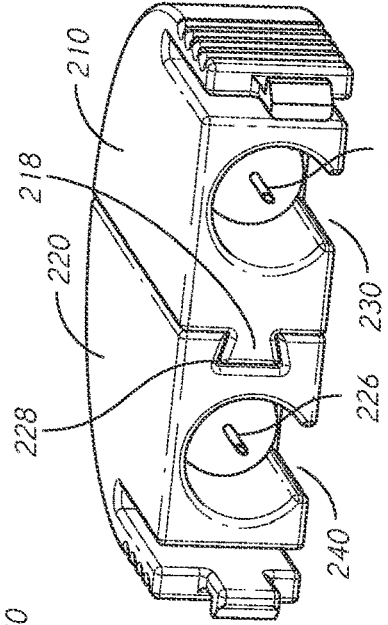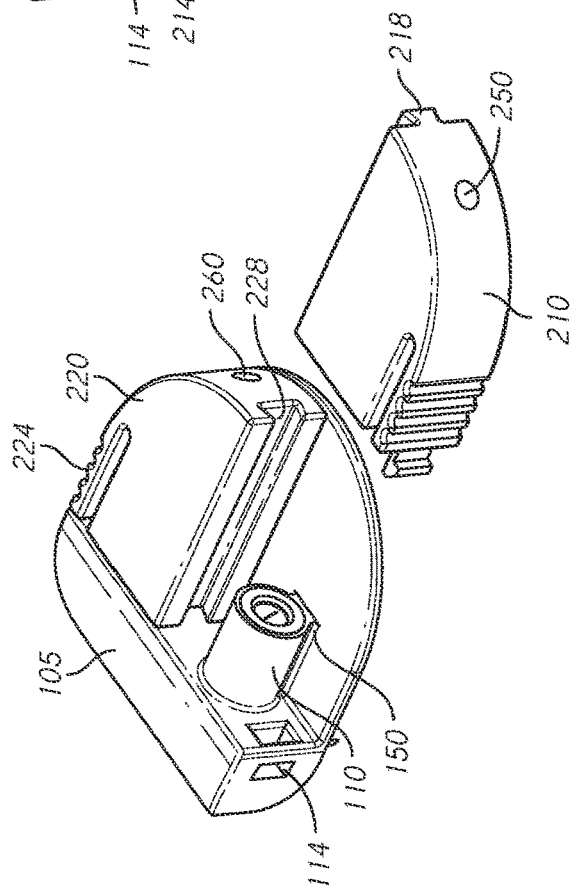
FIG. 8
FIG. 9
FIG. 10

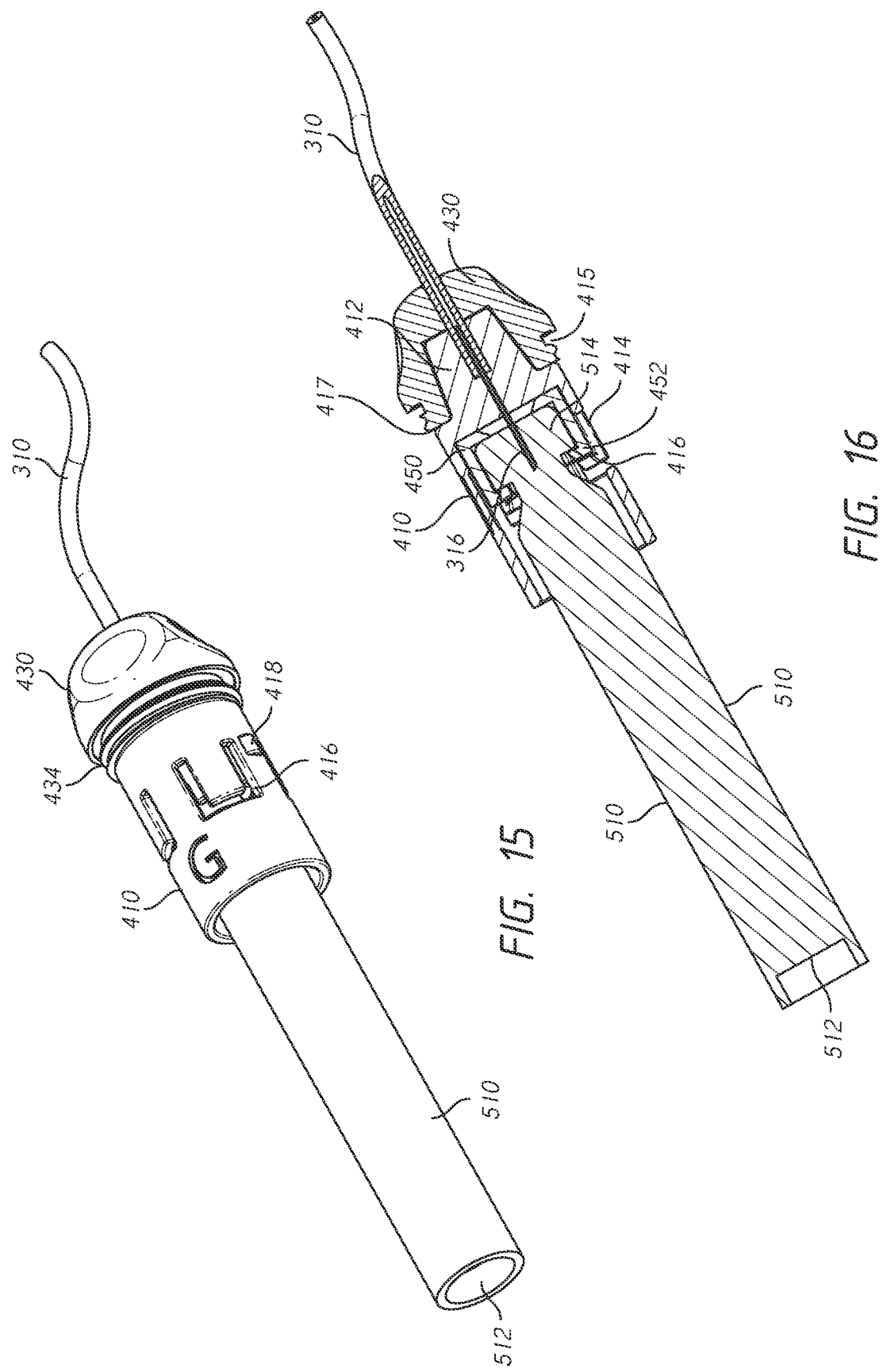

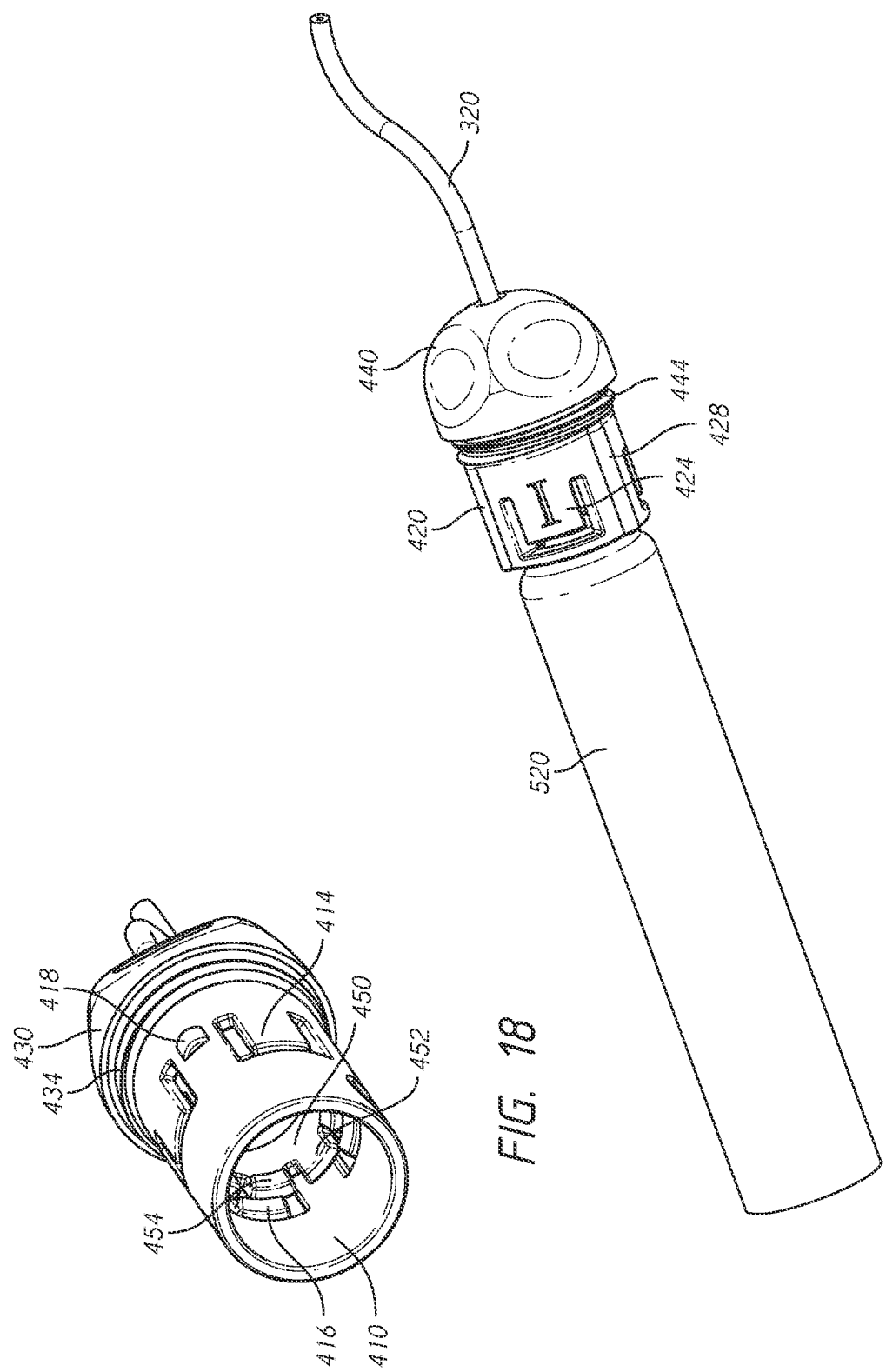

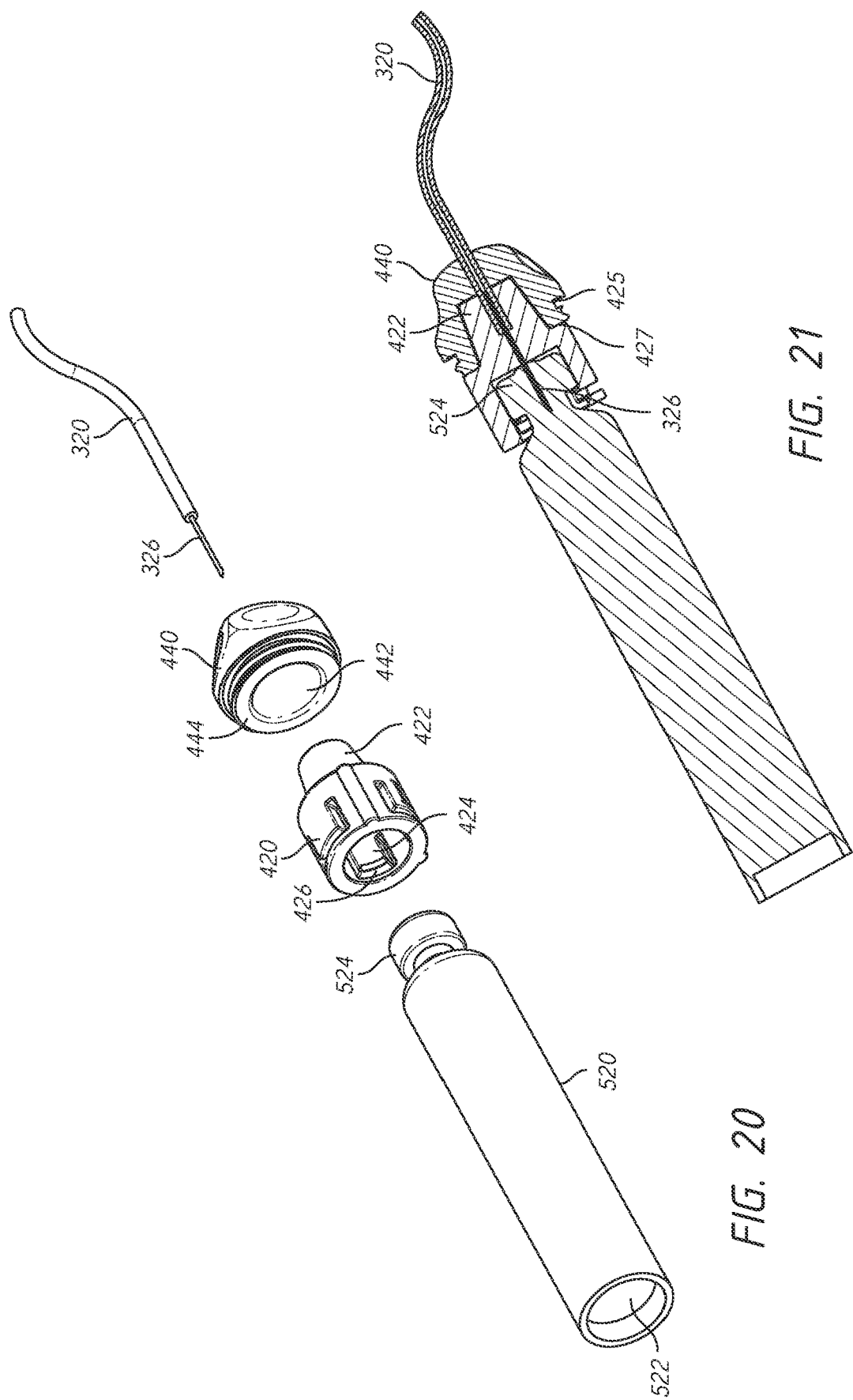

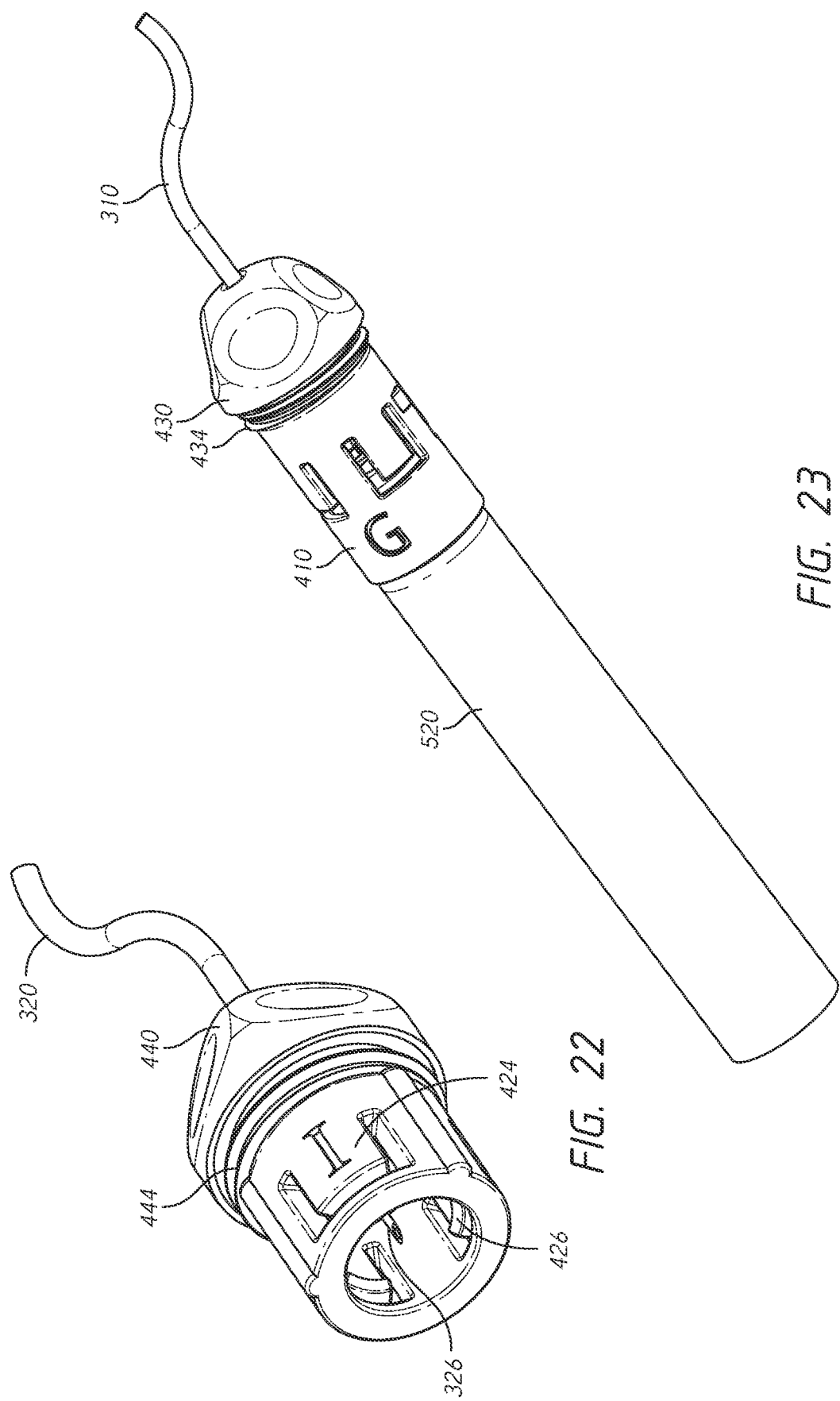

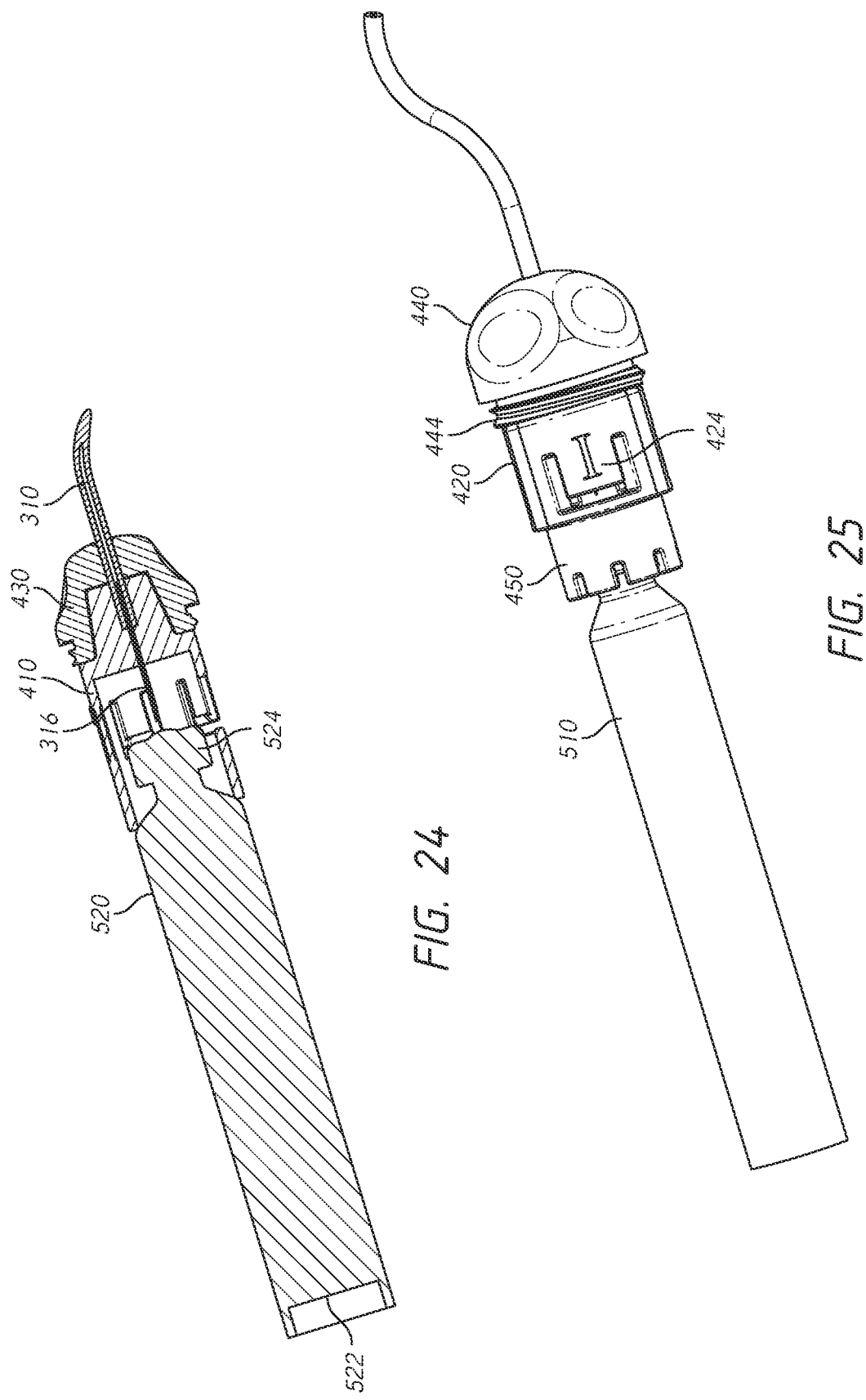

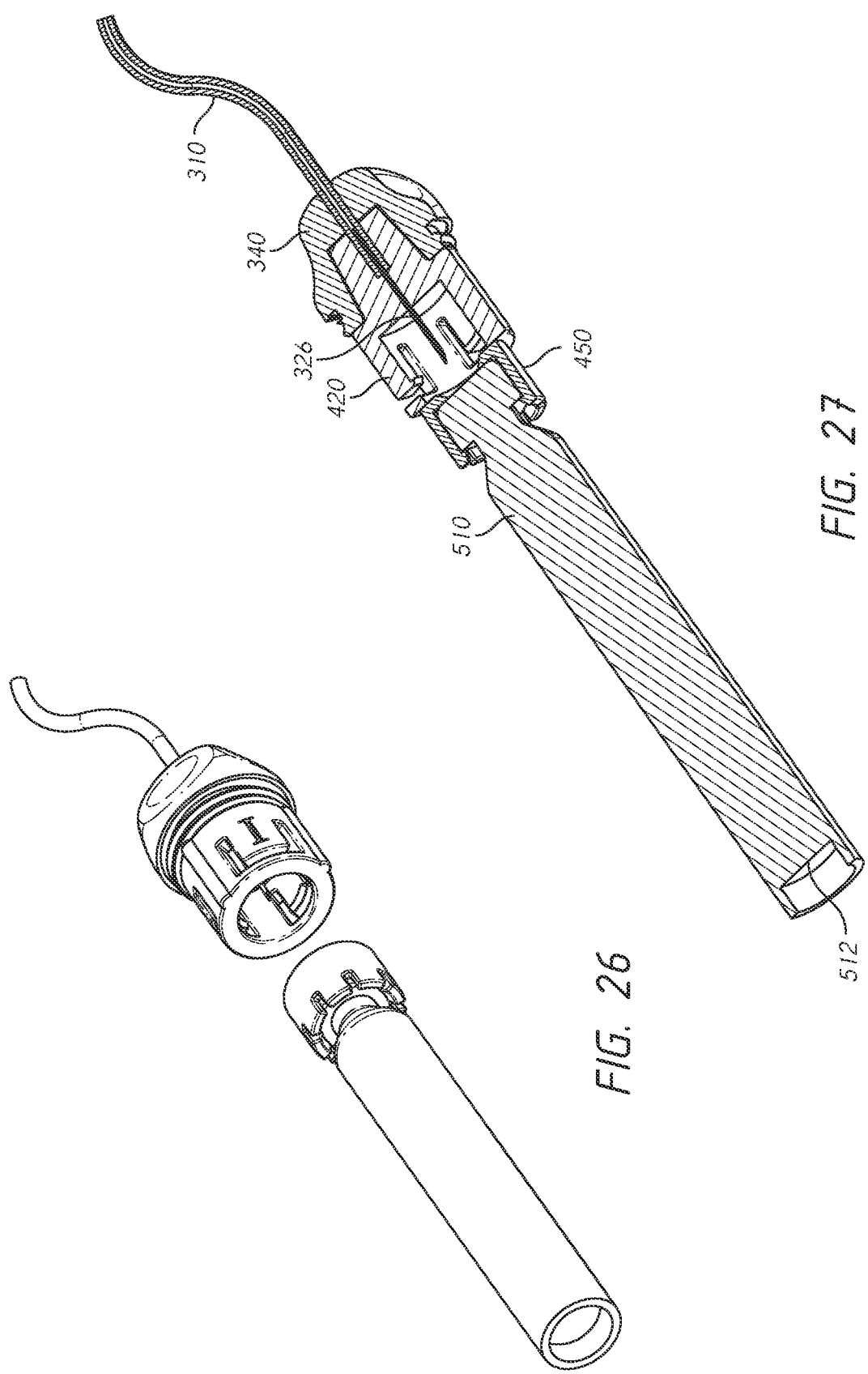

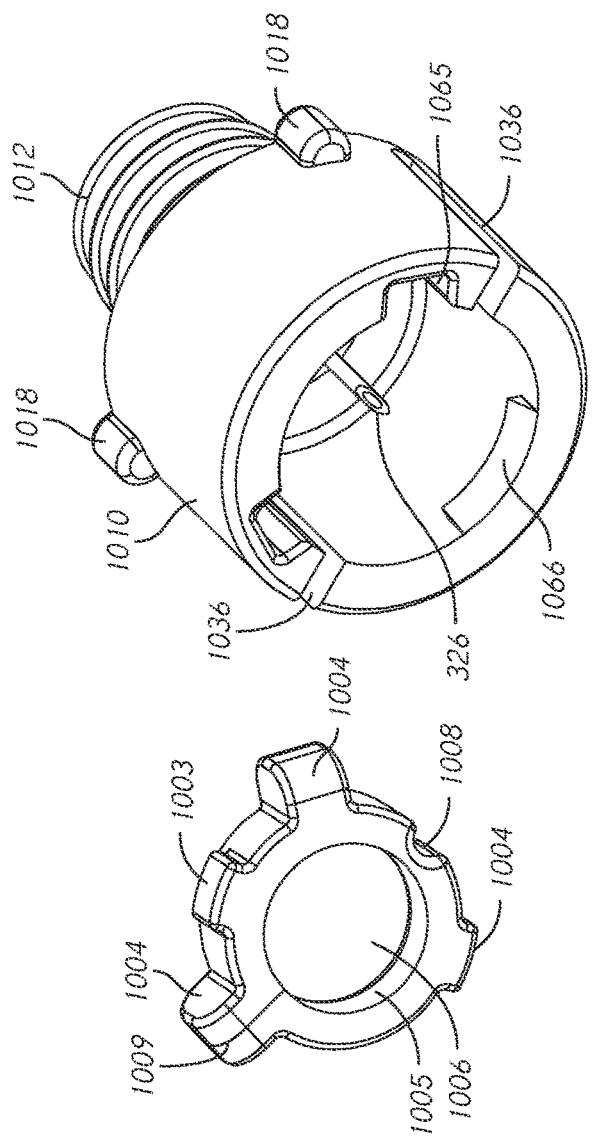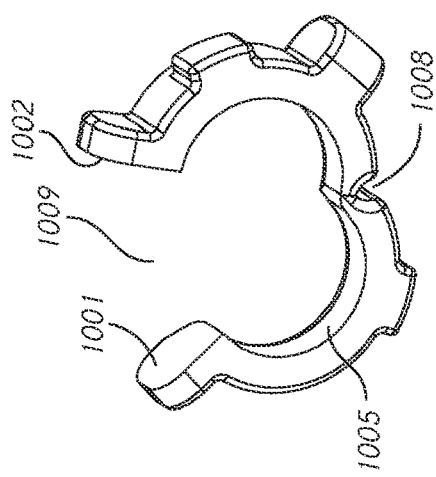
FIG. 40C
FIG. 40B
FIG. 40A

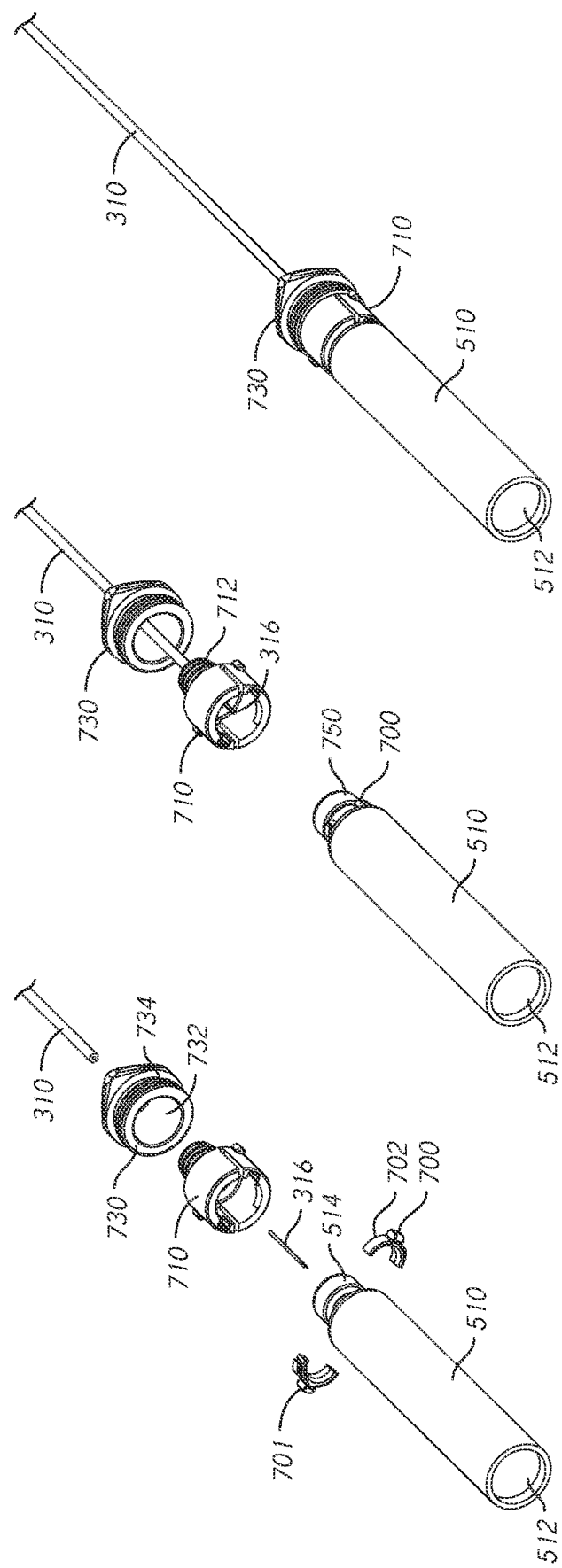

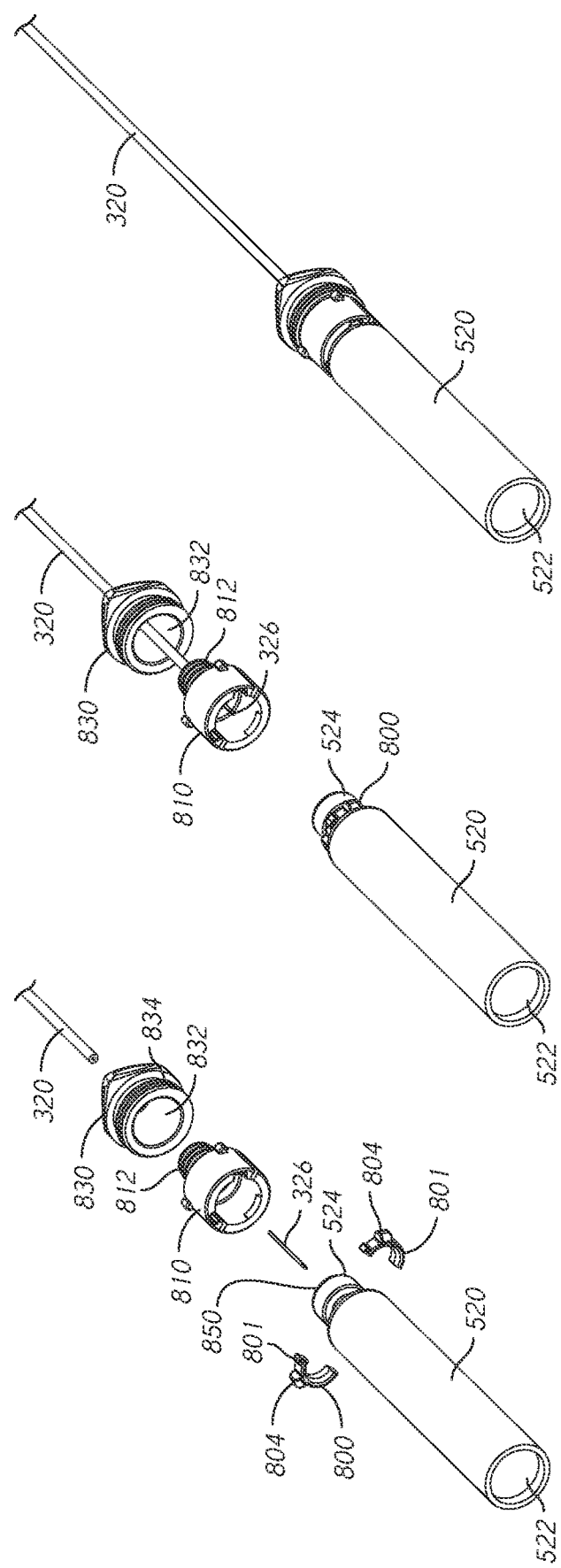

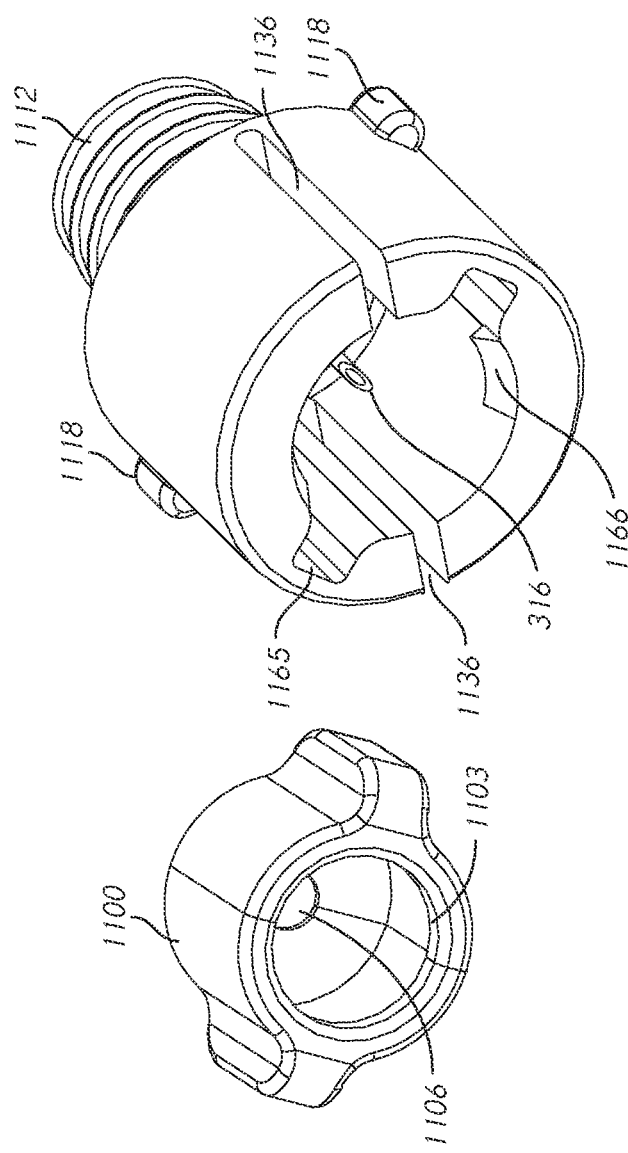
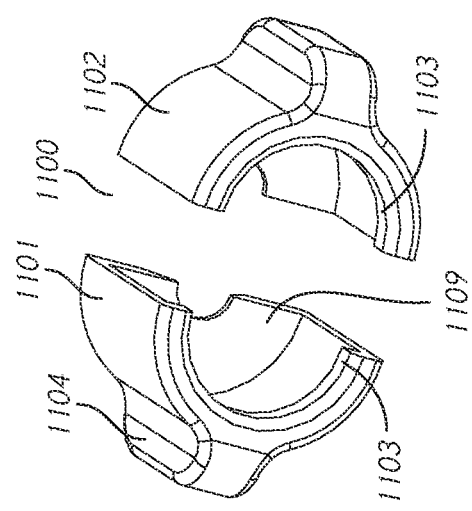
FIG. 44C
FIG. 44B
FIG. 44A

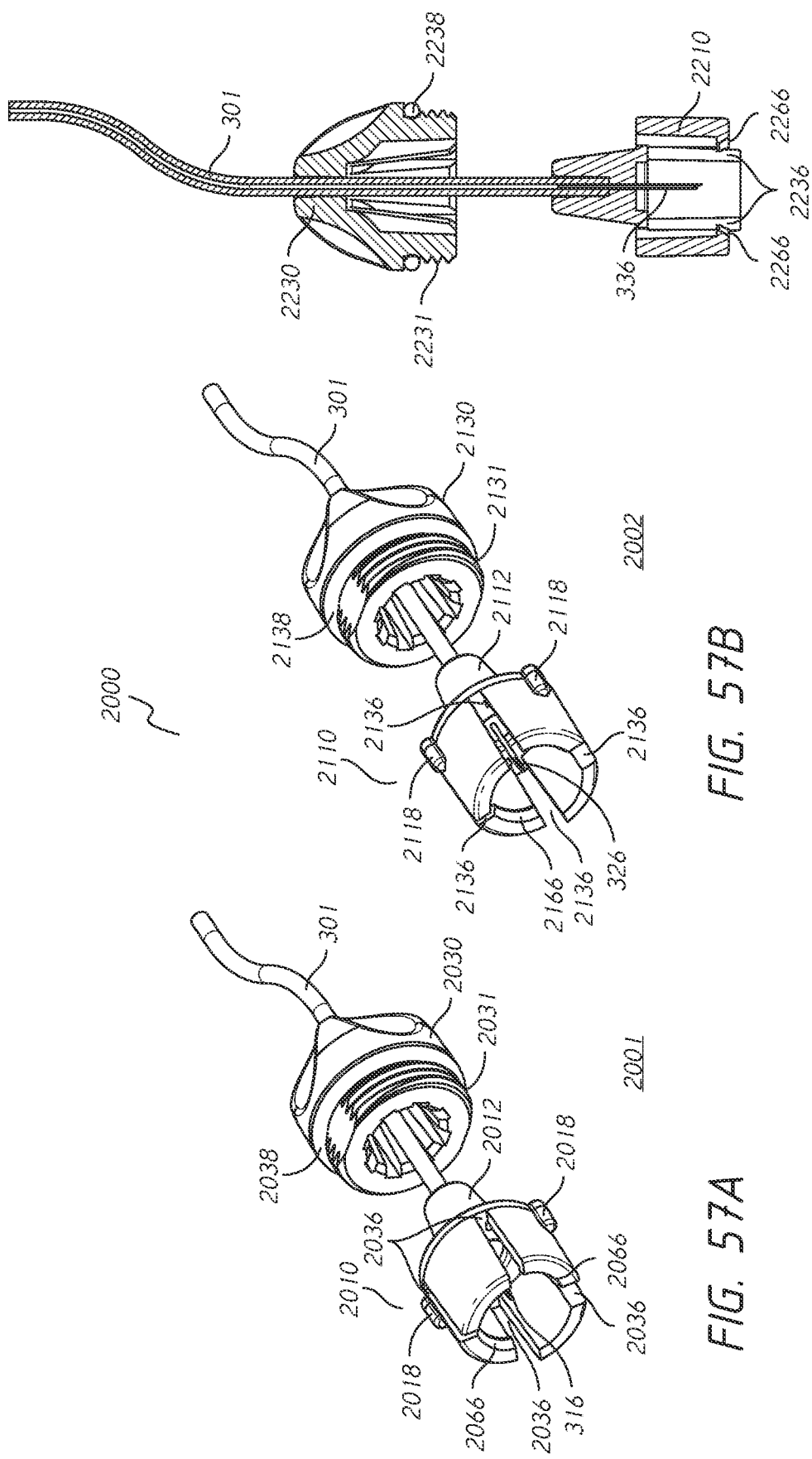

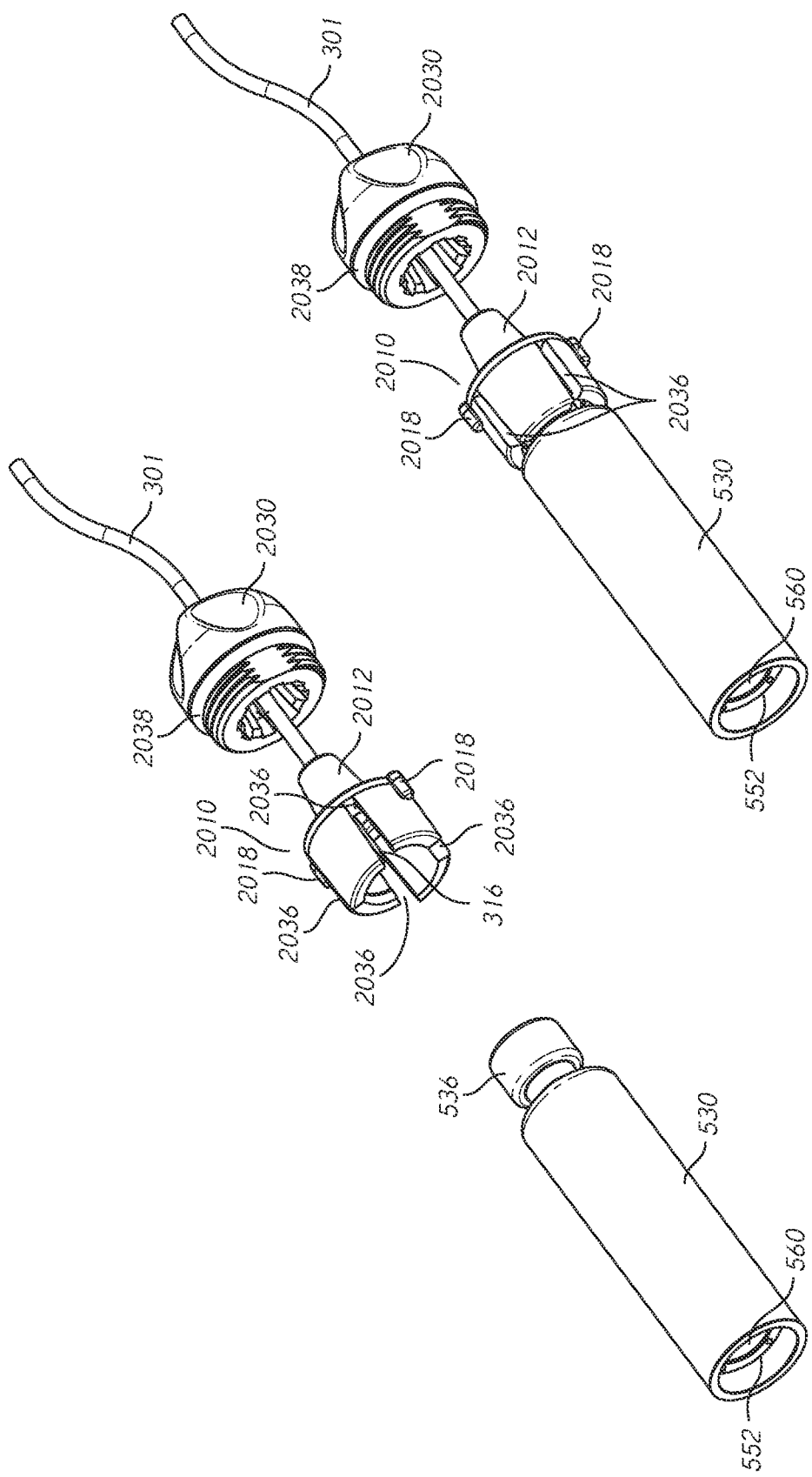

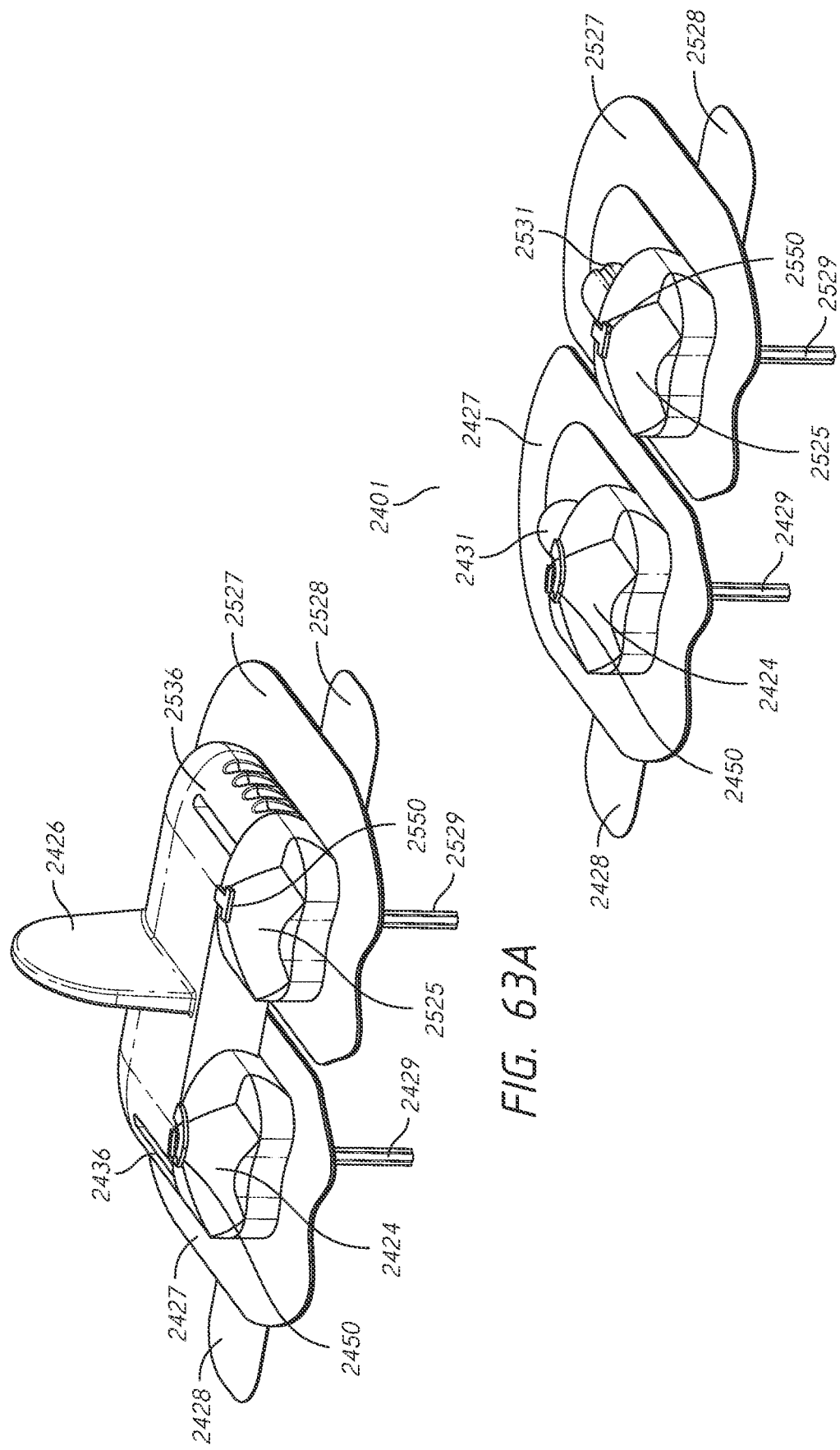

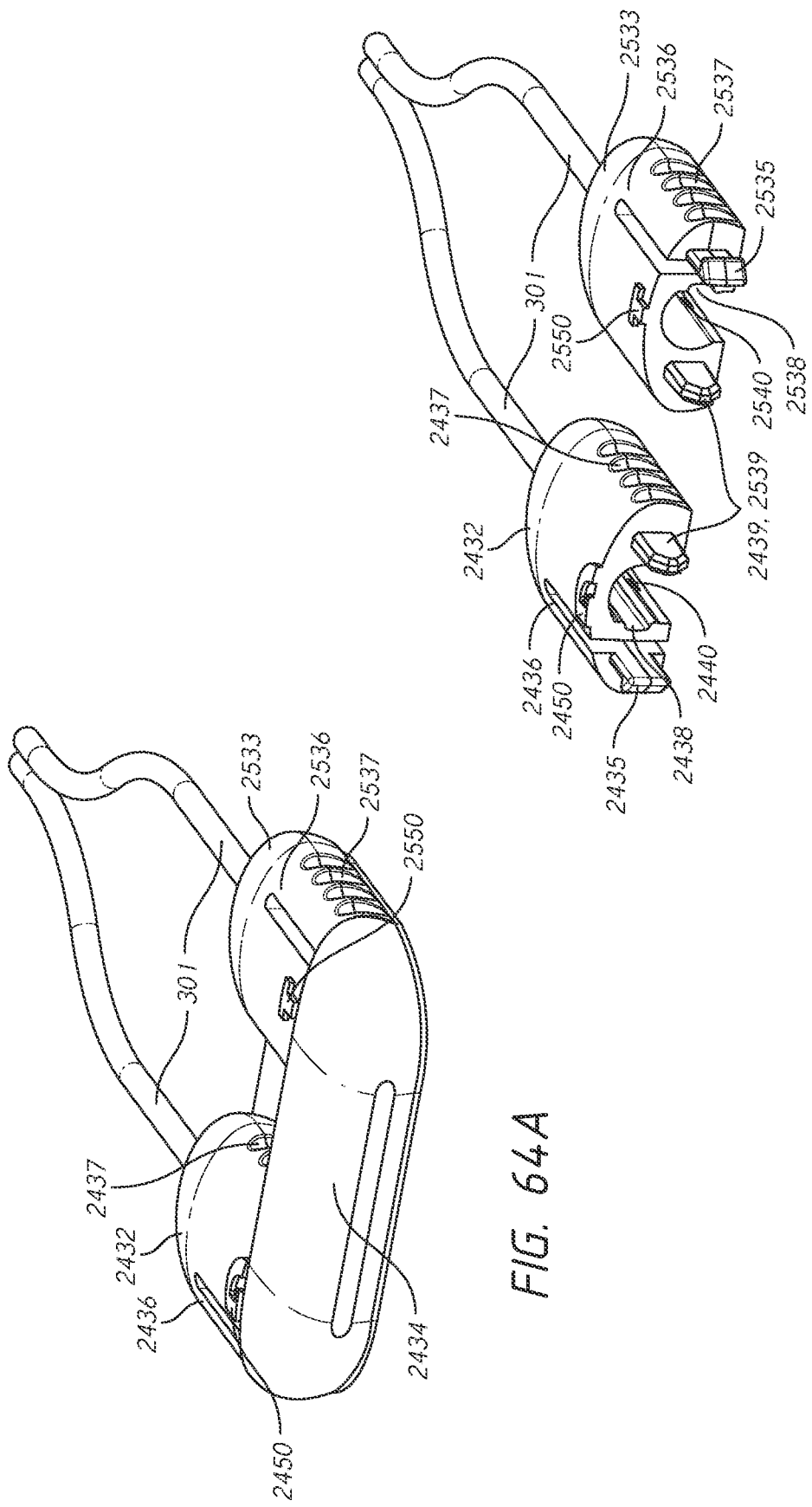

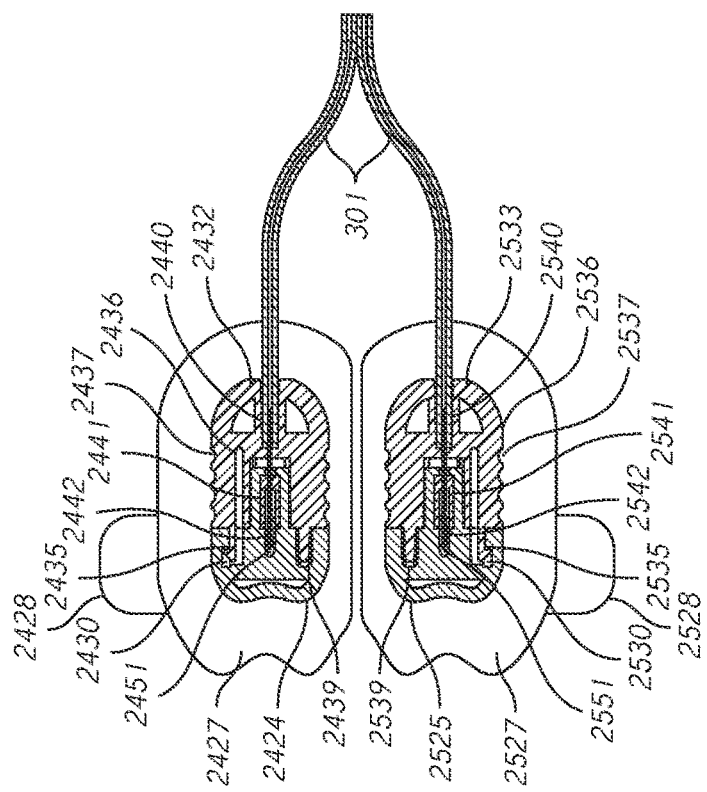
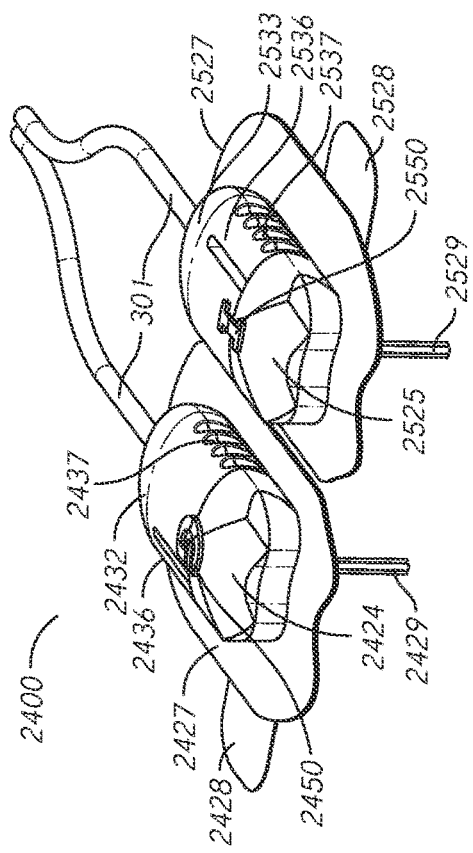
FIG. 65B
FIG. 65A

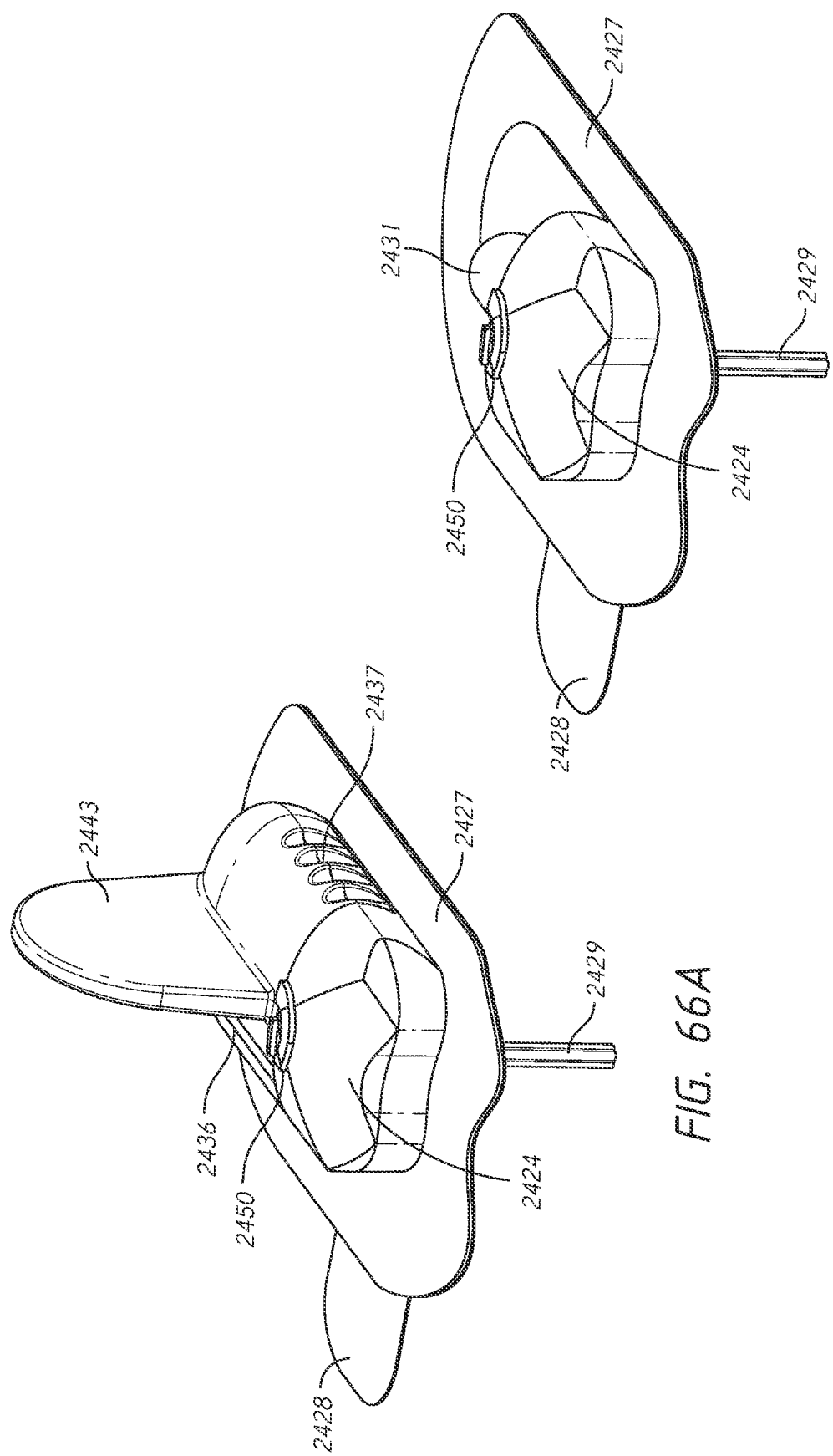

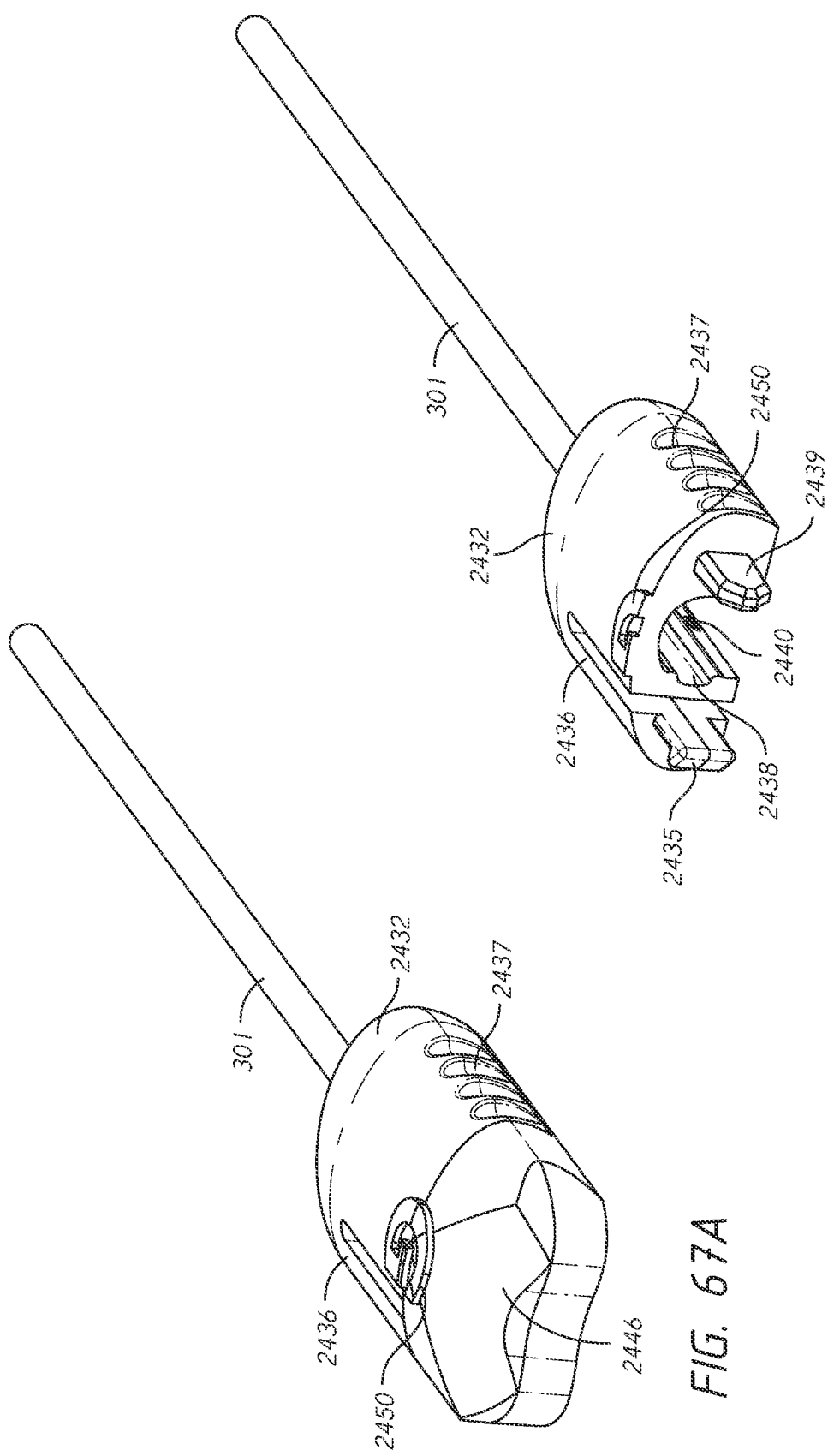

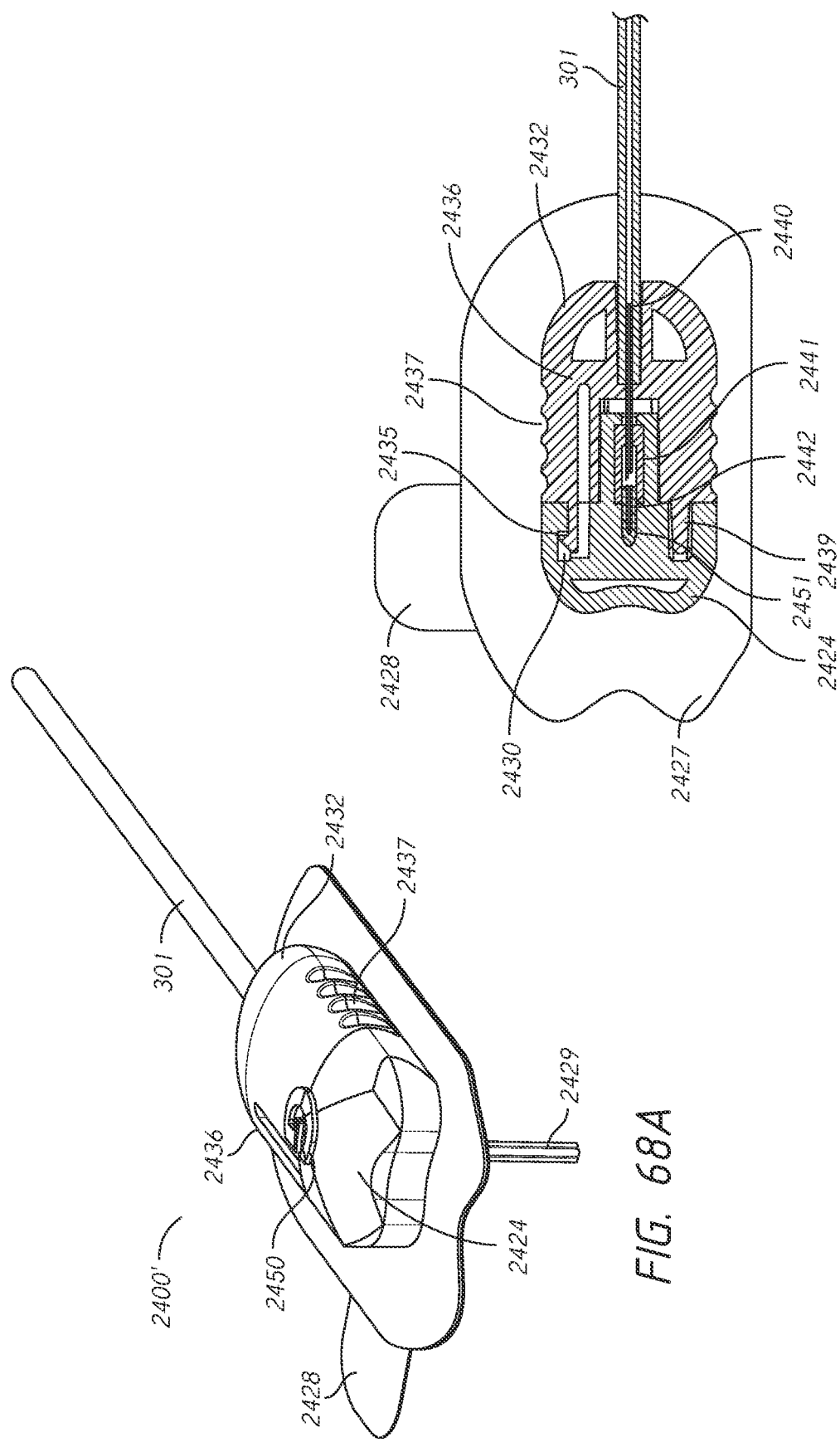

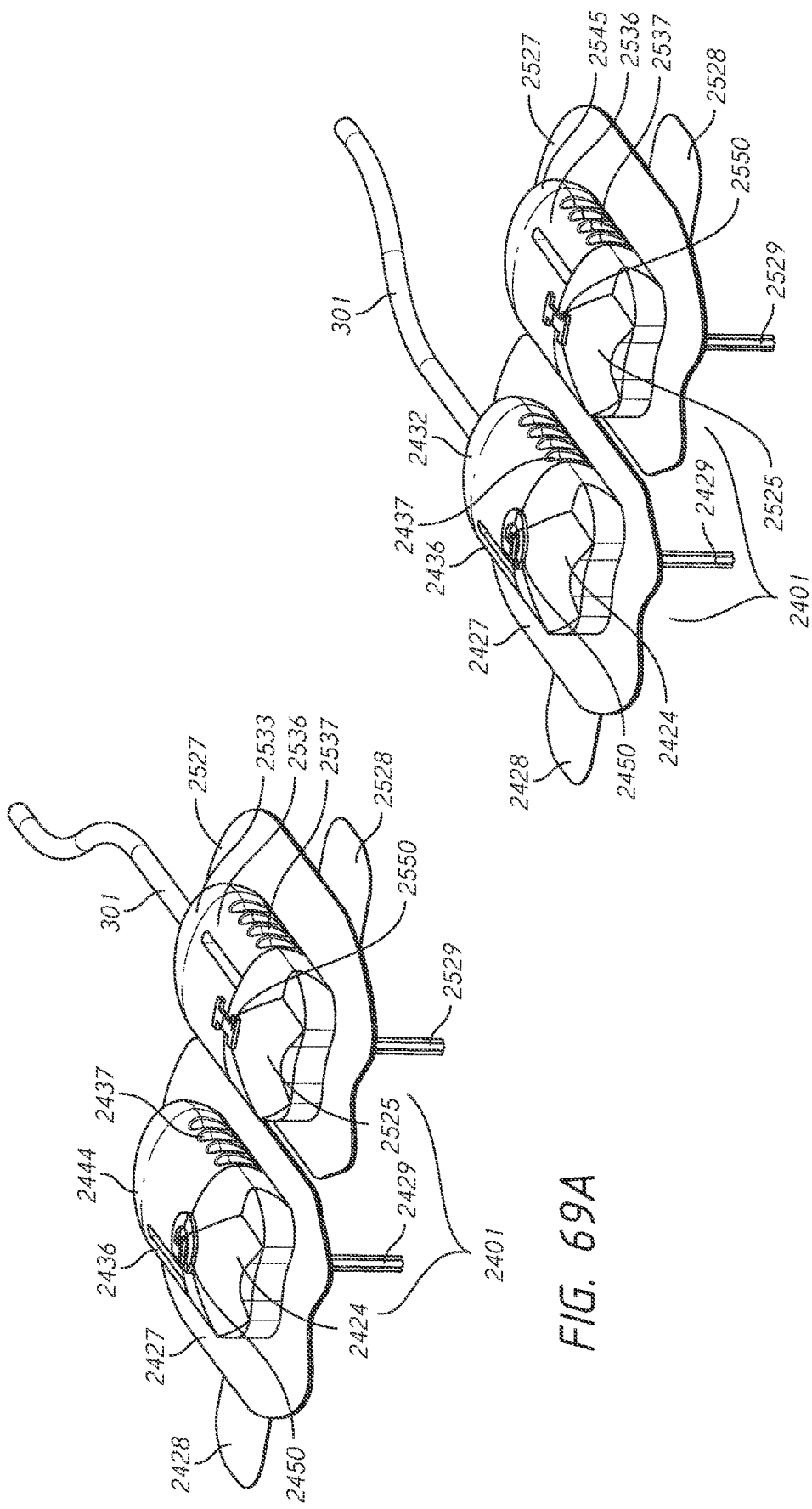

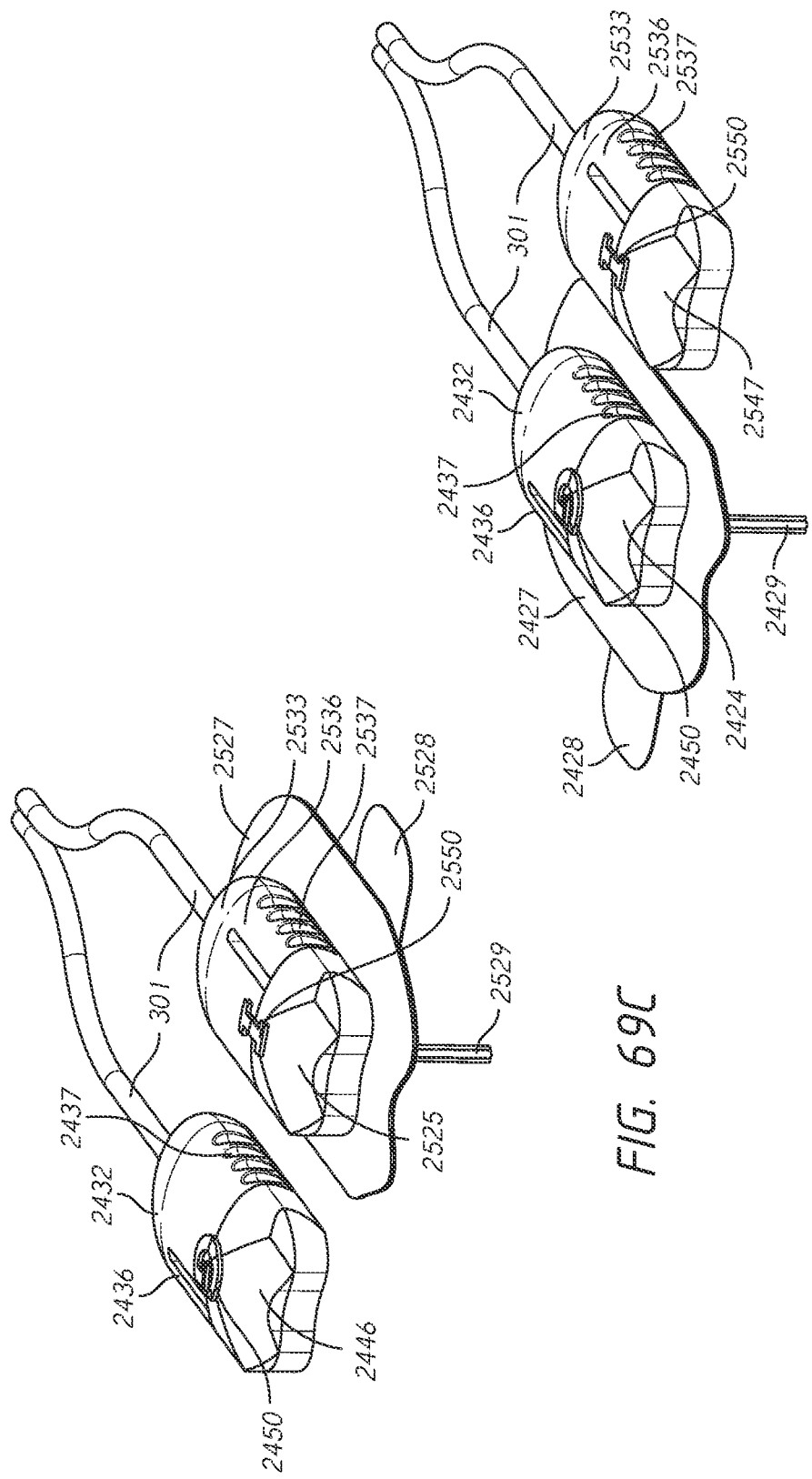

INFUSION SYSTEM AND COMPONENTS THEREOF

CROSS REFERENCE TO RELATED APPLICATIONS

This application is a continuation of U.S. application Ser. No. 17/988,449 filed Nov. 16, 2022, which is a continuation of U.S. application Ser. No. 17/723,769, filed Apr. 19, 2022, which is a continuation of U.S. application Ser. No. 15/848, 933, now U.S. Pat. No. 11,331,463, filed Dec. 20, 2017, which is a continuation of PCT application Serial No. PCT/US2016/041395, filed Jul. 7, 2016, which claims priority to U.S. Provisional Application Ser. No. 62/190,212, filed Jul. 8, 2015, U.S. Provisional Application Ser. No. 62/254,950, filed Nov. 13, 2015, and U.S. Provisional Application Ser. No. 62/353,210, filed Jun. 22, 2016. All of the foregoing applications are hereby incorporated herein by reference in their entireties.

STATEMENT REGARDING FEDERALLY SPONSORED R&D

This invention was made with Government Support under Contract No. DK097657 awarded by the National Institutes of Health. The Government has certain rights to the invention.

BACKGROUND OF THE INVENTION

Field

The disclosure relates generally to the field of infusion systems for medicaments and components thereof.

Description of the Related Art

Sustained delivery, pump driven medicament injection devices generally include a delivery cannula mounted in a subcutaneous manner through the skin of the patient at an infusion site. The pump draws medicine from a reservoir and delivers it to the patient via the cannula. The injection device typically includes a channel that transmits a medicament from an inlet port to the delivery cannula which results in delivery to the subcutaneous tissue layer of the in which the delivery cannula is located. Some infusion devices are configured to deliver one medicament to a patient while others are configured to deliver multiple medicaments to patient.

SUMMARY OF THE INVENTION

Certain embodiments pertain to an infusion set for delivering one or multiple medicaments to a patient. In some embodiments, the infusion set comprises a base unit. In some embodiments, the infusion set comprises a connector set. In some embodiments, the connector set is configured to couple to the base unit. In some embodiments, the connector set and the base unit are in fluidic communication through one or more fluid conduits or fluid pathways. In some embodiments, a fluid traveling through the connector set can travel through the base set and into a patient via one or more features attached to or coupled with the base set.

In some embodiments, the infusion set comprises a first connector. In some embodiments, the infusion set further comprises a second connector. In some embodiment, the infusion set comprises additional connectors (3, 4, 5, or more). In some embodiments, the base unit is a single piece that interacts simultaneously with multiple connectors (e.g., the first and second connector).

Any of the embodiments described above, or described elsewhere herein, can include one or more of the following features.

In certain variants, the base unit comprises a first port. In some embodiments, the base unit comprises a second port. In some embodiments, the base unit comprises additional ports. In some embodiments, the ports of the base unit are configured to interact with and/or engage with one or more connectors to provide a fluid pathway (or at least a portion of a fluid pathway) through a connector and the base unit to the patient.

In some embodiments, the first connector is configured to reversibly couple to the first port. In some embodiments, the interaction between the first connector and the first port of the base unit is facilitated by a first guide member. In some embodiments, the second connector is configured to reversibly couple to the second port. In some embodiments, the interaction between the second connector and the second port of the base unit is facilitated by a second guide member. In some embodiments, the first guide member prevents attachment of the second connector to the first port of the base unit. In some embodiments, the second guide member prevents attachment of the first connector to the second port of the base unit. In some embodiments, the second guide member prevents the engagement of the first connector to the second port and the first guide member prevents the engagement of the second connector to the first port.

In some embodiments, a base set comprising one or more base units is provided. In some embodiments, each base unit can interact with one or more separate connectors. For instance, in some embodiments, a first base unit and a second base unit are provided. In some embodiments, the first base unit interacts with the first connector only (e.g., via one or more coupling features, such as a guide member). In some embodiments, the second base unit interacts with the second connector only (e.g., via one or more coupling features, such as a guide member). In some embodiments, the first base unit interacts with one or more connectors and the second base unit interacts with one or more connectors that are different from the connectors that interact with the first base unit.

In some variants, the first port is in fluidic communication with a first inlet tube (e.g., a fluid conduit). In some embodiments, the first inlet tube extends from the first port. In some embodiments, the first guide member connects to a portion of the first inlet tube.

In certain implementations, the second port has a second inlet tube. In some embodiments, the second inlet tube extends from the second port. In certain variations, the second guide member connects to a portion of the second inlet tube.

In some embodiments, the base comprises a first and a second catheter. In certain embodiments, the first catheter is in fluidic communication with the first port and is configured to deliver a first agent subcutaneously to the patient via the base unit.

In some embodiments, the second catheter is in fluidic communication with the second port and is configured to deliver a second agent subcutaneously to the patient via the base unit.

In some embodiments, the first base unit of a base set comprises a first catheter. In some embodiments, the second base unit of a base set comprises a second catheter. In certain embodiments, the first catheter is in fluidic communication with the first port and is configured to deliver a first agent to the patient via first base unit. In certain embodiments, the second catheter is in fluidic communication with the second port and is configured to deliver a second agent to the patient via second base unit.

In some embodiments, the first connector comprises a first tab that audibly locks the first connector in place when in a coupled position with the first port. In some embodiments, the second connector comprises a second tab that audibly locks the first connector in place when in a coupled position with the first port. In some embodiments, the tabs are configured to be depressed to allow one-handed de-coupling of the one or both of the connectors from the base.

Some embodiments pertain to a device for delivering multiple agents to a patient, comprising a base unit (and/or base set with one or more base units). In some embodiments, the base unit (and/or first base unit of a base set) comprises a first port having a first inlet tube and a first guide member. In some embodiments, the first inlet tube and first guide member extend outwardly from the base unit (and/or first base unit of a base set). In some embodiments, the first inlet configured to receive a first agent. In some embodiments, the base unit comprises a first catheter in fluidic communication with the first port and configured to deliver the first agent to the patient via the base unit (and/or first base unit of a base set). In some variants, the device further comprises a second port having a second inlet tube and a second guide member extending outwardly from the base unit (and/or second base unit of a base set). In some embodiments, the second inlet tube and second guide member extend in the same direction as the first extension member. In some embodiments, the second inlet is configured to receive a second agent. In some embodiments, a second catheter is in fluidic communication with the second port and is configured to deliver the second agent to the patient via the base unit (and/or second base unit of a base set). In some embodiments, a first housing comprising a first outlet port configured to reversibly couple to the first port via the first guide member is provided. In some embodiments, a second housing comprising a second outlet port configured to reversibly couple to the second port via the second guide member is provided. In some embodiments the second guide member prevents the engagement of the first housing to the second port and the first guide member prevents the engagement of the second housing to the first port.

Certain embodiments pertain to a base unit (or base set) comprising a first port and a second port and a connector set configured to couple to the base unit (or base set). In some embodiments, the connector set comprises a first connector configured to reversibly couple to the first port and a second connector configured to reversibly couple to the second port. In some embodiments, the first connector comprises a male portion of an engaging fastener and the second connector comprises a female portion of the engaging fastener (or vice versa). In some embodiments, the first connector and second connector are linked via the engaging fastener.

In some embodiments, the engaging fastener comprises a tongue in channel configuration (or tongue in groove), wherein the tongue is located on the first connector and the channel (or groove) is located on the second connector.

Certain embodiments pertain to an apparatus for use with an infusion system, the apparatus comprising a fluid conduit comprising a first channel and a second channel. In some embodiments, the first channel comprises a first inlet connector attached to one terminus of the first channel. In some variants, the second channel comprises a second inlet connector attached at one terminus of the second channel. In some implementations the first inlet connector and the second inlet connector are differently shaped. In some embodiments, the first inlet connector engages a first fluid reservoir and the second inlet connector engages a second fluid reservoir.

In some embodiments, the first inlet connector comprises a first set external threads and the second inlet connector comprises a second set of threads. In some embodiments, the first set of threads is different from the second set of threads.

In certain implementations, the first set of threads is configured to engage a corresponding first configuration of threads located within a first aperture of an infusion pump. In some embodiments, the second set of threads is configured to engage a corresponding second configuration of threads located within a second aperture of the infusion pump.

Some embodiments pertain to a medicament delivery system for use with an infusion system. In some embodiments, the system comprises a first reservoir. In some embodiments, the first reservoir is configured to contain a first liquid solution of a first medicament. In some embodiments, the first reservoir comprises a first reservoir port that allows access to the first liquid solution. In some embodiments, the first reservoir interacts with a first collar. In some embodiments, the first collar comprises one or more projections extending (e.g., radially) outward from the first collar. In some embodiments, the first reservoir comprises a neck. In some embodiments, the first collar is configured to engage the first reservoir near the first reservoir port (e.g., around the neck) to provide a first collared reservoir.

In some embodiments, the system comprises a second reservoir. In some embodiments, the second reservoir is configured to contain a second liquid solution of a second medicament. In some embodiments, the second reservoir comprises a second reservoir port that allows access to the second liquid solution. In some embodiments, the second reservoir interacts with a second collar. In some embodiments, the second collar comprises one or more projections extending (e.g., radially) outward from the second collar. In some embodiments, the second reservoir comprises a neck. In some embodiments, the second collar is configured to engage the second reservoir near the second reservoir port (e.g., around the neck) to provide a second collared reservoir.

In some embodiments, a first inlet connector fits over at least a portion of the first reservoir to engage the first reservoir. In some embodiments, the first inlet connector also fits over at least a portion of the first port. In some embodiments, the first inlet connector is configured to engage at least a portion of the first collar of the first collared reservoir via the collar projections of the first collar. In some embodiments, the first inlet connector comprises a first needle configured to access the first liquid solution via the first port.

In some embodiments, a second inlet connector fits over at least a portion of the second reservoir to engage the second reservoir. In some embodiments, the second inlet connector also fits over at least a portion of the second port. In some embodiments, the second inlet connector is configured to engage at least a portion of the second collar of the second collared reservoir via the collar projections of the second collar. In some embodiments, the second inlet connector comprises a second needle configured to access the second liquid solution via the second port.

In some embodiments, the first collar further comprises one or more guiding elements. In some embodiments, the guiding element extends outward (e.g., radially) from the first collar. In some embodiments, the first inlet connector comprises a track (e.g., a trough, a groove, etc.) configured to receive the guiding element of the first collar.

In some embodiments, the second collar further comprises one or more guiding elements. In some embodiments, the guiding element extends outward (e.g., radially) from the second collar. In some embodiments, the second inlet connector comprises a track (e.g., a trough, a groove, etc.) configured to receive the guiding element of the second collar.

In some embodiments, the first collar (and/or first reservoir) is configured to interact with the first inlet connector and not the second inlet connector. In some embodiments, the projections and/or guide features of the first collar are configured to block engagement of the first collar with the second inlet connector. In some embodiments, features of the first reservoir (e.g., its diameter, neck position, etc.) are configured to block engagement of the first reservoir with the second inlet connector. In some embodiments, the second collar (and/or second reservoir) is configured to interact with the second inlet connector and not the first inlet connector. In some embodiments, the projections and/or guide features of the second collar are configured to block engagement of the second collar with the first inlet connector. In some embodiments, features of the second reservoir (e.g., its diameter, neck position, etc.) are configured to block engagement of the second reservoir with the first inlet connector.

In some embodiments, when an inlet connector is brought into proximity to the collared reservoir to engage the collared reservoir, the inlet connector and collared reservoir are not rotated axially with respect to each other. In some embodiments, when the inlet connector is brought into proximity to the collared reservoir to engage the collared reservoir, the inlet connector and collared reservoir are rotated axially with respect to each other. In some embodiments, when the inlet connector is brought into proximity to the collared reservoir to engage the collared reservoir, the inlet connector and collared reservoir are engaged linearly.

In some embodiments, the medicament delivery system further comprises a base unit (or base set) as described above. In embodiments, the medicament delivery system further comprises a connector set. In some embodiments, first reservoir and first inlet connector are in fluidic communication with the first connector (e.g., via a first fluid conduit). In some embodiments, second reservoir and second inlet connector are in fluidic communication with the second connector (e.g., via a first fluid conduit). In some embodiments, the first reservoir is configured to not interact with the second connector (e.g., through one or more features system). In some embodiments, the second reservoir is configured to not interact with the first connector (e.g., through one or more features of the system).

Some embodiments, pertain to a medicament delivery system for use with an infusion system, the system comprising a reservoir configured to contain a first liquid solution of a first medicament. In some embodiments, the reservoir comprises a port that allows access to the first liquid solution. In some embodiments, the system comprises a collar comprising a collar projection extending radially from the collar and a guiding element that extends radially from the collar, the collar configured to engage the reservoir near the port. In some embodiments, the system comprises an inlet connector that surrounds at least a portion of the reservoir covering the port, wherein the inlet connector engages at least a portion of the collar via the collar projection. In some embodiments, the inlet connector comprises a needle configured to access the first liquid solution via the port.

Some embodiments provide a medicament delivery system for use with an infusion system, the system comprises a reservoir configured to contain a first liquid solution of a first medicament, the reservoir comprising a port that allows access to the first liquid solution. In some embodiments, the medicament delivery system comprises a collar comprising a collar guiding element extending radially from the collar, the collar configured to engage the reservoir near the port to provide a collared reservoir. In some embodiments, the medicament delivery system comprises an inlet connector that fits over at least a portion of the collared reservoir and covers at least a portion of the port, wherein the inlet connector engages at least a portion of the collar via a collar guiding element track located within the inlet connector and configured to allow the collared reservoir to insert into the inlet connector. In some embodiments, the inlet connector comprises a needle configured to access the first liquid solution via the port.

In some embodiments, the collar further comprises a guiding element that extends radially outward from the collar and wherein the inlet connector comprises a track configured to receive the guiding element. In some embodiments, when the inlet connector is brought into proximity to engage the collared reservoir, the inlet connector and collared reservoir are not rotated axially with respect to each other. In some embodiments, when the inlet connector is brought into proximity to the collared reservoir to engage the collared reservoir, the inlet connector and collared reservoir are engaged linearly.

Some embodiments pertain to an infusion set for delivering a single or multiple medicaments to a patient. In some embodiments, the infusion set comprises a first base unit comprising a first port. In some embodiments, the infusion set a second base unit comprising a second port. In some embodiments, the infusion set comprises a first connector set configured to couple to the first base unit and not the second base unit, the first connector set comprising a first connector configured to reversibly couple to the first port via a first guide member. In some embodiments, the infusion set comprises a second connector set configured to couple to the second base unit and not the first base unit, the second connector set comprising a second connector configured to reversibly couple to the second port via a second guide member. In some embodiments, the infusion set the second guide member prevents the engagement of the first connector to the second port and the first guide member prevents the engagement of the second connector to the first port.

Some embodiments provide an infusion set for delivering a single or multiple medicaments to a patient. In some embodiments, the infusion set comprises a base set. In some embodiments, the base set comprises a first base unit having a first port and a first adhesive portion. In some embodiments, the first base unit comprises a first piercing element configured to deliver a first medicament to the patient. In some embodiments, the first adhesive portion is configured to adhere the first base unit to the patient. In some embodiments, the infusion set comprises a second base unit having a second port. In some embodiments, the second base unit comprises a second adhesive portion configured to adhere the second base unit to the patient.

In some embodiments, the infusion set further comprises a connector set. In some embodiments, the connector set comprises a first connector configured to reversibly couple to the first base unit via the first port. In some embodiments, the first connector provides a first fluid path from a first medicament reservoir to the first port of the first base.

In some embodiments, the infusion set comprises a second connector configured to reversibly couple to the second base unit.

In some embodiments, the first base unit comprises a first guide member that prevents engagement of the second connector to the first base unit. In some embodiments, the second base unit comprises a second guide member that prevents engagement of the first connector to the second base unit. In some embodiments, the first base unit and the second base unit are able to move independently with respect to each other to fit contours of the patient's body during movements made by the patient.

In some embodiments, the second base unit comprises a second piercing element configured to deliver a second medicament to the patient. In some embodiments, the second connector is configured to provide a second fluid path from a second medicament reservoir to the second port of the second base.

In some embodiments, the first piercing element is a catheter in fluidic communication with the first port and configured to deliver a first medicament to the patient via the first base unit.

In some embodiments, the first connector comprises a first retention clip that locks the first connector in place when in a coupled position with the first base unit.

In some embodiments, the first retention clip is configured to be depressed to allow one-handed de-coupling of the first connector from the first base unit.

In some embodiments, the second connector comprises a second retention clip that locks the second connector in place when in a coupled position with the second base unit. In some embodiments, the first retention clip is configured to prevent coupling of the first connector to the second base unit and the second retention clip is configured to prevent coupling of the second connector to the first base unit.

In some embodiments, the second tab is configured to be depressed to allow one-handed de-coupling of the second connector from the second port.

In some embodiments, the first connector comprises an alignment feature that guides the first connector in place when coupling it to the first base unit.

In some embodiments, the first connector set comprises a fluid conduit, wherein the fluid conduit is configured to allow fluidic communication with a first reservoir configured to contain a first liquid solution of a first medicament.

In some embodiments, the first base unit and first connector set, or the second base unit and second connector set, are used individually in a single medicament configuration or together in a dual-medicament configuration.

Some embodiments provide a medicament reservoir set for delivering a single or multiple medicaments to a patient. In some embodiments, the medicament reservoir set comprises a first reservoir comprising a first reservoir port and configured to contain a first medicament. In some embodiments, the medicament reservoir set comprises a first inlet connector that fits over at least a portion of the first reservoir and at least a portion of the first reservoir port. In some embodiments, the first inlet connector comprises a first needle configured to allow access to the first medicament. In some embodiments, the first inlet connector comprises a first engaging member that engages a portion of the first reservoir attaching the first inlet connector to the first reservoir. In some embodiments, the medicament reservoir set further comprises a first inlet connector cover configured to engage the first inlet connector. In some embodiments, the medicament reservoir set comprises a second medicament reservoir comprising a second reservoir port that allows access to a second medicament. In some embodiments, the medicament reservoir set comprises a second inlet connector that fits over at least a portion of the second reservoir and at least a portion of the second port. In some embodiments, the second inlet connector comprises a second needle configured to allow access a second medicament. In some embodiments, the second inlet connector comprises a second engaging member that engages a portion of the second reservoir attaching the second inlet connector to the second reservoir. In some embodiments, the medicament reservoir set comprises a second inlet connector cover configured to engage the second inlet connector.

In some embodiments, the medicament reservoir set comprises a first collar configured to engage the first reservoir near the first port to provide a first collared reservoir. In some embodiments, the first collar comprises a first collar projection extending radially outward from the first collar. In some embodiments, the first inlet connector engages at least a portion of the first collar of the first collared reservoir via the first collar projection. In some embodiments, the first collar is configured to prevent coupling to the second inlet connector.

In some embodiments, the medicament reservoir set further comprising a second collar configured to engage the second reservoir near the second port to provide a second collared reservoir. In some embodiments, the second collar comprises a second collar projection extending radially outward from the second collar. In some embodiments, the second inlet connector engages at least a portion of the second collar of the second collared reservoir via the second collar projection. In some embodiments, the second collar is configured to prevent coupling to the first inlet connector.

In some embodiments, the first inlet connector further comprises a first guiding element. In some embodiments, the second inlet connector further comprises a second guiding element. In some embodiments, the first guiding element is configured to guide the first medicament reservoir into a first pump receptacle having a first aperture that couples with the first guiding element. In some embodiments, the second guiding element is configured to guide the second medicament reservoir into a second pump receptacle having a second aperture that couples with the second guiding element. In some embodiments, the first guiding element is configured to prevent the placement of the first medicament reservoir into the second pump receptacle. In some embodiments, the second guiding element is configured to prevent the placement of the second medicament reservoir into the second pump receptacle.

In some embodiments, the first inlet connector cover is threaded to allow the first medicament reservoir to be screwed into place in the first pump receptacle. In some embodiments, the second inlet connector cover is threaded to allow the second medicament reservoir to be screwed into place in the second pump receptacle.

Some embodiments provide a medicament delivery system for delivering a single medicament or multiple medicaments to a patient. In some embodiments, the medicament delivery system comprises an infusion set, a medicament set, and a pump set.

In some embodiments, the infusion set comprises a base set. In some embodiments, the base set comprises a first base unit, the first base unit comprising a first base set piercing element configured to deliver a first medicament to the patient, a first port, and a first adhesive portion configured to adhere the first base unit to the patient. In some embodiments, the base set comprises a second base unit, the second base unit comprising a second adhesive portion configured to adhere the second base unit to the patient. In some embodiments, the infusion set comprises a connector set. In some embodiments, the connector set comprises a first connector configured to reversibly couple to the first base unit and to provide a first fluid path from a first medicament reservoir to the first port of the first base. In some embodiments, the connector set comprises a second connector configured to reversibly couple to the second base unit. In some embodiments, the first base unit comprises a feature that prevents engagement of the second connector to the first base unit. In some embodiments, the second base unit comprises a feature that prevents engagement of the first connector to the second base unit.

In some embodiments, a medicament set comprises a first reservoir and a first fluid conduit. In some embodiments, the first reservoir is configured to contain a first medicament accessible through a first reservoir port. In some embodiments, the first fluid conduit is configured to provide fluidic communication between the first reservoir and to the first base set piercing element In some embodiments, the medicament set comprises a first inlet connector and a first inlet connector cover. In some embodiments, the first inlet connector is configured to engage the first reservoir. In some embodiments, the first connector cover is configured to engage the first inlet connector.

In some embodiments, when not engaged to the inlet connector, the first connector cover is able to move along the first fluid conduit and/or to rotate freely around the first fluid conduit.

In some embodiments, the first reservoir comprises a first collar comprising a collar projection extending outward from the collar, the first collar configured to engage the reservoir near the port to provide a collared reservoir. In some embodiments, the first collar is configured to couple with matching projection apertures of the first inlet connector.

In some embodiments, the first inlet connector comprises a needle configured to access the first medicament via the first reservoir port.

In some embodiments, the second base unit comprises a second base unit piercing element and a second port, the second piercing element configured to deliver a second medicament to the patient. In some embodiments, the second connector is configured to provide a second fluid path from a second medicament reservoir to the second port of the second base unit.

In some embodiments, the medicament set comprises a first inlet connector and a first inlet connector cover, wherein the first inlet connector is configured to engage the first reservoir and wherein the first connector cover is configured to engage the first inlet connector. In some embodiments, the medicament set comprises a second inlet connector and a second inlet connector cover, wherein the second inlet connector is configured to engage the second reservoir and wherein the second connector cover is configured to engage the second inlet connector. In some embodiments, the second inlet connector is configured to not engage the first reservoir and the first inlet connector is configured to not engage the second reservoir.

Several illustrative embodiments are disclosed in this specification. Any feature, structure, or step disclosed in connection with any embodiment can be replaced with or combined with any other feature, structure, or step disclosed in connection with any other embodiment, or omitted.

Further, for purposes of summarizing the disclosure, certain aspects, advantages, and features of the inventions have been described herein. However, not all embodiments include or achieve any or all of those aspects, advantages, and features. No individual aspect of this disclosure is essential or indispensable.

BRIEF DESCRIPTION OF THE DRAWINGS

Various embodiments are depicted in the accompanying drawings for illustrative purposes, and should in no way be interpreted as limiting the scope of the embodiments. Any features, structures, components, materials, and/or steps of any of the embodiments can be combined or replaced with any features, structures, components, materials, and/or steps of any other of the embodiments to form additional embodiments, which are part of this disclosure.

FIGS. 3A and 3B illustrate front views of the system of FIG. 1.

FIG. 6 illustrates a view of a base and distribution connectors.

FIG. 7A-7D illustrates views of a base separated from distribution connectors.

FIG. 8 illustrates a view of a base and two distribution connectors where one distribution connector is disengaged from the base.

FIG. 9 illustrates a view of a base and two distribution connectors where one distribution connector is disengaged from the base.

FIG. 10 illustrates a front view of a distribution connection set.

FIG. 15 illustrates a reservoir coupled with an inlet connector with the cover engaged.

FIG. 16 illustrates a bisected view of a reservoir coupled with an inlet connector with the cover engaged.

FIG. 18 illustrates an inlet cover and components.

FIG. 19 illustrates a reservoir coupled with an inlet connector with the cover engaged.

FIG. 20 illustrates an exploded view of a reservoir, an inlet connector, and
a cover.

FIG. 21 illustrates a bisected view of a reservoir coupled with an inlet connector with the cover engaged.

FIG. 22 illustrates an inlet cover and components.

FIGS. 23-27 illustrate mismatched reservoir and inlet connector assemblies.

FIGS. 40A-C illustrate another embodiment of a collar assembly and a corresponding inlet connector.

FIGS. 41A-C illustrate an embodiment of a reservoir and inlet cover connector engaging with collar and inlet connector.

FIGS. 42A-C illustrate an embodiment of a reservoir and inlet cover connector engaging with collar and inlet connector.

FIGS. 44A-C illustrate another embodiment of a collar assembly and a corresponding inlet connector.

FIGS. 57A-C illustrate embodiments of inlet connectors, inlet connector covers, and components thereof.

FIGS. 58A-C illustrate exploded and partially assembled views of an embodiment of a reservoir, an inlet connector, an inlet connecting cover, and components thereof.

FIGS. 63A-B illustrate perspective views of a dual infusion set base where 63A also illustrates an insertion implement.

FIGS. 64A-B illustrate perspective views of dual medicament distribution connectors where 64A also illustrates a cover for the distribution connectors.

FIGS. 65A-B illustrate views of a dual medicament infusion set where 65B is a cross-sectional view from the top.

FIGS. 66A-B illustrate a single medicament infusion set base where an insertion implement is attached (66A) or detached (66B).

FIGS. 67A-B illustrate perspective views of a single medicament distribution connector where 67A also illustrates a cover for the distribution connector.

FIGS. 68A-B illustrate views of a single medicament infusion set where 68B is a cross-sectional view from the top.

FIGS. 69A-E illustrate various configurations of dual medicament infusion set bases, connectors, and covers.

DETAILED DESCRIPTION

Figure 1:
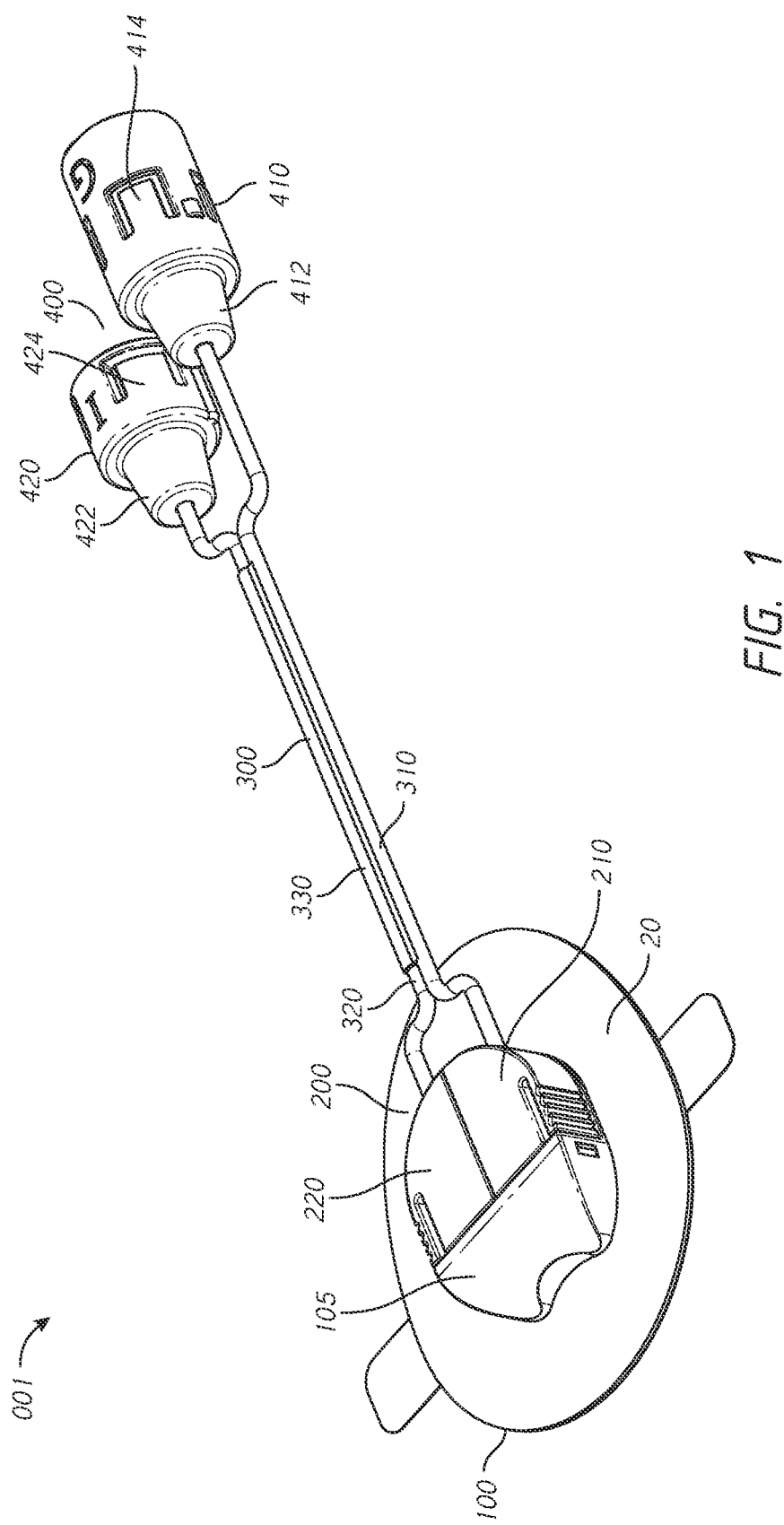
FIG. 1 illustrates a perspective view of an embodiment of a portion of an infusion system.
Figure 2:
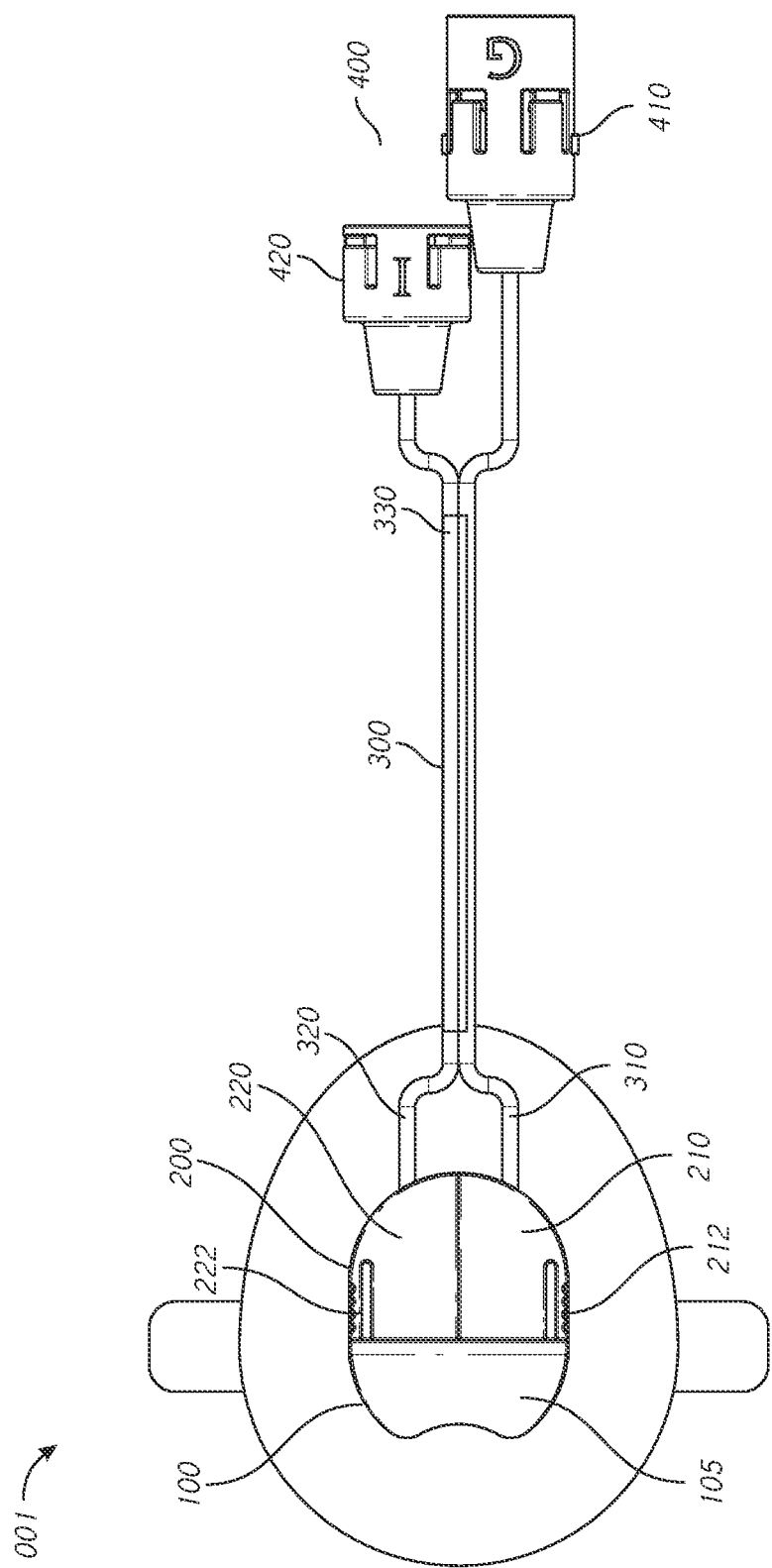
FIG. 2 illustrates a top view of the system of FIG. 1.

A drawback of multi-medicament (e.g., pharmaceutical, hormone, etc.) regimens is that the patient or physician may accidentally load, transfer, and/or administer the incorrect medicament. The accidental administration of the incorrect medicament to the patient can have serious and potentially fatal consequences. For example, standard-of-care insulin therapies for regulating blood glucose in diabetic patients may involve subcutaneous infusion of insulin via an insulin pump. If the amount of dosed insulin is excessive, it can lead to hypoglycemia or a situation of impending hypoglycemia. To combat and/or reverse such adverse situations, individuals typically consume additional carbohydrates (e.g. sweet juice or glucose tablets) and in some situations can also administer a so-called "rescue dose" of a counter regulatory agent, such as glucagon. In such an application, glucagon is typically reconstituted into solution from an emergency kit and manually administered intramuscularly. If, during a diabetic episode, a patient required insulin but was given glucagon accidentally, that administration could lead to devastating effects and potentially death.

The proper channeling in medicament dosing where one medicament is used to achieve one effect while the other is used to achieve the opposite effect (e.g., in the case of insulin and glucagon) is critical. While diabetic drugs are used as an example, improper channeling can have deleterious effects in many multi-medicament regimens (e.g., in drugs that regulate pancreatic enzymes, etc.) because a medicament is not administered to the patient at the necessary time or an incorrect medicament is administered at a dangerous level.

In a multi-medicament automated system, if the medicaments are accidentally loaded in the incorrect reservoirs, the automated system delivers an ineffective (and potentially harmful) medicament to the patient. This phenomenon of incorrect medicament administration in automated systems is called cross-channeling. Cross-channeling is dangerous because the wrong medicament could have the opposite of the intended effect or a side effect that is unanticipated. This improper channeling could not only fail to alleviate the patient's condition, but could make the patient's condition worse, or cause a new problem-state for the patient. For instance, this improper channeling could cause a negative feedback loop, wherein the control system attempts to adjust the patient's disease state in one direction, but the delivery of the incorrect medicament exacerbates or causes no effect on the disease state. Sensing this, the control system can trigger further doses of the wrong medicament in an attempt to control the patient's condition, while actually causing the patient's condition to further deteriorate (or causing overdosing of the incorrect medicament).

Certain embodiments, of infusion systems and components described herein are configured to minimize the occurrence of cross-channeling. Described herein are infusion systems for multiple medicaments and various connectors, tubes, and cartridges that ensure proper channeling of each medicament to the patient. While certain embodiments, of infusion systems and components are described below to illustrate various examples that may be employed to achieve one or more desired improvements, these examples are only illustrative and not intended in any way to restrict the general inventions presented and the various aspects and features of these inventions. The phraseology and terminology used herein is for the purpose of description and should not be regarded as limiting. No features, structure, or step disclosed herein is essential or indispensable.

Some embodiments described herein pertain to an infusion system for dosing multiple medicaments without cross-channeling by providing design features and/or mating connectors or adapters on certain components of the infusion system. In some embodiments, the infusion system consists of an infusion pump with two or more infusion chambers, drive shafts, or pump chambers, cartridges filled with different medicaments, and connectors and tubing that connect to the cartridge and to the infusion pump in such a way as to prevent mischanneling or cross-channeling of medicaments. In certain variants, each type of cartridge for each type of medicament has one or more unique differentiating features (either as an integral part of the cartridge or as a component attached or affixed to the cartridge), for example geometric or shape-based features, that allow for unique coupling with a type of connector that itself has unique differentiating features that engage corresponding features in the pump housing and allow for insertion of the proper cartridge into the proper infusion chamber, drive shaft, or pump chamber within the infusion pump.

In certain variants, the system comprises a base with a housing having one or more implements (e.g., delivery members) that allow delivery medicaments to the patient. In some variants of the system, the housing is connected to a distribution set comprising one or more distribution connectors that are configured to receive a medicament from one or more medicament reservoirs. In some embodiments of the system, one or more fluid conduits provide fluidic communication between the reservoirs and the connector set. In various implementations, a connector set comprising one or more connectors couples the fluid conduits to the reservoirs. In some variants of the system, the reservoirs are located in a pumping device configured to distribute the medicament from the reservoir to the conduit, thereby supplying the system with medicaments. In some embodiments, the fluid conduits provide separate pathways that terminate at designated delivery members (e.g., needles, cannulas, etc.) within the base enabling independent subcutaneous delivery of medicaments separately.

In some embodiments, unique mating connectors and design elements ensure that each portion of the system can only be connected within the system in a unique way or configuration, thus preventing the cross-channeling. In certain embodiments, the design features give rise to the following advantages: (1) the infusion system allows the user to easily connect and disconnect the channels independently from both medicament sources as well as from the infusion ports or sites; (2) the infusion system mitigates the possibility of mischanneling by accidentally connecting the wrong tubing to the wrong medicament source or infusion site (e.g., by having a connector that is disposed between one tube and one pump reservoir of one medicament system differ from the connector of the other tube and reservoir); and (3) the infusion system allows for a single or multistep insertion of the dual-cannula infusion site or port. In some embodiments, the components described herein (connectors, bases, ports, channels, etc.) can further comprise visual or brail call-outs in addition to or instead of various paired physical features disclosed herein. For instance, in some implementations, the components can comprise call-outs with wording indicating a proper medicament. In some variants, different colors or lengths (or other variables) to provide visual feedback regarding appropriate medicaments for appropriate components.

In some embodiments, as stated above, the infusion system can be used to provide separate fluid pathways for a variety of medicaments (e.g., drugs, hormones, proteins, pharmaceuticals, biologics, etc.) dissolved in a variety of liquid carriers. In certain embodiments, different liquid vehicles may be preferred based on the solubility, stability, or sensitivity of the medicament in a particular carrier. In some embodiments, aqueous solutions (buffers, etc.) are used as a delivery vehicle for the medicament. In certain variations, solvents such as DMSO are used to dissolve medicaments. In some embodiments, solvent/aqueous mixtures are used.

In instances where a solvent is used as a carrier for the medicament, such as when DMSO is used alone or as a partial aqueous solution, it is desirable to minimize potential contamination of medicaments from materials used for making the system. For instance, when solvents are used, each feature of the infusion system can be insert-molded to avoid glues and other materials that may dissolve in the medicament vehicle. In some embodiments, injection molding is not used. In some embodiments, the infusion systems described herein can be used to deliver drugs that are dissolved in weaker solvents and/or inorganic solutions (e.g., water) that do not dissolve glues and fixatives. In some embodiments, when such drug systems are used, features of the infusion system can be glued or otherwise affixed together.

In some variants, the infusion system comprises one or more of specifically shaped vials, vial caps, connections, and housings that can be configured to receive only medicaments supplied using the matched/paired components (e.g., threads, tubing, reservoirs, outlets, inlets, etc.) having coinciding shapes. In some variants, these paired connector sets help avoid mischanneling. In some embodiments, the features of the vials, vial caps, connections, and housings can only be paired with their mated fittings. In certain embodiments, for instance, a first medicament can only be delivered through a first medicament pathway and a second medicament can only be delivered through a second medicament pathway.

In some embodiments, as stated above, the infusion system comprises an infusion set, a fluid conduit, an infusion pump, and two or more medicament pathways. In certain implementations, the medicament pathways comprise design features preventing mixing and matching of design elements from one pathway with design elements of the other. For instance, in certain variants, the fluid conduit has two or more channels wherein each channel is configured to provide a different medicament pathway. In some embodiments, the infusion set comprises medicament pathways leading to separate distribution cannulas. In some embodiments, distribution connectors provide the medicament from the fluid pathways to the cannulas. In certain embodiments, these connectors are individually molded and can only engage specific ports within an infusion housing, so that the connections cannot be connected to other ports located on the housing.

In various embodiments, the two or more channels are configured to interact only with separate inlet connectors from medicament reservoirs. In some embodiments, these inlet connectors prevent the medicament from entering the incorrect medicament pathway. In certain embodiments, these connectors are individually molded and can only engage specific ports of the fluid conduit or of an infusion pump, so that the connections cannot be connected to other medicament pathways.

A variety of system components are described below to illustrate various examples that may be employed to achieve one or more desired improvements. These examples are only illustrative and not intended in any way to restrict the general inventions presented and the various aspects and features of these inventions. Furthermore, the phraseology and terminology used herein is for the purpose of description and should not be regarded as limiting. No features, structure, or step disclosed herein is essential or indispensable. For simplicity, the systems disclosed herein are shown as providing two medicaments pathways. However, additional pathways (3, 4, 5, 6, or more) can be prepared using this same strategy. Moreover, these pathways are shown as non-intersecting. It should be appreciated that, in some implementations, the pathways for particular medicament systems can be configured to intersect. In some embodiments, the intersection of certain pathways premixes medicaments separate from separate reservoirs just prior to infusion. For example, in a three medicament system, medicament A and B can share a fluid pathway, while medicament C has its own pathway configured not to interact with the A and B pathway. Medicament A and B can be mixed prior to injection, while medicament C remains free of other medicaments prior to injection.

Figure 4A:
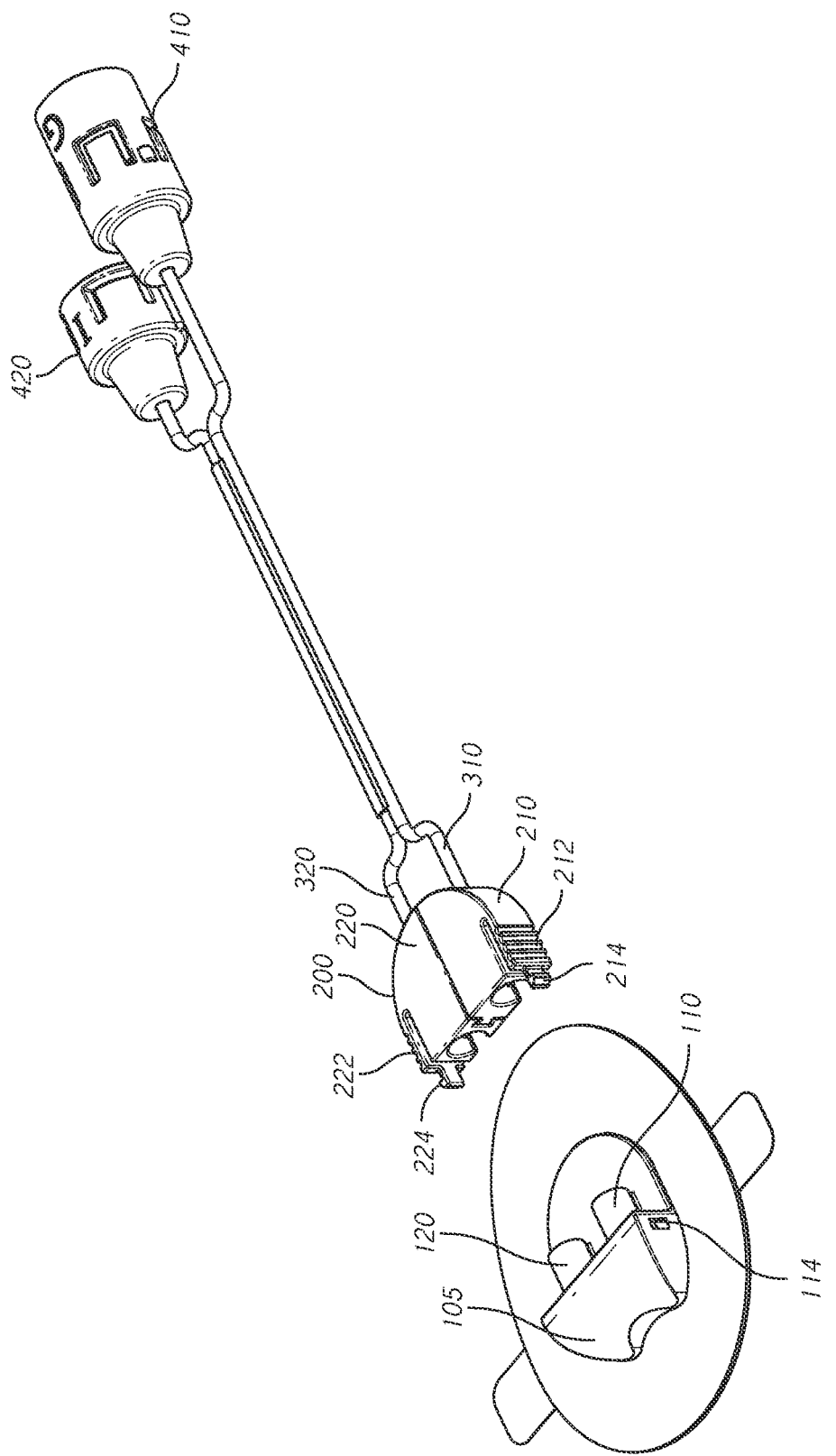
FIGS. 4A and 4B illustrate views of the system of FIG. 1 wherein portions of the system have been disconnected.
Figure 4B:
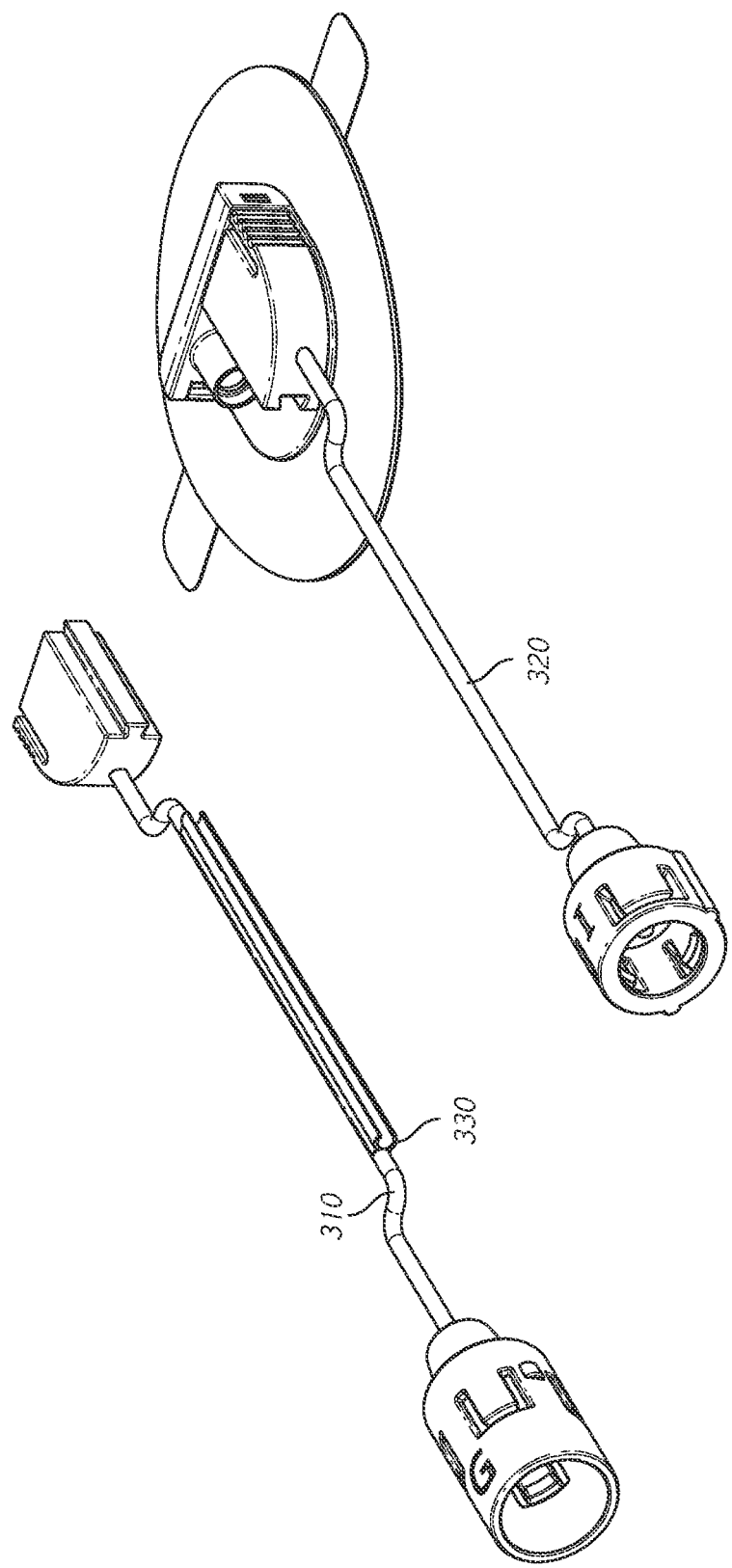

In some embodiments, as shown in FIGS. 1-4B, the infusion system 001 comprises a base 100. In some variants, the base comprises a housing 105 and is in communication with a distribution connector set 200. In certain implementations, the distribution set 200 comprises a first distribution connector 210 and a second distribution connector 220. In some variants, the first distribution connector 210 and a second distribution connector 220 are not interchangeable and, instead, are only able to interact with the base 105 at designated positions via design features of a housing 105. For example, as shown in FIGS. 4A and 4B, in some embodiments, the housing 105 comprises a first fluid inlet 110 and a second fluid inlet 120 shaped to interact only with the first distribution connectors 210 and the second distribution connector 220, respectively.

Figure 5:
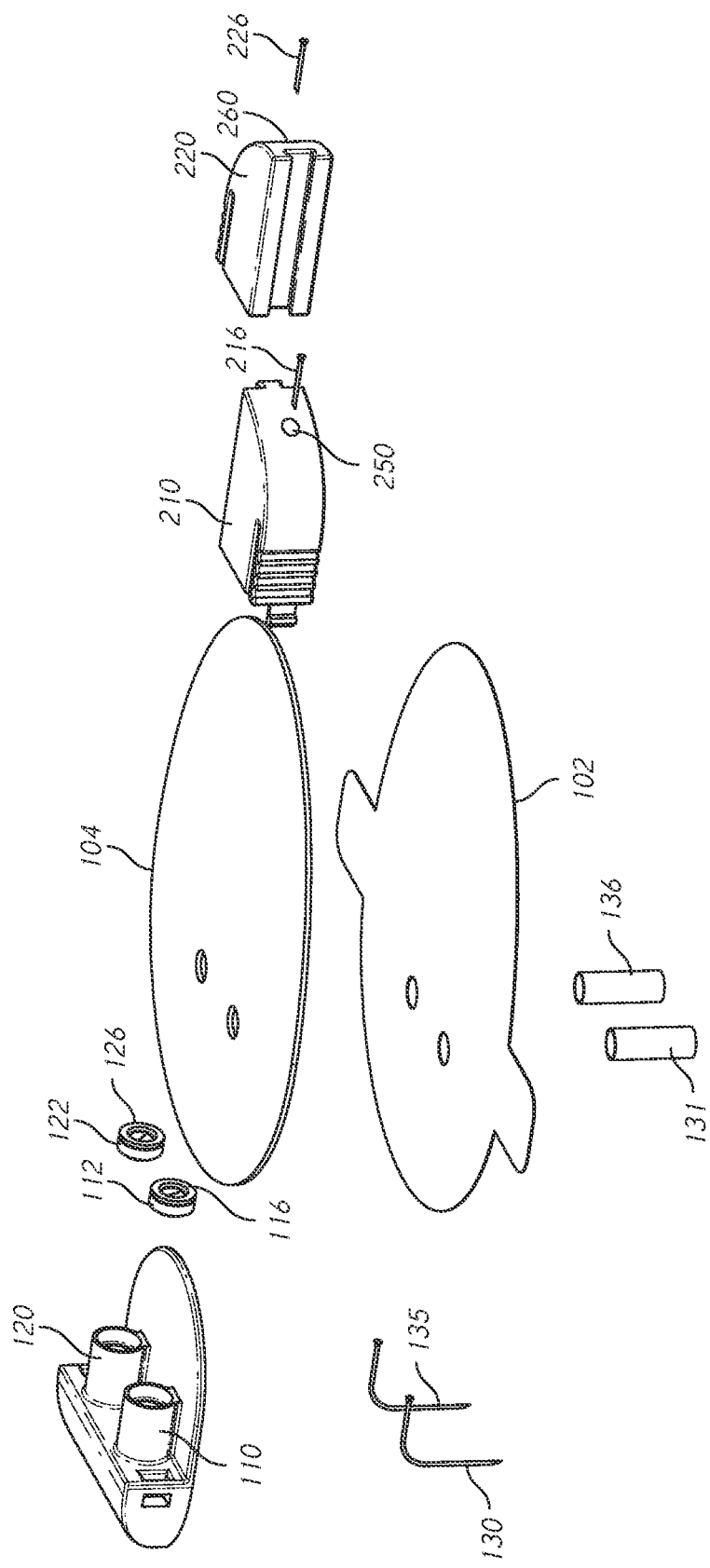
FIG. 5 illustrates an exploded view of an infusion set.

In some embodiments, the first distribution connector 210 and a second distribution connector 220 are independently or conjunctively reversibly couplable (as shown in FIGS. 4A-5) to the base 100 via design features of the housing 105 and of the connectors 210, 220.

In certain variants, as shown in FIGS. 3A-B and 5, the housing 105 comprises a first cannula 130 (e.g., needle, piercing implement, etc.) and a second cannula 135 (e.g., needle, piercing implement, etc.). In some embodiments, the piercing implement comprises material that can be rigid (e.g., stiff) or non-rigid (e.g., flexible). In certain implementations, the piercing implement comprises a metal material (e.g., iron, stainless steel, alloys, etc.), a polymeric material (e.g., plastic, Teflon, polyurethane, polyethylene, etc.), a composite material, or combinations thereof. In some embodiments, the first cannula 130 receives fluid only via the first distribution connector 210 and the second cannula receives fluid only via the second distribution connector 220. In certain embodiments, there is no cross contamination of fluids between distribution connectors 210, 220 and the first cannula 130 and the second cannula 135 because of separate features within the fluid pathways. In some embodiments, as shown in FIG. 5, the needles 130, 135 can be provided with protective covers 131, 136. These protective covers can prevent damage of the needles during manipulation of the assembly prior to use. The covers can also minimize risk of contamination of the needles prior to use. In some embodiments, the covers 131, 136 can be used as safety capture receptacles for used infusion sets. The covers can facilitate disposal of the infusion set and minimize risk of contamination.

In some embodiments, as shown in FIGS. 1-5, the infusion system further comprises a fluid conduit 300 having a plurality of channels 310, 320. In some embodiments, the fluid conduit comprises a first channel 310 and a second channel 320. In some variants, the first channel 310 and the second channel 320 are in fluidic communication with the first distribution connector 210 and the second distribution connector 220, respectively. In some embodiments, the first channel 310 is bonded (e.g., glued, welded, insert molded, or otherwise affixed) to the first distribution connector 210 and the second channel 320 is bonded to the second distribution connector 220 so that when one connector is replaced, the coinciding fluid channel is also replaced. In some embodiments, the channels are not bonded to the distribution connectors and instead have various attachment features (e.g., threads, projections, special configuration, channel couplers, etc.) that prevent cross mating of channels with incorrect distribution connectors.

In certain implementations, as shown in FIGS. 1-5, the first channel 310 and the second channel 320 are configured to be in fluidic communication with medicament reservoirs (not pictured) via inlet connectors. In some variants, the system comprises a first inlet connector 410 and a second inlet connector 420 (e.g., caps). In certain variants, the first inlet connector 410 and the second inlet connector 420 are configured to interact with differently shaped reservoirs. For instance, in some embodiments, a reservoir that interacts with the first inlet connector 410 will not interact with the second inlet connector 420 because of the shape of the reservoir and cap. Conversely, in some embodiments, a reservoir that interacts with the second inlet connector 420 will not interact with the first inlet connector 410 because of the shape of the reservoir and cap. In some embodiments, as shown in FIGS. 1-5, the first channel 310 and the second channel 320 are configured to be in fluidic communication with the first inlet connector 410 and the second inlet connector channel 420, respectively. In some embodiments, the first channel 310 is bonded to the first inlet connector 410 and the second channel 320 is bonded (welded, injected molded, glued, etc.) to the second inlet connector 420 so that when one inlet connector is replaced, the coinciding fluid channel is also replaced. In some embodiments, the channels are not bonded to the inlet connectors and instead have attachment features that prevent cross mating of channels with incorrect inlet connectors.

In some embodiments, the first channel is a different length than the second channel facilitating connection to the infusion pump in a specific configuration. In some embodiments, as shown in FIG. 1, the inlet connectors can be different colors to provide further indications to the user about which medicament should be delivered to a specific area of the infusion system.

In some embodiments, the first inlet connector 410 is configured to interact with specifically shaped and sized first medicament reservoirs (not shown) via mated design features (e.g., threads, caps, etc.) ensuring use with only those reservoirs. The second inlet connector 420 is also configured to interact with specifically shaped and sized medicament second reservoirs via a second configuration of reservoir connectors that are different from those that can be used on the first inlet connector. By providing conduits and connectors that are matched to form different pathways, medicaments from the first reservoir are only delivered to the first cannula 130 and medicaments from the second reservoir are only delivered to the second cannula 135. This feature helps prevent cross channeling of medicaments and to ensure safe use of a multi-medicament infusion system.

In some embodiments, as stated above, the infusion system also comprises a multi-medicament pump. In some embodiments, the pump also is shaped so that only specific configurations of medicament containers and specifically shaped reservoirs can be inserted into particular delivery pathways. The infusion pump serves to deliver (i.e., pump) the medicaments from the medicament reservoirs to the fluid conduit 300 (which can be a multi-lumen tube). The fluid conduit then carries the medicaments via individual fluid pathways to an infusion set 20 that subcutaneously delivers the medicaments to the patient.

In certain variants, as discussed above and as shown in FIGS. 3A and 3B, the base 100 comprises multiple designated needles 130, 135. While the needles 130, 135 shown in FIGS. 3A and 3B are of approximately the same length, the needles can be inserted to the same or different depths under the skin by using different lengths of needles. In some implementations, the ratio between the needles lengths is at least about: 1:1, 1:1.5, 1:2, 1:5, 1:10, values in between the aforementioned values, and otherwise. Moreover, the needles can have different shapes and profiles. In some embodiments, medicaments can separately or together be delivered transdermally, intradermally, subcutaneously, intramuscularly, or intravenously using separate piercing elements (e.g., needles or cannulas). While the term subcutaneous is used in several examples throughout this disclosure, the methods described herein are applicable to any of transdermal, intradermal, subcutaneous, intramuscular, or intravenous delivery, and the use of the term subcutaneous is used in an exemplary fashion. In some embodiments, during transdermal delivery, the medicament(s) can be delivered to, for example, a surface of the skin with or without the use of a permeation enhancing agent (e.g., a solvent such as DMSO, azone, pyrrolidones, fatty acids, essential oils, terpenes, terpenoids, oxazolidinones, urea, or the like). In certain implementations, during intradermal delivery, the medicament(s) can be delivered via a piercing element (e.g., a microneedle, etc.) that penetrates the skin by less than or equal to about 8 mm, about 6 mm, about 4 mm, about 2 mm, about 1 mm, or about 0.5 mm. In certain variants, the drug is delivered by catheters 130, 135 which can be placed under into the skin using trocars.

In some embodiments, cannula angles can be independently varied with respect to one another. For instance, in some embodiments, where the cannulas are at an angle of 0° with respect to each other, the needles that are aligned. In some embodiments, the cannulas are at angles with respect to one another that are more than about 0°, about 5°, about 10°, about 15°, about 20°, about 30°, or about 40°.

As shown in FIG. 4, in certain variants, the distribution connectors 210, 220 can be disengaged from the housing 105 and removed from the housing as a unit (e.g., as the connector set 200). As shown in FIGS. 1-5, in some embodiments, there is a left and a right side distribution connector. In some embodiments, the left side distribution connector 210 (i.e., the first distribution connector) is configured to only interact with the left side of the housing 105 via design elements of the housing 105 and/or the left side distribution connector 210. Similarly, in some embodiments, the right side distribution connector 220 (i.e., the second distribution connector) is configured to only interact with the right side of the housing 105. This capacity to engage only certain features of corresponding infusion system parts helps maintain separate medicament fluid paths (because distribution connectors cannot be simply switched from one side to the other).

In some embodiments, the connectors 210, 220 comprise tabs 212, 222. In some embodiments, the tabs 212, 222 (e.g., pads, levers, etc.) are textured (e.g., ribbed, knurled, abraded, etc.) to provide traction during depression or positioning of each of the distribution connectors 210, 220. In some embodiments, these pads allow single hand coupling and decoupling of the distribution connectors individually 210, 220 or as a set 200. This feature enables patients, even those with limited mobility and/or dexterity, to manipulate the connectors 210, 220 to engage and disengage them. In some embodiments, the pads click into place giving an auditory signal that the connectors are engaged. In some embodiments, visual verification of attachment is unnecessary.

In certain variants, as shown in FIGS. 4-7, the tabs 212, 222 comprise connection members 214, 224 (e.g., a flange, lip, groove, detent, etc.) that engage securing apertures 114, 124 on the housing 105 to secure the distribution connectors 210, 220. These features help tightly seal the distribution connectors 210, 220 to the housing 105. In some implementations, the tabs 212, 222 can be single-handedly be depressed to disengage the connection members 214, 224 and to release the distribution connectors 210, 220.

Figure 7C:
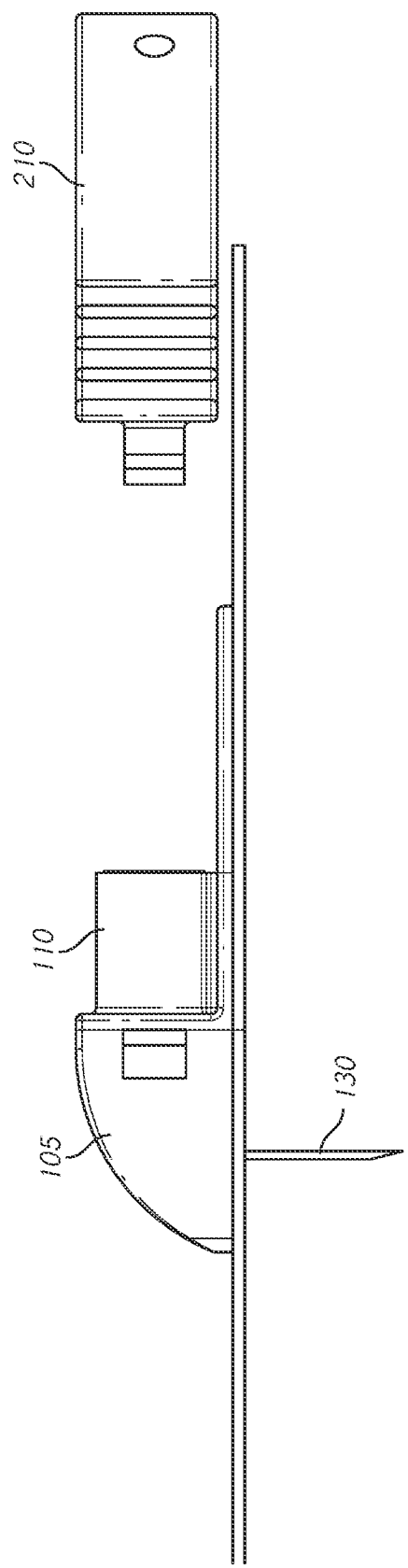

In some implementations, as shown in FIGS. 4, 5, and 7, the base 100 comprises a projecting first fluid inlet 110 and a second fluid inlet 120. These projecting fluid inlets 110, 120 are configured to engage corresponding connection apertures of the first distribution connector 210 and the second distribution connector 220, respectively. In some embodiments, the first fluid inlet 110 and a second fluid inlet 120 are shaped differently to match apertures of the first distribution connector 210 and the second distribution connector 220, respectively. This feature can also be implemented to prevent cross channeling of medicaments.

As shown in FIG. 5, in certain variants, the base 100 comprises an adhering surface 102 (adhesive tape, gel, etc.) configured to secure the infusion set to the skin of a patient. In some implementations, the base 100 comprises a support surface 104 (e.g., a foam pad) that engages the housing 105 and provides a connection point to the adhering surface 102 (e.g., a tacky foam). In some embodiments, the adhering surface 102, support surface 104, and housing 105 have apertures configured to align and to allow the needles 130, 135 to pass through. In some embodiments, an inserter can be provided to properly align the base before it is deployed. The inserted can comprise a spring loading to quickly insert the needles 130, 135 into the skin, allowing the patient (or doctor) to direct the location of the base.

Also as shown in FIG. 5, in certain implementations, the distribution connectors 210, 220 are configured to receive needles 216, 226. In certain embodiments, the needles 216, 226 can be heat bonded (or heat staked, insert molded, otherwise glued, welded, or affixed) in place within fluid conduit apertures 250, 260 of the distribution connectors 210, 220 during fabrication of the distribution connectors 210, 220. In some variants, the needles 216, 226 are removable and replaceable.

In some embodiments, as shown in FIGS. 7A-12, the first needle 216 and the second needle 226 of the distribution connectors 210, 220 are configured to pierce a first septum 112 and a second septum 122 residing within the first fluid inlet 110 and the second fluid inlet 120 of the housing 105, respectively.

These septa 112, 122 can be configured to prevent unwanted leaking of medicaments when connecting and disconnecting the distribution connectors 210, 220 via the first fluid inlet 110 and the second fluid inlet 120. In some embodiments, the septa 112, 122 comprise entrance slits 113, 123 that allow a needle to insert through the septa without friction. This feature minimizes buckling and back pressure in the fluid conduit. Buckling and/or back pressure can cause uneven delivery of the medicaments by causing bolus deposits to form within the connector (in, for instance the conical inlet 111) or by creating void spaces within a channel.

Figure 7D:
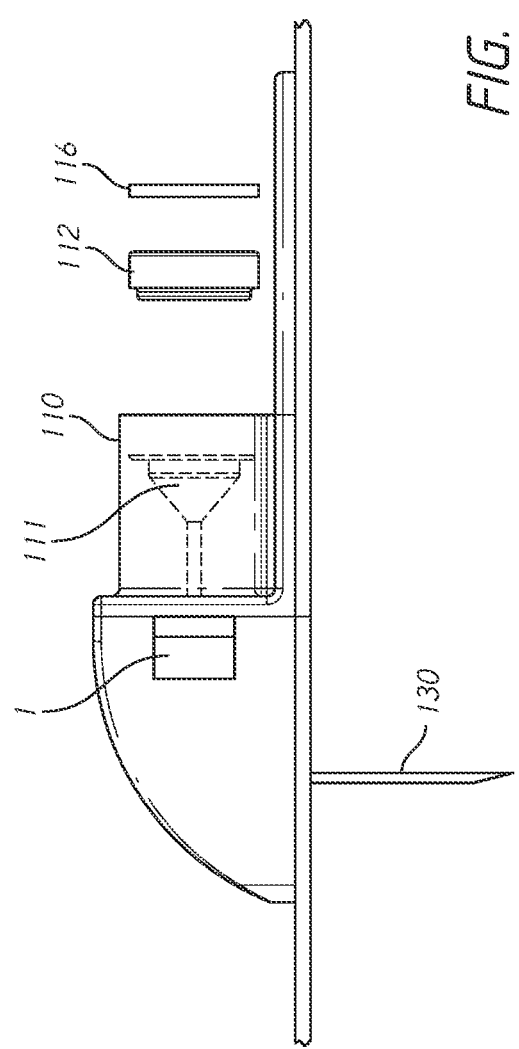

As shown in FIG. 7D, in some embodiments, the fluid inlets of the housing 105 can comprise a conical inlet 111 to guide the needle of the distribution connector into the fluid path of the housing 105. Once pierced the septa 112, 122 allow fluid to pass through the needles 216, 226 into the housing 105 and out of the needles 130, 135 keeping individual medicament pathways uncontaminated by other medicament pathways. In some embodiments, the needles 130, 135 affixed in place in the housing 105 (e.g., heat staked, insert molded, otherwise glued, welded, or affixed). In some instances, patients may be allergic to glues and adhesives present in needle fixing agents. Thus, heat staking can be used to seal the needles into the housing to avoid allergic reactions in these patients.

In some embodiments, as shown in FIGS. 7A-9 securing rings 116, 126 can be used secure the septa 112, 122 in place to avoid needle or channel buckling. In some embodiments, the rings are heat staked or ultrasonically welded into the base 100. In some implementations, rings are not used and the fluid inlets are melted or otherwise affixed in place. In some embodiments, the rings are replaceable.

Figure 11:
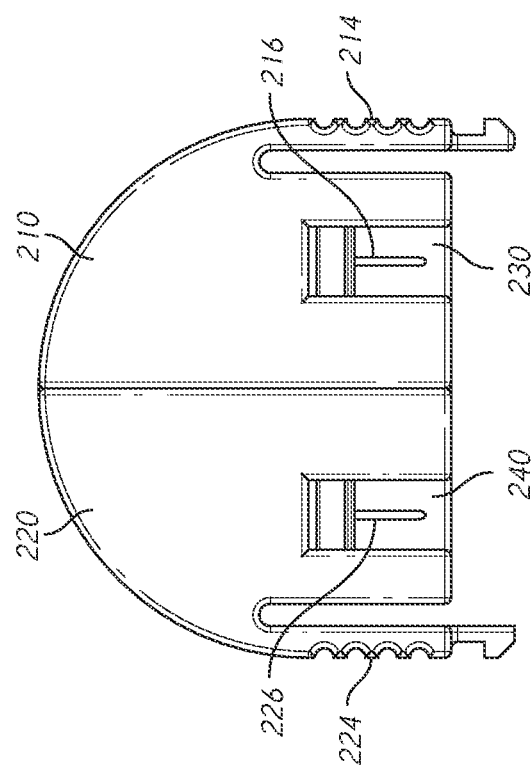
FIG. 11 illustrates a bottom view of the distribution connection set of FIG. 10.

In certain implementations, as shown in FIGS. 8 and 9 and as discussed elsewhere herein, the first distribution connector 210 and the second distribution connector 220 can be removed from the housing separately. As shown in FIGS. 10 and 11, they can also be removed from the housing 105 simultaneously as a unit (e.g., a distribution set 200).

The facile removal of the distribution connectors and the individual movability of the same help prevent cross-channeling. For instance, in certain instances, a user may wish to replace one of the distribution connectors and to leave the other in place. Given the design features and the chirality of the distribution connectors 210, 220, when replacing a faulty distribution connector, it can only be replaced by the same type of distribution connector (e.g., a first distribution connector can only be replaced by a replacement first distribution connector and not a replacement distribution connector that has the shape of the second distribution connector).

Figure 13:
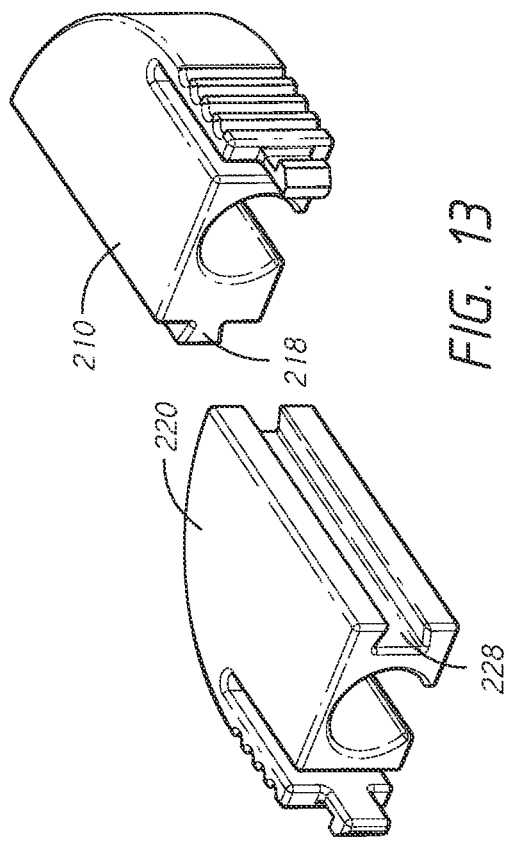
FIG. 13 illustrates connectors that are disengaged from each other.

In some variants, as shown in FIGS. 8, 9, and 13, the first distribution connector 210 is configured to engage the second distribution connector 220 via an engaging fastener 218 (e.g., a projection, dovetail, tongue, etc.) located on the first distribution connector 210 that interacts with a fastener aperture 228 (e.g., a groove) on the second distribution connector 220. This design element further aids in preventing the misplacement of distribution connectors during replacement (because two "second" distribution connectors cannot link together and two "first" distribution connectors could physically block each other from engagement on the housing via the dovetails). In some embodiments, these features are not present and other features of the connection/housing assembly ensure proper coupling.

In some embodiments, a groove and tongue can be included on an individual distribution connector. These can interact with coinciding features of an adjacent connector to provide asymmetric connectors that can only be used together in the desired specified way (thereby limiting cross-channeling).

Figure 12:
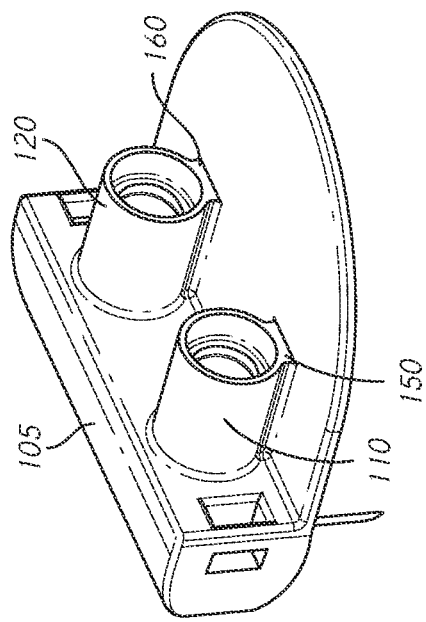
FIG. 12 illustrates a base with distribution connectors removed.

In some embodiments, the housing can comprise design elements that allow only desired interactions with connectors having complementary elements. For example, as shown in FIG. 12, in some variants, the housing 105 comprises a first guide member 150 and a second guide member 160. In certain implementations, the first guide member 150 engages a corresponding first slide aperture 230 of the first distribution connector 210 and the second slide member 160 engages a corresponding second slide aperture 240 of the second distribution connector 220. In some embodiments, these members are not present and other features of the connection/housing assembly ensure proper coupling.

When present, like others features described herein, the guide member/slide aperture configuration allows only the first distribution connector 210 to interact with the first fluid path and only the second distribution connector 220 to interact with the second fluid path. This is true even where the engaging fastener 218 and fastener aperture 228 are not present. For instance, the guide member/slide aperture configuration is configured in such a way as to prevent the misplacement of distribution connectors during replacement (because two "second" distribution connectors cannot link to the housing simultaneously—the slide aperture would be facing away from the slide member). Thus, this feature of the infusion system also ensures the fluid paths can be maintained and chances for cross channeling minimized. In some embodiments, where more than two medicaments are to be delivered independently, additional shapes and sizes of male and female connector configurations can be used to lock distribution connectors in place (first and second male shapes that fit into first and second female apertures, respectively).

In some embodiments, as shown in FIGS. 1-4, the distribution connector set 200 and the base 100 comprise an infusion set 20. As shown in FIGS. 1-4, the fluid conduit 300 can include two or more channels, where each channel is adapted to deliver a particular type of medicament to an appropriate inlet port on the infusion set 20. The multiple channels (e.g., fluid pathways) formed by the multi-channel lumen assembly 300 may be coupled and uncoupled together in order to assist the patient in assembling the infusion system, replacing one or more tubes of the assembly, or preventing the tubes of the lumen assembly from becoming tangled or caught on objects during daily use and during the performance of normal daily activities.

The multiple channels may bridge the span between the infusion pump and the infusion set 20 by independent channels where each channel can be a single or multiple-lumen channel, by channels joined by webbing or by some other manner where each channel can be a single or multiple-lumen channel, or by a single multiple-lumen channel where the enclosed lumens are arranged in an array or as concentric lumens.

In certain implementations, the fluid conduit 300 helps convey the medicaments from reservoirs located within the infusion pump to the infusion set 20. The infusion set 20 can also incorporate a channeling system that can pair with each of the tubes or channels of the fluid conduit assembly that spans the gap between the infusion pump and the site of infusion. The infusion set can be connected, disconnected, or reconnected to the fluid conduit and distribution connector set 200. In certain implementations, as discussed above, the infusion set 20 infuses medicaments to the patient through multiple channels.

As stated above, in some embodiments, the fluid conduit assembly 300 includes a first channel 310 and a second channel 320 forming medicament pathways or channels. The end portions of the first channel 310 and the second channel 320 can include if desired a feature element to help prevent the mischanneling of medicaments. For example, either or both end portions can employ features with different threads, sizes, and shapes to give it particular mating preferences.

As shown in FIGS. 1-4, the channels 310, 320 of the fluid conduit can be configured to be coupled together by a channel coupler 330. Then, if desired, detached or decoupled from each other. In some embodiments, this can be done repeatedly. For instance, the channels can be coupled together over at least a portion of the length of the tubes. In some embodiments, the channel coupler 330 prevents the channels from tangling. In some embodiments, as shown in FIG. 4B, the channel coupler 330 can be affixed to one channel 320 and the other channel 310 can be reversibly attached thereto. In some embodiments, the channel coupler 330 can be permanently coupled to one channel and a friction fit with the other, or it can be friction fit to both. In some embodiments, the channel coupler substantially the length of the channels or it can be less the full length of a channel. In some embodiments, the coupler is less than about 75%, about 50%, about 40%, about 30%, about 20%, or less than about 10% of the length of a channel. Shorter couplers are able to slide along the cables. Longer couplers enhance rigidity and to reduce the amount it will slide.

In some embodiments, the channel coupler 330 can run along a substantial length of the channels or a partial length of the channels. In some embodiments, the channel coupler 330 gives the channels rigidity preventing fluid pressure that could cause a bolus injection to the patient or a void space in the channel. In some embodiments, the rigidity allows the channels to be worn under the clothes without tangling or kinking.

In certain implementations, as shown in FIGS. 1-4 and 14, the first channel 310 engages a first inlet connector 410 via an aperture on the inlet connector 410. As shown in FIGS. 1-4, in some embodiments, the second channel 320 engages a second inlet connector 420 via an aperture on the inlet connector 420. As shown in FIGS. 1-4, the first inlet connector 410 and the second inlet connector 420 can be differently sized and shaped to prevent interactions with fluid reservoirs having incorrect medicaments, thereby minimizing risks of cross-channeling. As shown, the first inlet connector 410 can have a longer skirt with a larger outer diameter (OD) and the second inlet connector 420 can have a shorter skirt with a smaller OD. The different skirt sizes can give added selectivity during insertion of a connected reservoir into the skirts. For example, vials can be configured to not fit into certain skirts. Additionally, certain skirts can be configured to not insert into incorrect positions within an infusion pump.

Figure 14:
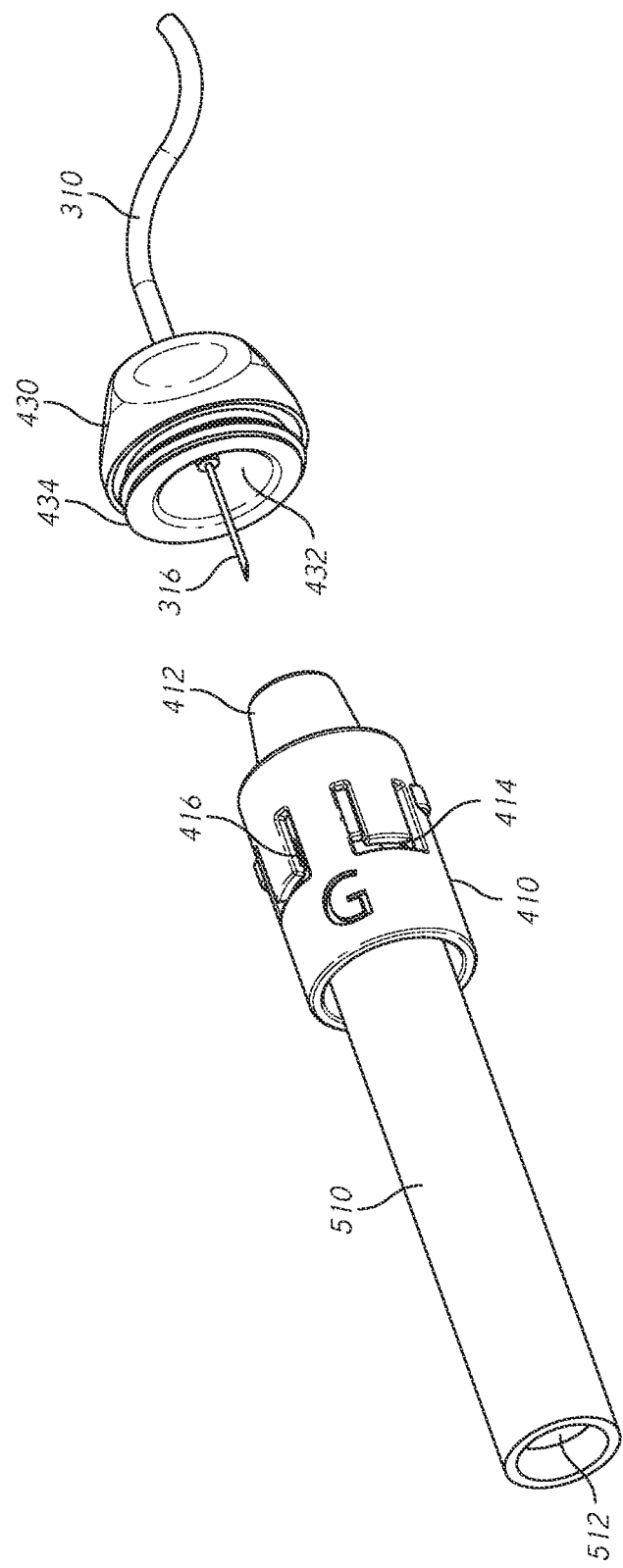
FIG. 14 illustrates a reservoir coupled with an inlet connector with the cover disengaged.

As shown in FIGS. 14-16, in some embodiments, the first channel 310 comprises a first piercing element 316 (e.g., a needle, cannula, etc.) configured to insert into a first medicament reservoir 510 that couples to the first inlet connector 410. In some embodiments, the needle 316 pierces a first reservoir septum 514 on the first medicament reservoir 510 by insertion through the pairing projection. In some embodiments, the first reservoir 510 has a first plunger 512 adapted to be depressed by a piston of an infusion pump.

In some embodiments, as shown in FIG. 14, a first inlet connector cover 430 (e.g., secondary cap, etc.) is configured to interact with the first inlet connector 410 via the first pairing projection 412. In certain variants, the cover 430 is molded and permanently attached to the first fluid conduit 310. In some embodiments, the cover 430 and the first fluid conduit 310 are reversibly attachable. In some embodiments, not pictured, the first inlet connector cover 430 is freely movable along the fluid conduit 310 while the needle 316 is molded to the first pairing projection 412 and fixed there. In some embodiments, the first inlet connector cover 430 is heat staked to the first inlet connector 410 via the first pairing projection 412. In some embodiments, the fluid conduit is able to freely rotate within the first inlet connector and cover. This helps avoid kinking of the fluid conduit. In some embodiments, the first inlet connector cover 430 and the first inlet connector are separated by a compressible O-ring 417. This O-ring allows the cover and connector to be tightly coupled to seal them together. In some embodiments, a compressible O-ring 415 resides around the first inlet connector cover 430 threads to facilitate tight connection to the fusion pump via the external threads.

In certain variants, the first cover 430 comprises a first external engagement implements 434 (e.g., external threads) configured to interact with and engage mated receptacles on an infusion pump. In some embodiments, the first cover 430 comprises a first pairing aperture 432 configured to engage with the first pairing projection 412. In some embodiments, the first cover 430 comprises a first pairing aperture 432 that is configured to not engage with the second pairing projection 422.

As shown in FIGS. 14-18, in certain implementations, the first inlet connector 410 is configured to interact with the first medicament reservoir 510. In some embodiments, the first inlet connector 410 is configured to receive an internal reservoir cover 450. In some embodiments, the internal reservoir cover 450 engages the reservoir septum 514 via one or more reservoir cover projections 454 residing on one or more internal cap extension members 452.

In some embodiments, to be inserted properly within the first inlet connector 410, the reservoir must be fitted with an internal reservoir cover 450. In some embodiments, the cover projections 454 can be configured to only interact with an appropriate reservoir, e.g., the first reservoir 510 and not the second reservoir 520. These features can further prevent cross-channeling of medicaments.

In some embodiments, as shown in FIG. 14-18, the first inlet connector 410 comprises a first inlet connector engaging member 414 with a first engaging member lip 416. In certain implementations, this lip 416 can interact with the internal reservoir cover 430 to engage the cover and an appropriate reservoir 510. These features also can be used to prevent mismatching of reservoirs, further prevent cross-channeling of medicaments.

As shown in FIGS. 20 and 21, in some embodiments, the second channel 320 comprises a second piercing element 326 (e.g., a needle, cannula, etc.). In some embodiments, the piercing element 326 is configured to insert into a second medicament reservoir 510, as shown in FIGS. 19-20, that couples to the second inlet connector 420. In some embodiments, the needle 326 pierces a second reservoir septum 524 on the first medicament reservoir 510 by insertion through the pairing projection.

In some embodiments, as shown in FIGS. 19-21, a second inlet connector cover 440 (e.g., secondary cap, etc.) is configured to interact with the second inlet connector 420 via the second pairing projection 422. In certain variants, the cover 440 is molded and permanently attached to the second fluid conduit 320. In some embodiments, the cover 440 and the second fluid conduit 320 are reversibly attachable. In some embodiments, the second inlet connector cover 440 is heat staked to the first inlet connector 420 via the first pairing projection 422. In some embodiments, not pictured, the second inlet connector cover 440 is freely movable along the fluid conduit 320 while the needle 326 is molded to the second pairing projection 422 and fixed there. In some embodiments, the fluid conduit is able to freely rotate within the second inlet connector and cover. This feature helps avoid kinking of the fluid conduit. In some embodiments, the second inlet connector cover 440 and the second inlet connector are separated by a compressible O-ring 427. This O-ring allows the cover and connector to be tightly coupled to seal them together. In some embodiments, a compressible O-ring 425 resides around the first inlet connector cover 430 threads to facilitate tight connection to the fusion pump via the external threads. In some embodiments, because solvents such as DMSO can be used to dissolve medicaments, each feature of the infusion system can be insert molded to avoid glues and other materials that may dissolve in DMSO or other organic solvents. In some embodiments, when weaker solvents or inorganic solvents are used (e.g., water), features of the infusion system can be glued or otherwise affixed together.

In certain variants, as shown in FIGS. 19-22, the second cover 440 comprises second external engagement implements 444 (e.g., external threads) configured to interact with and engage mated receptacles on an infusion pump. In some embodiments, the second cover 440 comprises a second pairing aperture 442 configured to engage with the second pairing projection 422. In some embodiments, the second cover 440 comprises a second pairing aperture 442 that is configured to not engage with the first pairing projection 412.

As shown in FIGS. 19-21, in certain implementations, the second inlet connector 420 is configured to interact with the second medicament reservoir 520. In some embodiments, the second reservoir 520 has a second plunger 522 adapted to be depressed by a piston of an infusion pump. In some embodiments, to be inserted properly within the second inlet connector 420, the reservoir must not be fitted with a reservoir cover 430. This feature can further prevent cross-channeling of medicaments.

In some embodiments, as shown in FIG. 19-22, the second inlet connector 420 comprises a second inlet connector engaging member 424 with a second engaging member lip 426. In certain implementations, this lip 426 can interact with the septum 524 of the second reservoir 520. These features also can be used to prevent mismatching of reservoirs, further preventing cross-channeling of medicaments.

Figure 17:
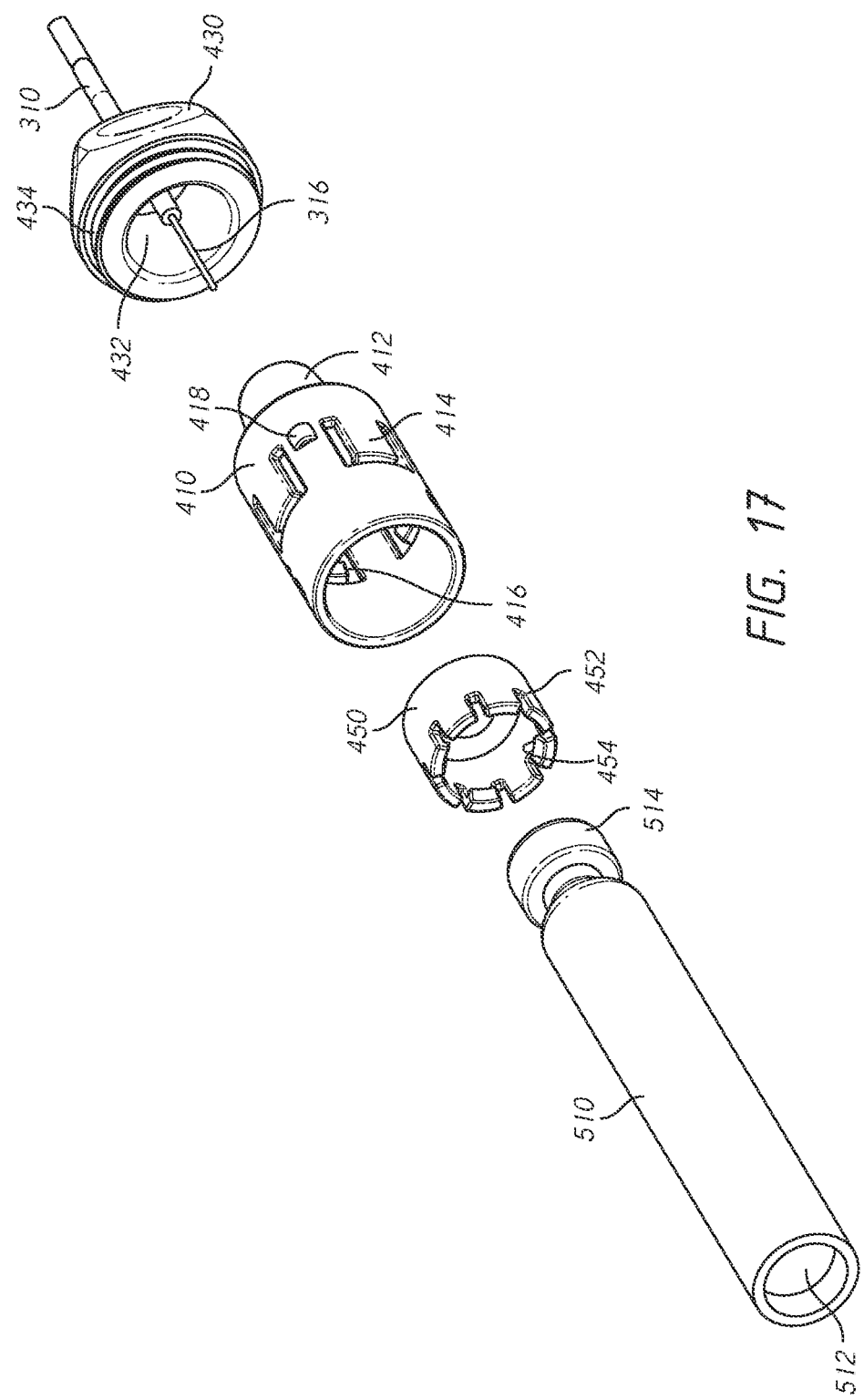
FIG. 17 illustrates an exploded view of a reservoir, an inlet connector, and
a cover.
Figure 28:
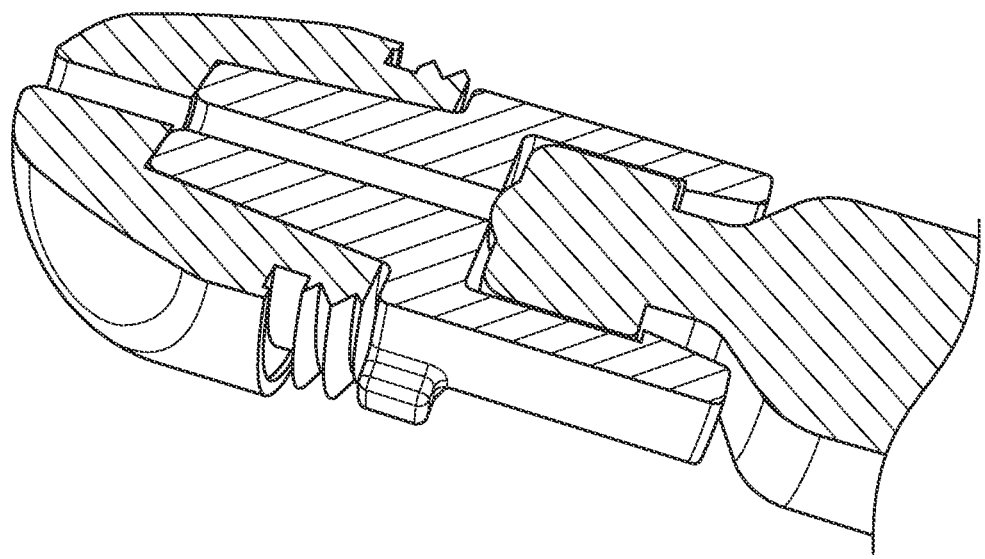
FIGS. 28-33 illustrate embodiments of reservoirs and inlet connector assemblies.
Figure 29:
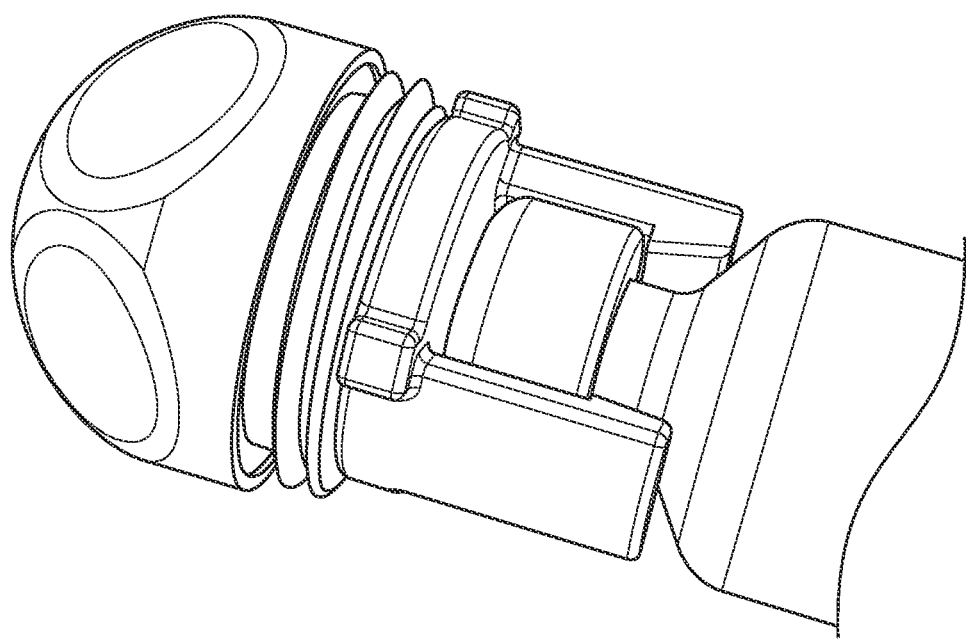
Figure 30:
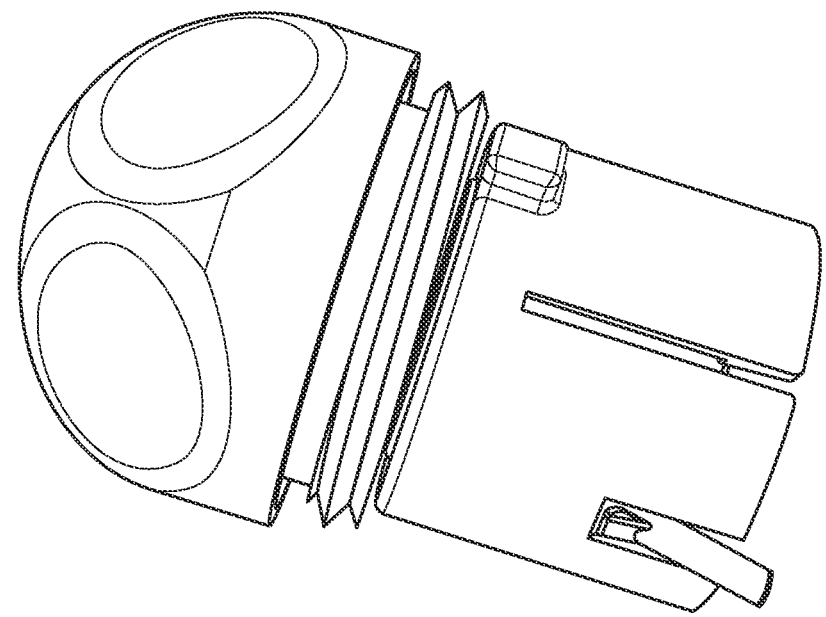
Figure 31:
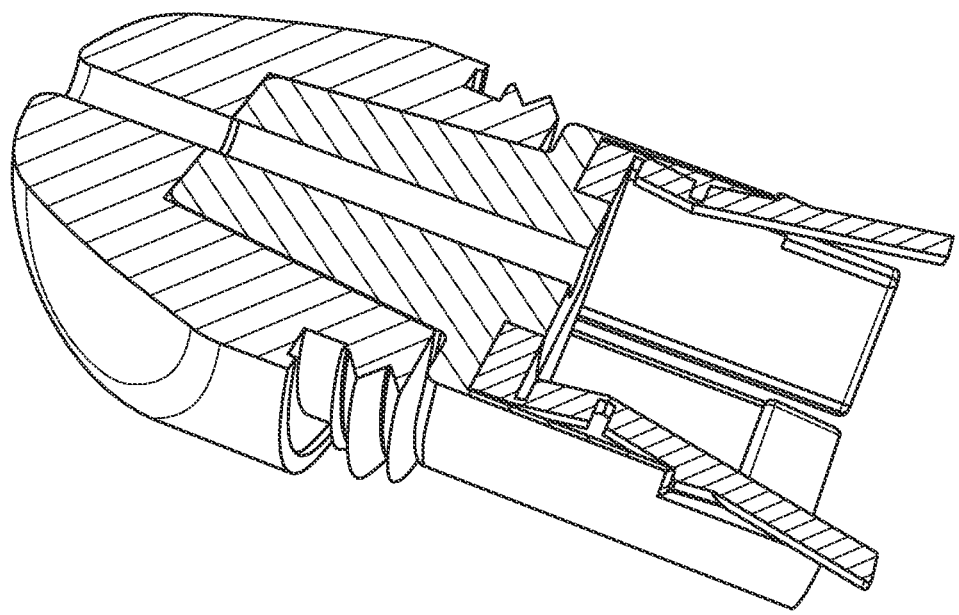
Figure 32:
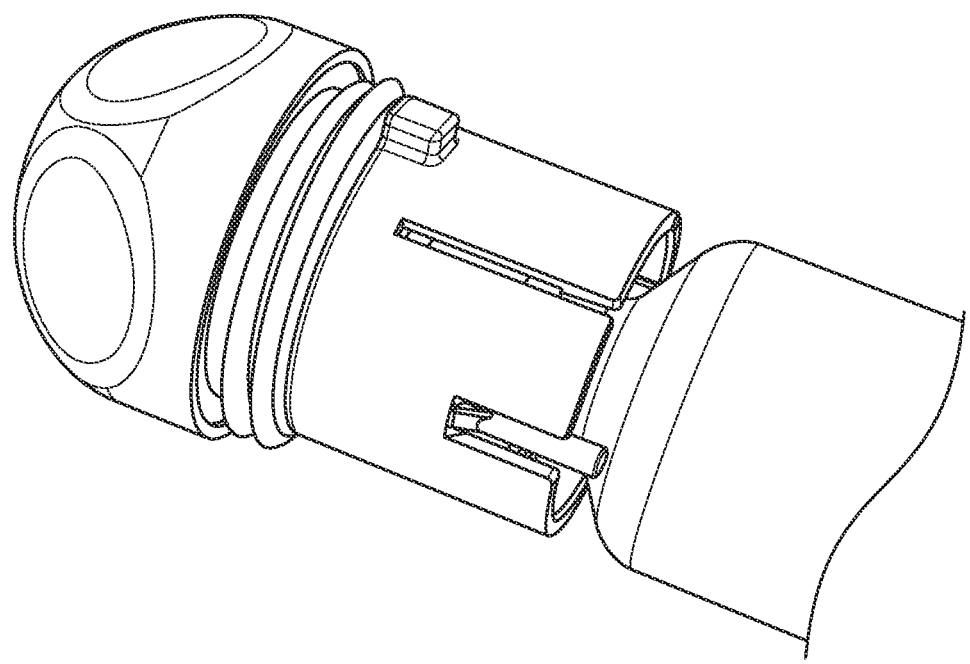
Figure 33:
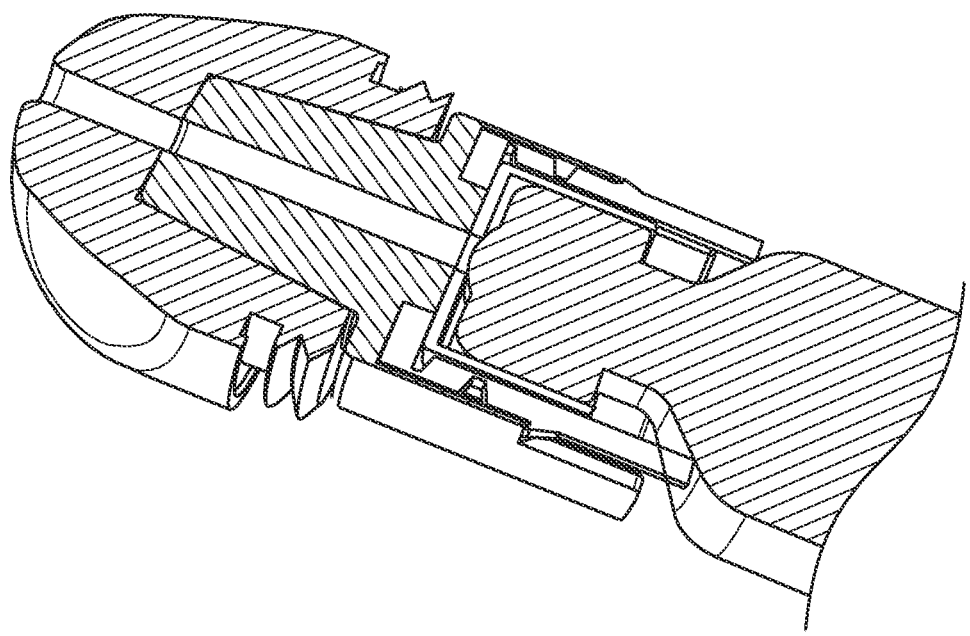
Figure 34A:
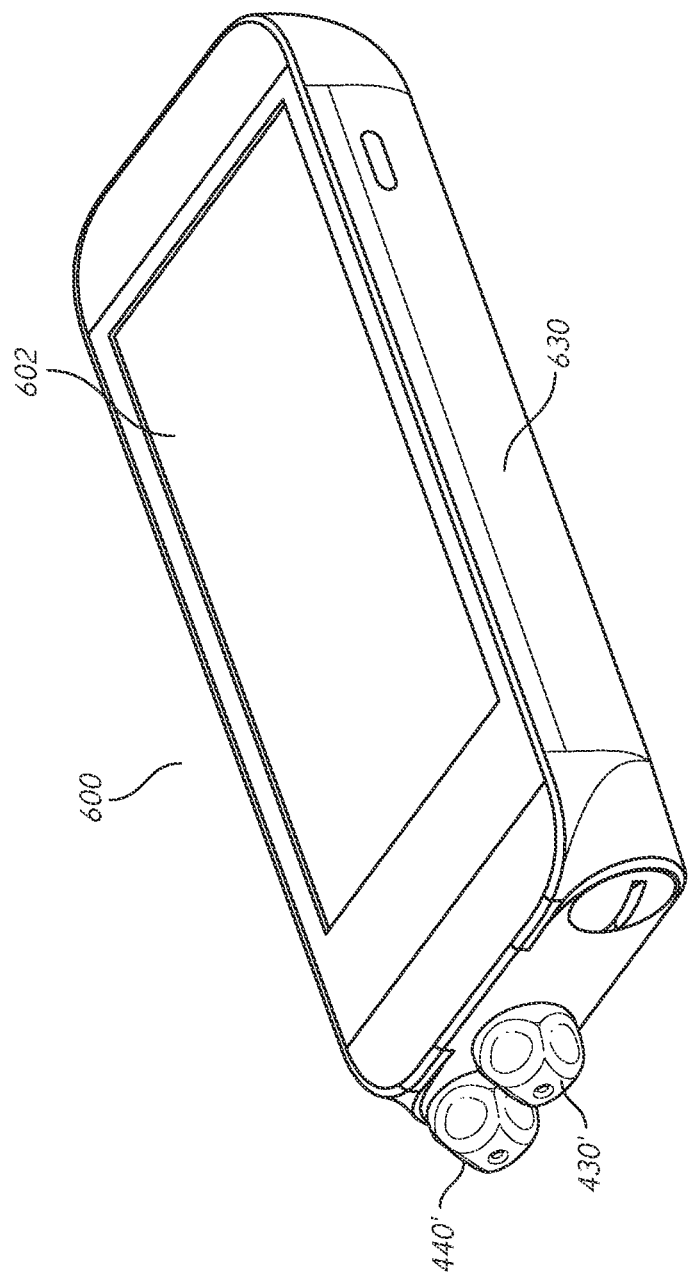
FIGS. 34A-36 illustrate a pump assembly configured for use with an infusion system.
Figure 34B:
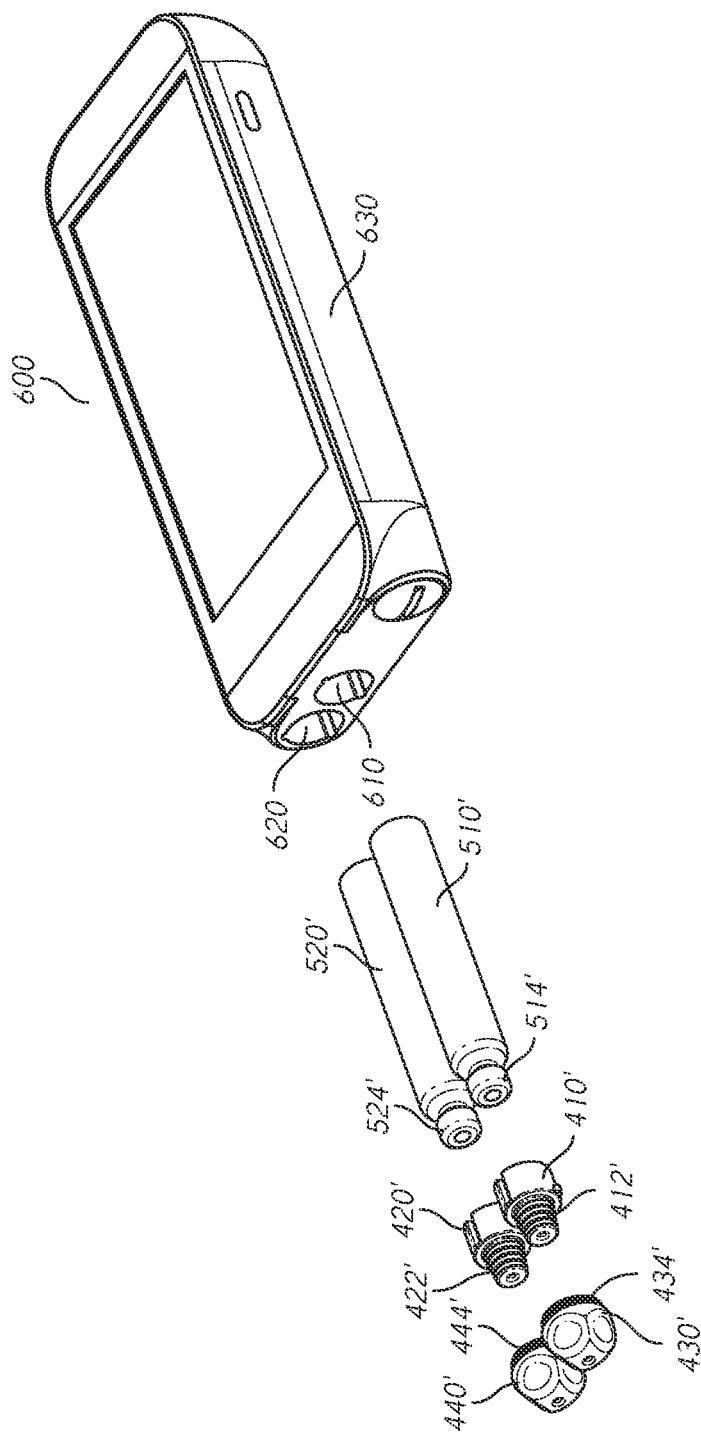

In some embodiments, as shown in FIGS. 17 and 18, the first inlet connector 410 comprises a first guiding element 418 (e.g., a projecting feature). In some embodiments, the second inlet connector 420 comprises a second guiding element 428 (e.g., a rail). In some embodiments these feature can facilitate placement in, for example, a specific aperture in an infusion pump, while discourage (or preventing) insertion into an incorrect aperture. In some embodiments, the second inlet connector comprises a second rolling element. The rolling elements can aid the user in placing the reservoirs within the pump as they are inserted into the infusion pump.

As shown in FIGS. 23 and 24, in some embodiments, when the second reservoir 520 is placed within the first inlet connector 410, they are unable to couple. For instance, as shown in FIG. 24, the second reservoir 520 body is of a sufficient diameter to not allow it to fully insert into the first inlet connector 410 or to be pierced by the first piercing element 316. Additionally, in some embodiments, features of the first inlet connector 410 (e.g., the engaging member lip 416) do not engage the second reservoir 520. This provides the patient or user immediate feedback indicating that the coupling is incorrect. Thus, in certain implementations, mismatching of reservoirs is avoided and cross-channeling can be prevented.

As shown in FIGS. 25-27, in some embodiments, when the first reservoir 510 is placed in proximity to the second inlet connector 420, they are unable to couple. For instance, as shown in FIGS. 25-27, in some embodiments, the internal reservoir cover 450 can be sized to block the first reservoir 510 from inserting into the second inlet connector 420. Thus, the reservoir 510 is not pierced by the second piercing element 326. This provides the patient or user immediate feedback indicating that the coupling is incorrect. Thus, in certain implementations, mismatching of reservoirs is avoided and cross-channeling can be prevented.

FIGS. 28-33 show various embodiments of inlet connectors. The inlet connectors of FIGS. 28 and 29 comprise projections that block their insertion into the incorrect positions of infusion pumps and facilitate their insertion into the correct positions. FIGS. 30-33 show views of inlet connectors that prevent facilitate coupling and placement of the correct reservoir into the correct infusion pump receptacle. For instance, as shown the inlet connector has a deployable kickstand that can be spring-loaded. When an incorrect vial is inserted the kickstand remains deployed. However, when an appropriate reservoir is added to the inlet, the kickstand retracts, allowing placement of the reservoir into an infusion pump receptacle. Features of each inlet connector can be mixed and matched to provide multiple types of connectors for use with 2, 3, 4, 5, 6 or more medicaments. In certain implementations, each embodiment is suited to aid in the prevention of cross-channeling.

In some embodiments, as shown in FIGS. 34A-36, the infusion system 001 further comprises a multi-medicament pump 600 comprising a pump body 630 and one or more reservoir receptacles 610, 620.

In certain embodiments, the pump 600 comprises a display region 602. In some embodiments, the display region provides the user with data regarding drug dosing or blood levels and allows the user to adjust the distribution of medicaments accordingly. In certain implementations, the drug dosing is controlled by algorithms and the pump automatically delivers doses based on patient status.

In some embodiments, the pump 600 also comprises design features and/or mating connectors or adapters on certain components to ensure that the system is connected appropriately to prevent cross-channeling. In some embodiments, the pump 600 reservoir receptacles 610, 620 are configured to receive different reservoirs 510', 520' which are configured to hold different medicaments. In certain implementations, as shown in FIGS. 34A-36, a first receptacle 610 is configured to receive a first reservoir 510' and a second receptacle 620 is configured to receive a second reservoir 520'. In certain variants, the first receptacle 610 is configured to not receive the second reservoir 520' and the second receptacle 620 is configured to not receive the second reservoir 510'.

In certain implementations, inlet connector covers 430', 440' having external threads 434', 444' can hold the reservoirs 510', 520' within the pump 600. Different pump bodies can be prepared to fit different inlet covers. For example a pump could be provided to provide different receptacles where one is configured to accommodate the external threads of the first connector cover 434 and the other is configured to accommodate the external threads of the second connector cover 444.

In some embodiments, the first inlet connector 410' comprises a first pairing projection 412' that is threaded or stepped to lock the first inlet connector cover 430' to the inlet connector 410' and reservoir 510'. In some embodiments, the second inlet connector 420' comprises a second pairing projection 422' that is threaded or stepped to lock the second inlet connector cover 440' to the inlet connector 420' and reservoir 520'. In some embodiments, when these stepped/snap-tight configurations are used, an audible click informs the user that the connectors are correctly engaged. In some embodiments, as with the embodiments disclosed elsewhere herein, the projections can be appropriately sized to allow pairing with only appropriately matched covers.

Figure 35:
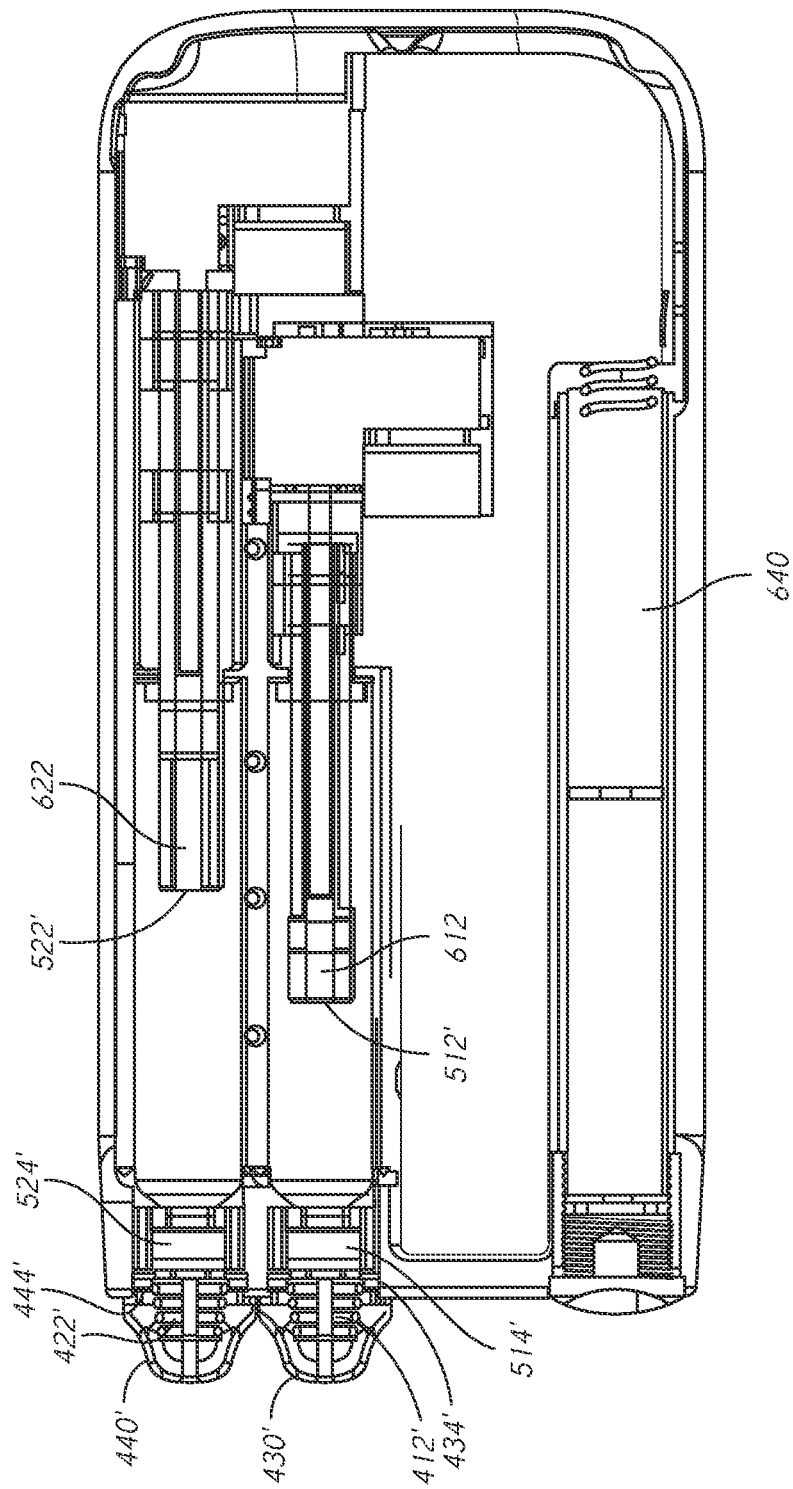
Figure 36:
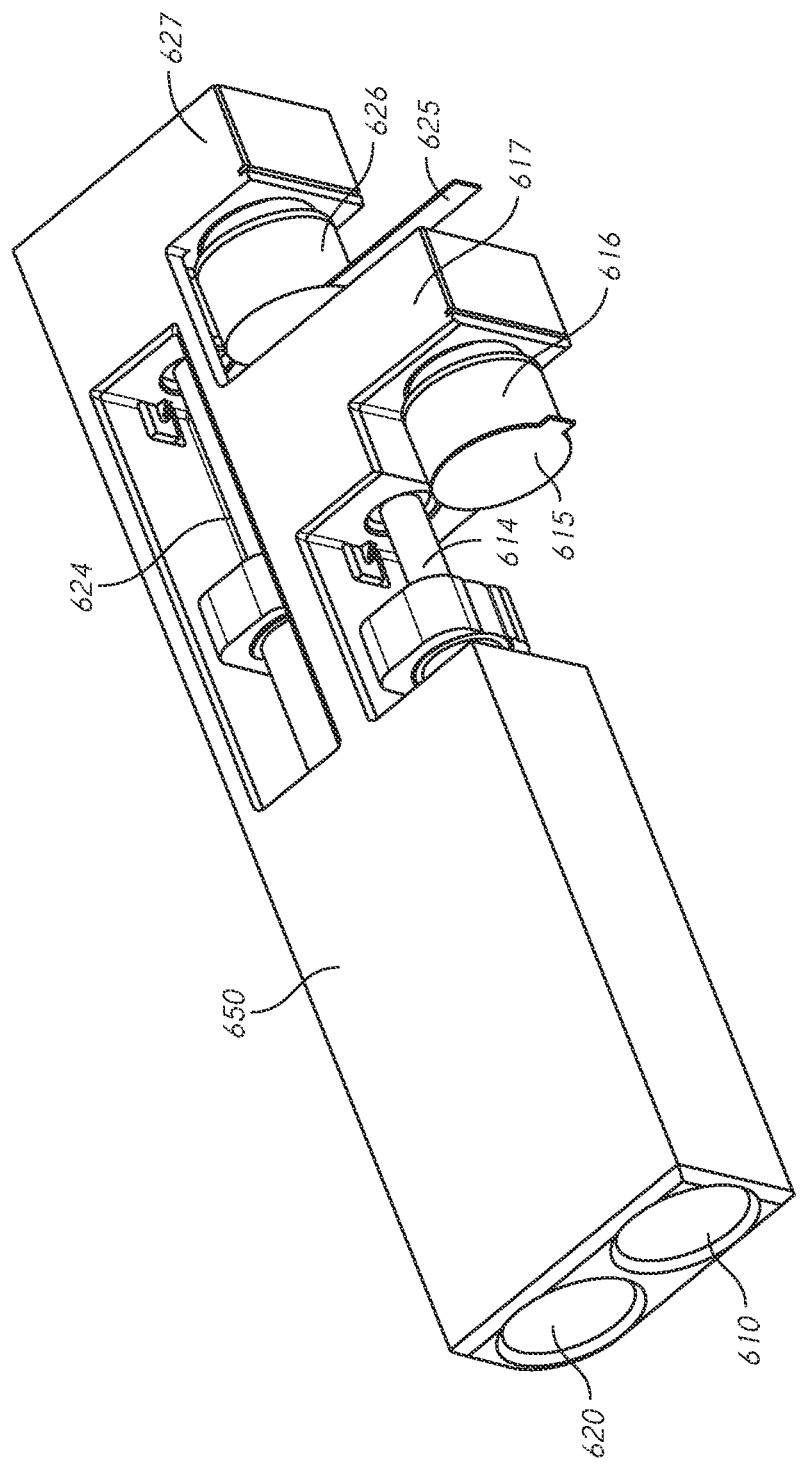

In some embodiments, as shown in FIGS. 35-36, the pump comprises pistons 612, 622 that engage plungers 512', 522' of the reservoirs. In some embodiments, the pistons 612, 622 are engaged by lead screws 614, 624 that can urge the pistons 612, 622 forward or backward.

In some embodiments, the pistons and reservoirs comprise a single assembly 650 that can be swapped out of the pump 600 to insert different configurations of medicaments and reservoirs.

In certain variants, an actuator, such as a button or a sensor (e.g., a capacitive touch sensor) is located behind a portion of the display 602 and can be activated by touching the display in designated locations. In some embodiments, the capacitive touch sensor sends signals to the pistons individually and allows the user to control one or more aspects of the drug delivered from the pistons. For instance, in some embodiments, a user can swipe (or drag) a finger in one direction (i.e., left, right, down, up, or otherwise) over the capacitive touch sensor change delivery capabilities.

In some embodiments, the pump is automated so that the PCBs activate the pistons 612, 622 based on one or more variables (e.g., time, patient data, etc.). The pump 600 can also include memory, such as firmware, to store the various user settings, control schemes, and algorithms, as well certain instructions and/or settings related to various characteristics of the patient. For example, the memory can include instructions and/or settings regarding when and how much to dose to the patient, and otherwise. The pump 600 can be configured such that a patient or doctor can modify (e.g., update, program, or otherwise) the memory, such as by connecting the pump to a computer (e.g., a smartphone, laptop, etc.) that is equipped with software or an "app" that is configured to enable the computer and/or pump to perform any of the functions, tasks, and/or steps described and/or illustrated herein.

In certain embodiments, as shown in FIG. 35, the pump 600 comprises a power source 640 (e.g., batteries). In certain variants, the infusion pump 600 is low profile to facilitate transport of the infusion pump in a pocket, on a belt, or under clothing. As shown in FIG. 36, flex cables 615, 625 provide input to the motors 616, 626 of the infusion pump. The motors 616, 626 drive gears in gear assemblies 617, 627 and facilitate movement of the lead screw. The drive access of the motor and the lead screws are each configured to be parallel to each other and in the same axis as the reservoirs. This gives the infusion pump a low profile design.

In some embodiments, collars can be used to avoid mischanneling of medicaments. For instance, one collar with various features, for example physical and/or geometric features, can be attached (clipped, glued, etc.) onto a vial of a particular medicament. A second different collar with different features can be attached (clipped, glued, etc.) onto a second vial of a different particular medicament. In some embodiments, collars can be configured to interact with only mated pump recesses, inlet connectors, etc. so that mischanneling is avoided. In some embodiments, collars (or other similar objects/implements that surround a portion of a reservoir, vial, or cartridge) can be added to reservoirs (e.g., vials, cartridges, etc.) at a single station at the end of each reservoir fill line. In some embodiments, collars allow a drug manufacturer to use the same cartridge (ampule, vial, etc.) for different medicament fill lines. In some embodiments, after coming off of the fill line, each reservoir could be rendered unique to a particular drug by the addition of a collar, while using a common cartridge for each medicament. In some embodiments, differently shaped vials and collars can be used, increasing the variability of possible configurations of medicament delivery systems that avoid mischanneling. In some embodiments, one or more collars can be used on a vial to mix and match features, increasing the variability of configurations. In some embodiments, the collars are either of a variety that connects to the head (or crown) of the cartridge or to the neck of the cartridge, to the body of the cartridge, or to combinations thereof.

As with other embodiments described herein, in some embodiments, mated collar components are applicable to multiple-medicament infusion pumps, reusable pens or syringes or other devices that use pre-filled cartridges and deliver medicaments (such as long-acting insulin analogs, rapid insulins and rapid insulin analogs, ultrarapid insulins and ultrarapid insulin analogs, insulin and insulin analogs of different concentration, etc.). In some embodiments, the mated features, when added to the cartridge, can engage corresponding features in the reusable pen or syringe (or pump body, connector inlets, caps, etc.) allowing for insertion of only the proper cartridge into the corresponding proper reusable pen or syringe (or pump body, connector inlets, caps, etc.).

In some embodiments, a collar (as shown by exemplary embodiments depicted in FIGS. 37-56) is provided. In certain variants, the collar is pre-fitted to medicament reservoirs (cartridges, vials, etc.) and can be attached to or fitted onto the neck (head or crown) of the reservoir, as shown in FIGS. 41 and 42. While variations are discussed with reference to specific collars, inlet connectors, caps, and pumps below, these variations are applicable to any collars, inlet connectors, caps, and pumps disclosed herein. Portions of different collars disclosed herein can be mixed and matched to provide different embodiments.

Figure 37C:
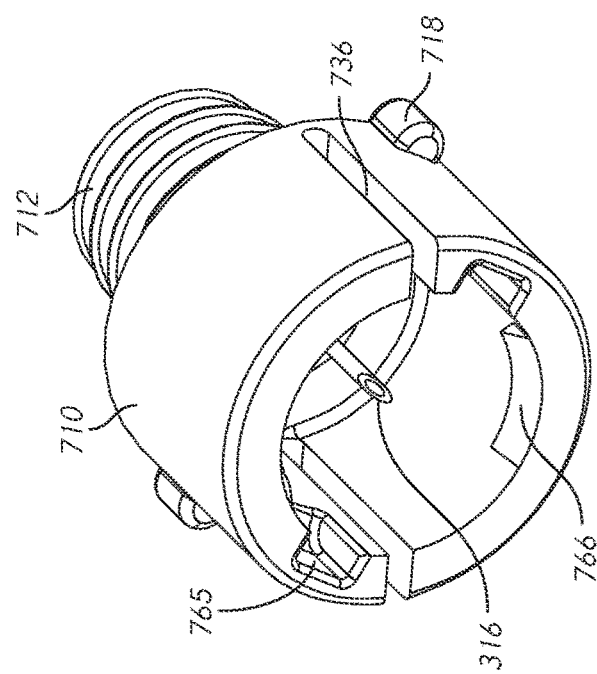
FIGS. 37A-C illustrate an embodiment of a collar assembly and a corresponding inlet connector.
Figure 37B:
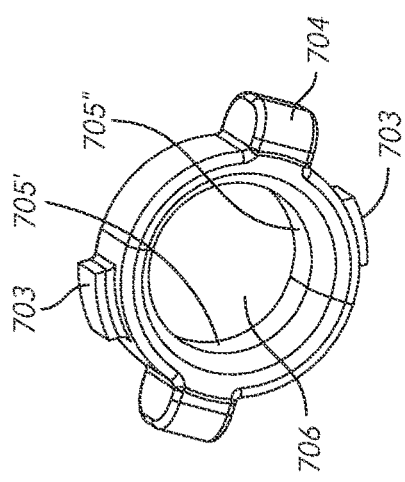
Figure 37A:
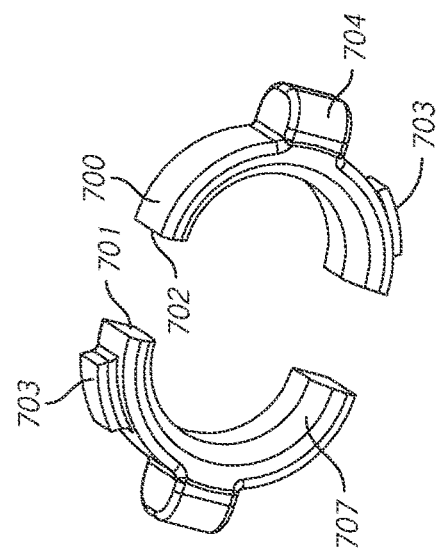

FIG. 37A shows an exploded view of an embodiment of a collar 700, showing a pre-fitted collar assembly that inserts around the neck of the cartridge. FIG. 37B shows an assembled view of the same pre-fitted collar 700 shown in FIG. 37A. FIG. 37C shows an inlet (or cap) connector 710 that inserts over the head (or crown) and neck of a reservoir and engages with the pre-fitted collar assembly shown in FIGS. 37A-B.

As shown in FIGS. 37A-B, in some embodiments, the collar 700 comprises a first collar portion 701 and a second collar portion 702. In some variants, as shown in FIGS. 37A-B, these portions 701, 702 can be equivalently shaped so that a single mold can be used to fabricate both portions 701, 702. In some implementations, the portions are differently shaped and sized. For instance, in some embodiments where the collar is circular, one portion could make up 75% of the circle and the other 25% (where another portion is present). This sizing could facilitate the larger portion of the collar snapping tightly over the reservoir, securing that portion in place, while the other piece is held (or fixed) in place during, for instance, capping of the collared reservoir. In some embodiments, the collar is substantially circular (or some other shape that fully surrounds a portion of the reservoir) and can be snapped into place via a single slit in the collar (e.g., a space or cut in the collar). For instance, a vial neck can be inserted through slit compressing the collar which then snaps back around the vial to its original shape. In some embodiments, the collar is flexible. In some embodiments, the collar can be deformed and returns back to its original shape. In some embodiments, the collar is arc shaped (making up 65%, 75%, 85% or more of a circle) and can be snapped around the neck. It should be noted that various shapes of collars could also be used (square, rectangular, triangular, etc.) depending on the shape of the vial or the shape of the inlet connector. In some embodiments, the collar comprises one, two, three, four, or more pieces (e.g., portions) that can be assembled to wrap a reservoir. In some embodiments, different collar portions can be mixed and matched, increasing the variability of possible configurations of medicament delivery systems that avoid mischanneling.

In some embodiments, as shown in FIG. 37B, different collar portions 701, 702 can be affixed (welded, glued, etc.) to one another to form a collar having a reservoir engaging aperture 706. In some embodiments, the collar can be attached permanently to a medicament reservoir (e.g., a vial, etc.). In certain embodiments, the medicament reservoir can be reused, being refilled using a bulk reservoir with corresponding features that match the features of the collar/collar-capping assembly/vial assembly.

In some embodiments, an adhesive, glue, rubberizing agent, or other applicant can be applied to mating surfaces 705', 705" of the engaging aperture 706 that contact the neck (or head, crown, etc.) of the cartridge. In some variants, the pre-fitted collar adhesive increases friction and reduces or prevents rotation of the pre-fitted collar relative to the reservoir. In some variants, the mating surfaces of the two-component pre-fitted collars 705', 705," as shown in FIGS. 37A-B, can be affixed (e.g., bonded, glued, laser welded, or otherwise attached) as the collar is assembled onto the neck of the cartridge. In some embodiments, the mating surfaces 705', 705" are compressible (sponge, foam, rubber, soft plastic, ribbed, fabric, etc.) to allow them to compress around a reservoir, locking it in place.

In certain implementations, the collar 700 comprises one or more form fitted edges 707 (beveled, squared, etc.) to allow the collar 700 to interact flushly with a reservoir having a corresponding shape.

In some embodiments, the pre-fitted collar contains one or more features that extend radially outwardly (teeth, tabs, protrusions, features, etc.) as in FIGS. 37A-C. In some embodiments, these protrusions allow coupling only with a corresponding cap connector (e.g., inlet connector) with corresponding receiving features. In some embodiments, the corresponding cap connector contains corresponding cavities, grooves, keyways, or slots to match with the unique differentiating tabs, protrusions, or features on the pre-fitted collar (as shown in FIG. 37C). In this way, only one type of pre-fitted collar can mate uniquely with one type of cap connector. In certain variants, the protrusions extend radially inwardly from a cap connector and engage receiving features located on the collar.

For instance, in certain implementations, the collar 700 comprises one or more (e.g., 1, 2, 3, 4, 5, or more) collar projections 703 (projections having an edge, lip, clips, etc.). The embodiment of FIG. 37A-B comprises two collar projections. In some embodiments, as shown, these projections extend radially outwardly away from the collar's reservoir engaging aperture 706. In some variants, these collar projections 703 are configured to interact with one or more (e.g., 1, 2, 3, 4, 5, or more) coinciding collar projection members or mates 766 (e.g., an engaging member, lips, edges, clips, cavities comprising the same, etc.) located on an inlet connector 710. As shown in FIGS. 37A-C, the collar projections 703 can interact with corresponding collar projection mates 766 of the inlet connector 710. In some embodiments, the collar projections 703 can engage the collar projection mates 766 to snap the collar into place holding the collar 700 and the inlet connector 710 together (e.g., flush to one another). In some variants, the inlet connector 710 has coinciding projection mates 766 that are mated with each configuration of collar projections 703. In some embodiments, the collar projection mates 766 act as a capture mechanism that engages a feature (e.g., collar projections 703) on the pre-fitted collar 700 and/or that engages the collar 700 itself. In some embodiments, the capture mechanism of the inlet connector 710 can expand slightly as it is pressed over the pre-fitted collar and then the inlet connector 710 would snap into place, engaging a tab, protrusion, or feature on the pre-fitted collar, or the bottom edge of the pre-fitted collar, and securely fasten the cap connector to the pre-fitted collar. The cartridge, pre-fitted collar, and cap connector subassembly could then be fastened into a pump housing unit. In some embodiments, projections and their corresponding mates are not present.

In some embodiments, where multiple collar projections 703 are present, the collar projections 703 can be spaced evenly about the collar 700 so that each collar projection is equidistant from the next. For instance, in an embodiment as shown in FIG. 37A-C, where two projections 703 are present, those projections can be positioned opposite of one another on the collar (180° apart from each other). In some variants of the collars disclosed herein, collar projections can be spaced unevenly about the collar so that some collar projections are closer and some are farther from adjacent collar projections. In some embodiments, adjacent collar projections are separated by values independently selected from about 180°, about 160°, about 140°, about 120°, about 100°, about 90°, about 80°, about 70°, about 60°, about 50°, about 40°, about 30°, about 20°, about 10°, values between the aforementioned values or otherwise. In some embodiments, multiple differently shaped collar projections can be used on a single collar. For instance, in some embodiments, the collar projections are polygonal (e.g., triangular shaped, squared, semi-circular), shape-and-stick (e.g., ball-and-stick) etc. This variability leads to almost unlimited variability in collar/inlet connector matings.

As shown in FIGS. 37A-C, the two collar guiding elements 704 are configured to interact with two corresponding collar guiding elements 765. In some variants, the collar comprises one or more (e.g., 1, 2, 3, 4, 5, or more) collar guiding elements (tabs, protrusions, etc.). In some embodiments, these collar guiding elements protrude radially from the collar extending away from the reservoir engaging aperture 706. In some embodiments, as shown in FIGS. 37A-C, these collar guiding elements 704 are configured to interact with one or more (e.g., 1, 2, 3, 4, 5, or more) coinciding collar guiding element tracks 765 (cavities, grooves, keyways, slots, apertures, etc.) located on an inlet connector 710. In some embodiments of the collars disclosed herein, similar to the collar projections above, the collar guiding elements 704 can be spaced evenly about the collar 700 so that each collar guiding element 704 is equidistant from the next. For instance, in the embodiment shown in FIG. 37A-C, two collar guiding elements 704 are present and are positioned opposite of one another on the collar 700 (about 180° apart from each other). In some variants of the collars disclosed herein, the collar guiding elements 704 can be spaced unevenly about the collar so that some projections are closer and some are farther. In some embodiments of the collars disclosed herein, adjacent collar guiding elements are separated apart by values independently selected from about 180°, about 160°, about 140°, about 120°, about 100°, about 90°, about 80°, about 70°, about 60°, about 50°, about 40°, about 30°, about 20°, about 10°, values between the aforementioned values or otherwise. In some embodiments, multiple differently shaped guiding elements can be used on a single collar. For instance, in some embodiments, the guiding elements are polygonal (e.g., triangularly-shaped, squared, semi-circular), shape-and-stick (e.g., ball-and-stick). This design can lead to multiple configurations of collars with almost unlimited variability. In some variants, the inlet connector 710 has coinciding collar guiding element tracks 765 (grooves, cavities, slots, key holes, etc.) that are mated with each configuration of collar guiding elements 704. In some embodiments, these tracks guide only properly matched collars into place on the inlet connector. In some embodiments, guiding elements and their corresponding mated tracks are not present.

In certain variants, the collar projections 703 (or inlet connector projections as the case may be) are at least as small or smaller than the collar guiding elements 704 (or inlet connector guiding elements as the case may be). In various embodiments, the collar projections 703 (or inlet connector projections as the case may be) are at least as large or larger than the collar guiding elements 704 (or inlet connector guiding elements as the case may be). In some embodiments, the ratio of the size of the collar projections to the collar guiding elements is about 1:10, about 1:5, about 1:2, about 1:1, about 2:1, about 5:1, or about 10:1, values between the aforementioned values or otherwise.

In some embodiments, when engaged with a cartridge, the collar 700 and the inlet connector 710 couple to one another without axial rotation of either the collared reservoir or the inlet connector 710. In some embodiments, as with other embodiments of collars and connectors disclosed herein, the collar (e.g., the collared cartridge) and the inlet connector are configured to directly couple and snap together in a linear direction during coupling.

In some embodiments, as shown in FIGS. 37A-C, similar in some aspects to embodiments described above, the inlet connector 710 can comprise a pairing projection 712. This pairing projection 712 is discussed in more detail elsewhere herein and can fit into an inlet connector cover (not shown).

In some embodiments, as shown in FIGS. 37A-C, similar in some aspects to embodiments described above, the inlet connector 710 can comprise one or more guiding elements 718 (tabs, protrusions, or features). In some embodiments, similar to the collar projections above, the guiding elements 718 can be spaced evenly about the inlet connector 710 so that each guiding element 718 is equidistant from the next. In some variants, the guiding elements 718 can be spaced unevenly about the collar so that some projections are closer and some are farther. In some embodiments, adjacent guiding elements are separated by values independently selected from about 180°, about 160°, about 140°, about 120°, about 100°, about 90°, about 80°, about 70°, about 60°, about 50°, about 40°, about 30°, about 20°, about 10°, values between the aforementioned values or otherwise. In some embodiments, the guiding elements can facilitate placement in, for example, a specific aperture in an infusion pump (e.g., the infusion pump housing) by interacting with a corresponding feature (e.g., aperture, cavity, etc.) within the pump body, while discouraging (or preventing) insertion into an incorrect aperture. In some embodiments, guiding elements and their corresponding mates are not present. In some embodiments, the cap comprises a piercing element 316 that can be heat staked (or otherwise affixed, glued, welded, etc.) in place.

In some embodiments, the cap connector's (i.e., inlet connector's) guiding elements allow insertion into an infusion chamber, drive shaft, or pump chamber of a pump housing unit that contains corresponding cavities, grooves, keyways, or slots to match with the unique differentiating tabs, protrusions, or features on the cap connector. In this way, only one type of cap connector can be inserted uniquely into one particular infusion chamber, drive shaft, or pump chamber. Alternatively, the inlet connector might contain cavities, grooves, keyways, or slots (not shown) that uniquely mate with one or more tabs, protrusions, or features in the infusion chamber, drive shaft, or pump chamber of a pump housing unit.

In certain variants, the guiding elements 718 are at least as small or smaller than the collar projections 703, or collar guiding elements 704. In various embodiments, the guiding elements 718 are at least as large as or larger than the collar projections 703 or collar guiding elements 704. In some embodiments, the ratio of the size of the guiding elements to the collar projections is about 1:10, about 1:5, about 1:2, about 1:1, about 2:1, about 5:1, or about 10:1, values between the aforementioned values or otherwise. In some embodiments, the ratio of the size of the guiding elements to the collar guiding elements is about 1:10, about 1:5, about 1:2, about 1:1, about 2:1, about 5:1, or about 10:1, values between the aforementioned values or otherwise.

In certain variants, the inlet connector 710 comprises one or more (2, 3, 4, 5, or more) inlet connector spacers 736 (e.g., relief slits, cavities, etc.). As shown, the two relief slits 736 of the inlet connector 710 of FIG. 37C are 180° apart. In some variants, where multiple relief slits are present, the relief slits can be spaced unevenly about the collar so that some projections are closer and some are farther. In some embodiments, adjacent relief slits are separated by values independently selected from about 180°, about 160°, about 140°, about 120°, about 100°, about 90°, about 80°, about 70°, about 60°, about 50°, about 40°, about 30°, about 20°, about 10°, values between the aforementioned values or otherwise. In some embodiments, this inlet connector spacer 736 allows the inlet connector 710 to be compressed as it inserts into a pump housing or expanded as it is slid over a collar/reservoir assembly. This can allow snap tight fitting into a pump housing or with a collar/reservoir assembly that comprises mated features. For instance, in some embodiments, once inserted all the way into the housing, the inlet connector spacers can re-expand, allowing the geometric features of the inlet connector 710 to interact with mated apertures or features of the pump housing. This feature, among others described herein, can allow the reservoir to be held in an appropriate position, with little movement, within the pump housing. In some embodiments, a single-component pre-fitted collar 700, such as the ones shown in FIGS. 37A-C, has relief slits 736 which allow the inlet connector to be pressed over the head (or crown) of the cartridge, and a locking mechanism, that snaps into place as it engages with the underside of the head (or crown) of the cartridge.

Figure 38C:
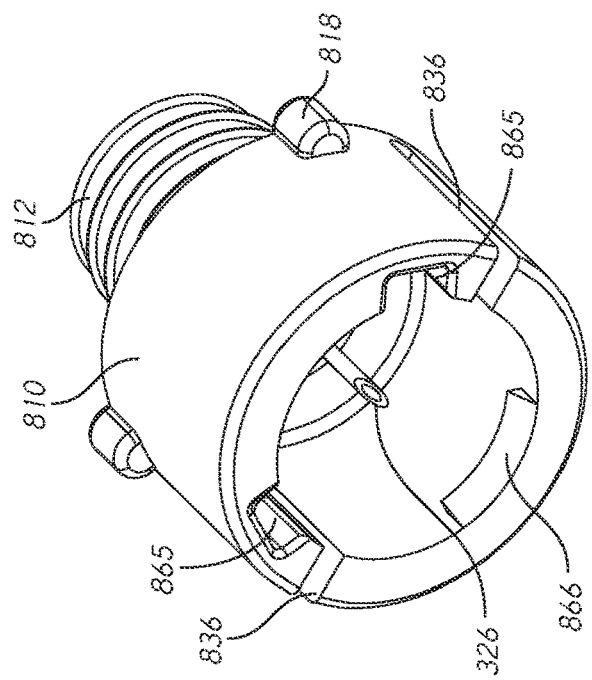
FIGS. 38A-C illustrate another embodiment of a collar assembly and a corresponding inlet connector.
Figure 38B:
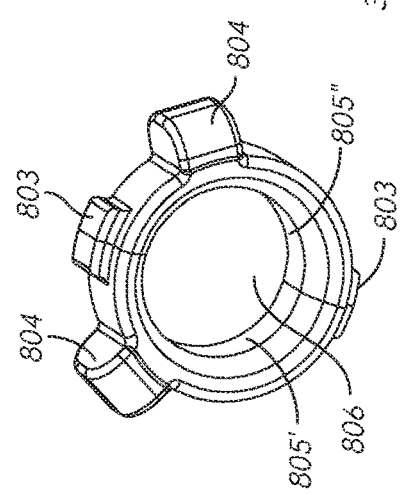
Figure 38A:
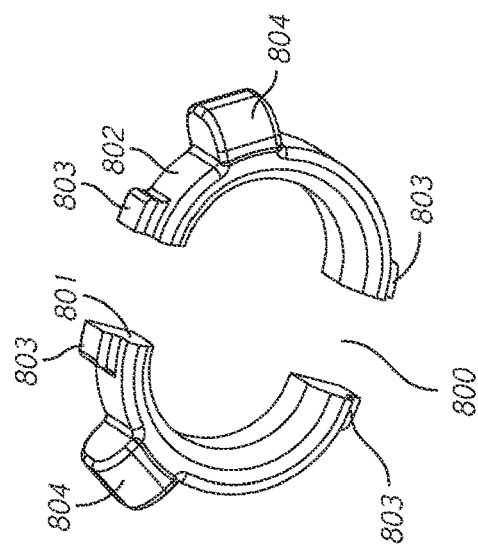

Another embodiment of a collar is shown in FIGS. 38A-C. The collar 800 can resemble or be identical to the above described collar 700 in many ways, yet can differ in certain respects. Some of the similarities and differences are discussed below.

As shown in FIGS. 38A-B, the collar 800 comprises a first portion 801 and a second portion 802. These portions 801, 802 are equivalent to one another and can be fabricated using a single mold. In some implementations, as discussed above, the portions are differently shaped and sized. FIG. 38A shows an exploded view of an embodiment of a collar 800, showing a pre-fitted collar assembly that inserts around the neck of the cartridge. FIG. 38B shows an assembled view of the same pre-fitted collar 800 shown in FIG. 38A. FIG. 38C shows an inlet (or cap) connector 810 that inserts over the head (or crown) and neck of a reservoir and engages with the pre-fitted collar assembly shown in FIGS. 38A-B. Throughout this disclosure, similar features for separate embodiments of a device component (e.g., collars, inlet connectors, inlet connector covers, etc.) can comprise one or more coinciding features offset numerically by a factors of 100 but having the same tens numerical value. For example, features of collar 800 and collar 900 that coincide to similar features of collar 700 will be offset by a 100 and 200, respectively (e.g., feature 703/803/903; feature 704/804/904, etc.).

In some embodiments, as shown in FIG. 38B, these portions 801, 802 can be affixed (welded, glued, etc.) to one another to form a collar having a reservoir engaging aperture 806 that can permanently hold a medicament reservoir (e.g., a vial, etc.). In some embodiments, an adhesive, glue, rubberizing agent, or other applicant can be applied to one or both of the mating surfaces 805', 805" of the engaging aperture 806 between the neck of the cartridge and the pre-fitted collar to increase friction and reduce or prevent rotation of the pre-fitted collar relative to the neck of the reservoir. In some variants, as discussed above, the mating surfaces of the two-component pre-fitted collars 805', 805," as shown in FIGS. 38A-B, can be bonded, glued, laser welded, or otherwise attached as the collar is assembled onto the neck of the cartridge. In some embodiments, the mating surfaces 805', 805" are compressible (sponge, foam, rubber, soft plastic, ribbed, fabric, etc.) to allow them to compress around a reservoir, locking it in place. In certain implementations, the collar 800 comprises one or more form fitted edges 807 (beveled, fitted, etc.) to allow the collar 800 to interact flushly with a reservoir.

As shown in FIGS. 38A-C, the pre-fitted collar contains one or more tabs, protrusions, features, which allow coupling only with the corresponding cap connector 810 (e.g., inlet connector) and the corresponding cap connector comprises cavities, grooves, keyways, or slots that match the unique differentiating tabs, protrusions, or features on the pre-fitted collar. As shown in FIG. 38A-B, the collar 800 comprises two collar projections 803 (projections having an edge, lip, etc.). As shown in FIG. 38A-C, the collar projections 803 (one or more) can be bisected by the separation of the collar pieces 801, 802. In some variants, these collar projections 803 interact with the coinciding collar projection mates 866 (lips, edges, clips, etc.) located on an inlet connector 810, as shown in FIGS. 38A-C. In some embodiments, the collar projections 803 engage the collar projection mates 866 to snap the collar into place holding the collar 800 and the inlet connector 810 flush to one another. In some variants, the inlet connector 810 has coinciding projection mates 866 that are mated with each configuration of collar projections 803. In some embodiments, the collar projection mates 866 act as a cap a capture mechanism that engages a feature (e.g., collar projections 803) on the pre-fitted collar 800 and/or that engages the collar 800 itself. In some embodiments, the collars are either of the variety that connects to the head (or crown) of the cartridge or to the neck of the cartridge. In some embodiments, the capture mechanism of the inlet connector 810 can expand slightly as it is pressed over the pre-fitted collar and then the inlet connector 810 can snap into place, engaging a tab, protrusion, or feature on the pre-fitted collar, or the bottom edge of the pre-fitted collar, and securely fasten the cap connector to the pre-fitted collar. The cartridge, pre-fitted collar, and cap connector subassembly could then be fastened into a pump housing unit.

In some embodiments, as shown in FIGS. 38A-B, the collar 800 comprises two collar projections 803 that are positioned opposite of one another on the collar (180° apart from each other). In some variants, as shown in FIGS. 38A-B, the collar 800 comprises two collar guiding elements 804 (tabs, protrusions, etc.). As shown, these collar guiding elements 804 are configured to interact two coinciding collar guiding element tracks 865 (cavities, grooves, keyways, slots, apertures, etc.) located on the corresponding inlet connector 810 shown in FIG. 38C. As shown in FIG. 38A-B, where two collar guiding elements 804 are present, those guiding elements can be positioned apart by about 120° from each other (or by about 240° traveling around the longer portion of the perimeter of the collar 800). As shown in FIG. 38C, the inlet connector 810 has coinciding collar guiding element tracks 865 that are mated with each configuration of collar guiding elements 804.

In some embodiments, as shown in FIGS. 38A-C, similar in some aspects to embodiments described above, the inlet connector 810 comprises a pairing projection 812. This pairing projection 812 is discussed in more detail elsewhere herein.

In some embodiments, as shown in FIGS. 38A-C, similar in some aspects to embodiments described above, the inlet connector 810 comprises three guiding elements 818 (tabs, protrusions, or features; where one is not shown). The guiding elements 818 can be spaced unevenly about the collar (as shown with a 120°/240° positioning in FIG. 48C). In some embodiments, as discussed above, the guiding elements facilitate placement in, for example, a specific aperture in an infusion pump (e.g., the infusion pump housing), while discouraging (or preventing) insertion into an incorrect aperture. In some embodiments, the cap connector's (i.e., inlet connector's) guiding elements would allow insertion into an infusion chamber, drive shaft, or pump chamber of a pump housing unit that contains corresponding cavities, grooves, keyways, or slots to match with the unique differentiating tabs, protrusions, or features on the cap connector.

In certain variants, the inlet connector 810, as shown, comprises two inlet connector spacers 836 (e.g., relief slits)

separated by 180°. In some embodiments, this inlet connector spacer 836 allows the inlet connector 810 to be compressed or expanded. These relief slits can be spaced about the connector in the same fashion as the guiding elements. As with the embodiment described in FIGS. 37C, the slits can allow snap tight fitting into a pump housing that comprises mated features. This feature, among others described herein, can allow the reservoir to be held in an appropriate position, with little movement, within the pump housing. In some embodiments, a single-component pre-fitted collar 800, such as the ones shown in FIGS. 38A-C, has relief slits 836 which allow the inlet connector to be pressed over the head (or crown) of the cartridge, and a locking mechanism, that snaps into place as it engages with the underside of the head (or crown) of the cartridge.

Figure 39C:
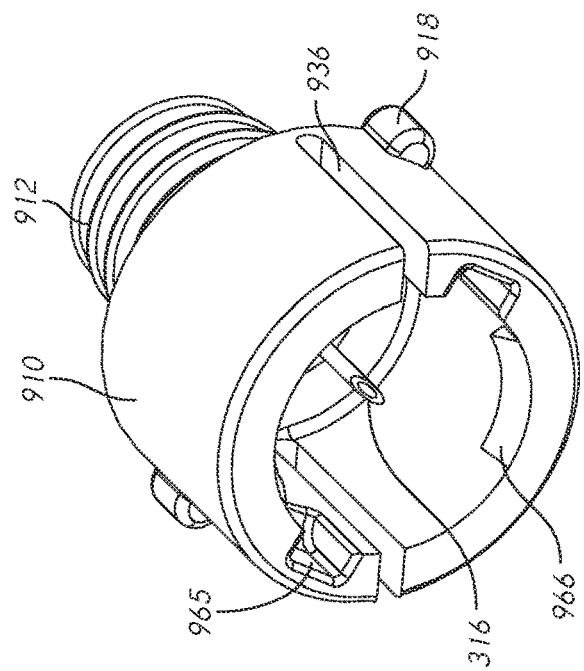
FIGS. 39A-C illustrate another embodiment of a collar assembly and a corresponding inlet connector.
Figure 39B:
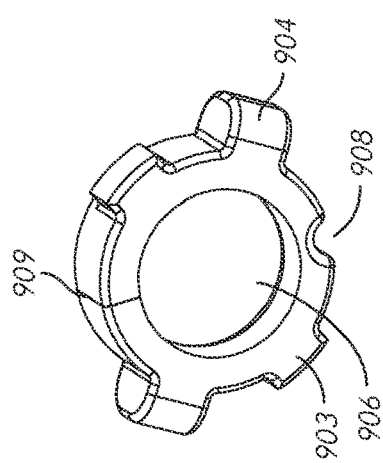
Figure 39A:
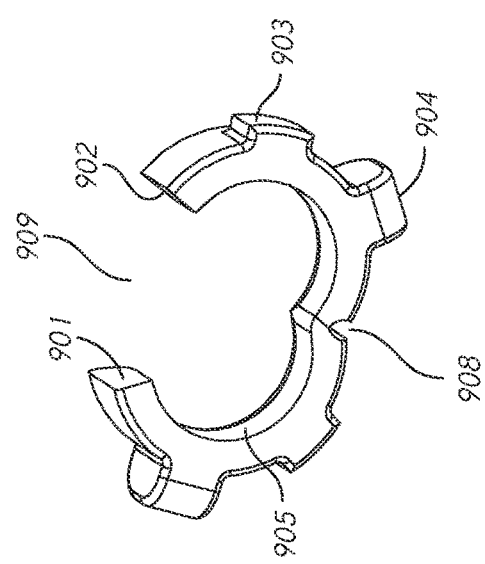

Another embodiment of a collar is shown in FIGS. 39A-C. The collar 900 is similar to the above described collar 700 except that it has a relief with fillet 908 and an opening 909 away from the fillet as opposed to being two distinct pieces. Given these similarities, in some embodiments, this assembly could fit into the same pump housings as would the embodiment of FIGS. 37A-C. FIG. 39A shows an open view of an embodiment of a collar 900, showing a pre-fitted collar assembly that inserts around the neck of the cartridge. FIG. 39B shows a closed view of the same pre-fitted collar 900 shown in FIG. 39A. FIG. 39C shows an inlet (or cap) connector 910 that inserts over the head (or crown) and neck of a reservoir and engages with the pre-fitted collar assembly shown in FIGS. 39A-B.

In some embodiments, the collar can automatically close around a reservoir by virtue of the elasticity of the collar 900. In some embodiments, a hinge, joint, or other swiveling mechanism can be used instead of the fillet 908, with the goal of having a closable (and, in some embodiments, an openable collar) in mind. In some embodiments, the collar 900 comprises surfaces 901, 902 that come into contact with one another when the collar 900 is in the closed position. In some embodiments, these surfaces 901, 902 can be affixed (welded, glued, etc.) to one another to form a collar having a reservoir engaging aperture 906 that can permanently hold a medicament reservoir (e.g., a vial, etc.). In some embodiments, an adhesive, glue, rubberizing agent, or other applicant can be applied to the mating surface 905 of the engaging aperture 906 between the neck of the cartridge and the pre-fitted collar 900 to increase friction and reduce or prevent rotation of the pre-fitted collar 900 relative to the neck of the reservoir. In some variants, as discussed above, the mating surface 905 can be bonded, glued, laser welded, or otherwise attached as the collar is assembled onto the neck of the cartridge. In some embodiments, the mating surface 905 is compressible (sponge, foam, rubber, soft plastic, ribbed, fabric, etc.) to allow them to compress around a reservoir, locking it in place. In certain implementations, the collar 900 comprises one or more form fitted edges (beveled, fitted, etc.; not shown) to allow the collar 900 to interact flushly with a reservoir.

In some embodiments, the pre-fitted collar contains one or more tabs, protrusions, features, as in FIGS. 39A-C, which allow coupling only with the corresponding cap connector (e.g., inlet connector), and the corresponding cap connector contains corresponding cavities, grooves, keyways, or slots to match with the unique differentiating tabs, protrusions, or features on the pre-fitted collar. In this way, only one type of pre-fitted collar can mate uniquely with one type of cap connector. For instance, the collar 900 comprises two collar projections 903 (projections having an edge, lip, etc.). In some variants, these collar projections 903 are configured to interact with two coinciding collar projection mates 966 (lips, edges, clips, etc.) located on an inlet connector 910, as shown in FIGS. 39A-C. In some embodiments, the collar projections 903 engage the collar projection mates 966 to snap the collar into place holding the collar 900 and the inlet connector 910 flush to one another. In some variants, the inlet connector 910 has coinciding projection mates 966 that are mated with each configuration of collar projections 903. In some embodiments, the collar projection mates 966 act as a cap a capture mechanism that engages a feature (e.g., collar projections 903) on the pre-fitted collar 900 and/or that engages the collar 900 itself. In some embodiments, the collars are either of the variety that connect to the head (or crown) of the cartridge or to the neck of the cartridge. In some embodiments, the capture mechanism of the inlet connector 910 can expand slightly as it is pressed over the pre-fitted collar and then the inlet connector 910 can snap into place, engaging a tab, protrusion, or feature on the pre-fitted collar, or the bottom edge of the pre-fitted collar, and securely fasten the cap connector to the pre-fitted collar. The cartridge, pre-fitted collar, and cap connector subassembly could then be fastened into a pump housing unit.

As shown in FIG. 39A-C, where two projections 903 are present, those projections can be positioned opposite of one another on the collar (180° apart from each other). In some variants, as shown in FIGS. 39A-B, the collar 900 comprises two collar guiding elements 904 (tabs, protrusions, etc.) configured to interact with two coinciding collar guiding element tracks 965 (cavities, grooves, keyways, slots, apertures, etc.) located on the inlet connector 910. These collar guiding elements are located about 180° apart on the collar. In some variants, the inlet connector 910 has coinciding collar guiding element tracks 965 that are mated with each configuration of collar guiding elements 904.

In some embodiments, as shown in FIGS. 39A-C, similar in some aspects to embodiments described above, the inlet connector 910 comprises a pairing projection 912.

In some embodiments, as shown in FIGS. 39A-C, similar in some aspects to embodiments described above, the inlet connector 910 can comprises guiding elements 918 (tabs, protrusions, or features) spaced 180° apart. In some embodiments, the guiding elements can facilitate placement in, for example, a specific aperture in an infusion pump (e.g., the infusion pump housing), while discouraging (or preventing) insertion into an incorrect aperture. In some embodiments, the cap connector's (i.e., inlet connector's) guiding elements would allow insertion into an infusion chamber, drive shaft, or pump chamber of a pump housing unit that contains corresponding cavities, grooves, keyways, or slots to match with the unique differentiating tabs, protrusions, or features on the cap connector.

In certain variants, as shown in FIG. 39C, the inlet connector 910 comprises two inlet connector spacers 936 (e.g., relief slits). In some embodiments, this inlet connector spacer 936 allows the inlet connector 910 to be compressed as it inserts into a pump housing. These relief slits can be spaced about the connector in the same fashion as the guiding elements. As with the embodiment described in FIGS. 37C, the slits can allow snap tight fitting into a pump housing that comprises mated features.

Another embodiment of a collar 1000 and its inlet connector 1010 is shown in FIGS. 40A-C. The collar 1000 is similar to the above described collars in many ways, yet can differ in certain respects. Some of the similarities and differences are discussed below. As shown in FIGS. 40A-B, the collar 1000 has a fillet 1008 and an opening 1009 away from the fillet 1008 as opposed to being two distinct pieces (for instance, collar 800's portions 801, 802). In some embodiments, this embodiment is substantially similar to that shown in FIGS. 38A-C except for the unitary collar that comprises a fillet. Given these similarities, in some embodiments, this assembly could fit into the same pump housings as would the embodiment of FIGS. 38A-C. FIG. 40A shows an open view of the collar 1000, showing a pre-fitted collar assembly that inserts around the neck of the cartridge. FIG. 40B shows a closed view of the same pre-fitted collar 1000 shown in FIG. 40A. FIG. 40C shows an inlet (or cap) connector 1010 that inserts over the head (or crown) and neck of a reservoir and engages with the pre-fitted collar assembly shown in FIGS. 40A-B.

In some embodiments, the filleted collar can automatically close around a reservoir by virtue of the elasticity of the collar 1000. In some embodiments, a hinge, joint, or other swiveling mechanism can be used instead of the fillet 1008, with the goal of having a closable (and, in some embodiments, an openable collar) in mind. In some embodiments, the collar 1000 comprises surfaces 1001, 1002 that come into contact with one another when the collar 1000 is in the closed position. In some embodiments, these surfaces 1001, 1002 can be affixed (welded, glued, etc.) to one another to form a collar having a reservoir engaging aperture 1006 that can permanently hold a medicament reservoir (e.g., a vial, etc.). In some embodiments, an adhesive, glue, rubberizing agent, or other applicant can be applied to the mating surface 1005 of the engaging aperture 1006 between the neck of the cartridge and the pre-fitted collar 1000 to increase friction and reduce or prevent rotation of the pre-fitted collar 1000 relative to the neck of the reservoir. In some variants, as discussed above, the mating surface 1005 can be bonded, glued, laser welded, or otherwise attached as the collar is assembled onto the neck of the cartridge. In some embodiments, the mating surface 1005 is compressible (sponge, foam, rubber, soft plastic, ribbed, fabric, etc.) to allow them to compress around a reservoir, locking it in place. In certain implementations, the collar 1000 comprises one or more form fitted edges (beveled, fitted, etc.; not shown) to allow the collar 1000 to interact flushly with a reservoir.

In some embodiments, the pre-fitted collar contains one or more tabs, protrusions, features, as shown in FIGS. 40A-C, which allow coupling only with the corresponding cap connector 1010 (e.g., inlet connector), and the corresponding cap connector would contain corresponding cavities, grooves, keyways, or slots to match with the unique differentiating tabs, protrusions, or features on the pre-fitted collar.

For instance, in certain implementations, as shown, the collar 1000 comprises two collar projections 1003 (projections having an edge, lip, etc.). In some variants, these collar projections 1003 are configured to interact with one or more coinciding collar projection mates 1066 (lips, edges, clips, etc.) located on an inlet connector 1010, as shown in FIGS. 40A-C (where only one is visible). In some embodiments, the collar projections 1003 engage the collar projection mates 1066 to snap the collar into place holding the collar 1000 and the inlet connector 1010 flush to one another. In some variants, the inlet connector 1010 has coinciding projection mates 1066 that are mated with each configuration of collar projections 1003. In some embodiments, the collar projection mates 1066 act as a cap a capture mechanism that engages a feature (e.g., collar projections 1003) on the pre-fitted collar 1000 and/or that engages the collar 1000 itself. In some embodiments, the collars are either of the variety that connect to the head (or crown) of the cartridge or to the neck of the cartridge. In some embodiments, the capture mechanism of the inlet connector 1010 can expand slightly as it is pressed over the pre-fitted collar and then the inlet connector 1010 can snap into place, engaging a tab, protrusion, or feature on the pre-fitted collar, or the bottom edge of the pre-fitted collar, and securely fasten the cap connector to the pre-fitted collar. The cartridge, pre-fitted collar, and cap connector subassembly could then be fastened into a pump housing unit.

In some embodiments, as shown, the collar projections 1003 are evenly spaced about the collar 1000 (at about 180° apart). In some variants, as shown in FIGS. 40A-B, the collar 1000 comprises two collar guiding elements 1004 (tabs, protrusions, etc.) configured to interact with one or more coinciding collar guiding element tracks 1065 (cavities, grooves, keyways, slots, apertures, etc.) located on an inlet connector 1010. As shown in FIG. 40B, the collar guiding elements are 120° apart with one being bisected by the opening 1009. In some variants, as shown, the inlet connector 1010 has coinciding collar guiding element tracks 1065 that are mated with each configuration of collar guiding elements 1004.

In some embodiments, as shown in FIGS. 40A-C, similar in some aspects to embodiments described above, the inlet connector 1010 can comprise a pairing projection 1012.

In some embodiments, as shown in FIGS. 40A-C, the inlet connector 1010 can comprise one or more guiding elements 1018 (tabs, protrusions, or features). For instance, as shown in FIG. 40C, the three guiding elements 1018 are 120° apart with one being hidden from view. In some embodiments, the guiding elements facilitate placement in, for example, a specific aperture in an infusion pump (e.g., the infusion pump housing), while discouraging (or preventing) insertion into an incorrect aperture. In some embodiments, the cap connector's (i.e., inlet connector's) guiding elements would allow insertion into an infusion chamber, drive shaft, or pump chamber of a pump housing unit that contains corresponding cavities, grooves, keyways, or slots to match with the unique differentiating tabs, protrusions, or features on the cap connector.

In certain variants, as shown in FIG. 40C, the inlet connector 1010 comprises two inlet connector spacers 1036 (e.g., relief slits) that are about 180° apart. In some embodiments, this inlet connector spacer 1036 allows the inlet connector 1010 to be compressed as it inserts into a pump housing or expanded as a reservoir and cap is inserted into it. These relief slits can be spaced about the connector in the same fashion as the guiding elements. The slits can allow snap tight fitting into a pump housing that comprises mated features.

FIGS. 41A-C show six separate components: the cartridge 510, the collar 700 of FIG. 37A-B (which, in some embodiments, inserts around the neck of the cartridge and contains unique differentiating tabs, keys, or protrusions as well as features that allow engagement with and locking with the cap connector), the inlet connector 710 (e.g., cap connector; which, in some embodiments, contains corresponding cavities, grooves, keyways, or slots to match with the unique differentiating tabs, protrusions, or features on the pre-fitted collar and a capture mechanism to lock with the features on the pre-fitted collar), inlet connector cover 730 (e.g., secondary cap, threaded coaxial cap, etc.; that, in some embodiments, can slide up and down the tubing, and that fits over the cap connector and threads into the pump housing), the needle 316 (which, in some embodiments, is overmolded, bonded, press-fitted, glued, solvent bonded, insert molded, or otherwise attached to the cap connector), and tubing 310

(that, in some embodiments, is overmolded, bonded, press-fitted, glued, solvent bonded, insert molded, or otherwise attached to both the cap connector). While FIGS. 41A-C show the interaction between the embodiment of FIGS. 37A-C with various other components, it should be understood that this is only an example configuration and other collar/inlet connector systems besides the one shown in FIGS. 37A-C could be used instead. For example, given the similar features of the embodiment described in FIGS. 39A-C, it could be used with the components of FIGS. 41A-C. As shown in FIGS. 41A-C and as described with respect to other embodiments herein, in some embodiments, the first channel 310 comprises a first piercing element 316 (e.g., a needle, cannula, etc.) configured to insert into a first medicament reservoir 510 that couples to the inlet connector 710. In some embodiments, the needle 316 pierces a reservoir septum 514 located within an internal reservoir cover 750 on the medicament reservoir 510 by insertion through the pairing projection 712. In some embodiments, as shown, the first reservoir 510 has a first plunger 512 adapted to be depressed by a piston of an infusion pump. In some embodiments, the needle is overmolded, bonded, press-fitted, glued, solvent bonded, insert molded, or otherwise attached to the inside of the inlet connector 710. In some embodiments, the hollow needle is recessed within the cap connector so as to be touch-proof. In this embodiment, the needle of FIG. 41C has pierced the septum 514 over the reservoir 510.

In some embodiments, as shown in FIGS. 41A-C and as described with respect to other embodiments herein, an inlet connector cover 730 (e.g., secondary cap, etc.) can be configured to interact with the inlet connector 710 via the pairing projection 712. In certain embodiments, the pairing projection is ribbed or threaded to allow snap or screw fitting to the inlet connector cover 730. In some embodiments the pairing projection does not snap or screw into the inlet connector cover 730 and is instead smooth. In certain variants, the cover 730 is molded and permanently attached to a fluid conduit 310. In some embodiments, tubing 310 is overmolded, bonded, press-fitted, glued, solvent bonded, insert molded, or otherwise attached to the cap connector and to the hollow needle in such a way as to allow a patent and continuous fluid path through the hollow needle, the cap connector, and the tubing. In some embodiments, the cover 730 and the fluid conduit 310 are reversibly attachable.

In some embodiments, as shown in FIG. 41B, the inlet connector cover 730 is freely movable along the fluid conduit 310. In some embodiments, a needle 316 is molded to the pairing projection 712 and fixed there. In some embodiments, the inlet connector cover 730 is heat staked to the inlet connector 710 via the pairing projection 712. In some embodiments, the fluid conduit is able to freely rotate within the first inlet connector and cover, which, as discussed above, helps avoid kinking of the fluid conduit. In certain variants, the inlet connector cover 730 and the inlet connector are separated by a compressible O-ring. This O-ring allows the cover and connector to be tightly coupled to seal them together. In some embodiments, a compressible O-ring (similar to that described above as 415) resides around the first inlet connector cover (similar to that described above as 430) threads to facilitate tight connection to the fusion pump via the external threads.

In certain variants, the cover 730 comprises external engagement implements 734 (e.g., external threads, ribbing, etc.) configured to interact with and engage mated receptacles on an infusion pump housing. These threadings can be configured to only interact with corresponding threads of a housing. In some embodiments, the cover 730 comprises a pairing aperture 732 configured to engage with the pairing projection 712. In some embodiments, the cover 730 comprises a pairing aperture 732 that is configured to not engage with a non-mated pairing projection.

As shown in FIGS. 41A-C, in certain implementations, the inlet connector 710 is configured to interact with the medicament reservoir 510. In some embodiments, to be inserted properly within the inlet connector 710, the reservoir must be fitted with a collar 700. In some embodiments, as described above, the projections of the collar can be configured to only interact with an appropriate inlet connector 710. In some embodiments, collars can be matched to specific size and diameter reservoirs. In some embodiments, the collars for these different reservoirs can interact with only certain reservoirs, thereby minimizing chances of mischanneling. In other embodiments, reservoirs that are the same can be used and mischanneling can be prevented by the selection of an appropriate collar. In some embodiments, the collars can be color coded to match reservoirs, inlets, and other components of the system to further prevent and/or discourage mischanneling.

FIGS. 42A-C show six separate components that are different from those of FIGS. 41A-C and that are used in conjunction with the system of FIGS. 41A-C to provide a drug delivery pump system that avoids mischanneling.

The components of the embodiment of FIGS. 42A-C include: the cartridge 520, the collar 800 of FIG. 38A-B (which, in some embodiments, inserts around the neck of the cartridge and contains unique differentiating tabs, keys, or protrusions as well as features that allow engagement with and locking with the cap connector), the inlet connector 810 (e.g., cap connector; which, in some embodiments, contains corresponding cavities, grooves, keyways, or slots to match with the unique differentiating tabs, protrusions, or features on the pre-fitted collar and a capture mechanism to lock with the features on the pre-fitted collar), inlet connector cover 830 (e.g., secondary cap, threaded coaxial cap, etc.; that, in some embodiments, can slide up and down the tubing, and that fits over the cap connector and threads into the pump housing), the needle 326 (which, in some embodiments, is overmolded, bonded, press-fitted, glued, solvent bonded, insert molded, or otherwise attached to the cap connector), and tubing 320 (that, in some embodiments, is overmolded, bonded, press-fitted, glued, solvent bonded, insert molded, or otherwise attached to both the cap connector). While FIGS. 42A-C show the interaction between the embodiment of FIGS. 38A-C with various other components, it should be understood that this is only an example configuration and other collar/inlet connector systems besides that shown in FIGS. 38A-C could be used instead. For example, given the similar features of the embodiment described in FIGS. 40A-C, it could be used with the components of FIGS. 42A-C. As shown in FIGS. 42A-C and as described with respect to other embodiments herein, in some embodiments, the second channel 320 comprises a second piercing element 326 (e.g., a needle, cannula, etc.) configured to insert into a second medicament reservoir 520 that couples to the inlet connector 810. In some embodiments, the needle 326 pierces a reservoir septum 524 located within an internal reservoir cover 850 on the medicament reservoir 520 by insertion through the pairing projection 812. In some embodiments, the second reservoir 520 has a second plunger 522 adapted to be depressed by a piston of an infusion pump. In some embodiments, the needle is overmolded, bonded, press-fitted, glued, solvent bonded, insert molded, or otherwise attached to the inside of the inlet connector 810. In some embodiments, the hollow needle is recessed within the cap connector so as to be touch-proof. In this embodiment, the needle of FIG. 42C has pierced the septum over the reservoir 520.

In some embodiments, as shown in FIGS. 42A-C and as described with respect to other embodiments herein, an inlet connector cover 830 (e.g., secondary cap, etc.) can be configured to interact with the inlet connector 810 via the pairing projection 812. In certain variants, the cover 830 is molded and permanently attached to a fluid conduit 320. In some embodiments, tubing 320 can be overmolded, bonded, press-fitted, glued, solvent bonded, insert molded, or otherwise attached to the cap connector and to the hollow needle in such a way as to allow a patent and continuous fluid path through the hollow needle, the cap connector, and the tubing. In some embodiments, the cover 830 and the fluid conduit 320 are reversibly attachable. In some embodiments, as shown in FIG. 42B, the inlet connector cover 830 is freely movable along the fluid conduit 320. In some embodiments, a needle 326 is molded to the pairing projection 812 and fixed there. In some embodiments, the inlet connector cover 830 is heat staked to the inlet connector 810 via the pairing projection 812. In some embodiments, the fluid conduit is able to freely rotate within the inlet connector and cover, which, as discussed above, helps avoid kinking of the fluid conduit. In certain variants, the inlet connector cover 830 and the inlet connector are separated by a compressible O-ring. This O-ring allows the cover and connector to be tightly coupled to seal them together. In some embodiments, a compressible O-ring (similar to that described above as 415) resides around the first inlet connector cover (similar to that described above as 430) threads to facilitate tight connection to the fusion pump via the external threads.

In certain variants, the cover 830 comprises external engagement implements 834 (e.g., external threads, ribbing, etc.) configured to specifically interact with and engage only mated receptacles on an infusion pump housing. In some embodiments, the cover 830 comprises a pairing aperture 832 configured to engage with the pairing projection 812. In some embodiments, the cover 830 comprises a pairing aperture 832 that is configured to not engage with a non-mated pairing projection.

As shown in FIGS. 42A-C, in certain implementations, the inlet connector 810 is configured to interact with the medicament reservoir 520. In some embodiments, to be inserted properly within the inlet connector 810, the reservoir must be fitted with a collar 800. In some embodiments, as described above, the projections of the collar can be configured to only interact with an appropriate inlet connector 810. In some embodiments, collars can be matched to specific size and diameter reservoirs. In some embodiments, the collars for these different reservoirs can interact with only certain reservoirs, thereby minimizing chances of mischanneling. In other embodiments, reservoirs that are the same can be used and mischanneling can be prevented by the selection of an appropriate collar. In some embodiments, the collars can be color coded to match reservoirs, inlets, and other components of the system to further prevent and/or discourage mischanneling.

Figure 43A:
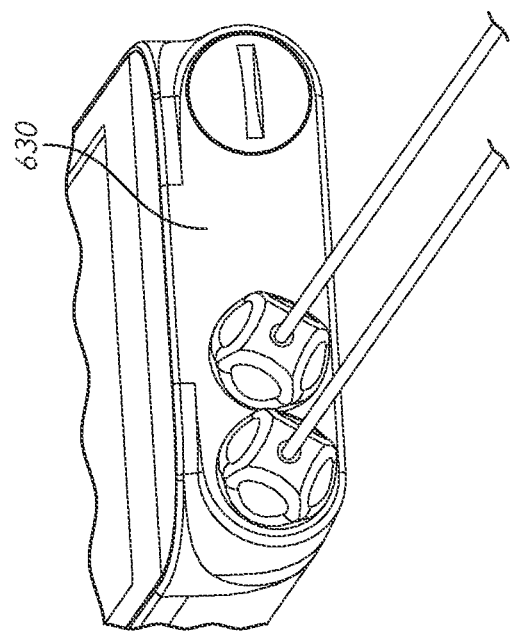
FIGS. 43A-B illustrate the assembly of FIG. 41A-C engaging with a pump device.
Figure 43B:
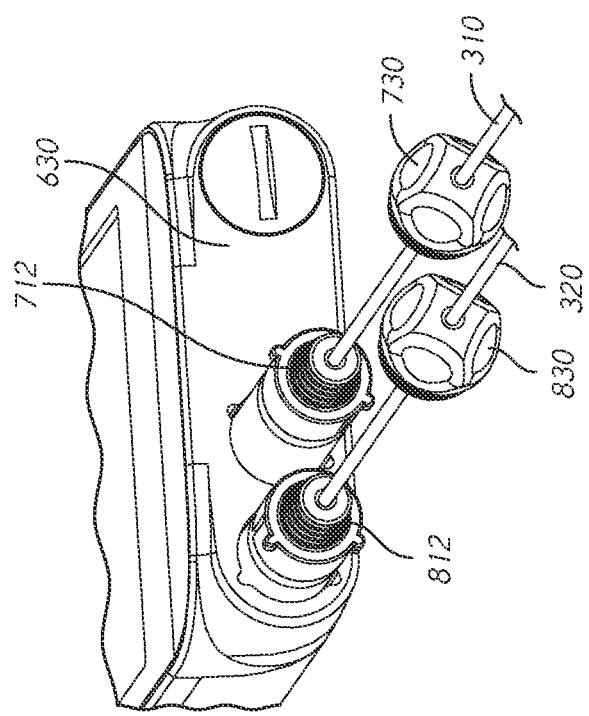

FIGS. 43A-B show a base of a dual-medicament pump housing 630 with the cartridge, cap connector, tubing, and threaded coaxial cap assembly partially loaded into each of the two infusion chambers, drive shafts, or pump chambers (FIG. 43A) or fully loaded (FIG. 43B). The three keyways or features on the left drive-shaft chamber of the pump housing are oriented at 120 degrees apart and the two keyways or features on the right driveshaft chamber of the pump housing are oriented at 180 degrees apart. The three external tabs 818 or protrusions on the cap connector on the left are oriented at 120 degrees apart and match the corresponding cavities, grooves, keyways, or slots on the left infusion chamber, drive shaft, or pump chamber of the pump housing, and the external tabs 718, protrusions, or features on the cap connector on the right are oriented at 180 degrees apart and match the corresponding cavities, grooves, keyways, or slots on the right infusion chamber, drive shaft, or pump chamber of the pump housing. In some embodiments, as shown, the threaded coaxial caps are free to slide along the tubing. Once each cartridge, cap connector, tubing, and threaded coaxial cap assembly are fully inserted, the threaded coaxial cap can slide down the tubing and screw into the threads in the pump housing, as in 43B. The cartridge, cap connector, tubing, and threaded coaxial cap assemblies shown here are the same components as are shown in FIGS. 41A-42C.

As shown in FIGS. 43A-B, in some embodiments, the first fluid conduit 310 (e.g., tubing) passes through a threaded coaxial cap (e.g., an inlet connector cover 730) that can slide up and down the tubing and thread into a pump housing unit (e.g., a pump body 630). In some embodiments, the second fluid conduit 320 (e.g., tubing) passes through a threaded coaxial cap (e.g., an inlet connector cover 830) that can slide up and down the tubing and thread into a pump housing unit (e.g., a pump body 630). In some embodiments, the fully assembled cartridge, cap, and tubing system (consisting of a cartridge with pre-fitted collar assembly engaged with the connected subassembly, consisting of the cap connector with capture mechanism, hollow needle, tubing, and threaded coaxial cap, as shown in 43A-B), inserts into an infusion chamber, drive shaft, or pump chamber of a pump housing unit that contains corresponding cavities, grooves, keyways, or slots to match with the unique differentiating tabs, protrusions, or features on the cap connector. In some embodiments, the threaded coaxial cap then screws into threads in the pump housing, as shown in FIG. 43A-B.

FIG. 44A-C shows another embodiment of a collar 1100 and a corresponding inlet connector 1110. The collar 1100 can resemble or be identical to the above described collars in many ways, yet can differ in certain respects. Some of the similarities and differences are discussed below.

FIG. 44A shows an exploded view of a collar 1100 that inserts around the neck of a reservoir (cartridge) via two pieces 1101, 1102. In this embodiment, the collar can comprise a crown of the reservoir or fits over the crown (or head) of the cartridge and engages with insert connector 1110 (shown in FIGS. 44A-C) via a lid 1109. In some embodiments, the lid 1109 comprises the lid aperture 1106. FIG. 44B is an assembled view of the same pre-fitted collar assembly shown in 44A. FIG. 44C shows an inlet connector 1110 (e.g., cap connector) that inserts over the head (e.g., crown) of the cartridge and engages the pre-fitted collar assembly shown in 44A and 44B. In this embodiment, two unique differentiating tabs or protrusions 1104 (e.g., collar guiding elements) shown in FIGS. 44A-B are positioned 180° apart from one another and couple with the corresponding inlet connector 1110 via collar guiding element tracks 1165 (visible in FIG. 44C). The corresponding cap connector 1110 shown in FIG. 44C contains two collar guiding element tracks 1165 (e.g., cavities, grooves, keyways, or slots) that pair with the two collar guiding elements 1104 (differentiating tabs, protrusions, or features) on the prefitted collar 1100. In some embodiments, as shown in FIGS. 44A-B, the bottom edge of the pre-fitted collar 1100 has a collar projection 1103 (lip, etc.) that can comprise the entire perimeter of the collar 1100. In some embodiments, the collar projection 1103 is sized and positioned appropriately to allow engagement by the two capture mechanisms 1166 shown in FIG. 44C (only one of which is visible). Also, in some embodiments, as shown in FIGS. 44A-C, the cap connector 1110 shown in FIG. 44C contains two guiding elements 1118 (tabs, protrusions, or features) positioned 180 degrees apart from one another, these allow insertion into an infusion chamber, drive shaft, or pump chamber of a pump housing unit that contains cavities, grooves, keyways, or slots to match with the unique differentiating tabs, protrusions, or features on the cap connector. Also, in some embodiments, as shown in FIGS. 44C, the cap connector 1110 contains two inlet connector spacers 1136 (tabs, protrusions, or features) positioned 180 degrees apart from one another. In some embodiments, the collar 1100 comprises a pairing projection 1112. The features of collar 1100 and inlet connector 1110 interact with corresponding inlet connecting covers 1130 (not shown) having pairing apertures 1132 and external engaging implements (e.g., threads) 1134.

Figure 45C:
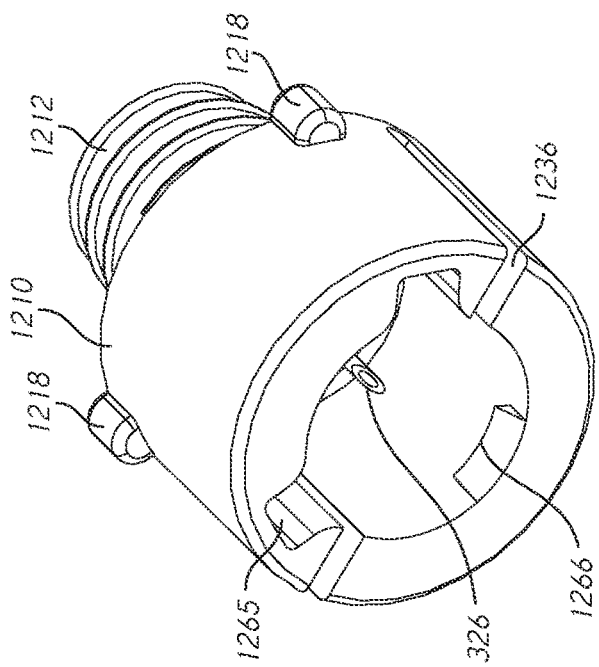
FIGS. 45A-C illustrate another embodiment of a collar assembly and a corresponding inlet connector.
Figure 45B:
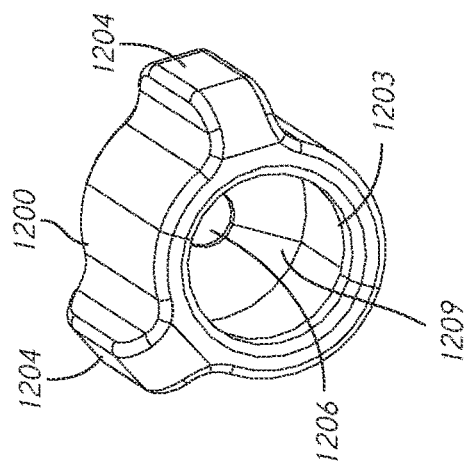
Figure 45A:
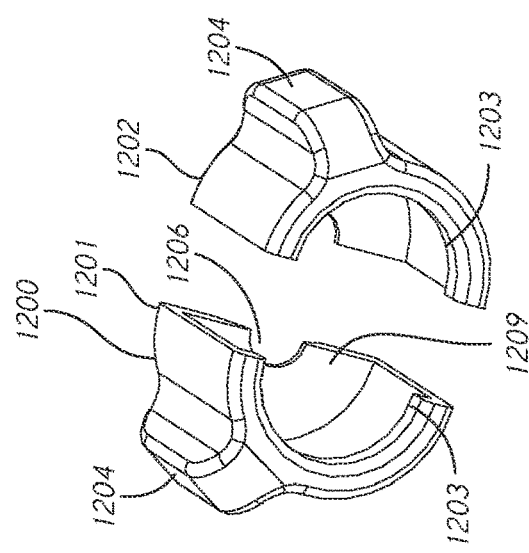

FIG. 45A-C shows another embodiment of a collar 1200 and a corresponding inlet connector 1210. The collar 1200 can resemble or be identical to the above described collars in many ways, yet can differ in certain respects. Some of the similarities and differences are discussed below.

FIG. 45A shows an exploded view of a collar 1200 that inserts around the neck of a reservoir (cartridge) via two pieces 1201, 1202. In this embodiment, the collar 1200 can comprise a crown of the reservoir or fits over the crown (or head) of a cartridge and engages with insert connector 1210 (shown in FIGS. 45A-C) via a lid 1209. In some embodiments, the lid 1209 comprises the lid aperture 1206. FIG. 45B is an assembled view of the same pre-fitted collar assembly shown in 45A. FIG. 45C shows an inlet connector 1210 (cap connector) that inserts over the head (or crown) of the cartridge and engages with the pre-fitted collar assembly shown in 45A and 45B. In this embodiment, two collar guiding elements 1204 (e.g., unique differentiating tabs or protrusions), shown in FIGS. 45A-B, are positioned 120° (or 240°) degrees apart from one another and couple with the corresponding inlet connector 1210 via collar guiding element tracks 1265 (both of which are visible in FIG. 45C). The corresponding cap connector 1210 shown in FIG. 45C contains collar guiding element tracks 1265 (two cavities, grooves, keyways, or slots) to match with the collar guiding elements 1204 (two unique differentiating tabs, protrusions, or features) on the prefitted collar 1200. In some embodiments, as shown in FIGS. 45A-B, the bottom edge of the pre-fitted collar 1200 has a collar projection 1203 (lip, etc.) running the entire perimeter of the collar 1200. In some embodiments, the collar projection 1203 is sized and positioned appropriately to allow engagement by the capture mechanisms 1266 shown in FIG. 45C (only one of which is visible). Also, in some embodiments, as shown in FIGS. 45A-C, the cap connector 1210 shown in FIG. 45C contains three guiding elements 1218 (tabs, protrusions, or features) positioned 120° apart from one another, which allow insertion into an infusion chamber, drive shaft, or pump chamber of a pump housing unit that contains cavities, grooves, keyways, or slots to match with the unique differentiating tabs, protrusions, or features on the cap connector. Other positions, as discussed elsewhere herein, are envisioned. Also, in some embodiments, as shown in FIGS. 45C, the cap connector 1210 contains two inlet connector spacers 1236 (tabs, protrusions, or features) positioned 180° apart from one another. In some embodiments, the collar 1200 comprises a pairing projection 1212. The features of collar 1200 and inlet connector 1210 interact with corresponding inlet connecting covers 1230 (not shown) having pairing apertures 1236 and external engaging implements 1234.

Figure 46B:
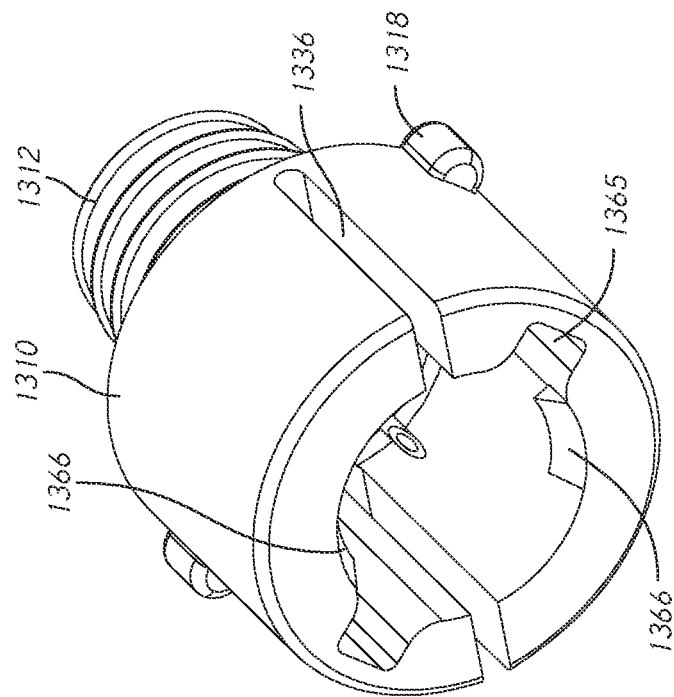
FIGS. 46A-B illustrate another embodiment of a collar assembly and a corresponding inlet connector.
Figure 46A:
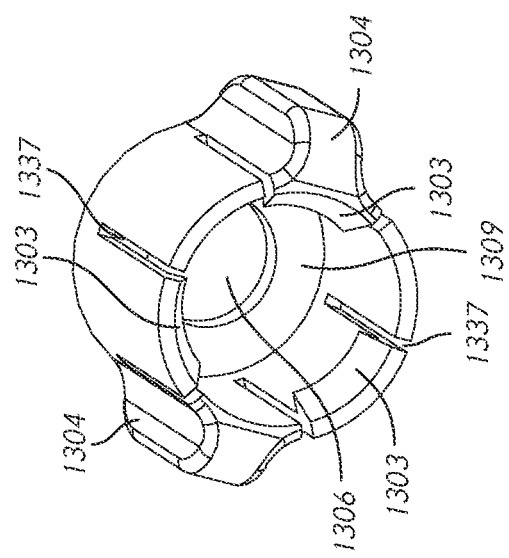

FIGS. 46A-B shows another embodiment of a collar 1300 and a corresponding inlet connector 1310. The collar 1300 can resemble or be identical to the above described collars in many ways, yet can differ in certain respects. Some of the similarities and differences are discussed below.

As shown in FIG. 46A the collar 1300 that inserts around the neck of a reservoir (cartridge) is a single piece (e.g., not comprising two pieces or a single piece with a fillet). In this embodiment, the collar can comprise a crown of the reservoir or fits over the crown (or head) of the cartridge and engages with insert connector 1310 (shown in FIGS. 46A-C) via a lid 1309. In some embodiments, the lid 1309 comprises the lid aperture 1306. In some embodiments, as shown in FIGS. 46A, the collar 1300 comprises one or more (1, 2, 3, 4, 5, 6, or more) collar spacers 1337. The embodiment of FIG. 46A has six collar spacers 1337. FIG. 46B shows an inlet connector 1310 (cap connector) that inserts over the head (or crown) of the cartridge and engages with the pre-fitted collar assembly shown in FIG. 46A. In this embodiment, three collar projections (e.g., unique differentiating tabs or protrusions) 1304 shown in FIG. 46A are positioned 120 degrees apart from one another and couple with the corresponding inlet connector 1310 via collar guiding element tracks 1365 (two of which are visible in FIG. 46B). The corresponding cap connector 1310 shown in FIG. 46C contains collar guiding element tracks 1365 (e.g., cavities, grooves, keyways, or slots) to match with the collar guiding elements 1304 on the prefitted collar. In some embodiments, the bottom edge of the pre-fitted collar 1300 has a collar projection 1303 (lip, etc.) running the entire perimeter of the collar 1300. In some embodiments, the collar projection is sized and positioned appropriately to allow engagement by the collar projection mates 1366 shown in FIG. 46C. Also, in some embodiments, the cap connector 1310 shown in FIG. 46B contains guiding elements 1318 (tabs, protrusions, or features) positioned 180 degrees apart from one another, which allow insertion into an infusion chamber, drive shaft, or pump chamber of a pump housing unit that contains cavities, grooves, keyways, or slots to match with the unique differentiating tabs, protrusions, or features on the cap connector. Also, in some embodiments, as shown in FIGS. 46B, the cap connector 1310 contains two inlet connector spacers 1336 (tabs, protrusions, or features) positioned 180° apart from one another. In some embodiments, the collar 1300 comprises a pairing projection 1312. The features of collar 1300 and inlet connector 1310 interact with corresponding inlet connecting covers 1330 (not shown) having pairing apertures 1336 and external engaging implements 1334.

Figure 47B:
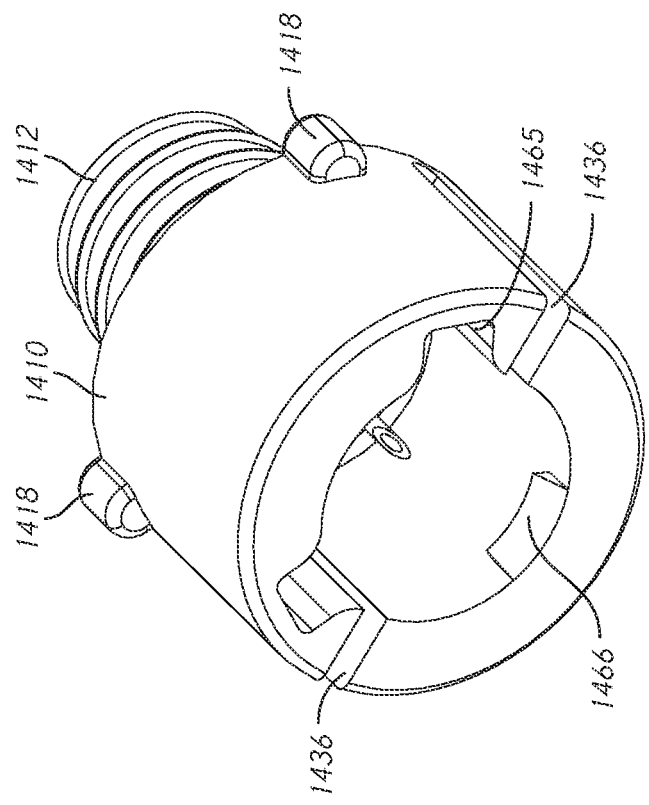
FIGS. 47A-B illustrate another embodiment of a collar assembly and a corresponding inlet connector.
Figure 47A:
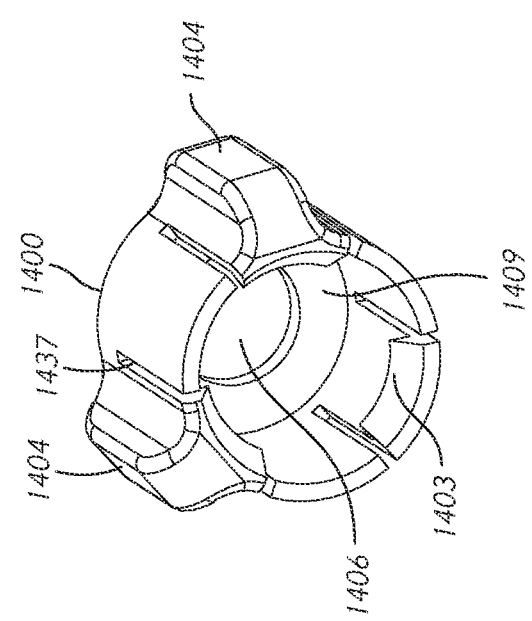

FIGS. 47A-B shows another embodiment of a collar 1400 and a corresponding inlet connector 1410. The collar 1400 can resemble or be identical to the above described collars in many ways, yet can differ in certain respects. Some of the similarities and differences are discussed below.

As shown in FIG. 47A the collar 1400 is configured to insert around the neck of a reservoir (cartridge) is a single piece. In this embodiment, the collar can comprise a crown of the reservoir or fits over the crown (or head) of the cartridge and engages with insert connector 1410 (shown in FIGS. 47A-C) via a lid portion 1409. In some embodiments, the lid 1409 comprises a lid aperture 1406. In some embodiments, as shown in FIGS. 47A, the collar 1400 comprises one or more (1, 2, 3, 4, 5, 6, or more) collar spacers 1437. The embodiment of FIG. 47A has six collar spacers 1437. FIG. 47B shows an inlet connector 1410 (cap connector) that inserts over the head (or crown) of the cartridge and engages with the pre-fitted collar assembly shown in FIG. 47A. In this embodiment, three collar projections (e.g., unique differentiating tabs or protrusions) 1404 shown in FIG. 47A are positioned 120 degrees apart from one another and couple with the corresponding inlet connector 1410 via collar guiding element tracks 1465. The corresponding cap connector 1410 shown in FIG. 47C contains collar guiding element tracks 1465 (e.g., cavities, grooves, keyways, or slots) to match with the collar guiding elements 1404 on the prefitted collar. In some embodiments, the bottom edge of the pre-fitted collar 1400 has a collar projection 1403 (lip, etc.). In some embodiments, the collar projection is sized and positioned appropriately to allow engagement by the collar projection mates 1466 shown in FIG. 47C. Also, in some embodiments, the cap connector 1410 shown in FIG. 47B contains guiding elements 1418 (tabs, protrusions, or features) positioned 120 degrees apart from one another, which allow insertion into an infusion chamber, drive shaft, or pump chamber of a pump housing unit that contains cavities, grooves, keyways, or slots to match with the unique differentiating tabs, protrusions, or features on the cap connector. Also, in some embodiments, as shown in FIGS. 47B, the cap connector 1410 contains two inlet connector spacers 1436 (tabs, protrusions, or features) positioned 180° apart from one another. In some embodiments, the collar 1400 comprises a pairing projection 1412. The features of collar 1400 and inlet connector 1410 interact with corresponding inlet connecting covers 1430 (not shown) having pairing apertures 1436 and external engaging implements 1434.

Figure 48C:
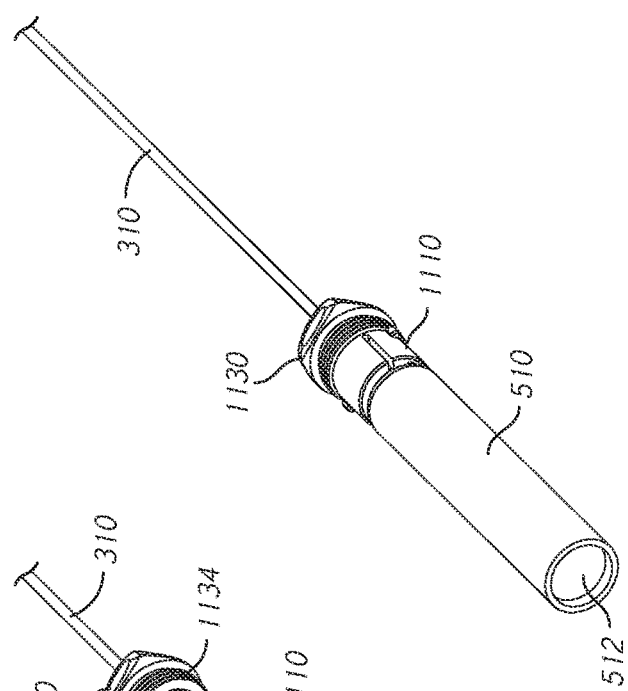
FIGS. 48A-C illustrate an embodiment of a reservoir and inlet cover connector engaging with collar and inlet connector.
Figure 48B:
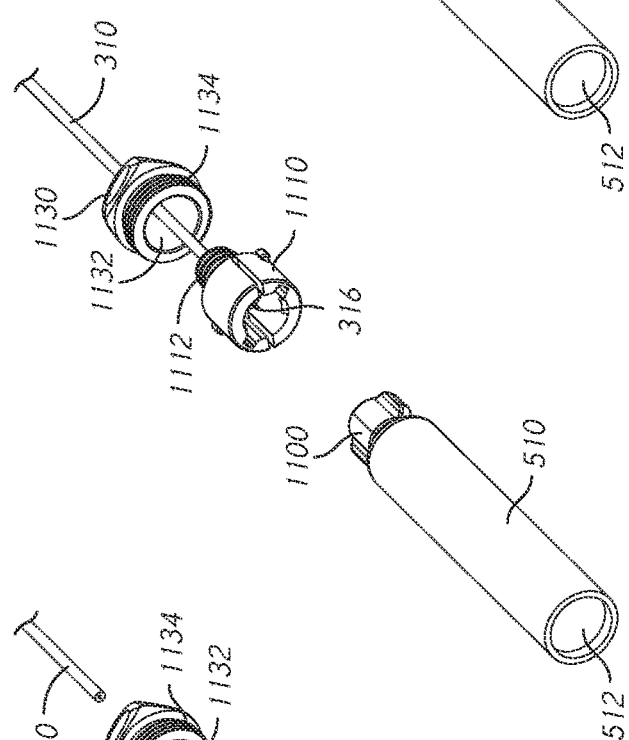
Figure 48A:
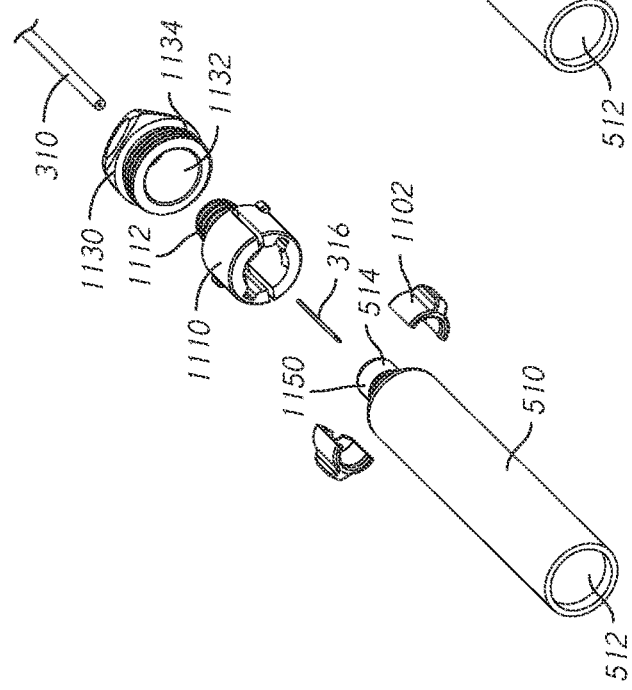

FIGS. 48A-C show six separate components: the cartridge 510, the collar 1100 of FIG. 44A-B (which, in some embodiments, inserts around the neck of the cartridge and contains unique differentiating tabs, keys, or protrusions as well as features that allow engagement with and locking with the cap connector), the inlet connector 1110 (e.g., cap connector; which, in some embodiments, contains corresponding cavities, grooves, keyways, or slots to match with the unique differentiating tabs, protrusions, or features on the pre-fitted collar and a capture mechanism to lock with the features on the pre-fitted collar), inlet connector cover 1130 (e.g., secondary cap, threaded coaxial cap, etc.; that, in some embodiments, can slide up and down the tubing, and that fits over the cap connector and threads into the pump housing), the needle 316 (which, in some embodiments, is overmolded, bonded, press-fitted, glued, solvent bonded, insert molded, or otherwise attached to the cap connector), and tubing 310 (that, in some embodiments, is overmolded, bonded, press-fitted, glued, solvent bonded, insert molded, or otherwise attached to both the cap connector). While FIGS. 48A-C show the interaction between the embodiment of FIG. 44A-C with various other components, it should be understood that this is only an example configuration and other collar/inlet connector systems could be used instead. For example, given the similar features of the embodiment described in FIG. 46A-C, it could be used with the components of FIGS. 48A-C. As shown in FIGS. 48A-C and as described with respect to other embodiments herein, in some embodiments, the first channel 310 comprises a first piercing element 316 (e.g., a needle, cannula, etc.) configured to insert into a first medicament reservoir 510 that couples to the inlet connector 1110. In some embodiments, the needle 316 pierces a reservoir septum 514 located within an internal reservoir cover 1150 on the medicament reservoir 510 by insertion through the pairing projection 1112. In some embodiments, the needle is heat staked or affixed within the inlet connector 1110. In some embodiments, the first reservoir 510 has a first plunger 512 adapted to be depressed by a piston of an infusion pump. In some embodiments, the needle is overmolded, bonded, press-fitted, glued, solvent bonded, insert molded, or otherwise attached to the inside of the inlet connector 1110. In some embodiments, the hollow needle is recessed within the cap connector so as to be touch-proof. In this embodiment, the needle of FIG. 48 has pierced the septum over the reservoir 510.

In some embodiments, as shown in FIGS. 48A-C and as described with respect to other embodiments herein, an inlet connector cover 1130 (e.g., secondary cap, etc.) can be configured to interact with the inlet connector 1110 via the pairing projection 1112. In certain variants, the cover 1130 is molded and permanently attached to a fluid conduit 310. In some embodiments, tubing 310 is overmolded, bonded, press-fitted, glued, solvent bonded, insert molded, or otherwise attached to the cap connector and to the hollow needle in such a way as to allow a patent and continuous fluid path through the hollow needle, the cap connector, and the tubing. In some embodiments, the cover 1130 and the fluid conduit 310 are reversibly attachable. In some embodiments, as shown in FIG. 48B, the inlet connector cover 1130 is freely movable along the fluid conduit 310. In some embodiments, a needle 316 is molded to the pairing projection 1112 and fixed there. In some embodiments, the inlet connector cover 1130 is heat staked to the inlet connector 1110 via the pairing projection 1112. In some embodiments, the fluid conduit is able to freely rotate within the first inlet connector and cover, which, as discussed above, helps avoid kinking of the fluid conduit. In certain variants, the inlet connector cover 1130 and the inlet connector are separated by a compressible O-ring. This O-ring allows the cover and connector to be tightly coupled to seal them together. In some embodiments, a compressible O-ring (similar to that described above as 415) resides around the first inlet connector cover (similar to that described above as 430) threads to facilitate tight connection to the fusion pump via the external threads.

In certain variants, the cover 1130 comprises external engagement implements 1134 (e.g., external threads, ribbing, etc.) configured to interact with and engage mated receptacles on an infusion pump housing. In some embodiments, the cover 1130 comprises a pairing aperture 1132 configured to engage with the pairing projection 1112. In some embodiments, the cover 1130 comprises a pairing aperture 1132 that is configured to not engage with a non-mated pairing projection.

As shown in FIGS. 48A-C, in certain implementations, the inlet connector 1110 is configured to interact with the medicament reservoir 510. In some embodiments, to be inserted properly within the inlet connector 1110, the reservoir must be fitted with a collar 1100. In some embodiments, as described above, the projections of the collar can be configured to only interact with an appropriate inlet connector 1110. In some embodiments, collars can be matched to specific size and diameter reservoirs. In some embodiments, the collars for these different reservoirs can interact with only certain reservoirs, thereby minimizing chances of mischanneling. In other embodiments, reservoirs that are the same can be used and mischanneling can be prevented by the selection of an appropriate collar. In some embodiments, the collars can be color coded to match reservoirs, inlets, and other components of the system to further prevent and/or discourage mischanneling.

Figure 49C:
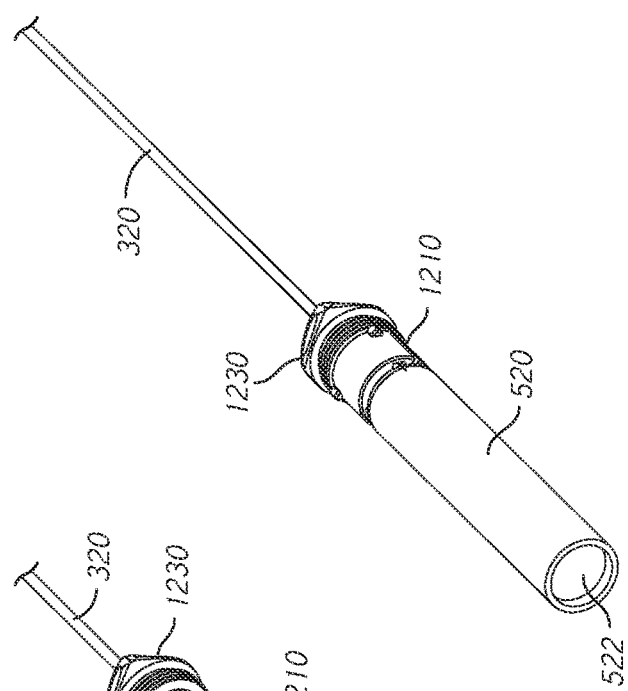
FIGS. 49A-C illustrate an embodiment of a reservoir and inlet cover connector engaging with collar and inlet connector.
Figure 49B:
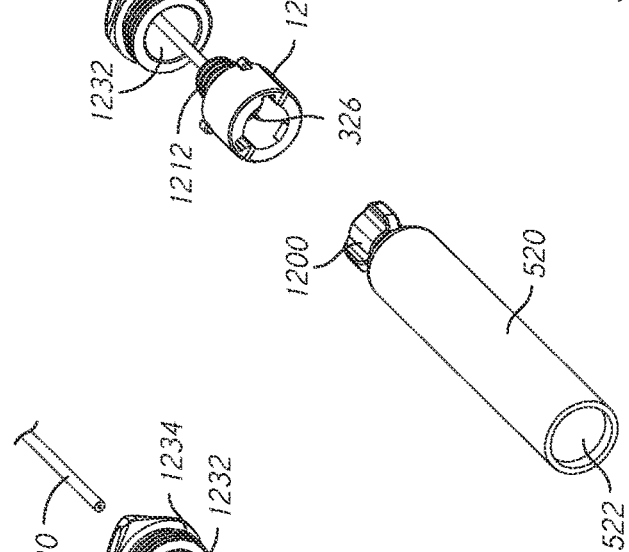
Figure 49A:
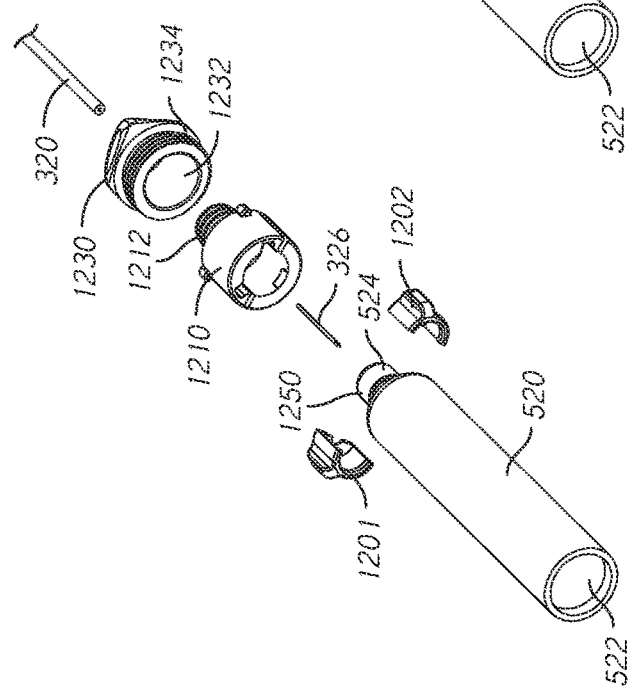

FIGS. 49A-C show six separate components that are different from those of FIGS. 48A-C and could be used in conjunction with the system of FIGS. 48A-C in a system that avoids mischanneling. The components include: the cartridge 520, the collar 1200 of FIG. 45A-B (which, in some embodiments, inserts around the neck of the cartridge and contains unique differentiating tabs, keys, or protrusions as well as features that allow engagement with and locking with the cap connector), the inlet connector 1210 (e.g., cap connector; which, in some embodiments, contains corresponding cavities, grooves, keyways, or slots to match with the unique differentiating tabs, protrusions, or features on the pre-fitted collar and a capture mechanism to lock with the features on the pre-fitted collar), inlet connector cover 1230 (e.g., secondary cap, threaded coaxial cap, etc.; that, in some embodiments, can slide up and down the tubing, and that fits over the cap connector and threads into the pump housing), the needle 326 (which, in some embodiments, is overmolded, bonded, press-fitted, glued, solvent bonded, insert molded, or otherwise attached to the cap connector), and tubing 320 (that, in some embodiments, is overmolded, bonded, press-fitted, glued, solvent bonded, insert molded, or otherwise attached to both the cap connector). While FIGS. 49A-C show the interaction between the embodiment of FIG. 45A-C with various other components, it should be understood that this is only an example configuration and other collar/inlet connector systems could be used instead. For example, given the similar features of the embodiment described in FIG. 47A-C, it could be used with the components of FIGS. 49A-C. As shown in FIGS. 49A-C and as described with respect to other embodiments herein, in some embodiments, the second channel 320 comprises a second piercing element 326 (e.g., a needle, cannula, etc.) configured to insert into a second medicament reservoir 520 that couples to the inlet connector 810. In some embodiments, the needle 326 pierces a reservoir septum 524 located within an internal reservoir cover 1250 on the medicament reservoir 520 by insertion through the pairing projection 1212. In some embodiments, the second reservoir 520 has a second plunger 522 adapted to be depressed by a piston of an infusion pump. In some embodiments, the needle is overmolded, bonded, press-fitted, glued, solvent bonded, insert molded, or otherwise attached to the inside of the inlet connector 1210. In some embodiments, the hollow needle is recessed within the cap connector so as to be touch-proof. In this embodiment, the needle of FIG. 49C has pierced the septum over the reservoir 520.

In some embodiments, as shown in FIGS. 49A-C and as described with respect to other embodiments herein, an inlet connector cover 1230 (e.g., secondary cap, etc.) can be configured to interact with the inlet connector 1210 via the pairing projection 1212. In certain variants, the cover 1230 is molded and permanently attached to a fluid conduit 320. In some embodiments, tubing 320 can be overmolded, bonded, press-fitted, glued, solvent bonded, insert molded, or otherwise attached to the cap connector and to the hollow needle in such a way as to allow a patent and continuous fluid path through the hollow needle, the cap connector, and the tubing. In some embodiments, the cover 1230 and the fluid conduit 320 are reversibly attachable. In some embodiments, as shown in FIG. 49B, the inlet connector cover 1230 is freely movable along the fluid conduit 320. In some embodiments, a needle 326 is molded to the pairing projection 1212 and fixed there. In some embodiments, the inlet connector cover 1230 is heat staked to the inlet connector 1210 via the pairing projection 1212. In some embodiments, the fluid conduit is able to freely rotate within the inlet connector and cover, which, as discussed above, helps avoid kinking of the fluid conduit. In certain variants, the inlet connector cover 1230 and the inlet connector are separated by a compressible O-ring. This O-ring allows the cover and connector to be tightly coupled to seal them together. In some embodiments, a compressible O-ring (similar to that described above as 415) resides around the first inlet connector cover (similar to that described above as 430) threads to facilitate tight connection to the fusion pump via the external threads.

In certain variants, the cover 1230 comprises external engagement implements 1234 (e.g., external threads, ribbing, etc.) configured to interact with and engage mated receptacles on an infusion pump housing. In some embodiments, the cover 1230 comprises a pairing aperture 1232 configured to engage with the pairing projection 1212. In some embodiments, the cover 1230 comprises a pairing aperture 1232 that is configured to not engage with a non-mated pairing projection.

As shown in FIGS. 49A-C, in certain implementations, the inlet connector 1210 is configured to interact with the medicament reservoir 520. In some embodiments, to be inserted properly within the inlet connector 1210, the reservoir must be fitted with a collar 1200. In some embodiments, as described above, the projections of the collar can be configured to only interact with an appropriate inlet connector 1210. In some embodiments, collars can be matched to specific size and diameter reservoirs. In some embodiments, the collars for these different reservoirs can interact with only certain reservoirs, thereby minimizing chances of mischanneling. In other embodiments, reservoirs that are the same can be used and mischanneling can be prevented by the selection of an appropriate collar. In some embodiments, the collars can be color coded to match reservoirs, inlets, and other components of the system to further prevent and/or discourage mischanneling.

In some embodiments, the configurations described in FIGS. 48A-C and FIGS. 49A-C could be used in a single pump system (similar to that depicted in FIG. 43A-B) to avoid mischanneling of medicaments.

Figure 50D:
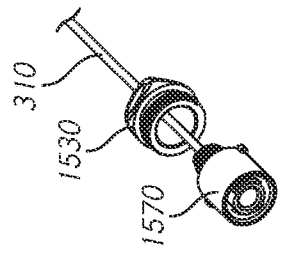
FIGS. 50A-D illustrate an embodiment of a luer lock collar system.
Figure 50C:
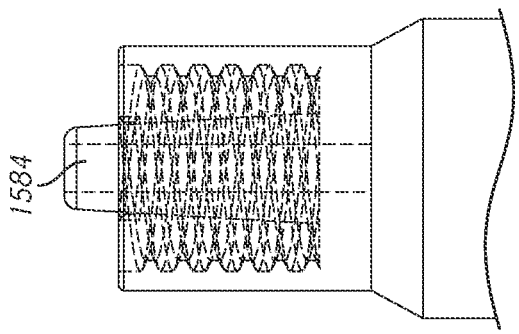
Figure 50B:
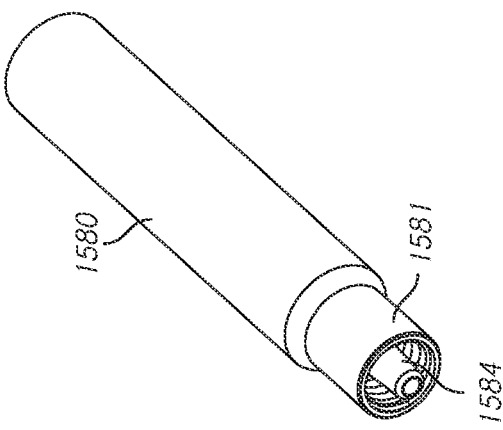
Figure 50A:
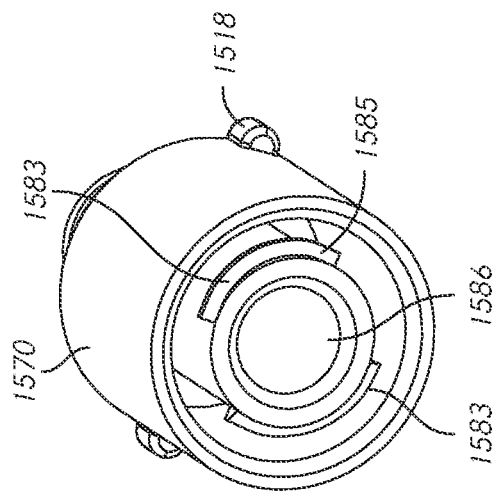

FIGS. 50A-D show an additional inlet connector 1570 assembly having a luer connection. In some embodiments, as shown in FIG. 50A, the inlet connector 1570 can comprise guiding elements 1518 similar to those described above. In this embodiment, the reservoir engaging aperture 1586 (e.g., internal cavity) of the cap connector shown in FIG. 50A contains female connector features 1585 of a standard luer lock, which engage with the male connector features of a standard luer lock 1584 integrated onto the end of the cartridge 1580 shown in 50B, with detail of the luer lock end of the cartridge shown in 50C. In this embodiment, the cap connector 1570 shown in 50A contains connector projections 1583 (e.g., two tabs, protrusions, or features) positioned 180 degrees apart from one another, which allow insertion into an infusion chamber, drive shaft, or pump chamber of a pump housing unit that contains corresponding cavities, grooves, keyways, or slots to match with the unique differentiating tabs, protrusions, or features on the cap connector 1570. In some embodiments, the cap connector 1570 in 50A does not contain a recessed needle or relief slits (as shown above), but rather couples with the cartridge shown in 50B and 50C using a standard luer lock mechanism, such that medicament can flow directly from the cartridge into the tubing 310 without first passing through a needle. Unlike the cartridges shown above, the cartridge 1580 shown in FIG. 50B might not be pre-filled with medicament at the point of care, and does not contain a crown with a septum, but rather contains the male connector features of a standard luer lock integrated onto the end 1581, of the cartridge. FIG. 50D shows a partially exploded view showing two separate subcomponents: (i) the cartridge with male connector features of a standard luer lock and (ii) the cap connector with female connector features of a standard luer lock, tubing, and threaded coaxial cap assembled into a single connected subassembly.

Figure 51C:
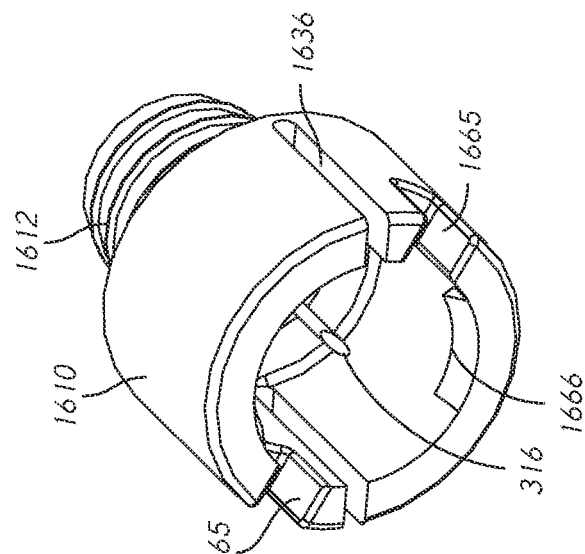
FIGS. 51A-C illustrate another embodiment of a collar assembly and a corresponding inlet connector.
Figure 51B:
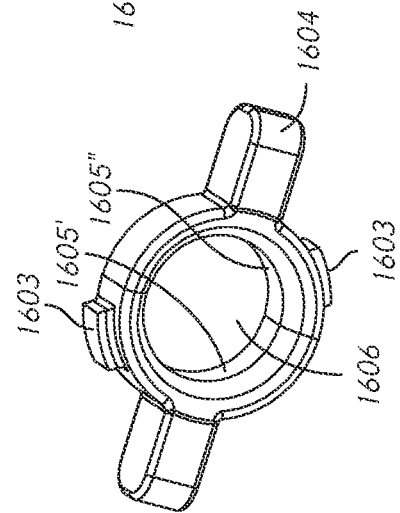
Figure 51A:
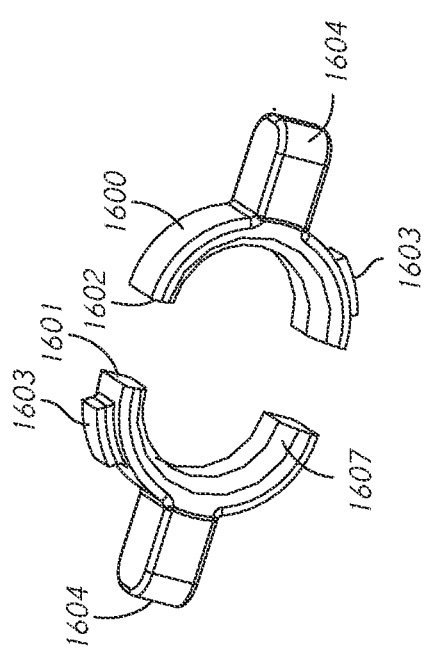

FIGS. 51A-C show another embodiment of a collar/inlet connector assembly. FIG. 51A shows an exploded view of an embodiment of a collar 1600, showing a pre-fitted collar assembly comprising two portions 1601, 1602 that insert around the neck of a cartridge. FIG. 51B shows an assembled view of the same pre-fitted collar 1600 shown in FIG. 51A. FIG. 51C shows an inlet (or cap) connector 1610 that inserts over the head (or crown) and neck of a reservoir that is collared and engages with the pre-fitted collar assembly shown in FIGS. 51A-B.

As shown in FIGS. 51A-B and similar to the collars disclosed elsewhere herein, in some embodiments, the collar 1600 comprises a first collar portion 1601 and a second collar portion 1602. In some variants, as shown in FIGS. 51A-B, these portions 1601, 1602 can be equivalently shaped so that a single mold can be used to fabricate both portions 1601, 1602. In some implementations, as with other collars disclosed herein, the portions are differently shaped and sized. For instance, in some embodiments, where the collar is circular, one portion could make up 75% of the circle and the other 25%. This sizing could facilitate the larger portion of the collar snapping tightly over the reservoir, securing that portion in place, while the other piece is held (or fixed) in place during, for instance, capping of the collared reservoir. It should be noted that various shapes of collars could also be used (square, rectangular, triangular, etc.) depending on the shape of the vial or the shape of the inlet connector, or the desired pairing between the two and/or the pump housing. In some embodiments, the collar comprises one, two, three, four, or more pieces (e.g., portions) that can be assembled to wrap a reservoir. In some embodiments, different collar portions can be mixed and matched, increasing the variability of possible configurations of medicament delivery systems that avoid mischanneling.

In some embodiments, as shown in FIG. 51B, different collar portions 1601, 1602 can be affixed (welded, glued, etc.) to one another to form a collar having a reservoir engaging aperture 1606. In some embodiments, the collar can be attached permanently to a medicament reservoir (e.g., a vial, etc.) which resides within the engaging aperture 1606 where it can be held. In certain embodiments, the medicament reservoir can be reused, being refilled using a bulk reservoir with corresponding features that match the features of the collar/collar-capping assembly/vial assembly.

In some embodiments, an adhesive, glue, rubberizing agent, or other applicant can be applied to mating surfaces 1605', 1605" of the engaging aperture 1606 that contact the neck (or head, crown, etc.) of the cartridge. In some variants, the pre-fitted collar adhesive increases friction and reduces or prevents rotation of the pre-fitted collar relative to the reservoir. In some variants, the mating surfaces of the two-component pre-fitted collars 1605', 1605," as shown in FIGS. 51A-B, can be affixed (e.g., bonded, glued, laser welded, or otherwise attached) as the collar is assembled onto the neck of the cartridge. In some embodiments, the mating surfaces 1605', 1605" are compressible (sponge, foam, rubber, soft plastic, ribbed, fabric, etc.) to allow them to compress around a reservoir, locking it in place.

In certain implementations, the collar 1600 comprises one or more form fitted edges 1607 (beveled, squared, etc.) to allow the collar 1600 to interact flushly with a reservoir having a corresponding shape.

In some embodiments, the pre-fitted collar contains one or more features that extend radially outwardly (teeth, tabs, protrusions, features, etc.) from the engaging aperture 1606, as shown in FIGS. 51A-C. In some embodiments, these protrusions allow coupling only with a corresponding cap connector 1610 (e.g., inlet connector) with corresponding receiving features. In some embodiments, the corresponding cap connector contains corresponding cavities, grooves, keyways, or slots to match with the unique differentiating tabs, protrusions, or features on the pre-fitted collar (as shown in FIG. 51C). In this way, only one type of pre-fitted collar can mate uniquely with one type of cap connector. In certain variants, the protrusions extend radially inwardly from a cap connector and engage receiving features located on the collar. In some embodiments, the cap connector has projections while the collar has corresponding cavities.

In certain implementations, the collar 1600 comprises one or more (e.g., 1, 2, 3, 4, 5, or more) collar projections 1603 (projections having an edge, lip, clips, etc.). In certain embodiments, as with the other collars described herein, the collar can lack collar projections. The embodiment of FIG. 51A-B comprises two collar projections. In some embodiments, as shown, these projections extend radially outwardly away from the collar's reservoir engaging aperture 1606. In some variants, these collar projections 1603 are configured to interact with one or more (e.g., 1, 2, 3, 4, 5, or more) coinciding collar projection mates 1666 (lips, edges, clips, cavities comprising the same, etc.) located on an inlet connector 1610. As shown in FIGS. 51A-C, the two collar projections 1603 would interact with two corresponding collar projection mates 1666 of the inlet connector 1610. In some embodiments, the collar projections 1603 engage the collar projection mates 1666 to snap the collar into place holding the collar 1600 and the inlet connector 1610 together (e.g., flush to one another). In some variants, the inlet connector 1610 has coinciding projection mates 1666 that are mated with each configuration of collar projections 1603. In some embodiments, the collar projection mates 1666 act as a capture mechanism that engages a feature (e.g., collar projections 1603) on the pre-fitted collar 1600 and/or that engages the collar 1600 itself. In some embodiments, the capture mechanism of the inlet connector 1610 can expand slightly as it is pressed over the pre-fitted collar and then the inlet connector 1610 would snap into place, engaging a tab, protrusion, or feature on the pre-fitted collar, or the bottom edge of the pre-fitted collar, and securely fasten the cap connector to the pre-fitted collar. The cartridge, pre-fitted collar, and cap connector subassembly could then be fastened into a pump housing unit.

In some embodiments, as with the other collars described herein, where multiple collar projections 1603 are present, the collar projections 1603 can be spaced evenly about the collar 1600 so that each collar projection is equidistant from the next. For instance, in an embodiment as shown in FIG. 51A-C, where two projections 1603 are present, those projections can be positioned opposite of one another on the collar (180° apart from each other). In some variants, as with the other collars described herein, the collar projections can be spaced unevenly about the collar so that some collar projections are closer and some are farther from adjacent collar projections. In some embodiments, as with other collars described herein, adjacent collar projections can be separated by values independently selected from about 180°, about 160°, about 140°, about 120°, about 100°, about 90°, about 80°, about 70°, about 60°, about 50°, about 40°, about 30°, about 20°, about 10°, values between the aforementioned values or otherwise. In some embodiments, as described above, collars can comprise one or more differently shaped collar projections on a single collar. In some embodiments, the collar projections can be one or more shapes selected from triangular shaped, squared, semi-circular, etc. This variability leads to almost unlimited variability in collar/inlet connector matings.

As shown in FIGS. 51A-C, in some embodiments, where present, collar guiding elements 1604 are configured to interact with corresponding collar guiding element tracks 1665. In some variants, the collar comprises one or more (e.g., 1, 2, 3, 4, 5, or more) collar guiding elements (tabs, protrusions, etc.). In some embodiments of the collars described herein, collar guiding elements are not present. In some embodiments, these collar guiding elements protrude radially from the collar extending away from the reservoir engaging aperture 1606. In some embodiments of the collars described herein, the collar guiding elements 1604 protrude radially from the collar 1600 and are long enough to extend outwardly from the inlet connector 1610 after insertion into the inlet connector 1610 (extending away from the reservoir engaging aperture 1606). In some embodiments, as shown in FIGS. 51A-C, these collar guiding elements 1604 are configured to interact with one or more (e.g., 1, 2, 3, 4, 5, or more) coinciding collar guiding element tracks 1665 (cavities, grooves, keyways, slots, apertures, etc.) located on an inlet connector 1610. In some embodiments, similar to the collar projections above and similar to any embodiment of collar described herein, the collar guiding elements 1604 can be spaced evenly about the collar 1600 so that each collar guiding element 1604 is equidistant from the next. For instance, in the embodiment shown in FIG. 51A-C, two collar guiding elements 1604 are present and are positioned opposite of one another on the collar 1600 (about 180° apart from each other). In some variants of the collars described herein, the collar guiding elements 1604 can be spaced unevenly about the collar so that some projections are closer and some are farther. In some embodiments of the collars described herein, adjacent collar guiding elements are separated apart by values independently selected from about 180°, about 160°, about 140°, about 120°, about 100°, about 90°, about 80°, about 70°, about 60°, about 50°, about 40°, about 30°, about 20°, about 10°, values between the aforementioned values or otherwise. In some embodiments, multiple differently shaped guiding elements can be used on a single collar. In some embodiments, the guiding elements of any of the collars described herein can be independently selected to be triangularly shaped, square-shaped, semi-circular, polygonal, ball-and-stick-shaped, polygon-and-stick-shaped, etc. This design can lead to multiple configurations of collars with almost unlimited variability. In some variants, the inlet connector 1610 has coinciding collar guiding element tracks 1665 (grooves, cavities, slots, key holes, etc.) that are mated with each configuration of collar guiding elements 1604. In some embodiments, these tracks guide only properly matched collars into place on the inlet connector.

In certain variants, the collar projections 1603 (or inlet connector projections as the case may be), as shown, are smaller than the collar guiding elements 1604 (or inlet connector guiding elements as the case may be). In some embodiments, the ratio of the size of the collar projections to the collar guiding elements is about 1:20, 1:10, about 1:5, about 1:2, values between the aforementioned values or otherwise.

In some embodiments, as shown in FIGS. 51A-C, similar in some aspects to embodiments described above, the inlet connector 1610 can comprise a pairing projection 1612. This pairing projection 1612 is discussed in more detail elsewhere herein and can fit into an inlet connector cover (not shown).

In some embodiments, once the collar 1600 is inserted into the inlet connector 1610, the collar guiding element 1604 can act as a guiding element (tabs, protrusions, or features) for the assembled collar 1600 and inlet connector 1610. In some embodiments, the collar guiding element 1604 protrudes through the inlet connector 1610 to facilitate placement in, for example, a specific, matching aperture in an infusion pump (e.g., the infusion pump housing), while discouraging (or preventing) insertion into an incorrect aperture (in some ways similar to, for example, the guiding elements 718 of the inlet connector 710 described above). In some embodiments, the cap comprises a piercing element 316 that can be heat staked (or otherwise affixed, glued, welded, etc.) in place. In some embodiments, the inlet connector also comprises guiding elements similar to those the guiding elements 718 show in FIG. 37C.

In some embodiments, the cap connector's (i.e., inlet connector's) guiding elements allow insertion into an infusion chamber, drive shaft, or pump chamber of a pump housing unit that contains corresponding cavities, grooves, keyways, or slots to match with the unique differentiating tabs, protrusions, or features on the cap connector. In this way, in some embodiments, only one type of cap connector can be inserted uniquely into one particular infusion chamber, drive shaft, or pump chamber. Alternatively, the inlet connector might contain cavities, grooves, keyways, or slots (not shown) that uniquely mate with one or more tabs, protrusions, or features in the infusion chamber, drive shaft, or pump chamber of a pump housing unit.

In certain variants, the distance the collar guiding elements 1604 protrude radially from the inlet connector 1610 when engaged can be compared to the radial distance the collar projections 1603 extend from the collar. In certain embodiments, the distance of extension from the inlet connector 1610 is at least as small or smaller than the distance the collar projections 1603 extend radially. In various embodiments, the ratio of the extension of the collar guiding elements from the inlet connector guiding elements to the collar projections from the collar is about 1:10, about 1:5, about 1:2, about 1:1, about 2:1, about 5:1, or about 10:1, values between the aforementioned values or otherwise.

In certain variants, the inlet connector 1610 comprises one or more (2, 3, 4, 5, or more) inlet connector spacers 1636 (e.g., relief slits, cavities, etc.). As shown, the two relief slits 1636 of the inlet connector 1610 of FIG. 51C are 180° apart. In some variants, where multiple relief slits are present, the relief slits can be spaced unevenly about the collar so that some projections are closer and some are farther. In some embodiments of the collars disclosed herein, adjacent relief slits are separated by values independently selected from about 180°, about 160°, about 140°, about 120°, about 100°, about 90°, about 80°, about 70°, about 60°, about 50°, about 40°, about 30°, about 20°, about 10°, values between the aforementioned values or otherwise. In some embodiments, inlet connector spacers 1636 allow the inlet connector 1610 to be compressed as it inserts into a pump housing or expanded as it is slid over a collar/reservoir assembly. In some embodiments, this can allow snap tight fitting into a pump housing or with a collar/reservoir assembly that comprises mated features. For instance, in some embodiments, once inserted all the way into the housing, the inlet connector spacers can re-expand, allowing the geometric features of the inlet connector 1610 to interact with mated apertures or features of the pump housing. This feature, among others described herein, can allow the reservoir to be held in an appropriate position, with little movement (e.g., substantially flush), within the pump housing. In some embodiments, a single-component pre-fitted collar 1600, such as the ones shown in FIGS. 51A-C, has relief slits 1636 which allow the inlet connector to be pressed over the head (or crown) of the cartridge, and a locking mechanism, that snaps into place as it engages with the underside of the head (or crown) of the cartridge.

Figure 52C:
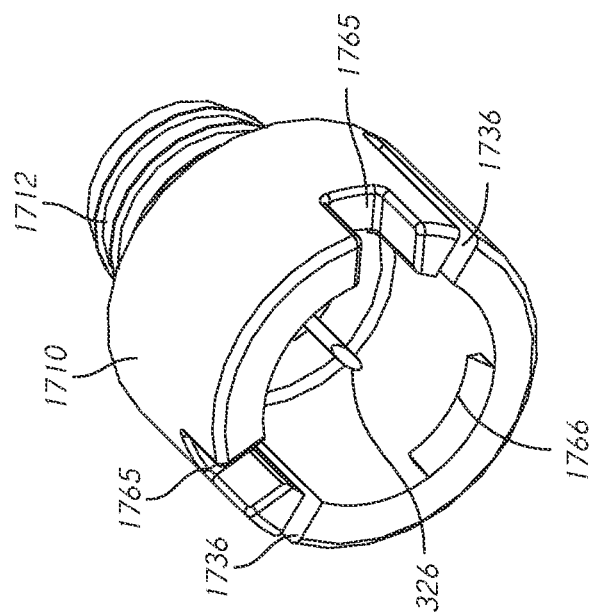
FIGS. 52A-C illustrate another embodiment of a collar assembly and a corresponding inlet connector.
Figure 52B:
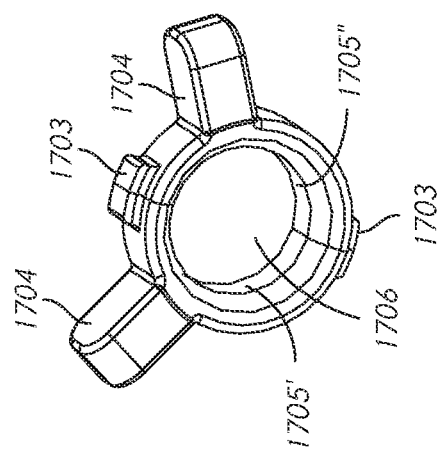
Figure 52A:
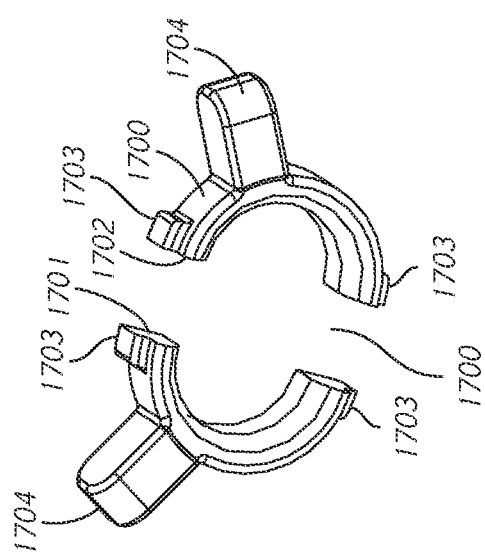

Another embodiment of a collar is shown in FIGS. 52A-C. The collar 1700 can resemble or be identical to the above described collar 1600 in many ways, yet can differ in certain respects. Some of the similarities and differences are discussed below.

As shown in FIGS. 52A-B, the collar 1700 comprises a first portion 1701 and a second portion 1702. As shown, these portions 1701, 1702 can be equivalent to one another and can be fabricated using a single mold. In some implementations, as discussed above, the portions are differently shaped and sized. FIG. 52A shows an exploded view of an embodiment of a collar 1700, showing a pre-fitted collar assembly that inserts around the neck of the cartridge. FIG. 52B shows an assembled view of the same pre-fitted collar 1700 shown in FIG. 52A. FIG. 52C shows an inlet (or cap) connector 1710 that inserts over the head (or crown) and neck of a reservoir and engages with the pre-fitted collar assembly shown in FIGS. 52A-B.

In some embodiments, as shown in FIG. 52B, these portions 1701, 1702 can be affixed (welded, glued, etc.) to one another to form a collar having a reservoir engaging aperture 1706 that can permanently hold a medicament reservoir (e.g., a vial, etc.). In some embodiments, an adhesive, glue, rubberizing agent, or other applicant can be applied to one or both of the mating surfaces 1705', 1705" of the engaging aperture 1706 between the neck of the cartridge and the pre-fitted collar to increase friction and reduce or prevent rotation of the pre-fitted collar relative to the neck of the reservoir. In some variants, as discussed above, the mating surfaces of the two-component pre-fitted collars 1705', 1705," as shown in FIGS. 52A-B, can be bonded, glued, laser welded, or otherwise attached as the collar is assembled onto the neck of the cartridge. In some embodiments, the mating surfaces 1705', 1705" are compressible (sponge, foam, rubber, soft plastic, ribbed, fabric, etc.) to allow them to compress around a reservoir, locking it in place. In certain implementations, the collar 1700 comprises one or more form fitted edges 1707 (beveled, fitted, etc.) to allow the collar 1700 to interact flushly with a reservoir.

As shown in FIGS. 52A-C, the pre-fitted collar contains one or more tabs, protrusions, features, which allow coupling only with the corresponding cap connector 1710 (e.g., inlet connector) and the corresponding cap connector comprises cavities, grooves, keyways, or slots that match the unique differentiating tabs, protrusions, or features on the pre-fitted collar. As shown in FIG. 52A-B, the collar 1700 comprises two collar projections 1703 (projections having an edge, lip, etc.). As shown in FIG. 52A-C, the collar projections 1703 (one or more) can be bisected by the separation of the collar pieces 1701, 1702. In some variants, these collar projections 1703 interact with the coinciding collar projection mates 1766 (lips, edges, clips, etc.) located on an inlet connector 1710, as shown in FIGS. 52A-C. In some embodiments, the collar projections 1703 engage the collar projection mates 1766 to snap the collar into place holding the collar 1700 and the inlet connector 1710 flush to one another. In some variants, the inlet connector 1710 has coinciding projection mates 1766 that are mated with each configuration of collar projections 1703. In some embodiments, the collar projection mates 1766 act as a cap a capture mechanism that engages a feature (e.g., collar projections 1703) on the pre-fitted collar 1700 and/or that engages the collar 1700 itself. In some embodiments, the collars are either of the variety that connects to the head (or crown) of the cartridge or to the neck of the cartridge. In some embodiments, the capture mechanism of the inlet connector 1710 can expand slightly as it is pressed over the pre-fitted collar and then the inlet connector 1710 can snap into place, engaging a tab, protrusion, or feature on the pre-fitted collar, or the bottom edge of the pre-fitted collar, and securely fasten the cap connector to the pre-fitted collar. The cartridge, pre-fitted collar, and cap connector subassembly could then be fastened into a pump housing unit.

In some embodiments, as shown in FIGS. 52A-B, the collar 1700 comprises two collar projections 1703 that are positioned opposite of one another on the collar (180° apart from each other). In some variants, as shown in FIGS. 52A-B, the collar 1700 comprises two collar guiding elements 1704 (tabs, protrusions, etc.). As shown, these collar guiding elements 1704 can be configured to interact coinciding collar guiding element tracks 1765 (cavities, grooves, keyways, slots, apertures, etc.) located on the corresponding inlet connector 1710 shown in FIG. 52C. In some embodiments, these collar guiding elements 1704 protrude radially from the collar 1700 and from the inlet connector 1710 after insertion into the inlet connector 1710 extending away from the reservoir engaging aperture 1706. As shown in FIG. 52A-B, and as described above, where two collar guiding elements 1704 are present, those guiding elements can be positioned apart by about 120° from each other (or by about 240° traveling around the longer portion of the perimeter of the collar 1700). As shown in FIG. 52C, the inlet connector 1710 can have coinciding collar guiding element tracks 1765 that are mated with each configuration of collar guiding elements 1704.

In some embodiments, as shown in FIGS. 52A-C, similar in some aspects to embodiments described above, the inlet connector 1710 comprises a pairing projection 1712. This pairing projection 1712 is discussed in more detail elsewhere herein.

In some embodiments, as is apparent from FIGS. 52A-C, similar in some aspects to embodiments described above, once the collar 1700 is inserted into the inlet connector 1710, the collar guiding element 1704 can act as a guiding element (a tab, a protrusion, or a feature) for the assembled collar 1700 and inlet connector 1710. In some embodiments, the collar guiding element 1704 protrudes through the inlet connector 1710 to facilitate placement in, for example, a specific, matching aperture in an infusion pump (e.g., the infusion pump housing), while discouraging (or preventing) insertion into an incorrect aperture (in some ways similar to, for example, the guiding elements 718 of the inlet connector 710 described above). In some embodiments, the cap comprises a piercing element 326 that can be heat staked (or otherwise affixed, glued, welded, etc.) in place. In some embodiments, the inlet connector also comprises guiding elements similar to those the guiding elements 718 show in FIG. 37C.

In certain variants, the inlet connector 1710, as shown, comprises two inlet connector spacers 1736 (e.g., relief slits) separated by 180°. In some embodiments, this inlet connector spacer 1736 allows the inlet connector 1710 to be compressed or expanded. These relief slits can be spaced about the connector in the same fashion as the guiding elements. As with the embodiment described in FIGS. 37C, the slits can allow snap tight fitting into a pump housing that comprises mated features. This feature, among others described herein, can allow the reservoir to be held in an appropriate position, with little movement, within the pump housing. In some embodiments, a single-component pre-fitted collar 1700, such as the ones shown in FIGS. 52A-C, has relief slits 1736 which allow the inlet connector to be pressed over the head (or crown) of the cartridge, and a locking mechanism, that snaps into place as it engages with the underside of the head (or crown) of the cartridge.

Figure 53C:
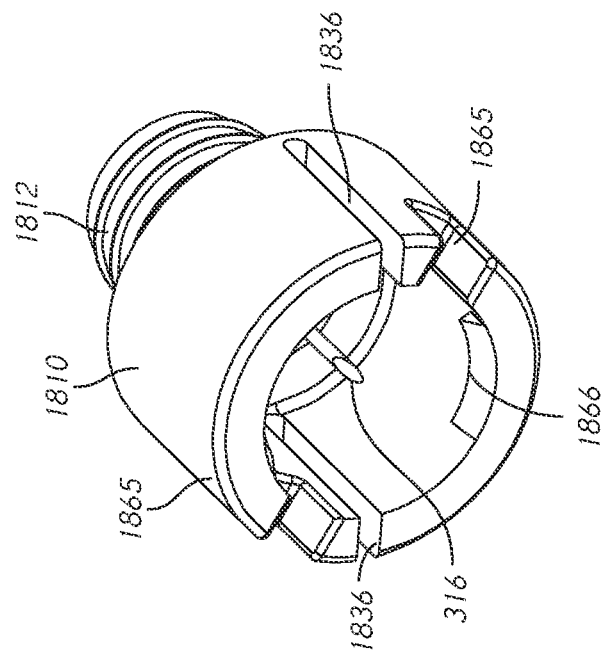
FIGS. 53A-C illustrate another embodiment of a collar assembly and a corresponding inlet connector.
Figure 53B:
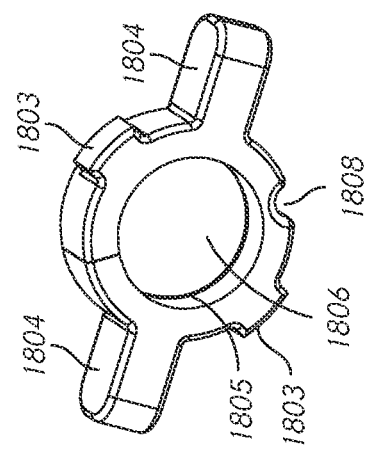
Figure 53A:
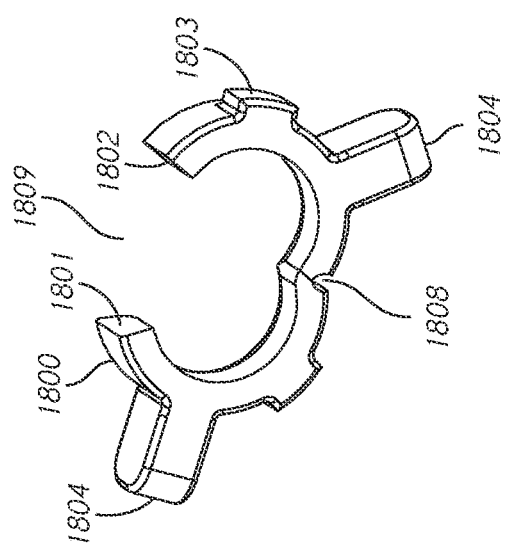

Another embodiment of a collar is shown in FIGS. 53A-C. The collar 1800 is similar to the above described collar 1600 except that it has a relief with fillet 1808 and an opening 1809 away from the fillet as opposed to being two distinct pieces. FIG. 54A shows an open view of an embodiment of a collar 1800, showing a pre-fitted collar assembly that inserts around the neck of the cartridge. FIG. 53B shows a closed view of the same pre-fitted collar 1800 shown in FIG. 53A. FIG. 53C shows an inlet (or cap) connector 1810 that inserts over the head (or crown) and neck of a reservoir and engages with the pre-fitted collar assembly shown in FIGS. 53A-B.

In some embodiments, the collar can automatically close around a reservoir by virtue of the elasticity of the collar 1800. In some embodiments, a hinge, joint, or other swiveling mechanism can be used instead of the fillet 1808, with the goal of having a closable (and, in some embodiments, an openable collar) in mind. In some embodiments, the collar 1800 comprises surfaces 1801, 1802 that come into contact with one another when the collar 1800 is in the closed position. In some embodiments, these surfaces 1801, 1802 can be affixed (welded, glued, etc.) to one another to form a collar having a reservoir engaging aperture 1806 that can permanently hold a medicament reservoir (e.g., a vial, etc.). In some embodiments, an adhesive, glue, rubberizing agent, or other applicant can be applied to the mating surface 1805 of the engaging aperture 1806 between the neck of the cartridge and the pre-fitted collar 1800 to increase friction and reduce or prevent rotation of the pre-fitted collar 1800 relative to the neck of the reservoir. In some variants, as discussed above, the mating surface 1805 can be bonded, glued, laser welded, or otherwise attached as the collar is assembled onto the neck of the cartridge. In some embodiments, the mating surface 1805 is compressible (sponge, foam, rubber, soft plastic, ribbed, fabric, etc.) to allow them to compress around a reservoir, locking it in place. In certain implementations, the collar 1800 comprises one or more form fitted edges (beveled, fitted, etc.; not shown) to allow the collar 1800 to interact flushly with a reservoir.

In some embodiments, the pre-fitted collar contains one or more tabs, protrusions, features, as in FIGS. 53A-C, which allow coupling only with the corresponding cap connector (e.g., inlet connector), and the corresponding cap connector contains corresponding cavities, grooves, keyways, or slots to match with the unique differentiating tabs, protrusions, or features on the pre-fitted collar. In this way, only one type of pre-fitted collar can mate uniquely with one type of cap connector. For instance, the collar 1800 comprises two collar projections 1803 (projections having an edge, lip, etc.). In some variants, these collar projections 1803 are configured to interact with coinciding collar projection mates 1866 (lips, edges, clips, etc.) located on an inlet connector 1810, as shown in FIGS. 53A-C. In some embodiments, the collar projections 1803 engage the collar projection mates 1866 to snap the collar into place holding the collar 1800 and the inlet connector 1810 flush to one another. In some variants, the inlet connector 1810 has coinciding projection mates 1866 that are mated with each configuration of collar projections 1803. In some embodiments, the collar projection mates 1866 act as a cap a capture mechanism that engages a feature (e.g., collar projections 1803) on the pre-fitted collar 1800 and/or that engages the collar 1800 itself. In some embodiments, the collars are either of the variety that connect to the head (or crown) of the cartridge or to the neck of the cartridge. In some embodiments, the capture mechanism of the inlet connector 1810 can expand slightly as it is pressed over the pre-fitted collar and then the inlet connector 1810 can snap into place, engaging a tab, protrusion, or feature on the pre-fitted collar, or the bottom edge of the pre-fitted collar, and securely fasten the cap connector to the pre-fitted collar. The cartridge, pre-fitted collar, and cap connector subassembly could then be fastened into a pump housing unit.

As shown in FIG. 53A-C, where two projections 1803 are present on a collar, those projections can be positioned opposite of one another on the collar (180° apart from each other). In some variants, as shown in FIGS. 53A-B, the collar 1800 comprises two collar guiding elements 1804 (tabs, protrusions, etc.) configured to interact with two coinciding collar guiding element tracks 1865 (cavities, grooves, keyways, slots, apertures, etc.) located on the inlet connector 1810. In some embodiments, these collar guiding elements 1804 protrude radially from the collar 1800 and from the inlet connector 1810 after insertion into the inlet connector 1810 extending away from the reservoir engaging aperture 1806. As shown, these collar guiding elements are located about 180° apart on the collar. In some embodiments, the collar guiding elements can be spaced apart by varying degrees as discussed above. In some variants, the inlet connector 1810 has coinciding collar guiding element tracks 1865 that are mated with each configuration of collar guiding elements 1804.

In some embodiments, as shown in FIGS. 53A-C, similar in some aspects to embodiments described above, the inlet connector 1810 comprises a pairing projection 1812.

In some embodiments, as shown in FIGS. 53A-C, similar in some aspects to embodiments described above, once the collar 1800 is inserted into the inlet connector 1810, the collar guiding element 1804 can act as a guiding element (tab, protrusions, or features) for the assembled collar 1800 and inlet connector 1810. In some embodiments, the collar guiding element 1804 protrudes through the inlet connector 1810 to facilitate placement in, for example, a specific, matching aperture in an infusion pump (e.g., the infusion pump housing), while discouraging (or preventing) insertion into an incorrect aperture (in some ways similar to, for example, the guiding elements 718 of the inlet connector 710 described above). In some embodiments, the cap comprises a piercing element 326 that can be heat staked (or otherwise affixed, glued, welded, etc.) in place. In some embodiments, the collar's guiding elements would allow insertion into an infusion chamber, drive shaft, or pump chamber of a pump housing unit that contains corresponding cavities, grooves, keyways, or slots to match with the unique differentiating tabs, protrusions, or features on the cap connector. In some embodiments, the inlet connector also comprises guiding elements similar to those the guiding elements 718 show in FIG. 37C.

In certain variants, as shown in FIG. 53C, the inlet connector 1810 comprises two inlet connector spacers 1836

(e.g., relief slits). In some embodiments, this inlet connector spacer 1836 allows the inlet connector 1810 to be compressed as it inserts into a pump housing. These relief slits can be spaced about the connector in the same fashion as the guiding elements. As with the embodiment described in FIGS. 37C, the slits can allow snap tight fitting into a pump housing that comprises mated features.

Figure 54C:
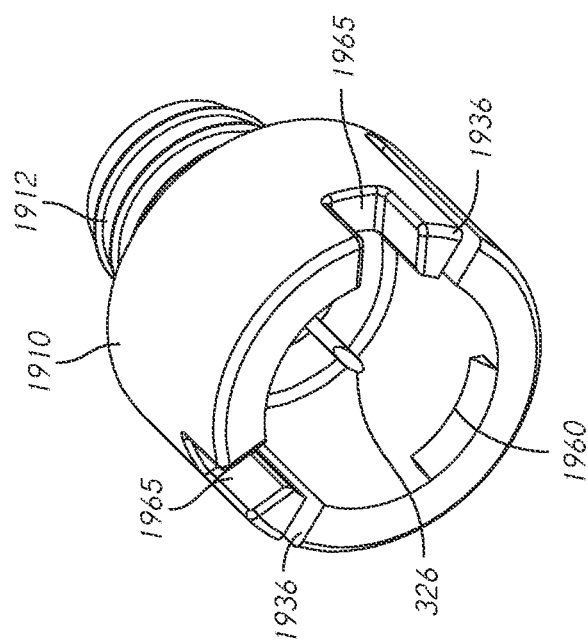
FIGS. 54A-C illustrate another embodiment of a collar assembly and a corresponding inlet connector.
Figure 54B:
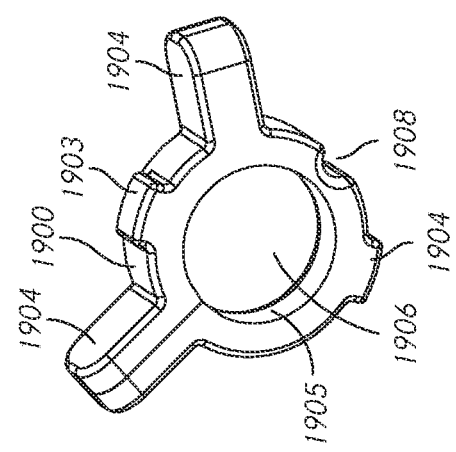
Figure 54A:
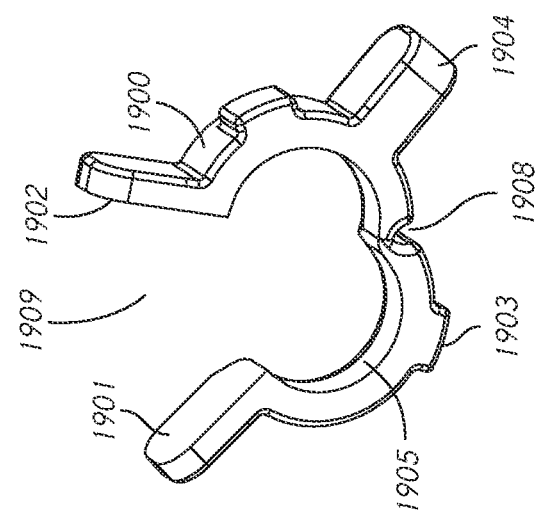

Another embodiment of a collar 1900 and its inlet connector 1910 is shown in FIGS. 54A-C. The collar 1900 is similar to the above described collars in many ways, yet can differ in certain respects. Some of the similarities and differences are discussed below. As shown in FIGS. 54A-B, the collar 1900 has a fillet 1908 and an opening 1909 away from the fillet 1908 as opposed to being two distinct pieces (for instance, collar 800's portions 801, 802). FIG. 54A shows an open view of the collar 1900, showing a pre-fitted collar assembly that inserts around the neck of the cartridge. FIG. 54B shows a closed view of the same pre-fitted collar 1900 shown in FIG. 54A. FIG. 54C shows an inlet (or cap) connector 1910 that inserts over the head (or crown) and neck of a reservoir and engages with the pre-fitted collar assembly shown in FIGS. 54A-B.

In some embodiments, the filleted collar can automatically close around a reservoir by virtue of the elasticity of the collar 1900. In some embodiments, a hinge, joint, or other swiveling mechanism can be used instead of the fillet 1908, with the goal of having a closable (and, in some embodiments, an openable collar) in mind. In some embodiments, the collar 1900 comprises surfaces 1901, 1902 that come into contact with one another when the collar 1900 is in the closed position. In some embodiments, these surfaces 1901, 1902 can be affixed (welded, glued, etc.) to one another to form a collar having a reservoir engaging aperture 1906 that can permanently hold a medicament reservoir (e.g., a vial, etc.). In some embodiments, an adhesive, glue, rubberizing agent, or other applicant can be applied to the mating surface 1905 of the engaging aperture 1906 between the neck of the cartridge and the pre-fitted collar 1900 to increase friction and reduce or prevent rotation of the pre-fitted collar 1900 relative to the neck of the reservoir. In some variants, as discussed above, the mating surface 1905 can be bonded, glued, laser welded, or otherwise attached as the collar is assembled onto the neck of the cartridge. In some embodiments, the mating surface 1905 is compressible (sponge, foam, rubber, soft plastic, ribbed, fabric, etc.) to allow them to compress around a reservoir, locking it in place. In certain implementations, the collar 1900 comprises one or more form fitted edges (beveled, fitted, etc.; not shown) to allow the collar 1900 to interact flushly with a reservoir.

In some embodiments, the pre-fitted collar contains one or more tabs, protrusions, features, as shown in FIGS. 54A-C, which allow coupling only with the corresponding cap connector 1910 (e.g., inlet connector), and the corresponding cap connector would contain corresponding cavities, grooves, keyways, or slots to match with the unique differentiating tabs, protrusions, or features on the pre-fitted collar.

For instance, in certain implementations, as shown, the collar 1900 comprises two collar projections 1903 (projections having an edge, lip, etc.). In some variants, these collar projections 1903 are configured to interact with one or more coinciding collar projection mates 1966 (lips, edges, clips, etc.) located on an inlet connector 1910, as shown in FIGS. 54A-C (where only one is visible). In some embodiments, the collar projections 1903 engage the collar projection mates 1966 to snap the collar into place holding the collar 1900 and the inlet connector 1910 flush to one another. In some variants, the inlet connector 1910 has coinciding projection mates 1966 that are mated with each configuration of collar projections 1903. In some embodiments, the collar projection mates 1966 act as a cap a capture mechanism that engages a feature (e.g., collar projections 1903) on the pre-fitted collar 1900 and/or that engages the collar 1900 itself. In some embodiments, the collars are either of the variety that connect to the head (or crown) of the cartridge or to the neck of the cartridge. In some embodiments, the capture mechanism of the inlet connector 1910 can expand slightly as it is pressed over the pre-fitted collar and then the inlet connector 1910 can snap into place, engaging a tab, protrusion, or feature on the pre-fitted collar, or the bottom edge of the pre-fitted collar, and securely fasten the cap connector to the pre-fitted collar. The cartridge, pre-fitted collar, and cap connector subassembly could then be fastened into a pump housing unit.

In some embodiments, as shown, the collar projections 1903 are evenly spaced about the collar 1900 (at about 180° apart). In some embodiments, as discussed with various embodiments above, the projections are distributed about the collar at various distances. In some variants, as shown in FIGS. 54A-B, the collar 1900 comprises two collar guiding elements 1904 (tabs, protrusions, etc.) configured to interact with one or more coinciding collar guiding element tracks 1965 (cavities, grooves, keyways, slots, apertures, etc.) located on an inlet connector 1910. As shown in FIG. 54B, the collar guiding elements are 120° apart with one being bisected by the opening 1909. In some variants, as shown, the inlet connector 1910 has coinciding collar guiding element tracks 1965 that are mated with each configuration of collar guiding elements 1904.

In some embodiments, as shown in FIGS. 54A-C, similar in some aspects to embodiments described above, the inlet connector 1910 can comprise a pairing projection 1912.

In some embodiments, as is apparent from FIGS. 54A-C, once the collar 1900 is inserted into the inlet connector 1910, the collar guiding element 1904 can act as a guiding element (tab, protrusions, or features) for the assembled collar 1900 and inlet connector 1910. In some embodiments, the collar guiding element 1904 protrudes through the inlet connector 1910 to facilitate placement in, for example, a specific, matching aperture in an infusion pump (e.g., the infusion pump housing), while discouraging (or preventing) insertion into an incorrect aperture (in some ways similar to, for example, the guiding elements 718 of the inlet connector 710 described above). In some embodiments, the cap comprises a piercing element 326 that can be heat staked (or otherwise affixed, glued, welded, etc.) in place. In some embodiments, the inlet connector also comprises guiding elements similar to those the guiding elements 718 show in FIG. 37C.

In certain variants, as shown in FIG. 54C, the inlet connector 1910 comprises two inlet connector spacers 1936 (e.g., relief slits) that are about 180° apart. In some embodiments, this inlet connector spacer 1936 allows the inlet connector 1910 to be compressed as it inserts into a pump housing or expanded as a reservoir and cap is inserted into it. These relief slits can be spaced about the connector in the same fashion as the guiding elements. The slits can allow snap tight fitting into a pump housing that comprises mated features.

Figure 55C:
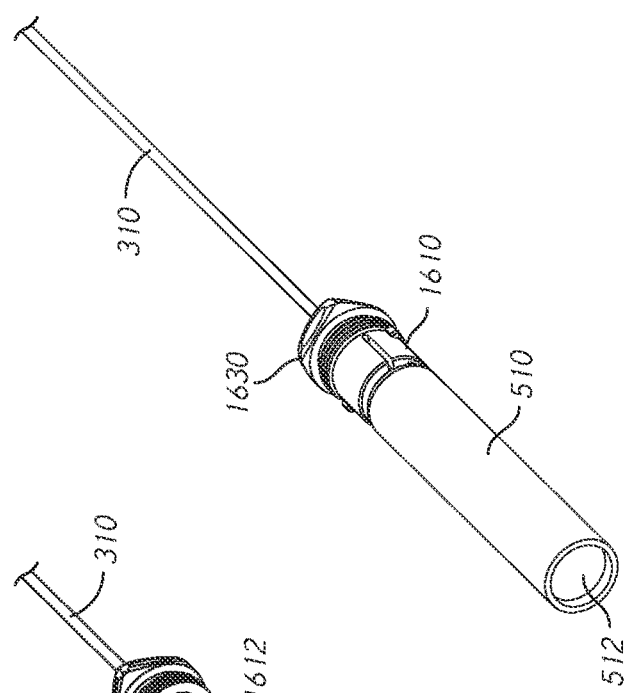
FIGS. 55A-C illustrate an embodiment of a reservoir and inlet cover connector engaging with collar and inlet connector.
Figure 55B:
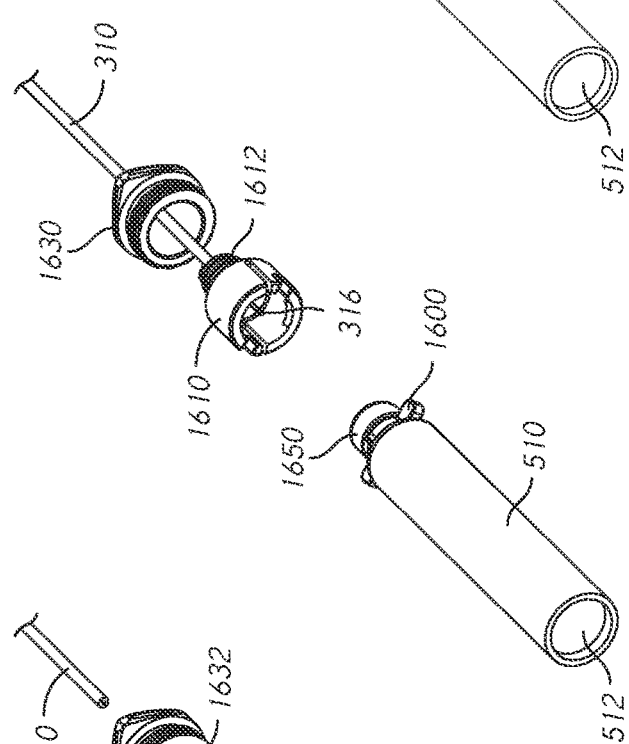
Figure 55A:
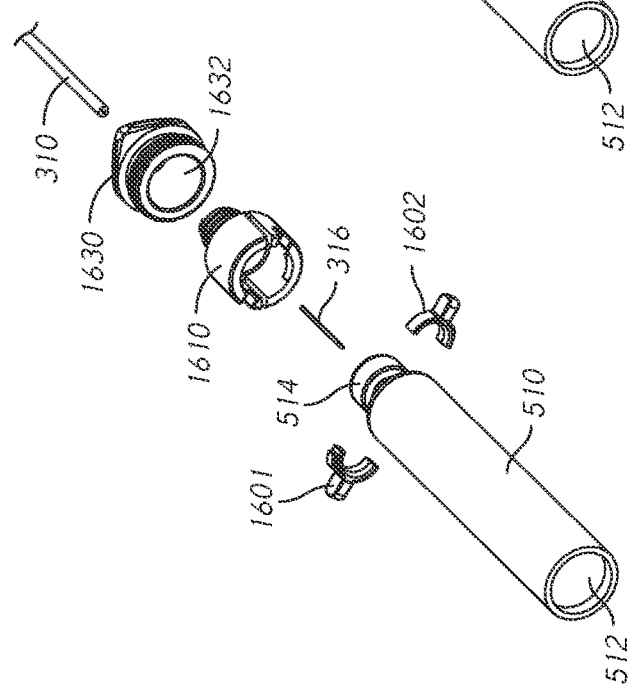

FIGS. 55A-C show six separate components: the cartridge 510, the collar 1600 of FIG. 51A-B (which, in some embodiments, inserts around the neck of the cartridge and contains unique differentiating tabs, keys, or protrusions as well as features that allow engagement with and locking with the cap connector), the inlet connector 1610 (e.g., cap connector; which, in some embodiments, contains corresponding cavities, grooves, keyways, or slots to match with the unique differentiating tabs, protrusions, or features on the pre-fitted collar and a capture mechanism to lock with the features on the pre-fitted collar), inlet connector cover 1630 (e.g., secondary cap, threaded coaxial cap, etc.; that, in some embodiments, can slide up and down the tubing, and that fits over the cap connector and threads into the pump housing), the needle 316 (which, in some embodiments, is overmolded, bonded, press-fitted, glued, solvent bonded, insert molded, or otherwise attached to the cap connector), and tubing 310 (that, in some embodiments, is overmolded, bonded, press-fitted, glued, solvent bonded, insert molded, or otherwise attached to both the cap connector). As shown in FIGS. 55A-C and as described with respect to other embodiments herein, in some embodiments, the first channel 310 comprises a first piercing element 316 (e.g., a needle, cannula, etc.) configured to insert into a first medicament reservoir 510 that couples to the inlet connector 1610. In some embodiments, the needle 316 pierces a reservoir septum 514 located within an internal reservoir cover 1650 on the medicament reservoir 510 by insertion through the pairing projection 1612. In some embodiments, as shown, the first reservoir 510 has a first plunger 512 adapted to be depressed by a piston of an infusion pump. In some embodiments, the needle is overmolded, bonded, press-fitted, glued, solvent bonded, insert molded, or otherwise attached to the inside of the inlet connector 1610. In some embodiments, the hollow needle is recessed within the cap connector so as to be touch-proof. In this embodiment, the needle of FIG. 55C has pierced the septum 514 over the reservoir 510.

In some embodiments, as shown in FIGS. 55A-C and as described with respect to other embodiments herein, an inlet connector cover 1630 (e.g., secondary cap, etc.) can be configured to interact with the inlet connector 1610 via the pairing projection 1612. In certain embodiments, the pairing projection is ribbed or threaded to allow snap or screw fitting to the inlet connector cover 1630. In some embodiments the pairing projection does not snap or screw into the inlet connector cover 1630 and is instead smooth. In certain variants, the cover 1630 is molded and permanently attached to a fluid conduit 310. In some embodiments, tubing 310 is overmolded, bonded, press-fitted, glued, solvent bonded, insert molded, or otherwise attached to the cap connector and to the hollow needle in such a way as to allow a patent and continuous fluid path through the hollow needle, the cap connector, and the tubing. In some embodiments, the cover 1630 and the fluid conduit 310 are reversibly attachable.

In some embodiments, as shown in FIG. 55B, the inlet connector cover 1630 is freely movable along the fluid conduit 310. In some embodiments, a needle 316 is molded to the pairing projection 1612 and fixed there. In some embodiments, the inlet connector cover 1630 is heat staked to the inlet connector 1610 via the pairing projection 1612. In some embodiments, the fluid conduit is able to freely rotate within the first inlet connector and cover, which, as discussed above, helps avoid kinking of the fluid conduit. In certain variants, the inlet connector cover 1630 and the inlet connector are separated by a compressible O-ring. This O-ring allows the cover and connector to be tightly coupled to seal them together. In some embodiments, a compressible O-ring (similar to that described above as 415) resides around the first inlet connector cover (similar to that described above as 430) threads to facilitate tight connection to the fusion pump via the external threads.

In certain variants, the cover 1630 comprises external engagement implements 1634 (e.g., external threads, ribbing, etc.) configured to interact with and engage mated receptacles on an infusion pump housing. These threadings can be configured to only interact with corresponding threads of a housing. In some embodiments, the cover 1630 comprises a pairing aperture 1632 configured to engage with the pairing projection 1612. In some embodiments, the cover 1630 comprises a pairing aperture 1632 that is configured to not engage with a non-mated pairing projection.

As shown in FIGS. 55A-C, in certain implementations, the inlet connector 1610 is configured to interact with the medicament reservoir 510. In some embodiments, to be inserted properly within the inlet connector 1610, the reservoir must be fitted with a collar 1600. In some embodiments, as described above, the projections of the collar can be configured to only interact with an appropriate inlet connector 1610. In some embodiments, collars can be matched to specific size and diameter reservoirs. In some embodiments, the collars for these different reservoirs can interact with only certain reservoirs, thereby minimizing chances of mischanneling. In other embodiments, reservoirs that are the same can be used and mischanneling can be prevented by the selection of an appropriate collar. In some embodiments, the collars can be color coded to match reservoirs, inlets, and other components of the system to further prevent and/or discourage mischanneling.

Figures 56A, 56B, 56C:
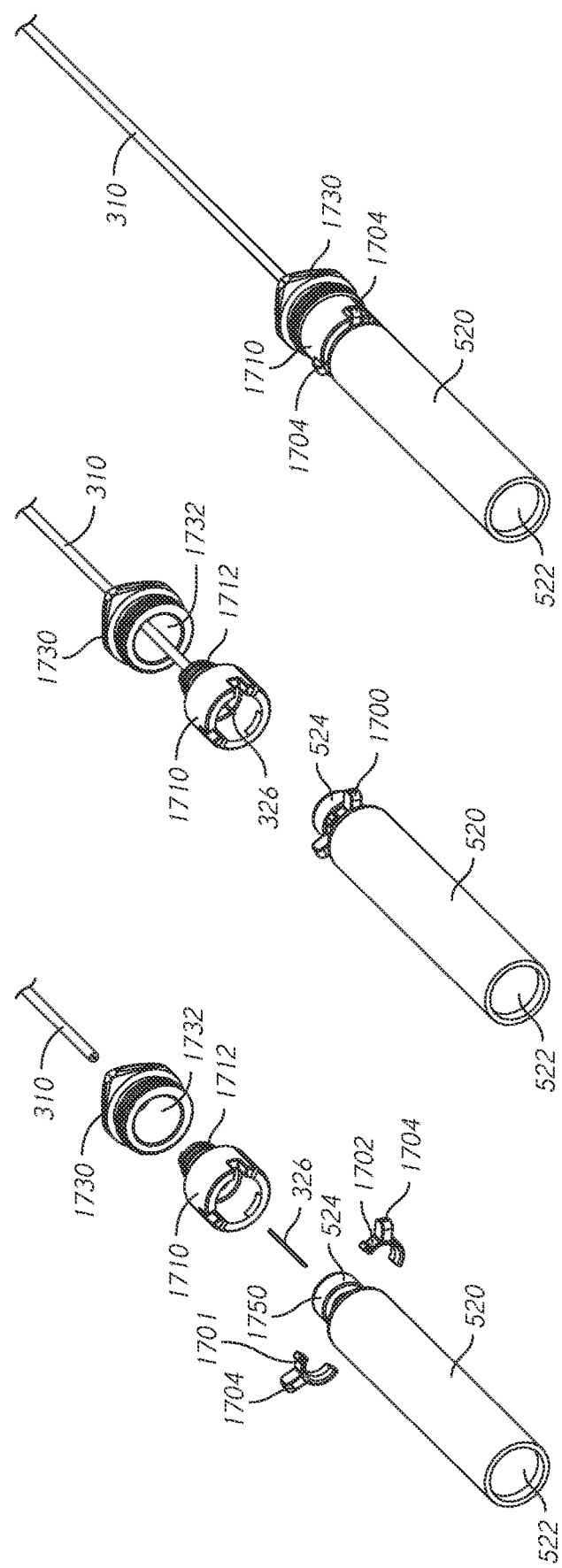
FIGS. 56A-C illustrate an embodiment of a reservoir and inlet cover connector engaging with collar and inlet connector.

FIGS. 56A-C show six separate components that are different from those of FIGS. 55A-C and that are used in conjunction with the system of FIGS. 56A-C to provide a drug delivery pump system that avoids mischanneling.

The components of the embodiment of FIGS. 56A-C include: the cartridge 520, the collar 1700 of FIG. 52A-B (which, in some embodiments, inserts around the neck of the cartridge and contains unique differentiating tabs, keys, or protrusions as well as features that allow engagement with and locking with the cap connector), the inlet connector 1710 (e.g., cap connector; which, in some embodiments, contains corresponding cavities, grooves, keyways, or slots to match with the unique differentiating tabs, protrusions, or features on the pre-fitted collar and a capture mechanism to lock with the features on the pre-fitted collar), inlet connector cover 1730 (e.g., secondary cap, threaded coaxial cap, etc.; that, in some embodiments, can slide up and down the tubing, and that fits over the cap connector and threads into the pump housing), the needle 326 (which, in some embodiments, is overmolded, bonded, press-fitted, glued, solvent bonded, insert molded, or otherwise attached to the cap connector), and tubing 320 (that, in some embodiments, is overmolded, bonded, press-fitted, glued, solvent bonded, insert molded, or otherwise attached to both the cap connector). As shown in FIGS. 55A-C and as described with respect to other embodiments herein, in some embodiments, the second channel 320 comprises a second piercing element 326 (e.g., a needle, cannula, etc.) configured to insert into a second medicament reservoir 520 that couples to the inlet connector 1710. In some embodiments, the needle 326 pierces a reservoir septum 524 located within an internal reservoir cover 1750 on the medicament reservoir 520 by insertion through the pairing projection 1712. In some embodiments, the second reservoir 520 has a second plunger 522 adapted to be depressed by a piston of an infusion pump. In some embodiments, the needle is overmolded, bonded, press-fitted, glued, solvent bonded, insert molded, or otherwise attached to the inside of the inlet connector 1710. In some embodiments, the hollow needle is recessed within the cap connector so as to be touch-proof. In this embodiment, the needle of FIG. 55C has pierced the septum over the reservoir 520.

In some embodiments, as shown in FIGS. 56A-C and as described with respect to other embodiments herein, an inlet connector cover 1730 (e.g., secondary cap, etc.) can be configured to interact with the inlet connector 1710 via the pairing projection 1712. In certain variants, the cover 1730 is molded and permanently attached to a fluid conduit 320. In some embodiments, tubing 320 can be overmolded, bonded, press-fitted, glued, solvent bonded, insert molded, or otherwise attached to the cap connector and to the hollow needle in such a way as to allow a patent and continuous fluid path through the hollow needle, the cap connector, and the tubing. In some embodiments, the cover 1730 and the fluid conduit 320 are reversibly attachable. In some embodiments, as shown in FIG. 56B, the inlet connector cover 1730 is freely movable along the fluid conduit 320. In some embodiments, a needle 326 is molded to the pairing projection 1712 and fixed there. In some embodiments, the inlet connector cover 1730 is heat staked to the inlet connector 1710 via the pairing projection 1712. In some embodiments, the fluid conduit is able to freely rotate within the inlet connector and cover, which, as discussed above, helps avoid kinking of the fluid conduit. In certain variants, the inlet connector cover 1730 and the inlet connector are separated by a compressible O-ring. This O-ring allows the cover and connector to be tightly coupled to seal them together. In some embodiments, a compressible O-ring (similar to that described above as 415) resides around the first inlet connector cover (similar to that described above as 430) threads to facilitate tight connection to the fusion pump via the external threads.

In certain variants, the cover 1730 comprises external engagement implements 1734 (e.g., external threads, ribbing, etc.) configured to specifically interact with and engage only mated receptacles on an infusion pump housing. In some embodiments, the cover 1730 comprises a pairing aperture 1732 configured to engage with the pairing projection 1712. In some embodiments, the cover 1730 comprises a pairing aperture 1732 that is configured to not engage with a non-mated pairing projection.

As shown in FIGS. 56A-C, in certain implementations, the inlet connector 1710 is configured to interact with the medicament reservoir 520. In some embodiments, to be inserted properly within the inlet connector 1710, the reservoir must be fitted with a collar 1700. In some embodiments, as described above, the projections of the collar can be configured to only interact with an appropriate inlet connector 1710. In some embodiments, collars can be matched to specific size and diameter reservoirs. In some embodiments, the collars for these different reservoirs can interact with only certain reservoirs, thereby minimizing chances of mischanneling. In other embodiments, reservoirs that are the same can be used and mischanneling can be prevented by the selection of an appropriate collar. In some embodiments, the collars can be color coded to match reservoirs, inlets, and other components of the system to further prevent and/or discourage mischanneling.

In some embodiments, the components of FIGS. 55A-C and 56A-C could be used in the housings similar to those shown in FIGS. 43A-B.

Figure 59B:
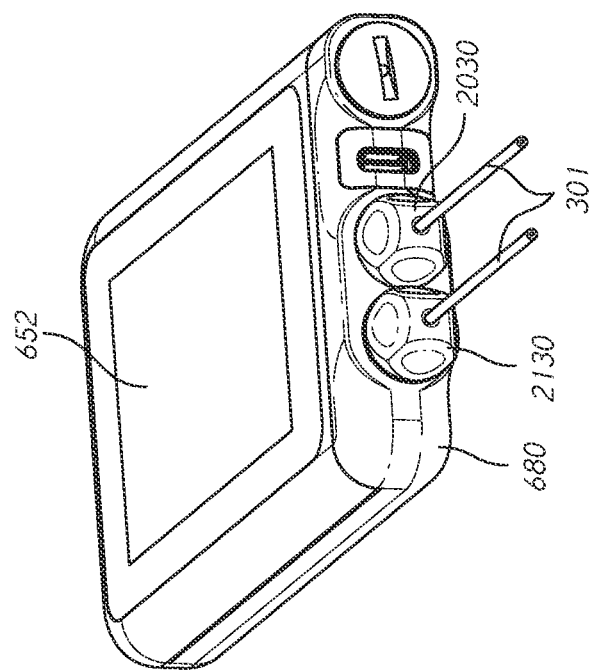
FIGS. 59A-B illustrate a pump assembly engaging with the inlet connectors and covers of FIGS. 57A-B and medicament reservoirs.
Figure 59A:
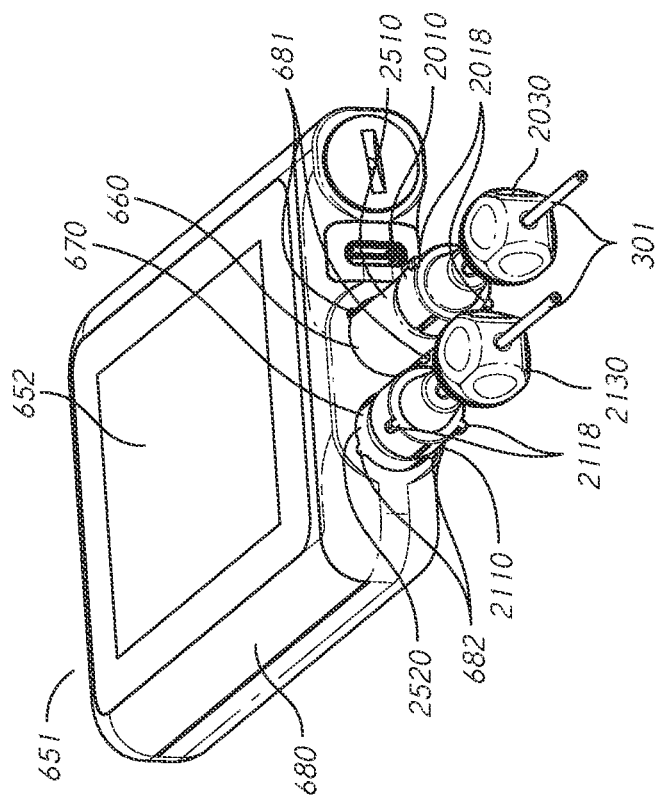

In some embodiments, as shown above, the medicament infusion system comprises an inlet system. In some embodiments, the inlet system comprises a connector set. In some embodiments, the connector set is configured (e.g., has pairing features) that prevent mischanneling of medicaments. FIGS. 57A-B show isometric views of a connector set 2000 comprising a first inlet connector 2010 and a second inlet connector 2110 adapted to prevent mischanneling. FIGS. 57A-B show two embodiments in which different needle connectors 2010, 2110 (e.g., the inlet connector), have unique differentiating guiding elements 2018, 2118 (e.g., tabs, features, or protrusions), separated by 180 degrees (FIG. 57A) and 120 degrees (FIG. 57B). In some embodiments, these unique differentiating guiding elements 2018, 2118 (e.g., tabs, features, or protrusions) mate uniquely with corresponding guiding element apertures 681, 682 (e.g., cavities, grooves, keyways, or slots) in the pump housing 680 of a pump 651 (as shown in FIGS. 59A-B) such that insertion of an inlet connector 2010, into the wrong pump receptacle 670 (e.g., chamber) is prevented. As shown in FIG. 57C, a cross-sectional view of the needle connector assembly, in some embodiments, the inlet connector 2210 lacks unique differentiating tabs, features, or protrusions.

In some embodiments, as shown in FIGS. 57A-B, the inlet connectors 2010, 2110 can have inlet connector spacers 2036, 2136 (e.g., relief slits). In some embodiments, the connector spacers allow the inlet connector to expand (e.g., over a vial to snap tight around the vial) and/or to contract (e.g., to snap into a pump receptacle). In some embodiments the inlet connectors 2010, 2110 comprise projection mates 2066, 2166 (e.g., capture-and-locking features) to facilitate interaction with a medicament cartridge (shown in FIGS. 58A-C).

In some embodiments, as shown in FIGS. 57A-C, tubing 301 is individually affixed (e.g., overmolded, bonded, press-fitted, glued, solvent bonded, insert molded, or otherwise attached) to individual inlet connectors 2010, 2110, 2210. In some embodiments, tubing 301 (e.g., channels, or other fluid conduits) connects to separate piercing elements 316, 326, 336 (e.g., a straight, beveled, hollow, stainless steel needle) in such a way as to allow a closed, independent, patent, and continuous fluid path from a medicament vial through piercing elements 316, 326, 336, inlet connectors 2010, 2110, 2210 and/or tubes 301 and on to an infusion set. In some embodiments, the piercing elements 316, 326, 336 can be recessed within the inlet connectors 2010, 2110, 2210 so as to be touch-proof (e.g., preventing the piercing element from pricking a user as the inlet connector is manipulated). In some embodiments, as shown in FIGS. 57A-C, the inlet systems comprise inlet connector covers 2030, 2130, 2230. In some embodiments, the inlet connector covers 2030, 2130, 2230 engage the inlet connectors 2010, 2110, 2210 via a pairing projection 2012, 2112, 2212. In some embodiments, the pairing projections comprise one or more features (e.g., tabs, slits, projections, etc.) that enable covers to engage only with paired inlet connectors (not shown). In some embodiments, as shown in FIGS. 57A-C, the inlet connector covers 2030, 2130, 2230 (e.g., caps) can comprise a tightening feature 2031, 2131, 2231 (e.g., threads, friction pairings, etc.) that allows them to be affixed into a pump receptacle. In some embodiments, the connector cap/cover 2030, 2130, 2230 is freely rotatable around the tubing 301. In some embodiments, the cap 2030, 2130, 2230 can slide up and down the tubing 301 and can be used to secure the cartridge (e.g., vial, medicament reservoir) and needle connector (e.g., inlet connector) sub-assembly to a pump housing (shown in FIG. 59B).

In some embodiments, an inlet connector, such as the ones shown in FIGS. 57A-61C, has relief slits on the sides, which allow it to expand slightly as it is pressed over the aluminum crimp seal around the head (or crown) of a medicament-filled cartridge, and a capture-and-locking feature, which snaps into place by engaging the underside of the aluminum crimp seal and simultaneously interlocking and securely fastening the needle connector with the aluminum crimp seal around the head (or crown) of the cartridge. In some embodiments, once fastened, the cartridge and needle connector subassembly can then be inserted and fastened into a pump housing 680 (as in FIGS. 59A-B).

In some embodiments, as shown in FIGS. 57A-B, the inlet connector system 2001, 2002 can comprise a gasket feature 2038, 2138 (e.g., an O-ring, or compressible feature) located around (e.g., around the periphery, external circumference, etc.) of an inlet connector cover 2030, 2130 or other inlet connector system feature. In some embodiments, the O-ring allows the connector cap 2030, 2130 to be securely fastened to the pump 651 such that the medicament vials have little or no movement when inserted into the pump 651 via the receptacles 660, 670 and tightened there using the tightening features 2031, 2131, 2231. Even though the medicament receptacles can be isolated from the rest of the pump housing, the O-ring also reduces (e.g., minimizes, lowers, etc.) fluid ingress into the medicament receptacle such that consequent pump damage is minimized.

Figure 58A:
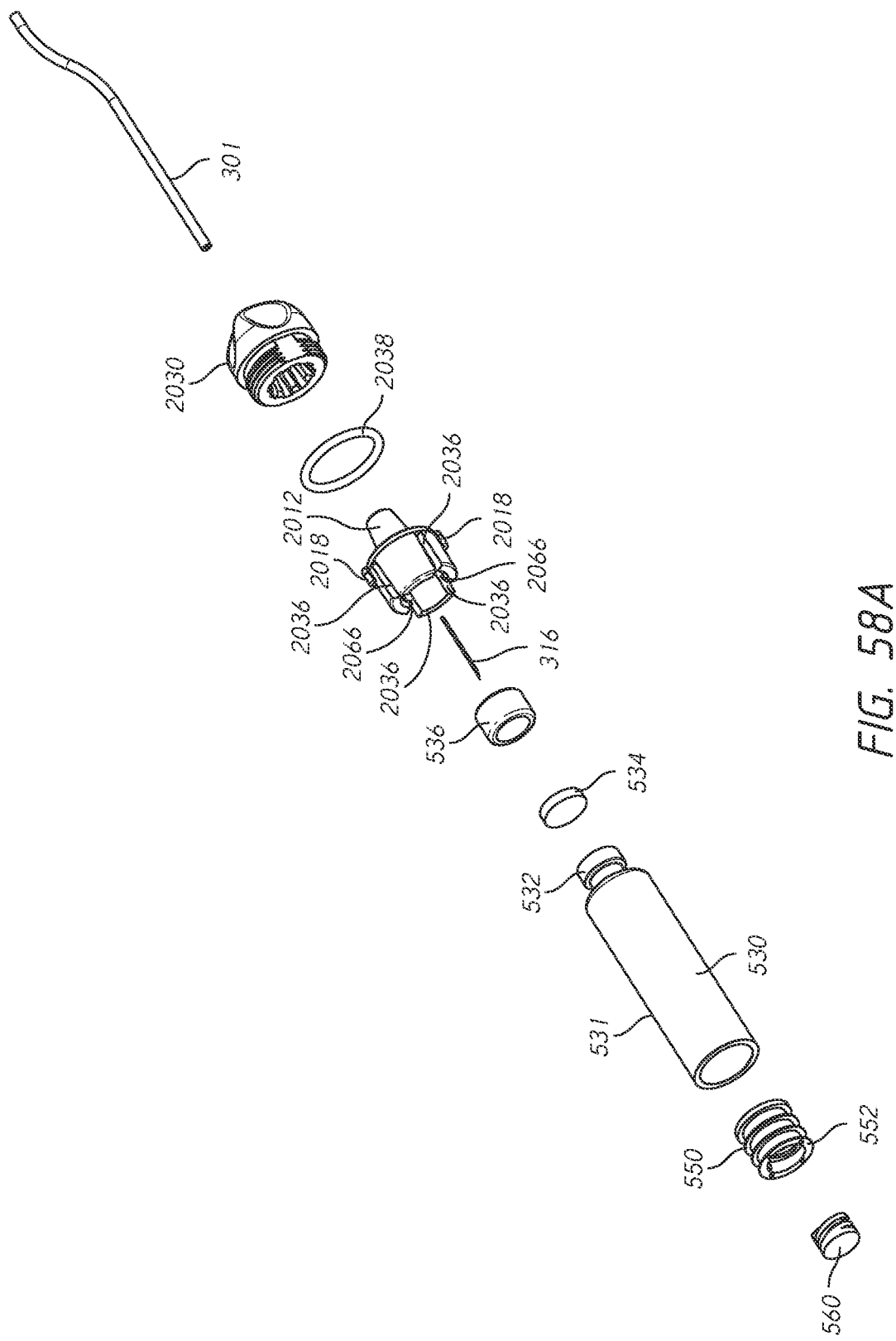

FIGS. 58A-C show various components and isometric views of (A) individual components that could be used in a cartridge and needle connector assembly, (B) the sub-assemblies that would be used in such an embodiment, and (C) the fully connected cartridge and needle connector assembly. To form the cartridge sub-assembly, a seal 536 (e.g., an aluminum crimp seal, etc.), wraps around the cartridge septum 534 and the head 532 (or crown) of the cartridge body 531. In some embodiments, the seal 536 and septum 534 can be used to create a sterile barrier and fluid seal on one end of the medicament reservoir 530.

In some embodiments, an elastomeric plunger 550 creates a sterile barrier and fluid seal on the other end of the cartridge 530. In some embodiments, the elastomeric plunger 550 has a receptacle 552 that captures (e.g., through threading, friction, etc.) an insert 560 (e.g., a ferrous insert). In some embodiments, as shown, the insert 560 is threaded to correspond and engage paired threads on the plunger 550. In some embodiments, the insert 560 could be used with a coupled piston (e.g., magnetically coupled) to prevent accidental medicament delivery caused by inadvertent separation of the piston from the elastomeric plunger 550. In some embodiments, this ferrous insert could facilitate magnetic coupling between a magnet at the end of the drive nut in a pump chamber and the elastomeric plunger such that it would prevent inadvertent departure or lift-off of the elastomeric plunger from the drive nut as in the case of unintentional medicament delivery caused by gravitationally induced changes in hydrostatic pressure between the patient and the infusion system, or any other changes in hydrostatic pressure that might arise between the patient and the infusion system. In some embodiments, the ferrous insert could be connected to the elastomeric plunger by means of a snug-fit or snap-fit.

In some embodiments, the inlet connector 2110 (i.e., needle connector) by virtue of its relief slits 2136 can expand around the head 532 (or crown) of the cartridge fitted with the crimp seal 536 allowing its capture-and-locking features/projection mate 2066 to snap into place by engaging the underside of the aluminum crimp seal 536 and simultaneously interlocking and securely fastening the inlet connector 2110 with the aluminum crimp seal 536. The cartridge and needle connector sub-assembly can be inserted into a pump housing and the threaded coaxial cap 2030 which is free to slide along the tubing 301, shown in FIG. 58C, is used to fasten the sub-assembly to the pump housing, with the O-ring 2038 protecting the pump chamber from external fluid (shown in FIGS. 59A-B).

As discussed above, FIGS. 59A-B are an illustration of one type of pump housing 680 that could be used with medicament cartridges and the needle connector assemblies (shown in FIGS. 57A-58C) showing the reservoir and inlet connector sub-assemblies (in FIG. 59A) partially loaded into the pump housing 680 and fully loaded into the pump housing 580 with the threaded coaxial caps 2030, 2130 completely screwed into the pump housing 580. In some embodiments, the pump 651 has a display 652 that can provide digital feedback to the user regarding, for example, blood glucose levels, remaining medicament amounts, battery life, etc.

Figures 60A, 60B:
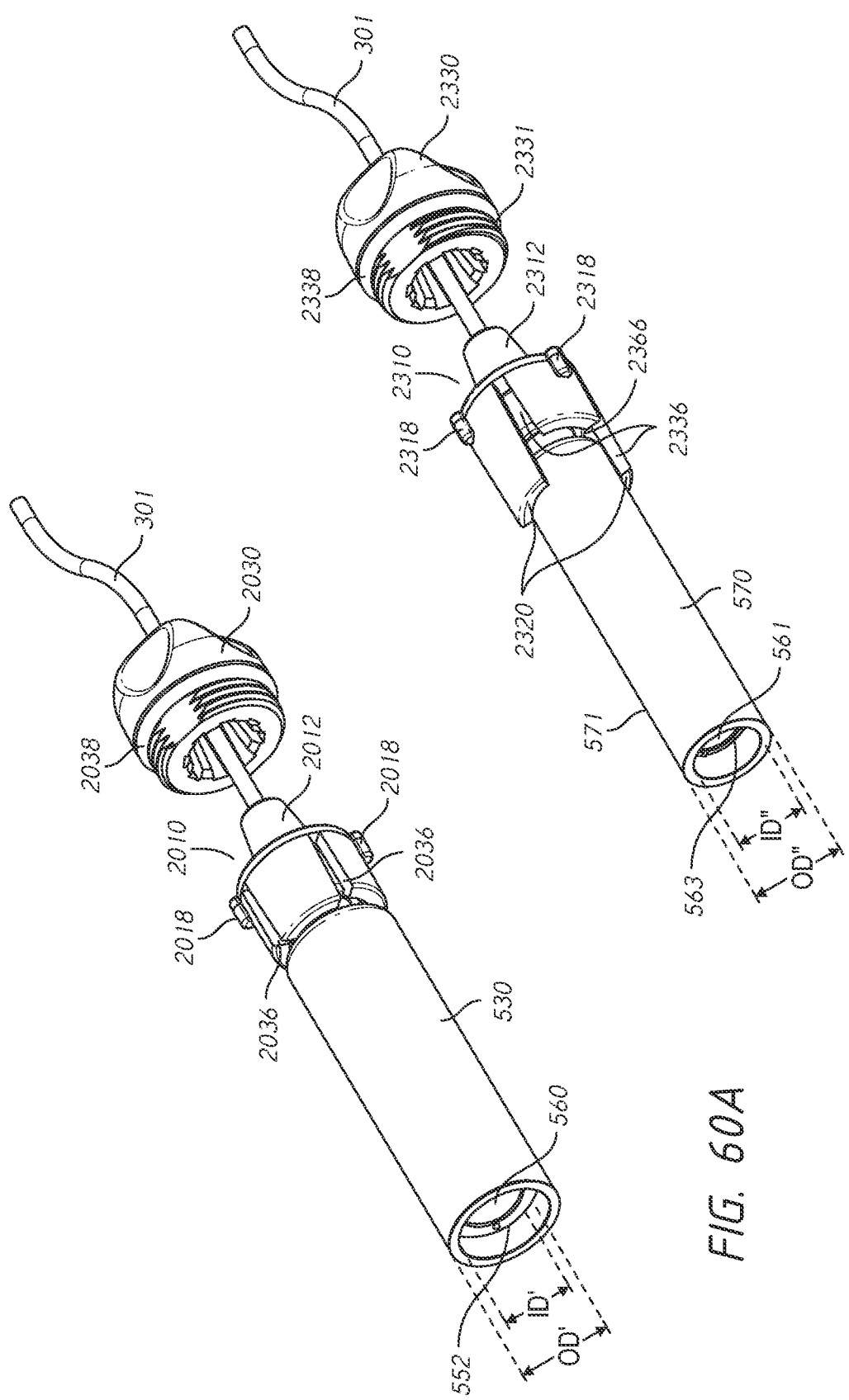
FIGS. 60A-B illustrate embodiments of inlet connectors, inlet connector covers, medicament reservoirs, and components thereof.

FIGS. 60A-B provide isometric views showing an embodiment with two cartridges and needle connector assemblies. In some embodiments, as shown in FIGS. 60A-B, the first medicament reservoir 530 has a larger outer diameter (OD') and a larger inner diameter (ID') than the second medicament reservoir 570 outer diameter (OD") and inner diameter (ID"), respectively. In some embodiments, the inlet connector 2310 has skirt features. When used with the smaller diameter cartridge 570, the inlet connector 2310 has skirt features 2320 that extend past the shoulder of the cartridge and hug the smaller diameter cartridge wall/body 571 closely. In some embodiments, accidental attempts to connect such an inlet connector 2310 with skirt features 2320 to a cartridge whose outer diameter is larger than that of the intended cartridge would be halted by the skirt features 2320 such that the capture-and-locking features (e.g., projection mate 2366) of the inlet connector 2310 would not be able to snap into place or engage the underside of the aluminum crimp seal 536 of the first medicament reservoir 530 (shown in FIGS. 58A-B) and the straight, beveled, hollow, stainless steel needle of the inlet connector 2310 (not shown) would not penetrate the cartridge septum 534 (shown in FIG. 58A) of the larger diameter cartridge 530. In this way, mis-connection of a needle connector 2310 to a cartridge with a larger diameter than the intended cartridge is prevented (not shown). Furthermore, the pump housing can be designed such that the cartridge 530 with a larger diameter is unable to fit into the pump chamber/receptacle intended for the smaller diameter cartridge. Whereas the two pump chambers/receptacles shown in FIG. 59A are of the same diameter and the two cartridges shown in FIG. 59A are of the same diameter, the pump chambers/receptacles could be of different diameters to accommodate cartridges having different diameters. This could be achieved either with different diameter sleeve inserts within the pump chambers/receptacles or different chamber/receptacle bore diameters. In some embodiments, the drive nut on the lead screw inside the pump chamber intended for the larger diameter cartridge cannot fit into the lumen of the smaller diameter cartridge 570 (not shown) because the internal diameter ID" is smaller than the drive nut. In this way, delivery of fluid when a cartridge is loaded into the wrong pump chamber is prevented.

In some embodiments involving two medicaments, the cartridge (cartridge A) containing one medicament (medicament A) has larger internal and external diameters than the corresponding diameters of the other cartridge (cartridge B) containing the other medicament (medicament B) (as shown in FIGS. 60A-B), such that cartridge A containing medicament A will not fit into the pump chamber intended for cartridge B containing medicament B, and the drive nut at the end of the lead screw in the pump chamber intended for medicament A is too large to fit into cartridge B containing medicament B.

In some embodiments involving two medicaments, the needle connector intended for cartridge B contains a skirt feature 2320 (as shown in FIG. 60B) that prevents the needle connector intended for cartridge B from penetrating and/or capturing cartridge A if the needle connector intended for cartridge B is accidentally placed on cartridge A.

In some embodiments involving two medicaments, the diameter of the aluminum crimp seal around the crown of one cartridge is identical to that of the other cartridge, but the height of the aluminum crimp seal around the crown of cartridge B is greater than that of cartridge A, such that the capture-and-locking feature 2366 within the needle connector 2310 intended for cartridge A will not be engaged if the needle connector intended for cartridge A is accidentally placed on cartridge B (not shown).

In some embodiments, as shown in FIGS. 57A-60B, the needle connector 2010, 2110, 2210, 2310 has any number of unique differentiating tabs, features, or protrusions, as shown in embodiments, which would allow insertion into the pump chamber of a pump housing that contains corresponding cavities, grooves, keyways, or slots to match with the unique differentiating tabs, features, or protrusions on the needle connector. In this way, only one type of needle connector can be inserted uniquely into one particular pump chamber. Alternatively, the needle connector might contain any number of cavities, grooves, keyways, or slots (not shown) that uniquely mate with tabs, features, or protrusions in the pump chamber of a pump housing.

In some embodiments (as shown in FIGS. 57A-60B), a straight, beveled, hollow, stainless steel needle is overmolded, bonded, press-fitted, glued, solvent bonded, insert molded, or otherwise attached to the inside of the needle connector 2010, 2110, 2210, 2310 and tubing 301 is overmolded, bonded, press-fitted, glued, solvent bonded, insert molded, or otherwise attached to the needle connector 2010, 2110, 2210, 2310 and to the straight, beveled, hollow, stainless steel needle in such a way as to allow a closed, independent, patent, and continuous fluid path through the straight, beveled, hollow, stainless steel needle, the needle connector, and the tubing. In some embodiments, the straight, beveled, hollow, stainless steel needle is recessed within the needle connector 2010, 2110, 2210, 2310 so as to be touch-proof.

In some embodiments, the tubing 301 passes through a threaded coaxial cap 2030, 2130, 2230, 2330, which is free to slide up and down the threaded coaxial cap and thread into a pump housing.

In some embodiments, the fully assembled cartridge assembly, comprising a cartridge, needle connector, and tubing system (consisting of a straight, beveled, hollow, stainless steel needle, a cartridge fastened to the needle connector with a capture-and-locking feature, tubing, and a threaded coaxial cap, as shown in FIGS. 58A-60B), inserts into a pump chamber of a pump housing that contains corresponding cavities, grooves, keyways, or slots to match the unique differentiating tabs, features, or protrusions on the needle connector. The threaded coaxial cap then screws into threads in the pump housing, as shown in FIGS. 59A-B.

Figure 61C:
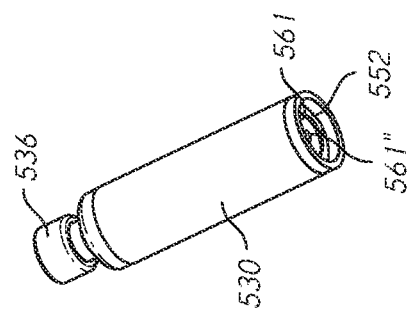
FIGS. 61A-C illustrate a system for filling a medicament reservoir.
Figure 61B:
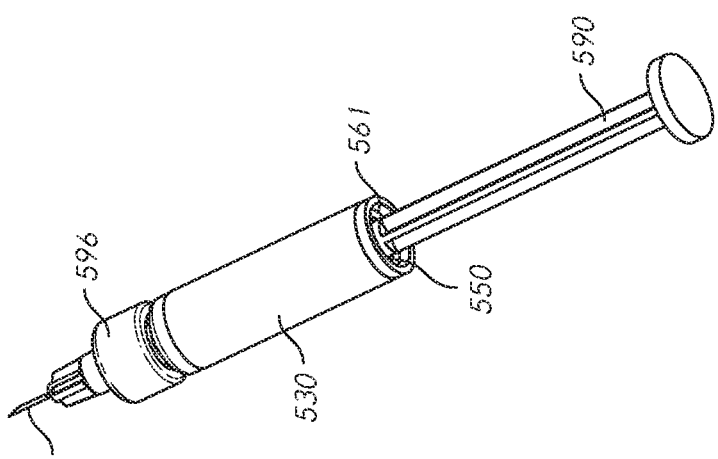
Figure 61A:
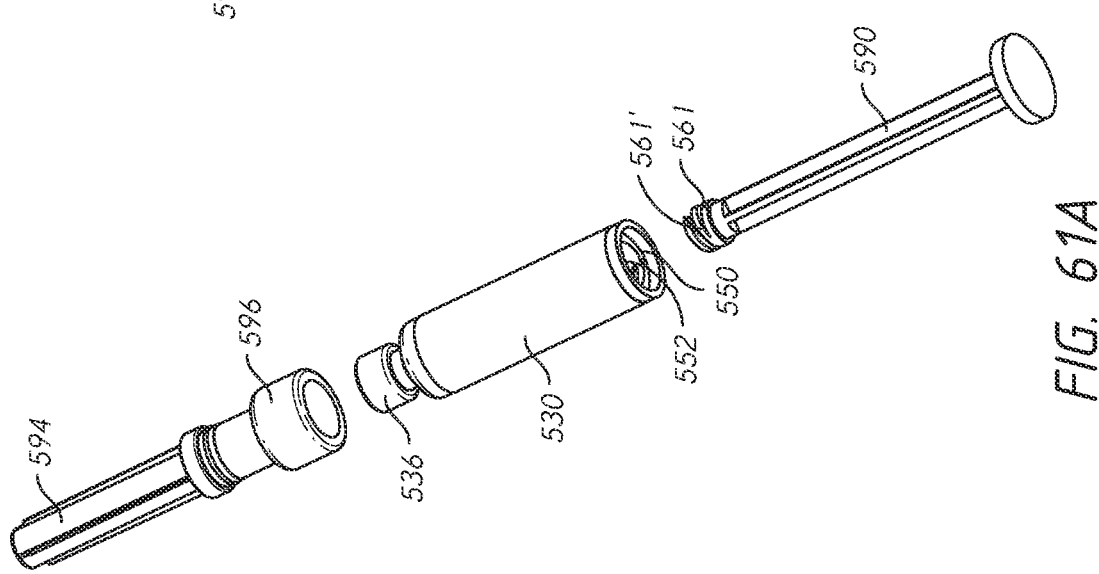

In some embodiments, a medicament reservoir filling system is provided, as shown in FIGS. 61A-B. FIG. 61A shows a rotated isometric view of a cartridge filling apparatus sub-assembly used to fill a medicament cartridge at the point of care. FIG. 61B shows a fillable cartridge assembly after the filling apparatus has been connected. FIG. 61C shows a fillable cartridge after the filling apparatus has been removed. In some embodiments, as shown, a fillable cartridge body 530, would be supplied and pre-assembled with the cartridge septum 534 (shown in FIG. 58A), the aluminum crimp seal 536 and the elastomeric plunger 550 with its threaded receptacle for a ferrous insert 552 exposed. In some embodiments, a needle transfer hub 596 containing a single needle 595 (with two beveled tips or two needles, each with a single beveled tip) would be attached to its needle guard 594 and provided along with the fillable cartridge 530. In some embodiments, a pushrod 590 would be attached to a threaded ferrous insert 561 by way of a breakable joint or threads and provided along with the fillable cartridge 530. In some embodiments, at the point of care (or at a site where filling is appropriate), the pushrod 590 would be used to thread (via an attaching feature 561') the threaded ferrous insert 561 into the threaded receptacle for a ferrous insert 552 present within the elastomeric plunger 550. In some embodiments, the needle transfer hub 596 would then be connected to the cartridge 530 such that the touch-proof needle or needle tip (not shown) within the needle transfer hub 596 would pierce the cartridge septum (shown in FIG. 58A), after which the needle guard 594 would be removed to reveal the needle or needle tip 595 designed to pierce the septum of the vial. The needle or needle tip designed to pierce the septum of the vial would then be inserted into a medicament vial (not shown), and the pushrod 590 would be used to fill the cartridge body 530 with the medicament (e.g., by inserting the needle 595 into a bulk medicament and depressing the plunger 550 into and back out of the medicament reservoir 530). After filling the cartridge 530, the needle transfer hub 596 and the pushrod 590 would be removed, revealing the threaded receptacle for a pushrod, or breakable joint remnant, and leaving the threaded ferrous insert 561 embedded within the elastomeric plunger 550 by virtue of its thread-locking barb 561'. Such a cartridge that is filled at the point of care could then be attached to a needle connector assembly (as in FIGS. 58A-C) and loaded into a pump housing (as in FIGS. 59A-B).

In some embodiments that utilize a needle transfer hub to transfer medicament from a vial to the cartridge, as in FIG. 61, a straight, beveled, hollow, stainless steel needle is overmolded, bonded, press-fitted, glued, solvent bonded, insert molded, or otherwise attached to the needle transfer hub in such a way as to allow a closed, independent, patent, and continuous fluid path through the straight, beveled, hollow, stainless steel needle. In some embodiments, the straight, beveled, hollow, stainless steel needle is beveled at both tips, where one tip would be designed to pierce the septum of the cartridge and the other tip would be designed to pierce the septum of the vial. In some embodiments, the tip that is designed to pierce the septum of the cartridge is recessed within the needle transfer hub so as to be touch-proof and the tip that is designed to pierce the septum of the vial can be concealed and protected by a needle guard which would be removed at the point of care before piercing the septum of the vial.

In some embodiments that utilize a needle transfer hub to transfer medicament from a vial to the cartridge, two separate, straight, beveled, hollow, stainless steel needles are overmolded, bonded, press-fitted, glued, solvent bonded, insert molded, or otherwise attached to the needle transfer hub in such a way as to allow a closed, independent, patent, and continuous fluid path through the straight, beveled, hollow, stainless steel needles. In some embodiments, each straight, beveled, hollow, stainless steel needle would be beveled only on one tip, where the beveled tip of one needle would be designed to pierce the septum of the cartridge and the beveled tip of the other needle would be designed to pierce the septum of the vial. In some embodiments, the tip that is designed to pierce the septum of the cartridge is recessed within the needle transfer hub so as to be touch-proof and the tip that is designed to pierce the septum of the vial can be concealed and protected by a needle guard which is to be removed at the point of care before piercing the septum of the vial. Alternatively, in some embodiments, the tip that is designed to pierce the septum of the vial can also be recessed so as to be touch-proof and a needle guard may not be supplied.

In some embodiments, involving two medicaments, mischanneling of medicaments can still be avoided if cartridge B is pre-filled with one medicament and cartridge A is filled at the point of care with a different medicament (using the embodiment described in FIGS. 61A-C). In some embodiments, as long as only one cartridge needs to be filled with one medicament at the point of care, and the other cartridge is pre-filled with another medicament, the designs described here can prevent medicament mischanneling. In some embodiments involving two medicaments, both cartridge A and cartridge B are pre-filled with medicament A and medicament B, respectively. In some embodiments involving two medicaments, cartridge A is filled at the point of care with medicament A and cartridge B is pre-filled with medicament B.

In some embodiments, the same dual-medicament infusion system could use identical needle sites, connectors, tubes, and cartridges in the configuration where both cartridge A is pre-filled with medicament A and cartridge B is pre-filled with medicament B, as in the configuration where cartridge A is filled at the point of care with medicament A and cartridge B is pre-filled with medicament B (or vice versa).

In some embodiments (as in FIGS. 61A-C) that require one cartridge to be filled at the point of care, medicament is transferred from a vial containing the medicament into the cartridge by way of a needle transfer hub and a pushrod that is connected to the elastomeric plunger residing in the cartridge by way of a breakable joint or threads such that the pushrod can be disconnected and discarded (or reused) upon completion of the filling procedure.

In some embodiments (as in FIGS. 61A-C) involving a cartridge containing a ferrous insert, the pushrod can be connected directly to the ferrous insert by means of a breakable joint or threads. Upon completion of the filling procedure, the pushrod can be disconnected and discarded (or reused), leaving the ferrous insert embedded within the elastomeric plunger. In some embodiments, in the case of a threaded connection between the ferrous insert and the pushrod, the threads on the ferrous insert could have a uni-directional burred surface (as in FIGS. 62A-F) that would allow it to easily thread into the elastomeric plunger, but would resist being threaded out of the elastomeric plunger. Whereas the threads on the pushrod would be smooth, and would not contain such a uni-directional burred surface, it would thread into and out of the ferrous insert easily, and without the ferrous insert threading out of the elastomeric plunger once the ferrous insert is fully threaded into the elastomeric plunger.

Figure 62C:
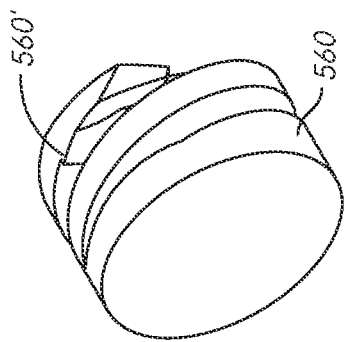
FIGS. 62A-F illustrate various inserts for engaging medicament reservoir pistons.
Figure 62F:
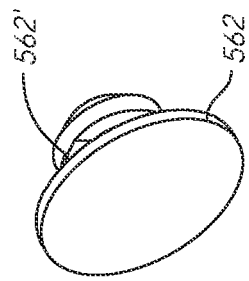
Figure 62B:
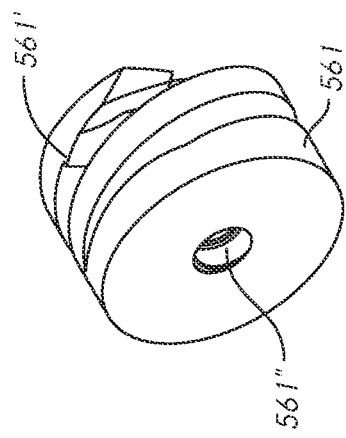
Figure 62E:
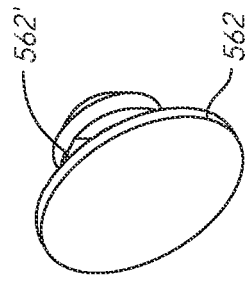
Figure 62A:
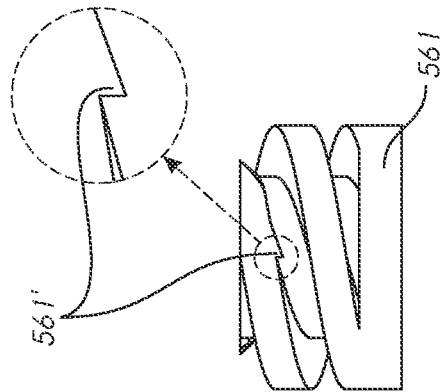
Figure 62D:
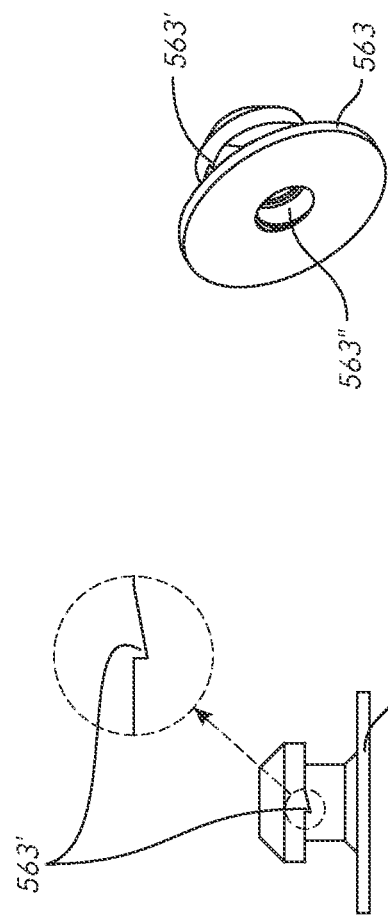

In some embodiments, as shown in FIG. 62A, a front view of the threaded ferrous insert 561, the insert 561 has a thread-locking barb 561'. An isometric view of the threaded ferrous insert 561 is shown in FIG. 62B with a threaded receptacle for a pushrod 561" and FIG. 62C shows an embodiment 560 without a threaded receptacle for a pushrod. FIG. 62D is a front view of the snug-fit metal insert 563 showing a thread-locking barb 563'. FIG. 62E is an isometric view of the snug-fit metal insert 563. FIG. 62E shows a threaded receptacle 563" for a pushrod. FIG. 62F shows an embodiment of a snug-fit insert 562 without a threaded receptacle for a pushrod. In some embodiments, the ferrous insert that is used to facilitate magnetic coupling between a magnet at the end of the drive nut in a pump chamber and the elastomeric plunger could be attached to the elastomeric plunger by way of threads (as in A, B, and C) or by way of snug-fit or snap-fit (as in D, E, and F). Regardless of the method of attachment to the elastomeric plunger, the ferrous insert could have a threaded receptacle for a pushrod (as in B and E). In some embodiments, in cases where a threaded receptacle for a pushrod is present, a pushrod could be pre-assembled with the ferrous insert. This sub-assembly could then be attached to the elastomeric plunger, either by way of threads, snug-fit, or snap-fit, and the pushrod could be used to fill an empty medicament cartridge. Upon filling the medicament cartridge, the pushrod could be detached from the ferrous insert while leaving the ferrous insert embedded within the elastomeric plunger (as in FIG. 61C). The metal insert may have thread-locking barbs to prevent the metal insert from backing out or rotating with the pushrod as the latter is being removed.

In some embodiments that utilize a needle transfer hub to transfer medicament from a vial to the cartridge, the body of the needle transfer hub could be manufactured from the same mold as the needle connector, except without the capture-and-locking feature as the needle transfer hub would need to be removed from the cartridge upon completing the filling procedure, whereas the needle connector would permanently capture the cartridge and would be disposed of along with the cartridge once the cartridge was emptied of its deliverable contents. Alternatively, the body of the needle transfer hub could be manufactured such that a weak capture and locking mechanism prevents the transfer hub from inadvertently pulling off the cartridge but can be overcome by intentional application of force.

In some embodiments involving a single medicament or multiple medicaments, the inlet end of each tubing is overmolded, bonded, press-fitted, glued, solvent bonded, insert molded, or otherwise attached to a needle connector (e.g., the inlet connector) and the outlet end of each tubing is overmolded, bonded, press-fitted, glued, solvent bonded, insert molded, or otherwise attached together with an infusion site and a cannula that delivers the medicament or medicaments to the delivery area (e.g., delivery transdermally, intradermally, subcutaneously, intramuscularly, intravenously, etc.).

In some embodiments involving a single medicament or multiple medicaments, the inlet end of each tubing is overmolded, bonded, press-fitted, glued, solvent bonded, insert molded, or otherwise attached to a needle connector (as in FIGS. 57A-60B) and the outlet end of each tubing is overmolded, bonded, press-fitted, glued, solvent bonded, insert molded, or otherwise attached to a straight, beveled, hollow, stainless steel needle and a component designed to connect to a subcutaneous or intradermal infusion site base (as in the dual-medicament infusion site connectors in FIGS. 64, 65, and 69, and the single-medicament infusion site connectors in FIGS. 67 and 68). For each medicament, this arrangement creates a closed, independent, patent, and continuous fluid path from the medicament reservoir to the end of the straight, beveled, hollow, stainless steel needle in the site connector. In some embodiments, each site connector can be physically independent and can connect to or disconnect from an infusion site base repeatedly.

FIGS. 63A-B are isometric views showing a portion of a dual-medicament infusion set. FIG. 63A shows an embodiment of a dual-medicament site base inserter 2426 attached. In FIG. 63B the dual-medicament site base inserter 2426 has been removed. In some embodiments involving two medicaments, the dual-medicament site base inserter 2426 couples two disjoint halves: the right site base 2424 (e.g., the first base, the glucagon base, etc.), and the left site base 2525 (e.g., the second base, the insulin base, etc.). In some embodiments, the inserter 2426 provides a handle for the application of the dual-medicament infusion site base 2401. In some embodiments, the base 2401 includes one or more needle guards 2429, 2529. In some embodiments, the infusion set base 2401 comprises one or more release liners 2428, 2528. In some embodiments, the infusion set base 2401 comprises an adhesive 2427, 2527 (e.g., a tape, gel, rubber adhesive, etc.). In some embodiments, once the two needle guards 2429, 2529 and the two release liners 2428, 2528 have been removed and discarded, the dual-medicament site base inserter 2426, can be used to apply the dual-medicament infusion set base 2401. In some embodiments, the adhesive tape 2427, 2527 can be used to adhere the dual-medicament infusion set 2401 to the surface of the skin. In some embodiments, after insertion, the dual-medicament site base inserter 2426 is disposable and is removed by activating the two living hinges 2436, 2536 and sliding the dual-medicament site base inserter 2426 out of the retention slots 2430, 2530 (shown in FIG. 65B) to reveal the two posts 2431, 2531 that are now ready to accept site connectors (see FIGS. 64A-B). In some embodiments, as shown in FIG. 63B, the posts 2431, 2531 are asymmetric. In some embodiments, the infusion set inserter 2426 is reusable and can be reattached to the site bases 2424, 2525.

In some embodiments, the infusion set includes a connector cover 2434. FIG. 64A is an isometric view showing the dual-medicament infusion site connectors 2432, 2533 with a dual-medicament site connector cover 2434 attached. FIG. 64B shows the dual-medicament infusion site connectors after the dual-medicament site connector cover 2434 has been removed. In some embodiments, the dual-medicament site connector cover 2434 couples the two disjoint halves: the first site connector 2432, and the second site connector 2533. In some embodiments, the site connector cover 2434 protects the site connectors 2432, 2533 from exposure (e.g., to dust, dirt, abrasion, physical damage, etc.) when they are not connected to the dual-medicament infusion site base 2401 (shown in FIG. 63B). In some embodiments, the second site connector 2533 can be disconnected from the dual-medicament site connector cover 2434 by activating the living hinge 2536 to release the retention clip 2535 and then sliding the second site connector 2533 out of the retention slot 2530 (shown in FIG. 65B). Disconnection of the second site connector 2533 from the dual-medicament site connector cover 2434 reveals the alignment posts 2539 and the asymmetric post receptacle 2538 which mate with corresponding features on the left site base 2525 (shown in FIG. 63B). The same procedure can be used to disconnect the first site connector 2432 from the dual-medicament site connector cover 2434, using corresponding features that are identifiable by enumerations that are identical in their last two digits (e.g., 2436 corresponds to 2536), except for the site connectors themselves, whose analogous enumerations are 2432 and 2533. The order of disconnection from the dual-medicament site connector cover 2434 and reconnection to the dual-medicament infusion site set base 2401 is arbitrary.

FIG. 65A shows an isometric view of the complete dual-medicament infusion set 2400 including the dual-medicament infusion site base 2401 (from FIG. 63B) assembled with the dual-medicament infusion site connectors (from FIG. 64B). In some embodiments, as shown, the infusion set comprises a first infusion assembly comprising a first base and a first connector and a second infusion assembly comprising a second base and a second connector. In some embodiments, having the bases separate prevents needle pull in a system where both needles are fixed to a single base. In some embodiments, this feature increases comfort when the infusion set is placed on an area where movement, pulling, and discomfort can occur. FIG. 65B shows a cross-sectional view revealing the internal components of the dual-medicament infusion set 2400. In some embodiments, after connection of the first site connector 2432 and the second site connector 2533, to the first site base 2424 and the left site base 2525, respectively, two closed, independent, patent, and continuous fluid paths are created. In some embodiments, the fluid paths terminate at 90 degree, beveled, hollow, piercing members 2442, 2542 (stainless steel needles). In some embodiments, each fluid path can begin in many types of connections to a fluid reservoir such as luer locks or custom cartridge connectors that eventually communicate with the lumen of the tubing 301 which is bonded together with a straight, beveled, hollow, stainless steel needle 2440, 2540 and an infusion site connector 2432, 2533, respectively. In some embodiments, upon connecting an infusion site connector(s) to an infusion site base(s), the straight, beveled, hollow, stainless steel needle 2440, 2540 pierces a site base septum 2441, 2541 respectively, allowing fluid to be pushed through the 90 degree, beveled, hollow, stainless steel needle 2442, 2542 for delivery to the patient. In some embodiments, lettering (or other visual indicators) 2450, 2550 are present on the infusion set 2400. In some embodiments, for example as shown in FIG. 65A, the indicators 2442, 2542 provide convenience to a user, though, in some embodiments, mis-connection of components is still mechanically prevented. In some embodiments, as shown, the indicators can be partial letters, with one portion on a base unit 2424 (e.g., a site base) and the other on a site connector 2432. In some embodiments, when the site base and site connector are properly connected, the indicators provide a completed letter (e.g., "I" and "G"). In some embodiments, when improperly connected, the indicators do not provide a compete letter (e.g., a mismatched letter), signaling visually to the user that the connector has been misplaced. In some embodiments, the 90 degree, beveled, hollow, stainless steel needle 2442, 2542 is placed in the site base using a sub-assembly consisting of itself, a soft durometer tube 2451, 2551 and the site base septum 2441, 2541 which is then secured with a plug that can be affixed to the site base with adhesive, snap-fit, or one-way capture-and-locking features (not shown).

FIG. 66A is an isometric view showing the first site base 2424 (also shown in FIG. 63B), as it would be used in the single-medicament configuration. In some embodiments, a first site base inserter 2443 can be attached as shown. FIG. 66B shows the first base 2424 after the first site base inserter 2443 has been removed. In some embodiments, the first site base inserter 2443 provides a handle for the application of the single-medicament infusion site base 2424. In some embodiments, after insertion, the first site base inserter 2443 is removed by activating the living hinge 2436 and sliding the right site base inserter 2443 out of the retention slot, 2430 (shown in FIG. 68B), to reveal the asymmetric post, 2431 that is now ready to accept a site connector 2432 (see FIGS. 67A-B). Although only the first half of the dual-medicament infusion site base 2401 (shown in FIG. 63B) is shown, the second half 2433 could also be used in a single-medicament configuration. In some embodiments, the second half 2433 could be attached using the same strategy as for the first half 2432, but with components having uniquely pairing features, hinges, etc.

FIG. 67A shows an isometric view of the first site connector 2432 (shown in FIGS. 64A-B), as it would be used in the single-medicament configuration, with the first site connector cover 2446. FIG. 67B shows the first site connector 2432 after the first site connector cover 2446 has been removed. In some embodiments, the first site connector cover 2446 protects the first site connector 2432 from exposure (e.g., to dirt, grime, debris, physical damage from bumps, etc.) and can be removed by activating the living hinge 2436, to release the retention clip 2435 and then sliding the first site connector 2432 out of the retention slot 2430 (shown in FIG. 68B). In some embodiments, disconnection of the first site connector 2432 from the first site connector cover 2446 reveals the alignment post 2439 and the asymmetric post receptacle 2438, which mate with corresponding features on the first site base 2424 (shown in FIGS. 66A-B). Although this depiction describes only the first half of the dual-medicament infusion site connectors (shown in FIGS. 64A-B), the second half could also be used in a single-medicament configuration with similarly numbered features.

FIG. 68A shows an isometric view of the complete single-medicament infusion set 2400' including the single-medicament infusion site base 2424 assembled with the single-medicament infusion site connector 2432. FIG. 68B shows a cross-sectional view revealing the internal components of the single-medicament infusion set 2400'. In some embodiments, after connection of the first site connector 2432 to the first site base 2424, a closed, independent, patent, and continuous fluid path is created. In some embodiments, the closed fluid path terminates in a 90 degree piercing member, 2442 (e.g., a beveled, hollow, stainless steel needle). In some embodiments, the fluid path can begin in many types of connections to a fluid reservoir such as luer locks or custom cartridge connectors that eventually communicate with the lumen of the tubing 301. In some embodiments, the tubing 301 is bonded together with a straight piercing element 2440 (e.g., a beveled, hollow, stainless steel needle) and, in this depiction, the first site connector 2432. In some embodiments, upon connecting the first site connector 2432 to the right site base 2424, the straight, beveled, hollow, stainless steel needle 2440 pierces the site base septum 2441, allowing fluid to be pushed through the 90 degree, beveled, hollow, stainless steel needle 2442, for delivery to the patient. In some embodiments, although this depiction is analogous only to the first half of the dual-medicament infusion set (shown in FIGS. 65A-B), the second half of the infusion set (e.g., the left half) could also be used in a single-medicament configuration. In some embodiments, lettering or other visual indicators 2450, 2550 are present and provide convenience to a user. In some embodiments, beside the visual indicators, mis-connection of components is still mechanically prevented. In some embodiments, the 90 degree, beveled, hollow, stainless steel needle 2442 is placed into the site base using a sub-assembly consisting of itself, a soft durometer tube 2451 and the site base septum 2441 which is then secured with a plug that can be affixed to the site base with adhesive, snap-fit, or one-way capture-and-locking features (not shown).

Figure 69E:
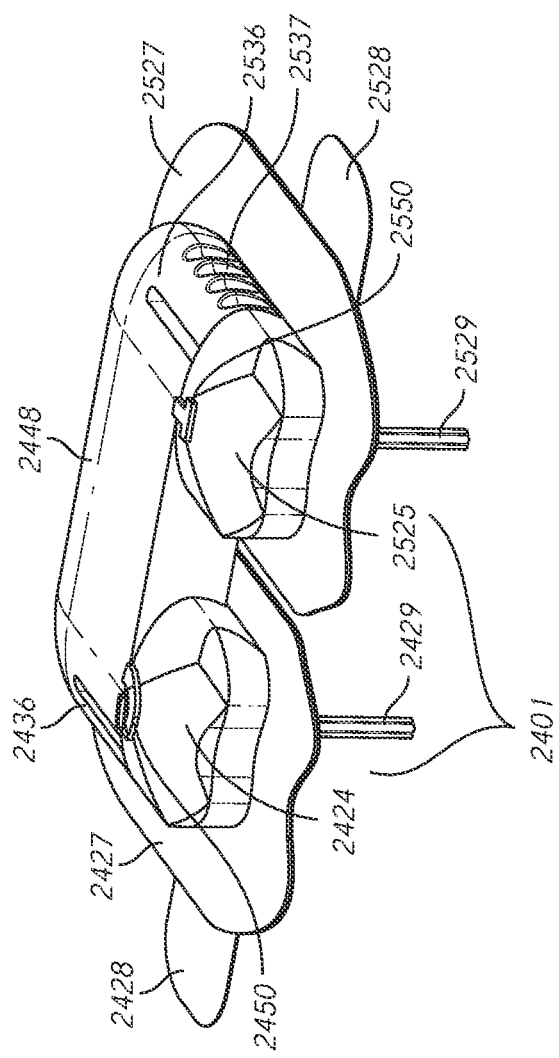

FIGS. 69A-E show isometric views of embodiments of a dual-medicament infusion set. FIG. 69A with the right site base 2424, connected to a right site base cover 2444. FIG. 69B shows the second site base 2525 connected to a second site base cover 2545. FIG. 69C shows the first site connector 2432 connected to a first site connector cover 2446. FIG. 69D shows the second (left) site connector 2533 connected to a second (left) site connector cover 2547. FIG. 69E shows the dual-medicament infusion site base 2401 connected to a dual-medicament site base cover 2448. In some embodiments, when an individual site connector must be replaced, it can be disconnected from its site base and a site base cover can be temporarily connected to the site base thereby protecting it from exposure (as in A and B) until the site connector can be replaced. In some embodiments, if both site connectors are removed together, a dual-medicament site base cover 2448 can be connected temporarily to both site bases to protect them from exposure until the site connectors can be replaced (as in E). In some embodiments, when any individual site base must be replaced, it can be disconnected from its site connector and a site connector cover is temporarily connected to the site connector thereby protecting it from exposure (as in C and D) until the site base can be replaced. In some embodiments, if both site bases are removed together, a dual-medicament site connector cover can be connected temporarily to both site connectors to protect them from exposure until the site bases can be replaced (as in FIG. 64A). A single-medicament embodiment could operate in the same manner as the right site half of A and C or the left site half of B and D.

In some embodiments, a single-medicament implementation of the infusion system that infuses only medicament A can use one of the two single-medicament infusion site connectors of the dual-medicament infusion site connectors. Similarly, the other single-medicament infusion site connector, which is distinct from the single-medicament infusion site connector for medicament A, can be used for a single-medicament implementation of the infusion system that infuses only medicament B. In some embodiments, asymmetric features in the dual-medicament infusion site connectors, such as any combination of asymmetric posts, asymmetric post receptacles, retention clips, alignment posts, and/or keys and keyways can be used to differentiate the single-medicament infusion site connector for medicament A from medicament B. In some embodiments, such features can also be used to ensure that a single-medicament implementation of the infusion system that infuses only medicament A uses only the medicament A chamber in the pump housing, and a single-medicament implementation of the infusion system that infuses only medicament B uses only the medicament B chamber in the pump housing. In some embodiments, in this way, the same molds used to manufacture the dual-medicament infusion site connectors will serve for the single-medicament infusion site connectors for a single-medicament implementation of the infusion system that infuses only medicament A or only medicament B. Thus, the constituent components of the dual-medicament infusion site base, dual-medicament infusion site connectors, tubing, and needle connectors, which serve a dual-medicament implementation of the infusion system, can be used to serve one of two distinct single-medicament implementations of the infusion system, one for medicament A and one for medicament B.

In some embodiments, software (either integrated into the infusion system or run on an auxiliary device such as a smart-phone or tablet) can be used to configure (automatically and/or manually) the infusion system to be configured either as a dual-medicament infusion system, as a single-medicament infusion system that uses only the medicament A chamber in the pump housing, or a single-medicament infusion system that uses only the medicament B chamber in the pump housing. In some embodiments, once any of these three configurations is implemented, the dual-medicament infusion site connectors or appropriate single-medicament infusion site connectors (either pertaining to medicament A or medicament B) can be chosen to match the particular configuration.

In some embodiments involving a site connector or site connectors, each site connector can be designed to connect to a site base by the action of at least one retention clip. Connection of a site connector to a site base allows a straight, beveled, hollow, stainless steel needle to pierce a septum in the site base (as in FIGS. 65 and 68). In some embodiments, once the straight, beveled, hollow, stainless steel needle in a site connector pierces the site base septum in a site base, it is brought into fluid continuity with a 90 degree, beveled, hollow, stainless steel needle, which can deliver the medicament to the delivery space. In some embodiments, this arrangement creates, for each medicament, a closed, independent, patent, and continuous fluid path from the medicament reservoir to the patient (e.g., for delivery transdermally, intradermally, subcutaneously, intramuscularly, intravenously, etc.). In some embodiments, each site base can be physically independent and can connect to or disconnect from a site connector repeatedly.

In some embodiments involving the use of a site base, the 90 degree, beveled, hollow, stainless steel needle can be overmolded, bonded, press-fitted, glued, solvent bonded, insert molded, or otherwise attached to the site base. In some embodiments, as an example other than insert molding, such a 90-degree, beveled, hollow, stainless steel needle may be sheathed with a soft durometer tube, which is in turn press-fit into the site base septum to create a sub-assembly outside the site base. In some embodiments, this sub-assembly can then be placed into a cavity in the site base (as shown in FIGS. 65 and 68) and a plug (not shown) can be used to hold the sub-assembly firmly in place while simultaneously ensuring a fluid seal.

In some embodiments involving the use of a site base, the 90 degree, beveled, hollow, stainless steel needle, the needle may be designed to protrude from the center or near the center of the site base. In some embodiments, this arrangement increases the likelihood that the site base will remain adhered to the surface of the skin for the entirety of its intended use.

In some embodiments involving multiple medicaments where a site connector can be connected to or disconnected from a site base, the site connectors and site bases can contain features such as lettering or other visual indicators to help prevent mis-connection of a site base or a site connector to incorrect site connectors or site bases. In some embodiments, such lettering or other visual indicators (colors, etc.) can be used in addition to physical features that mechanically prevent mis-connection. In some embodiments, the lettering or other visual indicators can be raised and colored differently from the base material to enhance visibility.

In some embodiments involving multiple medicaments where a site connector can be connected to or disconnected from a site base, the site connectors and the site bases can contain features such as asymmetric post receptacles, retention clips, alignment posts, and/or keys and keyways that prevent mis-connection of a site base or a site connector to incorrect site connectors or site bases.

In some embodiments involving a site connector or site connectors, each site connector can be designed to connect to a site base by the action of at least one retention clip that fits into at least one retention slot. In some embodiments involving two medicaments where only one retention clip and retention slot pair is used on each site connector and site base pair, the retention clips and retention slots may be present on the medial or lateral (as in FIGS. 63-65) sides of the site connectors and site bases. If the retention clips and retention slots are present on the lateral side of one site connector and site base pair, and on the medial site of the other site connector and site base pair, convenience is afforded to the user by allowing for the same finger to activate the living hinges. In this case, mis-connection of the site connectors to incorrect site bases is still prevented by the presence of the asymmetric posts and asymmetric post receptacles.

In some embodiments involving two medicaments, a right site connector and a left site connector (as in FIGS. 64, 65, and 69) comprise the dual-medicament infusion site connectors, can be physically independent, and can contain features such as asymmetric post receptacles, retention clips, alignment posts, and/or keys and keyways that prevent mis-connection of the dual-medicament infusion site connectors to a dual-medicament infusion site base.

In some embodiments involving two medicaments, a right (first) site base and a left (second) site base (as in FIGS. 63, 65, and 69) comprise the dual-medicament infusion site base, can be physically independent, and can contain features such as retention slots (shown in FIG. 65), asymmetric posts, and alignment post receptacles that prevent mis-connection of the dual-medicament infusion site connectors to the dual-medicament infusion site base.

In some embodiments the site connectors and site bases are designed such that any site connector and site base pair from a multiple medicament configuration can be used individually in a single medicament configuration (as in FIGS. 66-68) such that the single medicament site connectors and site bases can be manufactured from the same tools as the multiple medicament site connectors and site bases.

In some embodiments involving multiple medicaments, the site connectors can be supplied with one or more site connector covers that may couple all of the site connectors, certain groups of the site connectors, or none of the site connectors such that each site connector can be supplied with its own site connector cover. The site connector cover can be connected to and disconnected from the site connectors repeatedly and protects them from exposure (as in FIG. 64A). Likewise, the site bases can be supplied with one or more site base covers that may couple all of the site bases, certain groups of the site bases, or none of the site bases such that each site base can be supplied with its own site base cover. The site base cover can be connected to and disconnected from the site bases repeatedly and protects them from exposure (as in FIG. 69).

In some embodiments involving a single medicament or multiple medicaments wherein each site base is supplied with its own site base cover and each site connector is supplied with its own site connector cover, the site base covers and the site connector covers could be manufactured from the same tools as the site bases and the site connectors respectively. In some embodiments, each site base cover may not contain the straight, beveled, hollow, stainless steel needle and the tubing and each site connector cover may not contain the 90 degree, beveled, hollow, stainless steel needle and the site base septum.

In some embodiments involving a single medicament or multiple medicaments, the site base or site bases can be supplied with a site base inserter that connects to the site base or site bases in the same manner as the site connectors and provides a handle for the application of site base or site bases (as in FIGS. 63 and 66). In some embodiments, the handle provided by the site base inserter may be used to apply the site base manually or to load the site base(s) into an automated insertion device, such as a spring loaded inserter. In some embodiments, in the case of multiple site bases, one or more site base inserters may couple all of the site bases, certain groups of the site bases, or none of the site bases such that each site base can be supplied with its own site base inserter. In some embodiments, removal of a site base inserter would decouple any coupled site bases.

In some embodiments, the infusion pump may be equipped with a cartridge detection hardware-software system that would detect, separately, whenever each cartridge is fully loaded and secured in its corresponding pump chamber. In some embodiments, since the design described herein can ensure that only the correct medicament cartridge can be fully loaded and secured in its corresponding pump chamber, the cartridge detection system can, when functioning in conjunction with the design described herein, effectively and conclusively inform the infusion pump system of which specific medicaments are available for potential infusion. In some embodiments, the availability status of each medicament for potential infusion at any point in time would also allow the infusion pump system to set its mode of operation accordingly. In some embodiments, for example, in the case of a dual-chamber pump, the detection of both cartridges being in place would allow the infusion pump system to operate in dual-infusion mode, whereas the detection of one cartridge being in place but not the other would lead the infusion pump system to operate in a single-infusion mode that is specific to the medicament that corresponds to the cartridge that is detected to be in place. In some embodiments, this detection capability would be determined autonomously in real time, including when a cartridge is in place or out of place transiently or temporarily.

In some embodiments, the infusion pump may also be equipped with a delivery occlusion hardware-software detection system that would detect, separately, whenever the fluid-delivery path associated with each cartridge is impeded or obstructed anywhere from the cartridge, all the way through the corresponding tubing, and out to the distal end of the corresponding site base. In some embodiments, since the design described herein can ensure that only the correct tubing assembly and site base can be connected to their corresponding cartridge, the occlusion detection system would, when functioning in conjunction with the design described herein, effectively and conclusively inform the infusion pump system of which specific medicaments have a patent fluid-delivery path.

In some embodiments, with both cartridge and occlusion detection systems simultaneously present, the infusion pump may at any point in time conclusively determines which medicament is possible to deliver to the user. In some embodiments, the infusion pump could then autonomously set its mode of operation, as per the detection of which of the cartridges are in place along with the patency of their corresponding fluid-delivery paths. In some embodiments, in a specialized example of a dual-chamber pump that autonomously controls blood glucose levels by delivering insulin or an insulin analog, as well as a counter-regulatory agent (e.g. glucagon, a glucagon analog, or dextrose), such cartridge and occlusion detection systems, when functioning in conjunction with the design described here, would practically allow the infusion pump system to be prescribed in a particular configuration to deliver only insulin, or only the counter-regulatory agent, or both. Moreover, in some embodiments, such an implementation would also allow the dual-chamber infusion pump system to autonomously switch its mode of operation in real time whenever either delivery channel becomes unavailable for delivery (whether informed by cartridge detection, occlusion detection, or both), including in cases where channel availability may alternate in real time. In some embodiments, the cartridge and occlusion detection methods could be realized through a variety of hardware and software implementations, including, but not limited to, techniques that rely on magnetic field or electrical signal feedback in the case of cartridge detection, or techniques that rely on back pressure detection or flow sensor technology in the case of occlusion detection, to mention but a few.

In some embodiments, the features described in the context of one base, connector, housing, inlet connector, inlet connector cover, collar, medicament reservoir, or pump assembly can be mixed and matched and used in different combinations on other bases, connectors, housings, inlet connectors, inlet connector covers, collars, medicament reservoirs, or pump assemblies. For instance, any feature described above to prevent mischanneling can be deleted from or added to other embodiments. Redundant features can be added or deleted from the components of the medicament delivery systems.

The examples shown here are meant to be representative of a general approach to the design of an infusion system for multiple medicaments and various connectors, tubes, and cartridges to ensure proper channeling of each medicament to the patient. The geometric shapes, sizes, orientations, locations, and number of tabs, protrusions, and features, as well as the corresponding cavities, grooves, keyways, or slots are merely meant to be examples of a much greater abundance of variations on the particular examples shown here.

For instance, as described elsewhere herein, the degrees of separation between the tabs, protrusions, and features on the cap connectors and on the corresponding cavities, grooves, keyways, or slots in the pump housing, or the degrees of separation between the tabs, protrusions, and features on the pre-fitted collar assembly and the corresponding cavities, grooves, keyways, or slots on the cap connector shown here can be generalized to be placed closer together or farther apart than in the examples shown here. Additionally, the number of tabs, protrusions, and features on the cap connectors and on the corresponding cavities, grooves, keyways, or slots in the pump housing, or the number of tabs, protrusions, and features on the pre-fitted collar assembly and the corresponding cavities, grooves, keyways, or slots on the cap connector designs shown here can be generalized to one, two, three or more such features, which might have different sizes, shapes, orientations, and locations from the examples shown here. Moreover, as discussed above, the locations of the tabs, protrusions, and features on the pre-fitted collar assembly and the corresponding cavities, grooves, keyways, or slots on the cap connector designs shown here need not be limited to the neck or head (or crown) regions of the cartridge. For instance, the point of engagement between the pre-fitted collar assembly and the cap connector could alternatively occur elsewhere on the body of the cartridge, or extend over the entire length of the cartridge. In some embodiments, the tabs, protrusions, and features on the pre-fitted collar assemblies described here could instead appear directly on the surface of the cartridge (such as in the case of an injection molded cartridge), which is either pre-filled with medicament or not pre-filled with medicament.

In some embodiments, the cartridges described here can either be pre-filled with medicament or not pre-filled with medicament before or after the pre-fitted collar assemblies described here are installed onto the cartridge. In the case of the latter, such cartridges can be filled with medicament sometime after the manufacturing process, including at the point of care.

In some embodiments, for example in the case of a cartridge that is filled with medicament at the point of care, the cap connector might not contain a recessed needle, but rather might couple with said cartridge using a standard luer lock or other mechanism, as in FIG. 50, in which the medicament flows directly from the cartridge into the tubing without first passing through a needle. In this case, the tabs, protrusions, and features on the pre-fitted collar assemblies described here would still appear on the surface of the cap connector.

In some embodiments, mischanneling of medicaments can still be avoided if one cartridge is prefilled with one medicament and a second cartridge is filled at the point of care with a different medicament (using the embodiment described in FIG. 50 or FIGS. 61A-C). So long as only one cartridge needs to be filled with medicament at the point of care, and all other cartridges are pre-filled with medicaments, the designs described here can prevent medicament mischanneling.

In some embodiments, the features and components described above are applicable to reusable injection pens (e.g., insulin pens, etc.). In some embodiments, each collar, cap, input connector, etc. could be applied to prevent incorrect dosing of drugs delivered by injection pens. For example, one unique cartridge, having a first set of unique features as described above could be used to deliver long-acting insulin to a patient via a mated injection pen. Another unique cartridge, with a second set of unique features as described above could be used to deliver fast-acting or ultra-rapid insulin analogs to a patient via a different mated injection pen. As a further example, these features can be used to differentiate between more and less concentrated insulin analogs (e.g. U100, U200, or U500 insulin analogs).

The medicament described above for any embodiment can include any suitable compound or drug for treating, regulating, controlling or addressing one or more conditions of the patient. While diabetes mellitus is a target, other conditions can be addressed as well (e.g., pancreatic misfunction). The medicament can include for example a regulating agent, such as insulin, for regulating the blood glucose levels in the patient and/or a counter-regulatory agent, such as glucose or glucagon, for more effective blood glucose regulation in certain circumstances. Other type of agents can be used as well.

In some embodiments, an infusion system for multiple medicaments involving various needle sites, connectors, tubes, and cartridges that ensure proper channeling of each medicament to the patient is provided. In some embodiments, the infusion system comprises an infusion pump. In some embodiments, the infusion system comprises an infusion pump with two or more pump chambers. In some embodiments, the infusion system comprises cartridges that can be filled at the point of care with different medicaments (or may be pre-filled with different medicaments). In some embodiments, the infusion system comprises connectors and tubing that connect the cartridges to the infusion pump in such a way as to prevent mischanneling or cross-channeling of medicaments. In some embodiments, each type of cartridge for each type of medicament has unique differentiating sizes, shapes, and/or geometrical features (either as an integral part of the cartridge or as a component attached or affixed to the cartridge) that allow for unique coupling with a type of connector that itself has unique differentiating features that engage corresponding features in the pump housing and only allow for insertion of the proper cartridge into the proper pump chamber within the infusion pump.

In some embodiments, the systems described above can be used for the delivery of single medicaments, or combinations of medicaments. For instance, in some embodiments, the infusion set can be used to deliver agent A (e.g., insulin), while the features of that infusion set would be incompatible with the medicament reservoir for agent B (e.g., glucagon). Alternatively, in some embodiments, the infusion set can be used to deliver agent B, while the features of that infusion set would be incompatible with the medicament reservoir for agent A. Additionally, in some embodiments, as described above, dual medicaments can be delivered without mischanneling (e.g., bi-hormonal delivery, dual drug delivery, etc.). As is apparent from the disclosure above, configurations for the delivery of a plurality of medicaments (e.g., two, three, four, or more) without mischanneling can be provided.

Some embodiments provide methods of using the medicament delivery system. In some embodiments, the base set, the connector set, and the medicament reservoir set are provided together fully assembled, partially assembled, or disassembled in packaging. For instance, in some embodiments, the base is attached to the connector set in the package. In some embodiments, the connector set is attached to the medicament reservoir set in the package. In some embodiments, each of the base set, the connector set, and the medicament reservoir set are provided together or packaged separately.

In some embodiments, the base is removed from its packaging. In some embodiments, where present, the needle guards are then removed from the needles of the base set prior to insertion into a patient. In some embodiments, the release liners are removed from the base set. In some embodiments, the base set is then positioned over the skin and affixed there manually, by inserting the needles into the skin.

In some embodiments, a base inserter is provided on the packaged base. In some embodiments, the base set can be positioned for insertion into the patient manually by holding the base inserter. In some embodiments, the base inserter is gripped between the finger and thumb of a user (e.g., a patient or doctor) and plunged into the skin to manually insert the piercing elements of the base set into patient and to affix the base set on the patient (e.g., via an adhesive on the set). In some embodiments, the base inserter is can be loaded into a positioning device that projects (e.g., shoots, or delivers) the base unit automatically into the skin of the patient at an appropriate angle and position. In some embodiments, the positioning device is provided already attached to the packaged based set.

In some embodiments, after injecting the base set, the connector set is engaged to the base set. In some embodiments, the connector set is already engaged to the base set in the package. In some embodiments, the connector set is then connected via tubing to the inlet connectors. In some embodiments, after connecting the connector set to the base set, the medicament reservoir(s) can be attached to the inlet connectors and secured there by one or more features of the inlet connector. In some embodiments, prefilled medicament reservoirs are already attached to the base set via the connector set in the package.

In some embodiments, the medicament reservoirs are then placed into corresponding receptacles within a pump. In some embodiments, the reservoirs are tightened in place within the receptacle of the pump by threading an inlet connector cover into the pump. In some embodiments, the pump can then be activated to allow one or more medicaments to be delivered to the patient.

Any terms generally associated with circles, such as "radius" or "radial" or "diameter" or "circumference" or "circumferential" or any derivatives or similar types of terms are intended to be used to designate any corresponding structure in any type of geometry, not just circular structures. For example, "radial" as applied to another geometric structure should be understood to refer to a direction or distance between a location corresponding to a general geometric center of such structure to a perimeter of such structure; "diameter" as applied to another geometric structure should be understood to refer to a cross sectional width of such structure; and "circumference" as applied to another geometric structure should be understood to refer to a perimeter region. Nothing in this specification or drawings should be interpreted to limit these terms to only circles or circular structures.

What is claimed is:

1. An infusion set for delivering a single or multiple medicaments to a patient, the infusion set comprising:
  (i) a base set comprising:
    a first base unit having a first port and a first adhesive portion, the first base unit comprising a first piercing element configured to deliver a first medicament to the patient, the first adhesive portion configured to adhere the first base unit to the patient; and
    a second base unit having a second port, the second base unit comprising a second adhesive portion configured to adhere the second base unit to the patient; and
  (ii) a connector set comprising:
    a first distribution connector configured to reversibly couple to the first base unit via the first port and to provide a first fluid path from a first medicament reservoir to the first port of the first base; and
    a second distribution connector configured to reversibly couple to the second base unit;
  wherein the first base unit comprises a first feature that prevents engagement of the second distribution connector to the first base unit;
  wherein the second base unit comprises a second feature that prevents engagement of the first distribution connector to the second base unit; and
  wherein the first base unit and the second base unit are able to move independently with respect to each other and are configured to fit contours of the patient's body during movements made by the patient,
  wherein the first distribution connector comprises a single retention clip that locks the first distribution connector in place when in a coupled position with the first base unit;
  wherein the single retention clip is configured to be depressed to allow one-handed de-coupling of the first distribution connector from the first base unit; and
  wherein the first distribution connector and second distribution connector are each asymmetric.

2. The infusion set of claim 1, wherein the first piercing element is a catheter in fluidic communication with the first port and configured to deliver the first medicament to the patient via the first base unit.

3. The infusion set of claim 1, wherein the second distribution connector comprises a single retention clip that locks the second distribution connector in place when in a coupled position with the second base unit, wherein the single retention clip of the first distribution connector is configured to prevent coupling of the first distribution connector to the second base unit and wherein the single retention clip of the second distribution connector is configured to prevent coupling of the second distribution connector to the first base unit.

4. The infusion set of claim 3, wherein the single retention clip of the second distribution connector is configured to be depressed to allow one-handed de-coupling of the second distribution connector from the second port.

5. The infusion set of claim 1, wherein the first distribution connector comprises an alignment feature that guides the first distribution connector in place when coupling it to the first base unit.

6. The infusion set of claim 1, wherein the first piercing element is flexible.

7. The infusion set of claim 1, further comprising a first inlet connector and a first fluid conduit, the first fluid conduit being in fluidic communication with the first distribution connector;
  wherein the first fluid path extends through the first inlet connector, the first fluid conduit, and the first distribution connector; and
  wherein the first inlet connector is configured to engage the first medicament reservoir and to allow fluidic communication with the first medicament within the first medicament reservoir.

8. The infusion set of claim 7, further comprising a second inlet connector and a second fluid conduit, the second fluid conduit being in fluidic communication with the second distribution connector;
  wherein a second fluid path extends through the second inlet connector, the second fluid conduit, and the second distribution connector; and
  wherein the second inlet connector is configured to engage a second medicament reservoir and to allow fluidic communication with a second medicament within the second medicament reservoir.

9. The infusion set of claim 8, wherein the first inlet connector comprises engagement elements configured to engage a first receptacle of an infusion pump.

10. The infusion set of claim 9, wherein the engagement features of the first inlet connector are configured to prevent engagement of the first inlet connector with a second receptacle of the infusion pump.

11. The infusion set of claim 10, wherein the second inlet connector comprises engagement elements configured to engage a second receptacle of the infusion pump and wherein the engagement elements of the second inlet connector are configured to prevent engagement of the second inlet connector with the first receptacle of the infusion pump.

12. The infusion set of claim 8, wherein the first inlet connector and the second inlet connector are shaped differently and wherein the first inlet connector comprises features that are configured to prevent engagement with the second medicament reservoir.

13. The infusion set of claim 12, wherein the second inlet connector comprises features that are configured to prevent engagement with the first medicament reservoir.

14. The infusion set of claim 8, wherein the first inlet connector comprises a third piercing element configured to insert into the first medicament reservoir to allow the first medicament to enter the first fluid path.

15. The infusion set of claim 14, wherein the second inlet connector comprises a fourth piercing element configured to insert into the second medicament reservoir to allow the second medicament to enter the second fluid path.

* * * * *